(12) United States Patent
Franke et al.

(10) Patent No.: US 11,950,931 B2
(45) Date of Patent: Apr. 9, 2024

(54) ELECTRODE CURABLE AND MOLDABLE TO CONTOURS OF A TARGET IN BODILY TISSUE AND METHODS OF MANUFACTURING AND PLACEMENT AND DISPENSERS THEREFOR

(71) Applicant: Neuronoff, Inc., Valencia, CA (US)

(72) Inventors: Manfred Franke, Valencia, CA (US); Andrew Shoffstall, Valencia, CA (US); John W. Sheets, Jr., Valencia, CA (US)

(73) Assignee: NEURONOFF, INC., Cleveland, OH (US)

( * ) Notice: Subject to any disclaimer, the term of this patent is extended or adjusted under 35 U.S.C. 154(b) by 1337 days.

(21) Appl. No.: 16/439,323

(22) Filed: Jun. 12, 2019

(65) Prior Publication Data
US 2019/0357847 A1 Nov. 28, 2019

Related U.S. Application Data

(63) Continuation of application No. PCT/US2017/065929, filed on Dec. 12, 2017.
(Continued)

(51) Int. Cl.
*A61B 5/268* (2021.01)
*A61B 5/00* (2006.01)
(Continued)

(52) U.S. Cl.
CPC ............. *A61B 5/686* (2013.01); *A61B 5/268* (2021.01); *A61B 5/6868* (2013.01);
(Continued)

(58) Field of Classification Search
CPC ......... A61B 5/263; A61B 5/266; A61B 5/268; A61B 5/6877; A61B 5/686; A61B 5/6868
See application file for complete search history.

(56) References Cited

U.S. PATENT DOCUMENTS

| | | |
|---|---|---|
| 3,587,982 A | 6/1971 | Campbell |
| 4,525,147 A | 6/1985 | Pitz |

(Continued)

FOREIGN PATENT DOCUMENTS

WO 2015149070 10/2015

OTHER PUBLICATIONS

Coghlan, Judith, "Response to Extended Search Report for Europe Patent App No. 17880495.1," filed with European Patent Office dated Mar. 31, 2021.
(Continued)

*Primary Examiner* — Eun Hwa Kim
(74) *Attorney, Agent, or Firm* — Joseph S. Bird, III; Maynard, Cooper & Gale, PC

(57) ABSTRACT

A cured electrode comprising a mixture comprising conductive elements and a carrier which, upon injection into a body, cures from a liquid phase at a first time to a biocompatible solid phase at a second time at or on a target tissue within the body. The cured electrode is capable of being molded around contours of the target tissue so that, after curing, the cured electrode retains the contours of the target tissue. The cured electrode is capable of conducting electricity at a resistance of less than 10 ohm meters in the liquid or the solid phases. Carrier materials include hydgrogel, silicone, bone cement, cyanoacrylate, dental resin and a fibrin mix. The carrier material may also be used to anchor the cured electrode and provide great stability.

45 Claims, 74 Drawing Sheets

Related U.S. Application Data

(60) Provisional application No. 62/564,809, filed on Sep. 28, 2017, provisional application No. 62/479,117, filed on Mar. 30, 2017, provisional application No. 62/432,747, filed on Dec. 12, 2016.

(51) Int. Cl.

| | | |
|---|---|---|
| *A61L 24/02* | (2006.01) | |
| *A61L 24/06* | (2006.01) | |
| *A61L 31/02* | (2006.01) | |
| *A61L 31/04* | (2006.01) | |
| *A61L 31/06* | (2006.01) | |
| *A61L 31/14* | (2006.01) | |
| *A61L 31/16* | (2006.01) | |
| *A61N 1/05* | (2006.01) | |

(52) U.S. Cl.
CPC ............ *A61B 5/6877* (2013.01); *A61L 24/02* (2013.01); *A61L 24/06* (2013.01); *A61L 31/022* (2013.01); *A61L 31/041* (2013.01); *A61L 31/06* (2013.01); *A61L 31/145* (2013.01); *A61L 31/148* (2013.01); *A61L 31/16* (2013.01); *A61N 1/0558* (2013.01); *A61L 2300/402* (2013.01); *A61L 2300/404* (2013.01); *A61L 2300/406* (2013.01); *A61L 2300/41* (2013.01); *A61L 2400/06* (2013.01); *A61N 1/0534* (2013.01)

(56) References Cited

U.S. PATENT DOCUMENTS

| | | | |
|---|---|---|---|
| 4,722,761 | A | 2/1988 | Cartmell |
| 5,063,257 | A | 11/1991 | Akahane |
| 5,286,415 | A | 2/1994 | Buckley |
| 5,622,168 | A | 4/1997 | Keusch |
| 5,814,022 | A | 9/1998 | Antanavich |
| 6,305,934 | B1 | 10/2001 | Hatley |
| 6,610,033 | B1 | 8/2003 | Melanson |
| 8,828,433 | B2 | 9/2014 | Claude |
| 2003/0170906 | A1 | 9/2003 | Swain |
| 2004/0159833 | A1 | 8/2004 | Rueckes |
| 2005/0154434 | A1 | 7/2005 | Simon |
| 2006/0195146 | A1 | 8/2006 | Tracey |
| 2007/0051307 | A1 | 3/2007 | Babaev |
| 2007/0093748 | A1 | 4/2007 | Nayak |
| 2008/0260802 | A1 | 10/2008 | Sawhney |
| 2011/0087315 | A1 | 4/2011 | Richardson-Burns |
| 2011/0257504 | A1* | 10/2011 | Hendricks ................ A61N 1/05 607/45 |
| 2014/0276247 | A1 | 9/2014 | Hall |
| 2015/0066125 | A1 | 3/2015 | Osypka |
| 2015/0238754 | A1 | 8/2015 | Loudin |
| 2016/0120472 | A1 | 5/2016 | Kub |

OTHER PUBLICATIONS

Knupling, Moritz, "European Search Report for Europe App No. 17880495.1," European Patent Office; dated Apr. 24, 2020.

Heo, Dong Nyoung, et al., "Multifunctional hydrogel coatings on the surface of neural cuff electrode for improving electrode-nerve tissue interfaces," Acta Biomaterialia, vol. 39, May 6, 2016; pp. 25,33.

Hong, Guosong, et al., "Syringe Injectable Electronics: Precise Targeted Delivery with Quantitative Input/Output Connectivity," NanoLett, Sep. 28, 2015.

Ghatee, Rosa, "Injectable Conductive Hydrogels for Use in Neuroprosthetic Intervention," Thesis in electrical engineering at University of Rhode Island; Jan. 1, 2015, pp. 1-45.

Liu, Jia, et al., "Syringe-injectable electronics," Nature Nanotechnology, vol. 10, Jun. 8, 2015, pp. 629-637.

Sekitani, Tsuyoshi, et al., "Ultraflexible organic amplifier with biocompatible gel electrodes," Nature Communications, Apr. 29, 2016; pp. 1-11; and supplemental information pp. 1-26.

Sui, Kunyan, "Injectable Supramolecular Hybrid Hydrogels Formed by MWNT-grafted -Poly(ethylene glycol) and x-Cyclodextrix," Journal of Polymer Science: Part A: Polymer Chemistry, vol. 48, Apr. 21, 2010, pp. 3145-3151.

Baei, Payam, "Electrically conductive gold nanoparticle-chitosan thermosensitive hydrogels for cardiac tissue engineering," Materials Science and Engineering, vol. 62, Feb. 19, 2016, pp. 131-141.

Dong, Ruonan, et al., "Self-Healing Conductive Injectable Hydrogels with Antibacterial Activity as Cell Delivery Carrier for Cardiac Cell Therapy," ACS Applied Materials & Interfaces, vol. 8, Jun. 16, 2016; pp. 171389-17150.

Young, Lee, "International Search Report and Written Opinion for International App No. PCT/US2018/36773," US International Searching Authority, dated Sep. 20, 2018.

Young, Lee, "International Search Report and Written Opinion for International App No. PCT/US2017/65929," US International Searching Authority, dated Apr. 25, 2018.

\* cited by examiner

Pierce the skin and advance with ultrasound guidance

Advance

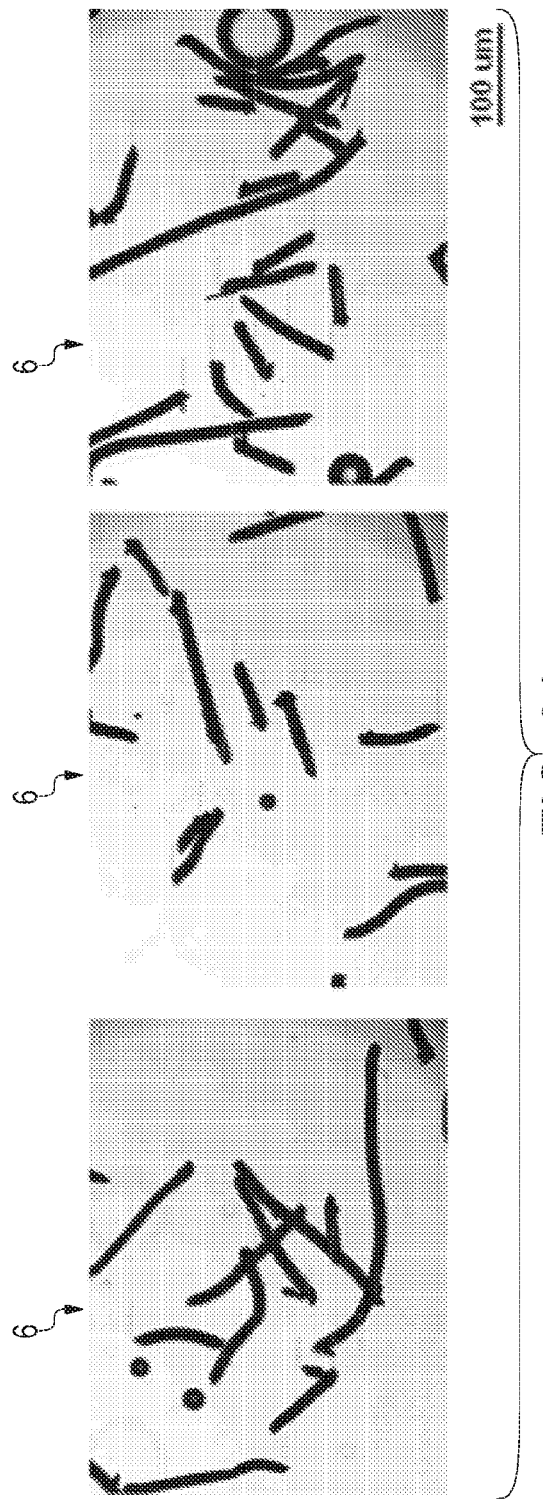
FIG. 34
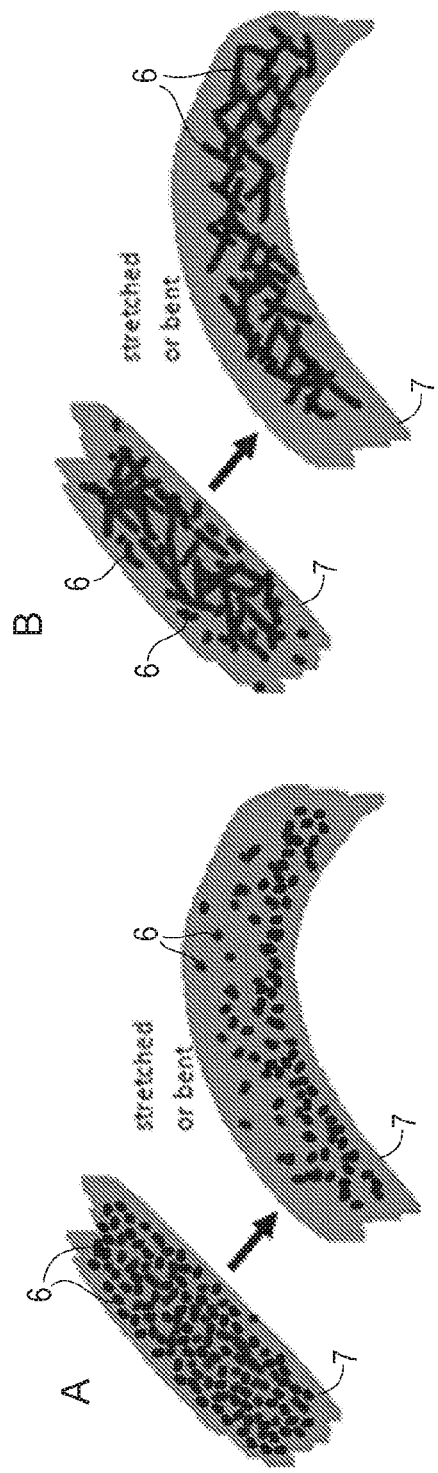
FIG. 35A
FIG. 35B

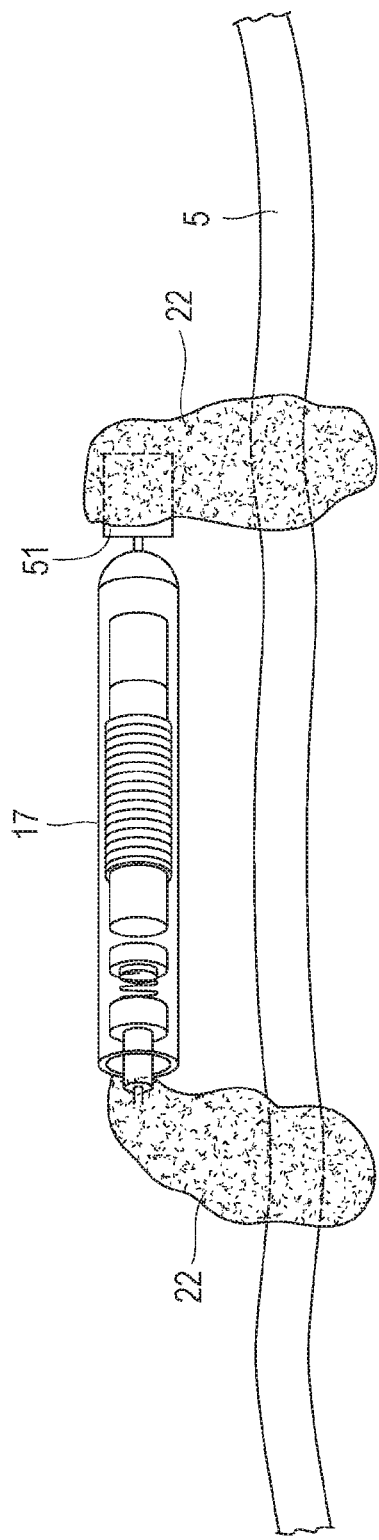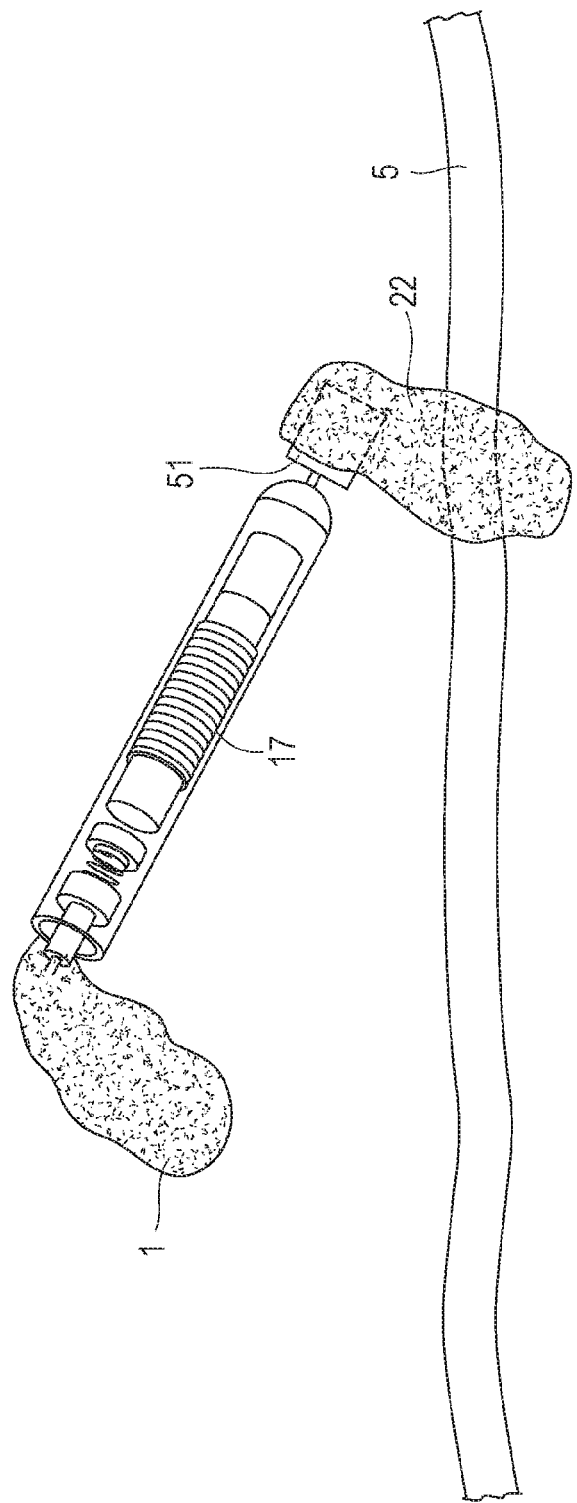
FIG. 44
FIG. 45

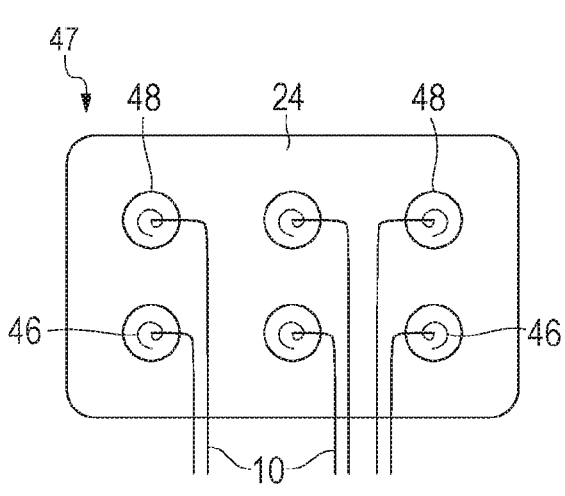
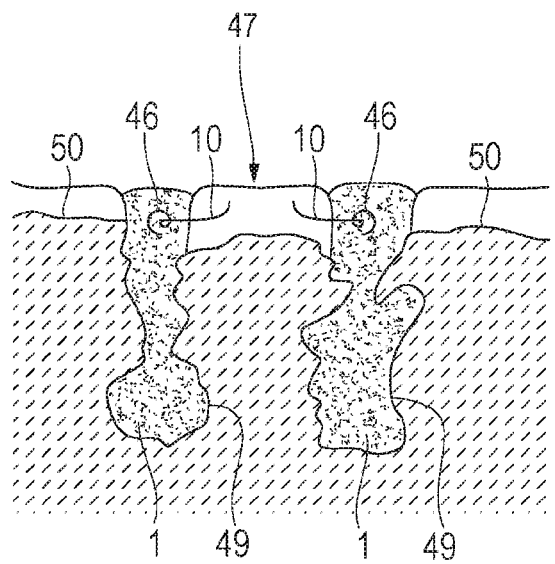
FIG. 56A  FIG. 56B
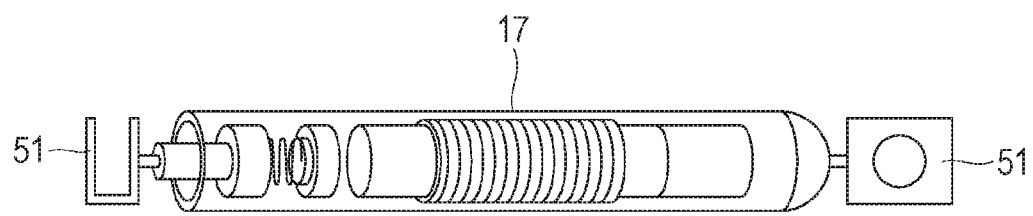
FIG. 57

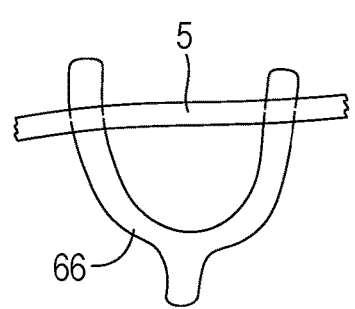 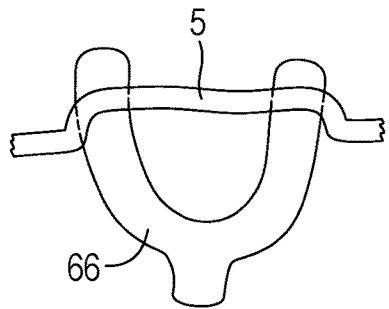 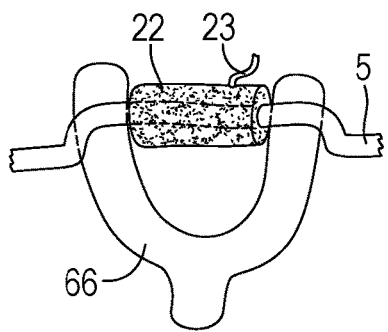
FIG. 70A          FIG. 70B          FIG. 70C
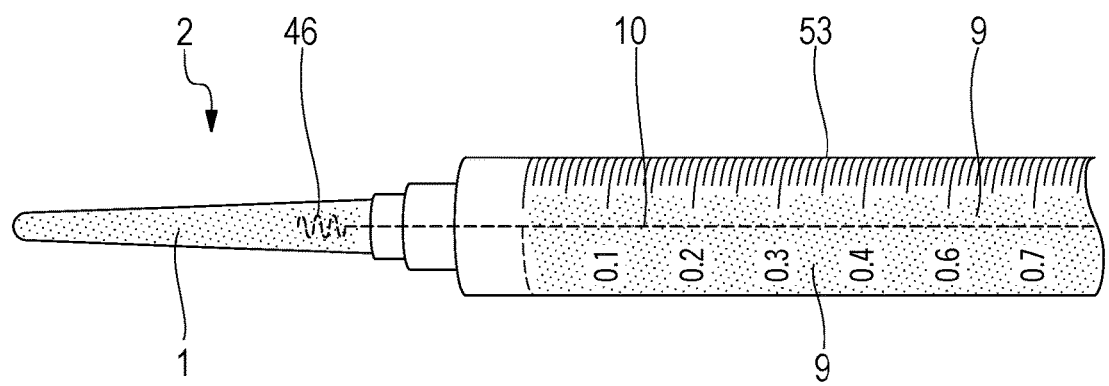
FIG. 71

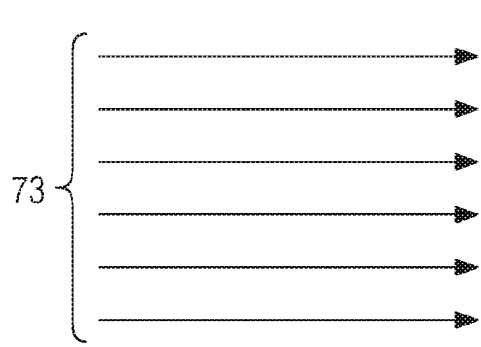
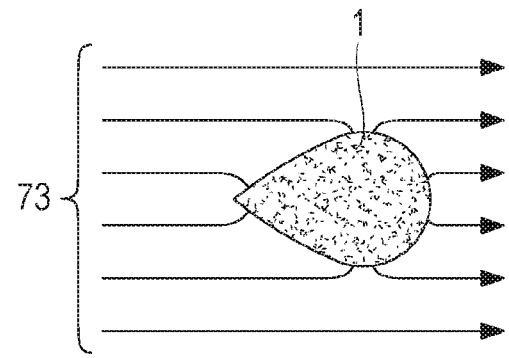
FIG. 81A          FIG. 81B
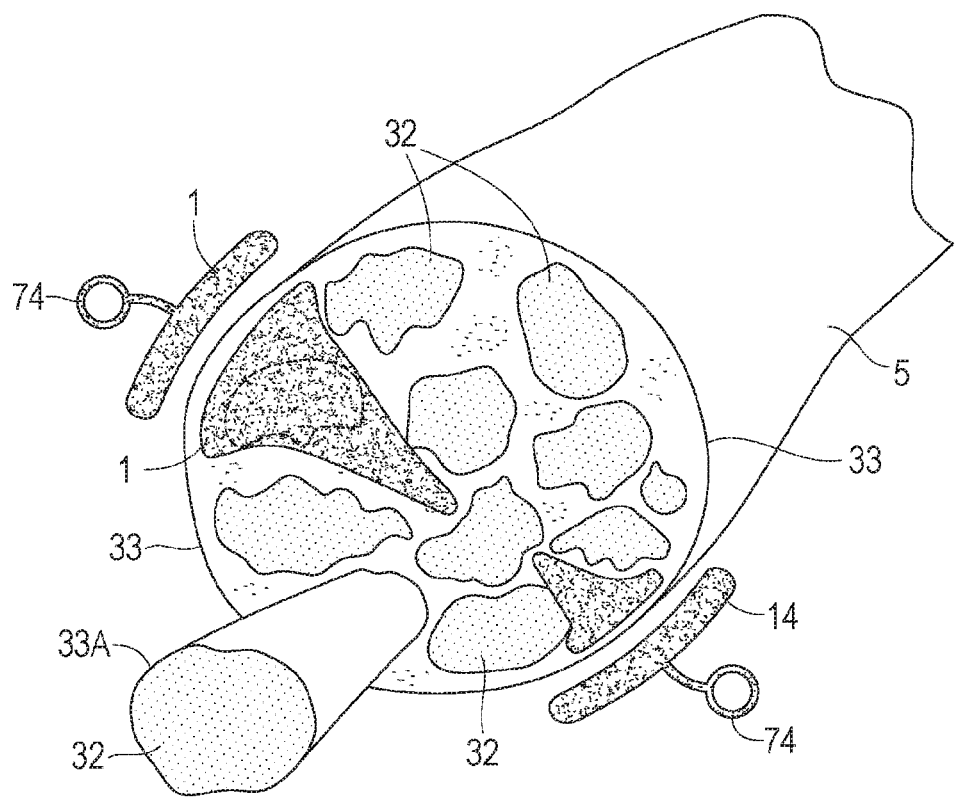
FIG. 82

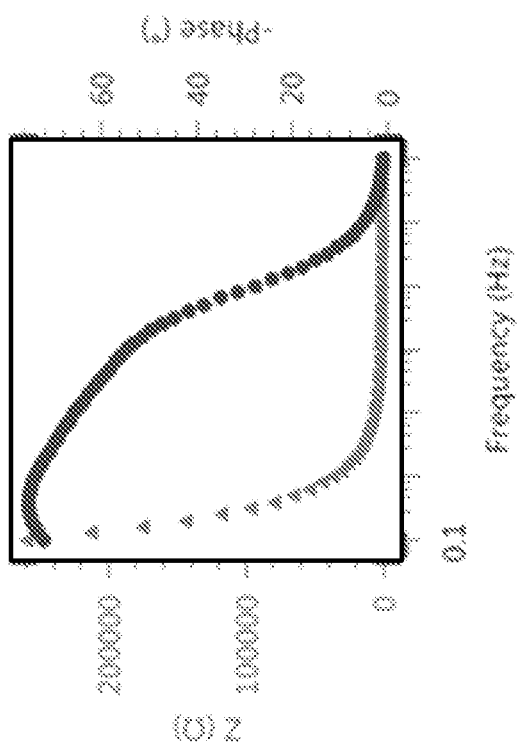
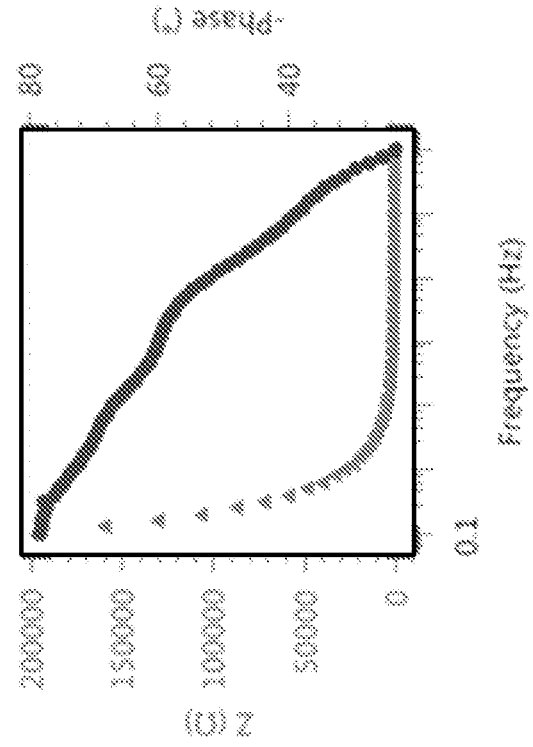
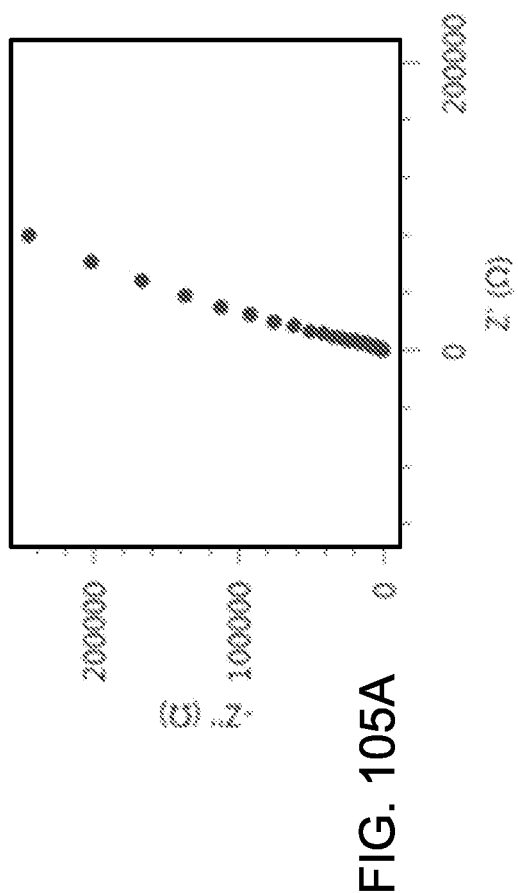
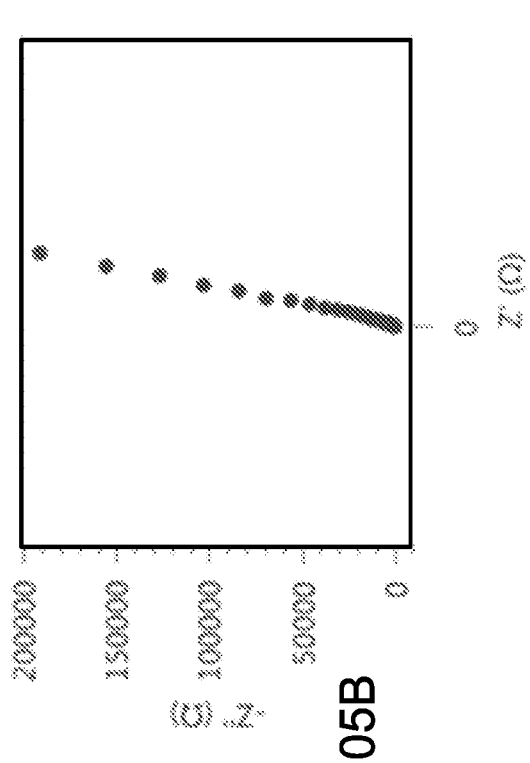
FIG. 105A
FIG. 105B

ELECTRODE CURABLE AND MOLDABLE TO CONTOURS OF A TARGET IN BODILY TISSUE AND METHODS OF MANUFACTURING AND PLACEMENT AND DISPENSERS THEREFOR

This is a continuation of which claims priority to, and the full benefit of, PCT/US2017/065,929 filed on Dec. 12, 2017, and incorporates the latter fully as if set forth herein. PCT/US2017/065,929 claims priority to the following U.S. Provisional Patent Applications, 62/432,747 filed on Dec. 12, 2016, 62/479,117 filed on Mar. 30, 2017, and 62/564,809 filed on Sep. 28, 2017, and incorporates each of them fully as if set forth herein.

BACKGROUND

Bioelectronic medicine is the application of electronic devices to address medical problems. Prior art biocompatible electrodes, however, have many problems and limitations which have limited bioelectronic medicine to date. Electrodes provide the interface from the metallic mixture of electrical current to the ionic mixture surrounding a target such as the interstitial fluid inside in a bodily tissue, whether in a body or in a sample severed for research purposes. In prior art electrodes, regardless of the electrode's material that supplies the mechanical structure, the metal at the actual contact with the target in bodily tissue ("the interface") is comprised of pre-shaped wires or metallic traces having limited flexibility or ability to be shaped to conform to the unique contours of a target in a bodily tissue. The targets in bodily tissue vary greatly in size and shape. For example, in the peripheral nervous system ("PNS") neural plexi are highly irregularly shaped bundles of nerves, an example of which is a human brachial plexus as shown in the diagram in FIG. 1A. Similarly, PNS ganglia differ from the cylindrical or oval shape of a PNS nerve like the median nerve in the arm, and ganglia have many different shapes. An image of a rat cranial nerve ganglion is shown in FIG. 1B. A single peripheral nerve in a limb can be cylindrical and fall within a wide range of diameter, from 1 to 15 mm. The range of sizes of the same ganglia also varies greatly among individual humans. One study reports human superior cervical sympathetic chain ganglia as having an axial diameter of 7.7 mm+/−1.8 mm with a range of 4.8-13.2 mm., showing very wide variability among only 53 subjects. Lee, et al., Superior Cervical Sympathetic Ganglion: Normal Imaging Appearance on 3T-MRI, Korean J. Radiol 1016 September-October; 17(5): 657-663 and a cranial nerve can be, at the point of interface, between about 1 and 5 mm and cylindrical. Thus, there is great variability among the sizes and particular shapes of a particular target from individual to individual. A one-size-fits-all electrode has many problems relating to fit.

Implantation of prior art electrodes requires a surgical approach far more invasive than the injection of a drug by needle. In fact, most prior art electrodes designed for a good signal to noise ratio ("SNR") in neural sensing or selective stimulation applications for the PNS require the surgeon to have a line of sight access to the target in bodily tissue which generally requires a reasonably large incision, blunt dissection and release of the nerve from the adjoining tissue. To describe the invention herein, it is first helpful to point to several prior art electrodes, and to set forth figures showing them.

Most prior art devices for use in bodily tissues do not conform to the contours of the target in bodily tissue, and their shapes in fact are sometimes dictated by the production processes by which they are made. For example, a flat electrode is produced by silicon wafer production techniques with needles extending from the metal contacts from a planar surface, as shown in FIG. 2A and FIG. 2A from U.S. Pat. No. 5,215,088. Another prior art planar electrode from US20150367124 is shown in FIG. 3A and FIG. 3B. These prior art electrodes cannot be easily modified or adapted for use on other targets besides the specific location for which they are designed, and they are not sized according to the individual, and they are therefore limited in adaptability to the many different anatomical shapes and sizes and varied targets. For example, PNS ganglia and plexi have a host of irregular shapes whereas the median nerve in the arm is linear. Not only does the general size of prior art devices result in target mismatch, but the preset locations of the individual electrical contacts in prior art devices also present great potential for mismatch in a given implantation.

Another prior art device is a cuff electrode which is generally a strip of non-conductive material with wiring to metal electrode contacts and the device is wrapped around a PNS target, as shown in the diagram in FIG. 4A from US20060030919 A1 and the drawing in FIG. 4B.

Prior art deep brain stimulation electrodes have a generally rod-like shape, as shown for example in FIG. 5, which is from US20110191275. Another rod shaped electrode is FIG. 6 from US8473062. FIG. 5 and FIG. 6 depict rod-shaped electrode configurations with one or several electrode contacts aligned linearly. Electrical field lines between two contacts on the same electrode and a distal return are not equidistant and not homogeneous. Attempting to stimulate a neural target next to the rod is not an easy task when other neural side targets are close by. One advantage of rod shaped electrodes is that they are, compared to other prior art electrodes, easier to place through a tunneled approach. That is, the rod shape has a narrow width and the surgeon can implant the entire electrode and electrode system through a keyhole incision and advance the electrode deep into the body to the neural stimulation target structure. There are, however, significant disadvantages. The electrical field emanating from these electrodes is that of a point source instead of a homogeneous field like inside a ring electrode that is placed around a nerve. FIG. 7 shows the rod-shaped electrode configurations in FIG. 5 and electrical contacts which may have a single electrode contact or a multitude of electrode contacts, here labeled 1-4. Electrical field lines 73 B between contacts 1 and 4 and field lines 73 A between contacts 2 and 3 on the same electrode and a distal return are not equidistant and not homogeneous. Also, field lines 73 C are directed in almost 360 degrees, and can have unintended effects. Attempting to stimulate a neural target (shaded area in FIG. 7 to the right of the electrode) next to the rod is not an easy task when other neural side targets are close by.

The process of encapsulation of the electrode by connective tissue can migrate the electrode away from the nerve. This can change the electrical field lines 73 so much that waveform parameters used for successful stimulation of said nerve might not work after a few weeks. The point source will generally depolarize the fascicle(s) inside the nerve that are mechanically closest to the electrode. While this may add selectivity, it also can add unwanted effects of stimulating all small and large fibers of a fascicle closer to the electrode while the large fibers in a more distant fascicle might not be activated, even though the goal of the stimulation might be to activate all large fibers in all the fascicles of a given nerve. A uniform electrical field as may be provided by a ring of metal placed around the nerve as done with a cuff electrode can achieve this equal activation of fibers of the same size in a nerve.

There are additional problems as well. The surgical procedure necessary to insert a large pre-configured electrode next to a biological target can cause great trauma to the target 5 or in the immediate area, causing bleeding and a large inflammatory response which leads to growth of connective tissue between the electrode interface and the target (data shown in FIG. 8). The distance between the prior art device and the target contours can be too great, allowing an insufficient transfer of current and providing unneeded space allowing growth of connective tissue which has far higher impedance than interstitial fluid. The fall off of an electric field from a bipolar electrode is 1/r2, where r is the distance from the electrode. This means for a unipolar electrode that the normalized field strength at 100 µm distance from the edge of the electrode and mostly only partly into the nerve, only 10% of the initial field strength at the electrode edge may be available. This value drops to about ¹⁄₁₀₀th for a tri-polar electrode. It is thus not only possible but to be expected that electrodes that fit more tightly and provide a more uniform field throughout the nerve are able to achieve a control more primarily based on fiber diameter and less on fiber location with respect to the edge of the electrode, causing only the outside fibers in a nerve to depolarize if at all. Plonsey, R. Quantitative formulations of electrophysiological sources of potential fields in volume mixtures. IEEE Trans Biomed Eng 31, 868-872 (1984), and Barr, R. C. & Plonsey, R. Propagation of excitation in idealized anisotropic two-dimensional tissue. Biophys J 45, 1191-1202 (1984). Post-implantation in chronic usage, prior art devices have great potential to cause irritation of surrounding tissues and further inflammatory action. Also, a prior art device placed next to a target (without enveloping it) will depolarize the target partially but likely not fully (i.e., the areas more distant from the location of the lead remain in their pre-implantation voltage states). Many prior art devices are also not anchored to the target and so they are pulled away from the target by the normal movements of the body in which it is implanted. Thus a prior art device may have some functionality in the days or weeks following surgery, but the inflammatory process soon operates to wall the interface off from the target, and reduce or eliminate the functionality.

The surgical procedure for prior art devices itself is an additional deterrent for doctors who are aware of risks from surgery such as general anesthesia and infection, and time in an operating room is expensive. A patient can also be discouraged from undergoing an elective surgical procedure for implantation by his or her less than optimum health and also by large insurance co-payments necessitated in significant surgery.

The electrical properties of prior art electrodes are also in need of improvement, in that their charge transfer often may incorporate a significant resistive current component in addition to the capacitive charge injections that is fully reversible, and resistive current is likely to produce corrosive by-products over stimulation time.

There is therefore a need for a biocompatible electrode which can be injected, cured and molded to surround and conform to the contours of a target in or on bodily tissue in a minimally invasive or external procedure, and produce far better chronic results at the interface with the target in bodily tissue.

Terms

In addition to additional definitions and explanations supplied throughout this written description, the following definitions apply.

(1) "Capacitive charge" means charge injected that can be extracted fully without any charge components causing irreversible chemical reactions.
(2) "Carrier material" means any biocompatible material comprising a liquid (or less viscous) phase curing to a solid or a more viscous phase. A carrier material is one selected from a group consisting of a hydrogel, an elastomer such as silicone, bone cement, cyanoacrylate, dental amalgam, dental resin, fibrin glue, or their components and others.
(3) "Collagen" and "gelatin" are synonymous, unless specifically differentiated.
(4) "Conductive elements" are particles of conductive material comprising at least one dimension of at least one micron produced by a process selected from a group include cutting, grinding, etching and extruding.
(5) "Cure" includes, without limitation, polymerizing, crosslinking, going through precipitation and/or going through solvent phase inversion, gelation or other phase transition to a solid which retains its shape when subjected to shear forces expected for a living body in non-extreme conditions. The curing may be substantially instantaneous, a few seconds or minutes, or may occur over a longer period of time.
(6) "Elastomer" means any of various elastic substances resembling rubber, e.g., polyvinyl elastomers which comprise a liquid phase and a solid phase, including without limitation siloxane
(5) "Inject" means introducing into bodily tissue through (a) a dispenser by means of a needle or needle-like structure without the need of an incision besides that of the needle, (b) a catheter in a blood vessel or other bodily structure with a lumen, (c) a pump through a laparoscopic device inserted through a small incision, (d) a hole that has been created with a separate incision, or (e) an auger system transporting the injectable material inside a lumen from which it is expressed near, into or around an interface target.
(6) "Liquid mixture," means a carrier material in a liquid phase which also comprises solid conductive elements dispersed throughout, and the liquid carrier material is capable of curing to a solid phase. "Liquid mixture" means not only the liquid carrier material but also the solid conductive elements contained within it. When the combination of phrases, "liquid mixture/cured electrode," is used this refers to the same material in either the liquid or solid phases, and that as used in this way the only difference in the material is the phase.
(7) "Liquid nonmixture," means a carrier material in a liquid phase and without conductive elements, either the same material as the liquid mixture (or not), which is also capable of curing to a solid phase and bonding to the liquid mixture. A liquid mixture cures to a solid phase termed a "nonconductive layer."
(8) "Liquid phase," means a state in which liquid or semi-solid material may flow by, for example, injection prior to curing to a later solid phase. "Liquid phase" includes, without limitation, a paste or other configurations which do not hold their shape when subjected to shear forces expected for a living body.
(9) "Network," means an irregular structure comprising numerous conductive elements of either regular or irregular shape, said conductive elements being either touching one another or disposed in very close proximity to one another.
(10) "Nonconductive layer" is liquid nonmixture which has cured to the solid phase.

(11) "Percolation" means the ability to disperse throughout a mixture.
(12) "Phase transition" includes, without limitation, curing, cross-linking (chemical, ionic or other), polymerization, gelation, self-assembly, or fusion/solidification
(13) "Resistive charge injection" means current which causes irreversible reactions to occur in the vicinity of the electrode/electrolyte interface.
(14) "Solid" means a material which has undergone a phase transition away from the liquid phase and has substantially polymerized, crosslinked, precipitated, gelled, gone through solvent phase inversion, or transitioned otherwise, and retains its shape under shear forces expected for a living body in non-extreme conditions.
(15) "Solid phase," means a state in which a material has cured substantially to a solid and at least partially retains a shape under shear forces expected for a living body in non-extreme conditions, either flexible or hard and either hydrous or anhydrous, or having these qualities partially or in combination.
(16) "Target" means nervous tissue including a nerve, plexus, ganglion, brain, spinal cord and the like, and any other tissue for which electrical stimulation may have an effect such as for example, muscle, organs and tumors.

BRIEF DESCRIPTION OF THE FIGURES

In FIG. 5, from US Patent Application Publication No. 20110191275, the electrode contacts are represented by the darker bands, and dimensions of the electrode contacts and spacing between them are depicted. In FIG. 6, from U.S. Pat. No. 8,473,062, the electrode contacts are represented by pairs of lines.

In FIG. 12A the liquid conductor is outside the body and the white background represents air filling any pores. FIG. 12B depicts the pores after the liquid conductor has been injected into a body and interstitial fluid (darkened background) immediately fills up at least a portion of the pores. FIG. 12C represents the cured electrode four to eight weeks post-injection after resorption of carrier material.

FIG. 34 contains images of high-aspect ratio conductive elements such as gold bonding wire bits.

FIGS. 35A and 35B are idealized section views of a cured electrode in an original linear shape and a subsequent bent position showing, after bending, the high aspect conductive elements (35B) maintain connectivity compared to lower aspect ratio (35A).

FIG. 44 is a diagram of two embodiments of the ring-like portion of a cured electrode, and a first side of each being connected with either the anode or cathode end of a signal generator and each of the other ends being connected optionally to a nerve target.

FIG. 45 depicts a ring like portion of a cured electrode connected to one end of the signal generator and also to the nerve (active cathode), or can be placed at another location to provide a better electrical interface to the surrounding tissue at the location of the distal anode.

FIG. 56A is a representation of a portion of the ECoG electrode matrix in FIG. 54 from the top showing the matrix and wires terminating in holes where the wires make electrical contact with the liquid mixture (as shown in FIG. 56B) injected into the sulci.

FIG. 56B is a cross-section of neocortex and the ECoG electrode matrix including the holes allowing injection of the liquid mixture material deep into the sulci, as shown.

FIG. 57 is a representation of two types of connectors of a neural signal generator to enable an excellent mechanical and electrical connection to the cured electrode.

FIG. 62C depicts a two chamber dispenser tip, with each chamber loaded with a wire embedded in liquid mixture, and a portion of the same extruded from both chambers.

FIG. 70A, FIG. 70B and FIG. 70C are a sequence of diagrams depicting use of a pre-formed mold, here an inflatable balloon, to facilitate placement of a cured electrode.

FIG. 71 depicts a syringe with a wire with a connecting feature at its forward most point embedded in the liquid conductor.

FIG. 72A and FIG. 72B show two syringes without needles joined by a connector. FIG. 72C depicts the syringes and the connector prior to being joined. FIG. 72D is an image of the manual mixer comprising a baffle in the lumen of the connector.

FIG. 76C shows that by placing the liquid conductor all around the connection point of the three side arms forming the Y provides a means to stimulate all nerve fibers entering and exiting the Y-junction.

FIG. 81A is a diagram depicting homogenous electrical field lines and FIG. 81B depicts electrical field lines distorted by examples of placement of liquid conductor "blobs" to align field lines through a target.

FIG. 82 is a diagram showing liquid conductor blobs injected into a nerve without leaving a trace through the epineurium, and cured electrodes outside the epineurium.

FIG. 85, though, illustrates that electrical field lines can be redirected in a revision procedure, by placing liquid conductor just underneath the two cuff electrode contacts on opposite sides of the nerve just inside the cuff electrode, and also placing liquid nonconductor in the fibrous tissue to prevent circumferential electrical field lines.

Figure 100:
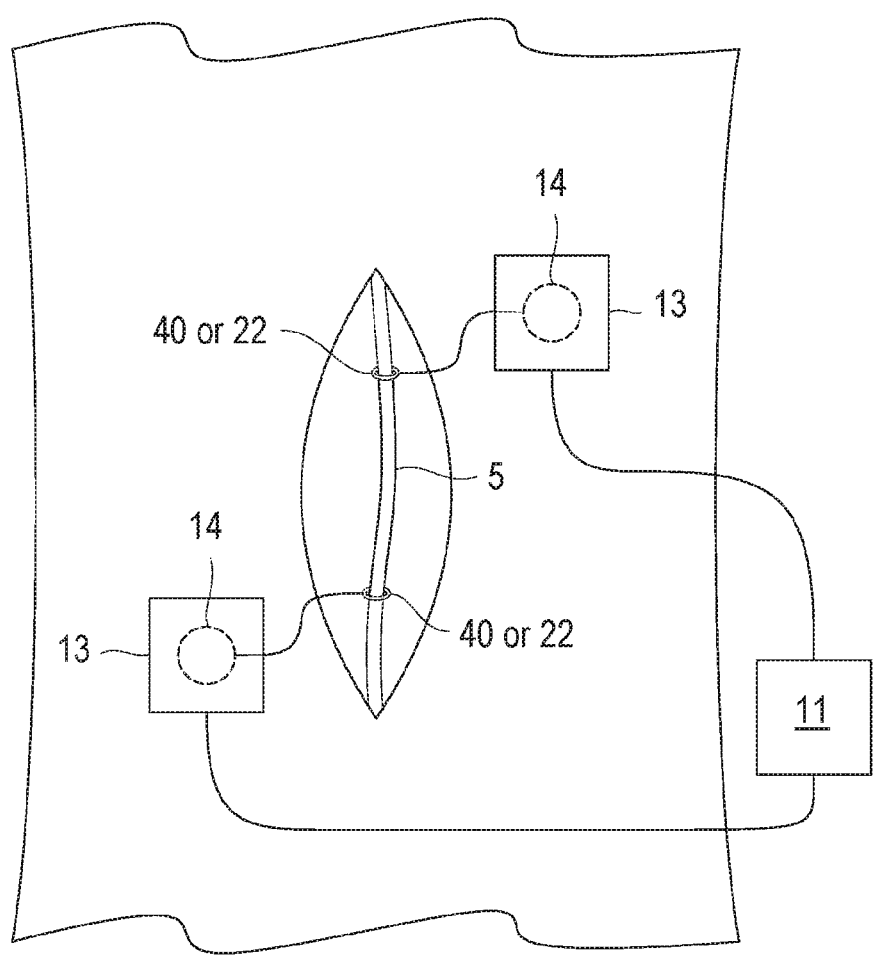
FIG. 100 is a diagram showing placement of TENS patch electrodes on the outside of the skin of a pig, each patch electrode on top of a corresponding cured electrode as a subcutaneous contact pad, each contact pad being connected to a ring electrode attached by a wire acutely to the vagus nerve.
Figure 102:
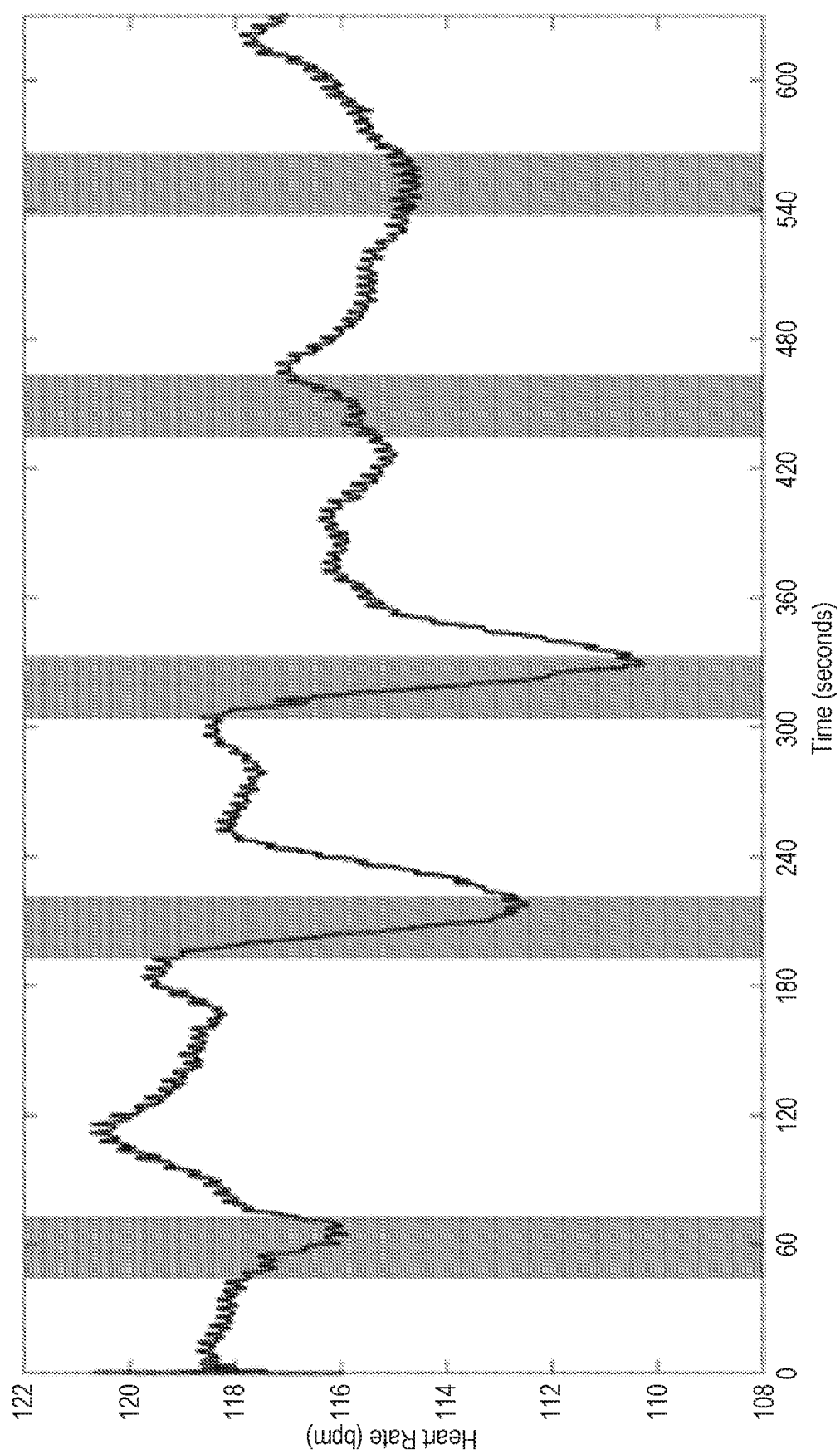

FIG. 102 is a chart which plots heart rate (bpm) versus time (seconds) observed from stimulation of the vagus nerve in pigs in the set up diagrammed in FIG. 100, under five different conditions: (1) low amplitude stimulation, (2) mid amplitude stimulation, (3) high amplitude stimulation, (4) removal of the subcutaneously placed contact pad 14 that connected to the cathode to test for leakage driving the HR reduction, with no leakage detected, and (5) removal of the subcutaneously placed contact pad 14.

Figure 103A:
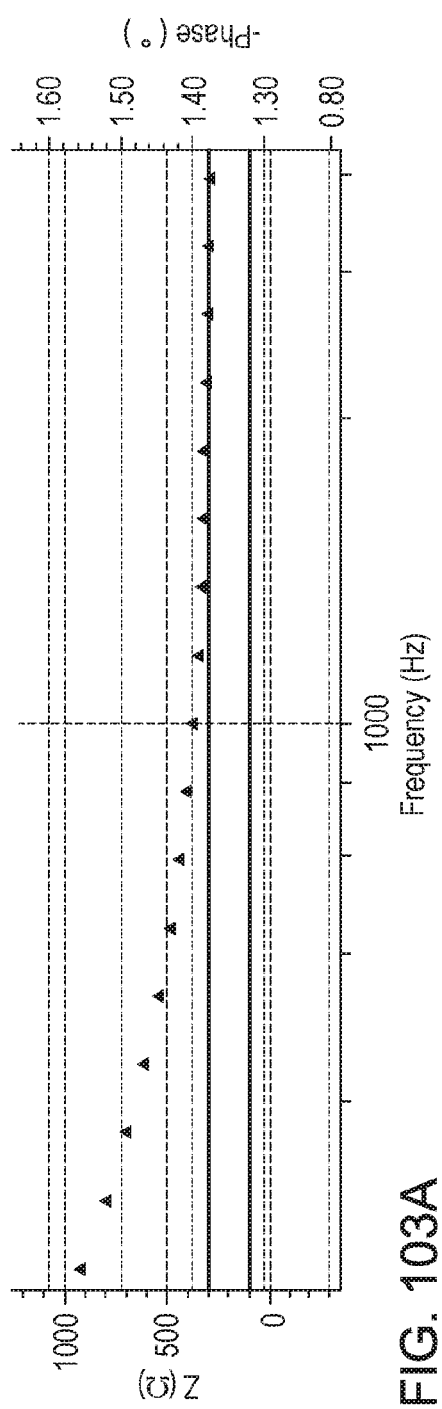
Figure 103B:
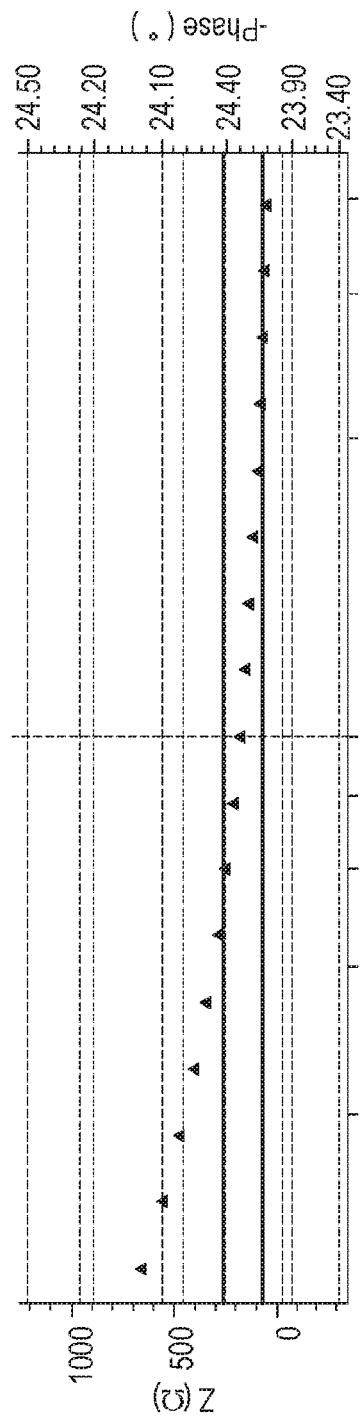

FIGS. 103A and 103B are two charts showing a comparison of electrodes and their capacitive charge injection capabilities: a prior art cuff (LivaNova) 103A and the cured electrode 103B.

Figure 104A:
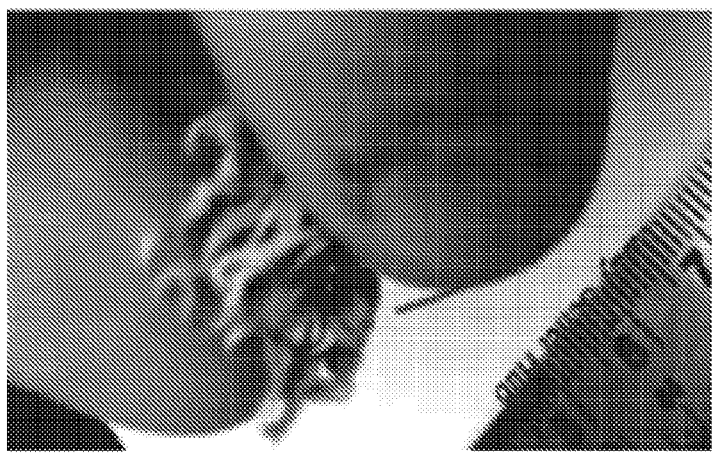
Figure 104B:
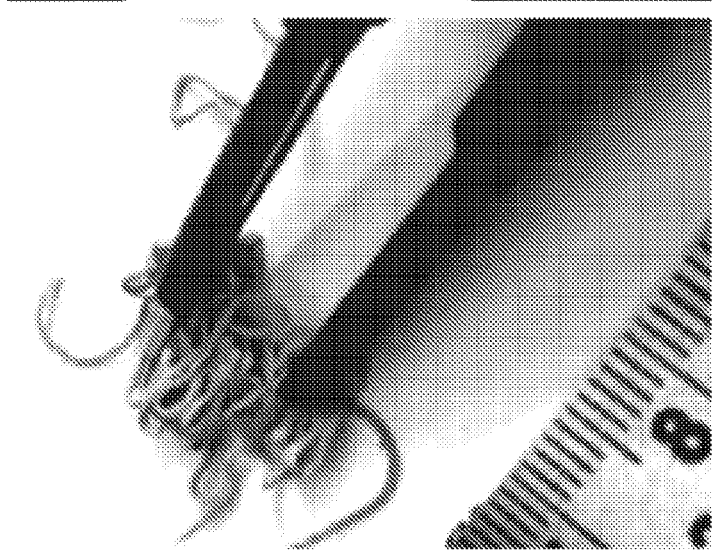
Figure 104C:
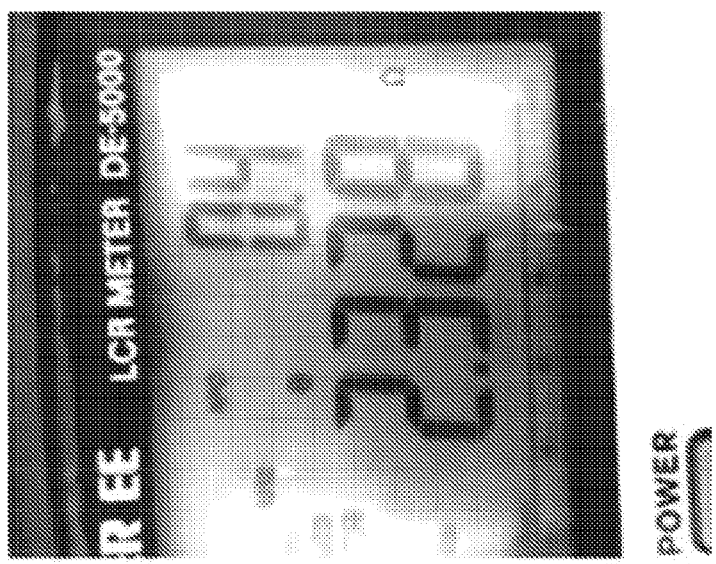

FIG. 104A is an image of the readout of impedance on an LCR meter as 2.328 ohms, measured across the length of several turns and twists of the extruded very thin cured electrodes and wires (<1 mm) as shown in FIGS. 104B and 104C.

FIGS. 105A and 105B depict differences in impedance spectrometry for a prior art device (105A) and the cured electrode (105B) of the present invention.

GENERAL

The present invention solves the above problems, and provides additional advantages unknown in the prior art. The cured electrode 1 of the present invention, in one embodiment, first comprises a liquid mixture in a liquid phase which is capable of being injected through a dispenser 2 comprising a needle 3 to the target 5 without a surgical procedure, where it may be pushed from the needle 3 and molded to the contours of the target and is capable of curing to a solid phase which is capable of retaining the shape of the contours of the target. The present invention produces low impedance values (<100Ω or even <10Ω or <1Ω), thus providing a simple approach to connect electrically to a target in bodily tissue in various locations, different patients and within a shorter procedure time when compared to the time needed to place prior art electrodes, especially cuff electrodes.

Another advantage of the present invention is that it is injectable without surgical dissection of tissue leading up to the target by means of scalpel, scissors and the like prior to electrode placement, that is, with little or no disruption to the target or surrounding tissues. The present invention has the ability to form a "negative" from the "positive" target contours. The novel property of curing to the contours of the target not only provides a better electrical connection to the target, but also a better mechanical adherence to it, thereby anchoring it. Anchors 4 for the cured electrode 1 may additionally be achieved by injecting either liquid mixture, or liquid nonmixture bonded to the liquid mixture, to non-target structures such as bones.

Moreover, through injection the cured electrode of the present invention may be placed in hard to reach locations in the body which a surgeon might be unwilling to place a prior art device with elective general surgery, e.g., ganglia of the sympathetic chain or nerves of the PNS adjacent to major blood vessels and located medially in the body which are difficult to access on a direct line from outside of the body. See e.g., FIG. 9I.

The particular mechanical and structural properties of the cured electrode 1 may be varied to match the properties of the tissue targeted, by the choice of the liquid carrier material 7 or by additives thereto, and by the selection of the conductive elements 6. The curing process, i.e., by introducing additional conditions or energies during curing such as ultrasound, cooling or heating or radio-frequency radiation may furthermore be utilized to change the physical properties of what becomes the cured electrode 1.

Additionally, the present invention is put into place without the far greater costs of general surgery, and the attendant risks from general anesthesia and infection. The present invention may be placed by pain physicians accustomed to the placement of pharmacological nerve blocks with or without the aid of ultrasound or angiography as means for visualization.

Figure 9:
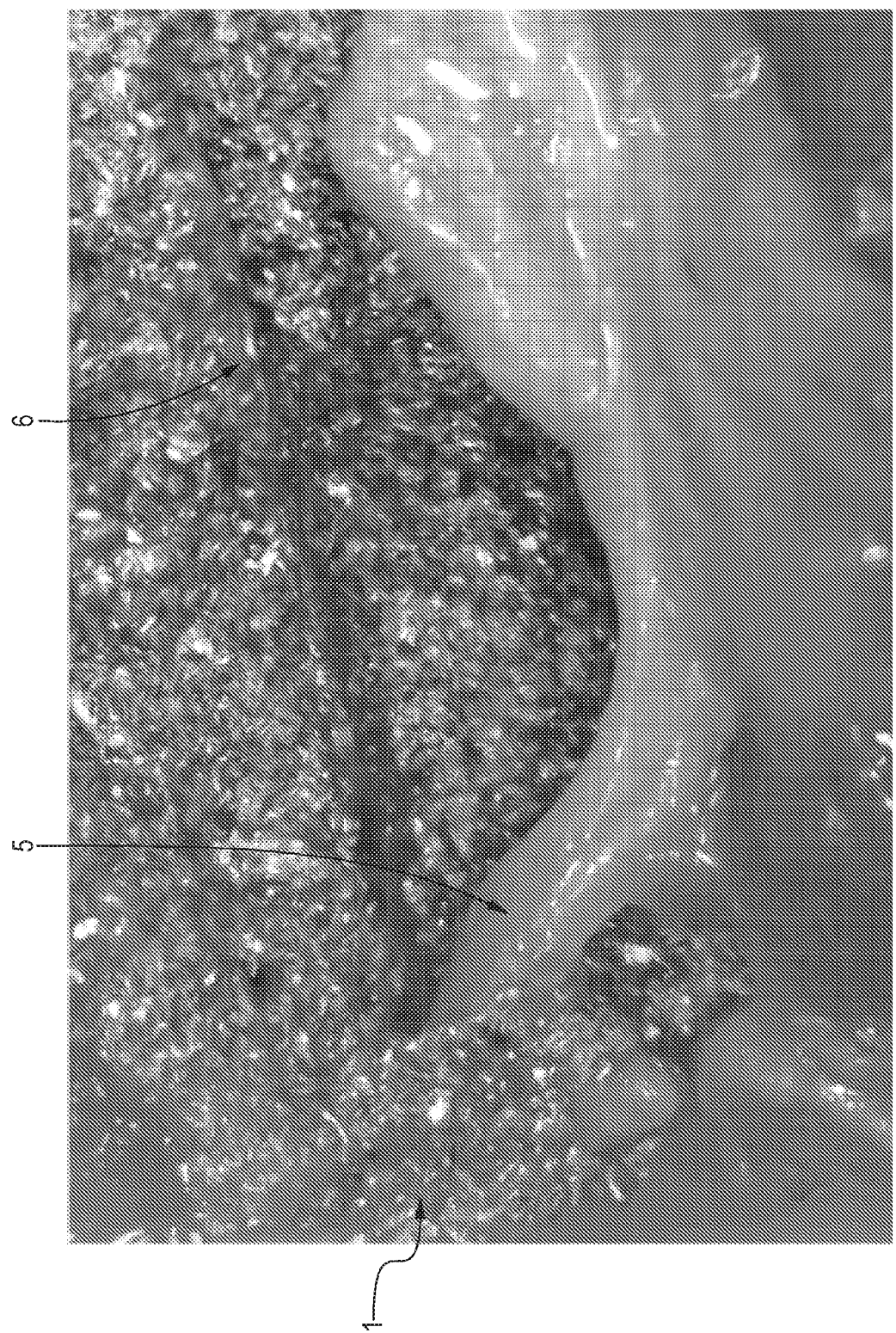
FIG. 9 is an image of an embodiment of the cured electrode comprising a silicone carrier material injected into chicken meat. The nerve has been pulled partially out of the cured electrode, i.e., from the groove in the upper middle of the image, which is a portion of the area of the cured electrode in closest contact with the nerve upon curing.

FIG. 9 is an image of an embodiment of the cured electrode 1 with a silicone carrier material injected into chicken meat. The silicone was molded against, and cured to a solid against a target 5, here a nerve partially on the right side of the image and fully on the left side of the image. A few minutes after the injection, the nerve was pulled back from the cured electrode 1. Note the 360 degree covering on the left, the 180+ degree interface on the right, the groove on the left indicating the mechanical match between the nerve and the cured electrode and how well the material matches with the nerve's mechanical structure. This is a fundamental example showing that it is possible to intentionally encase 180-360 degrees around a nerve. The impedance of muscle tissue as measured in rats, chicken and pork is approximately 500 to 700Ω at 1 kHz sinusoidal waveforms. Impedance values of different embodiments of the cured electrode are provided herein. Any material providing a lower impedance than 100Ω is thus at least five times more conductive and any mixture of <10Ω is at least 50 times more conductive than the surrounding bulk, not yet taking into account the additional impedance added by the encapsulation which encases any electrode placed into the body over time in the chronically implanted case, i.e. after three to four weeks post implantation.

Figure 10:
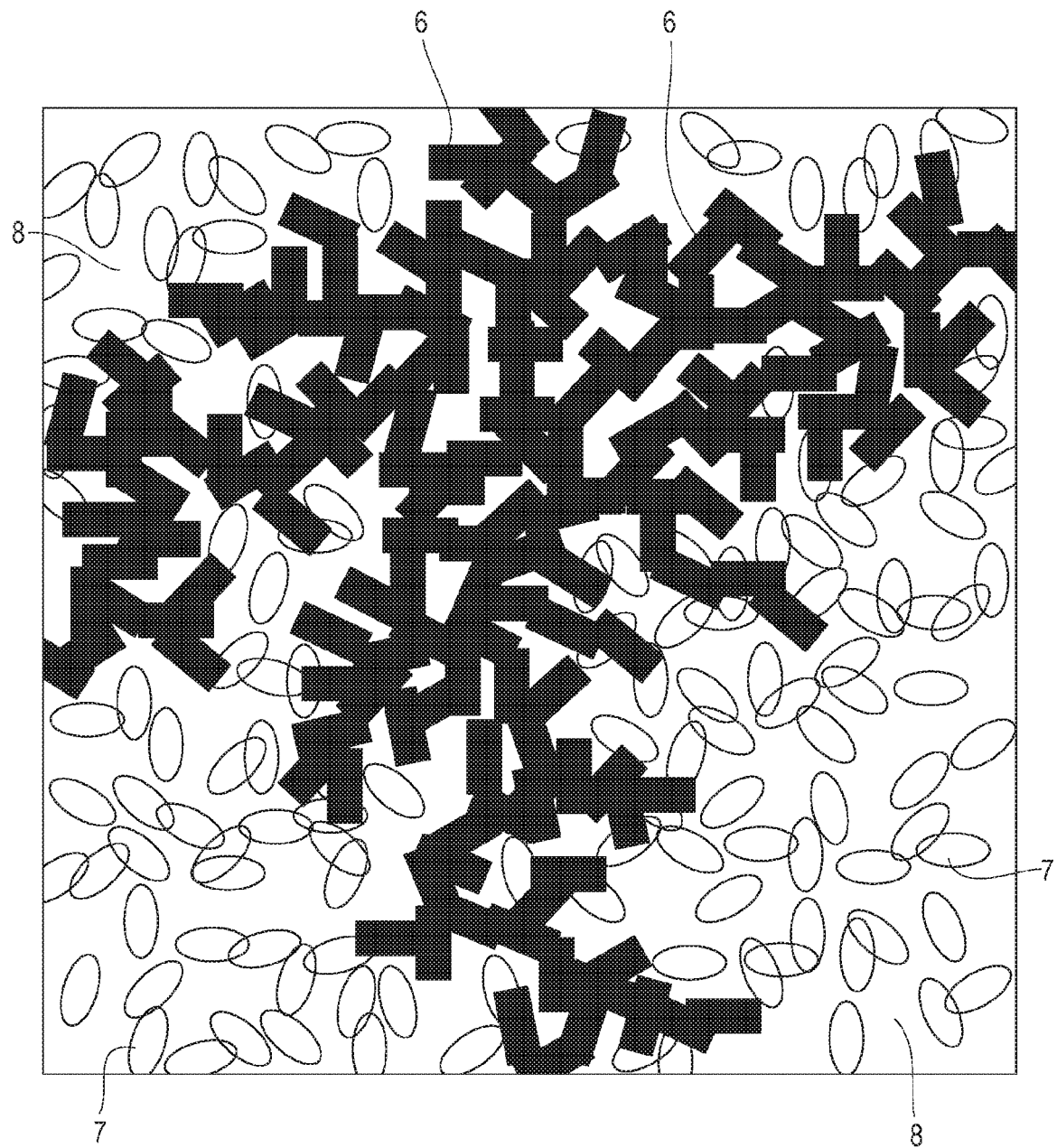
FIG. 10 is a conceptual diagram of the distribution of conductive elements (represented as dark bars) in the carrier material (represented as open ovals) in a cured electrode. The empty space represents pores.

A conceptual diagram of the distribution of conductive elements 6 (represented as bars) in the carrier material 7 (represented as ovals) is in FIG. 10. The conductive elements form a conductive pathway through the carrier material, either in a liquid phase or a solid phase after curing. The open space between the conductive elements 6 and the carrier material 7 represents pores 8.

Figure 11:
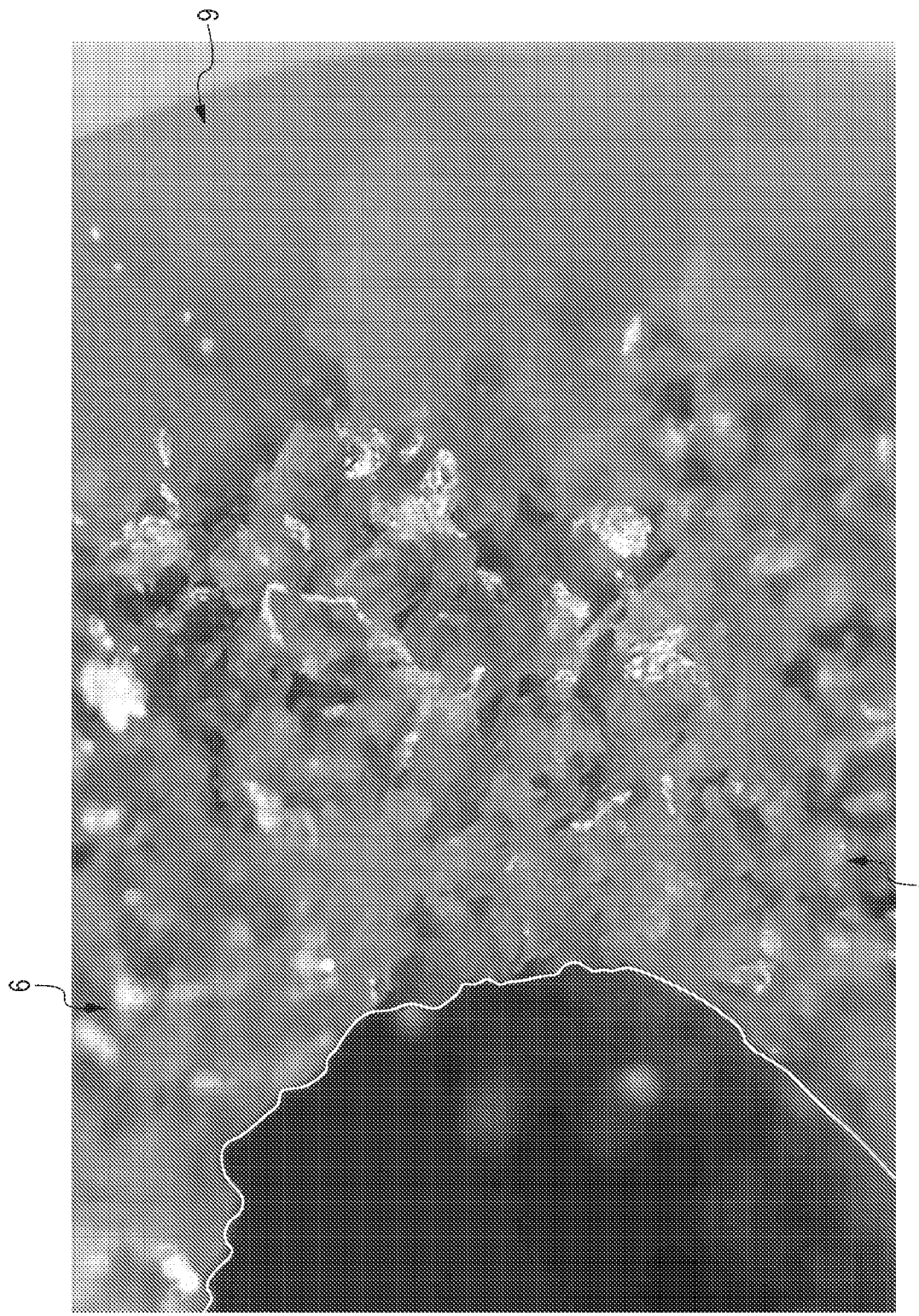
FIG. 11 is an image of a portion of a cured electrode including a nonconductive layer (right side of image) after the cured electrode was removed from a nerve target. The white line is drawn to demarcate the cured electrode from the dark space (left side of image) where the nerve target was formerly located before removal of the cured electrode.

FIG. 11 is an image of a cured electrode 1 including a nonconductive layer 9 removed from a nerve target. The curved space on the left was produced by the molding of liquid mixture/cured electrode against the target (not shown), surrounded by the inner cured electrode with silver conductive elements 6, and the outer portion with few or no conductive elements is the nonconductive layer 9. Note the white line drawn to show how the cured electrode after curing retains the shape of the nerve target.

Figure 2A:
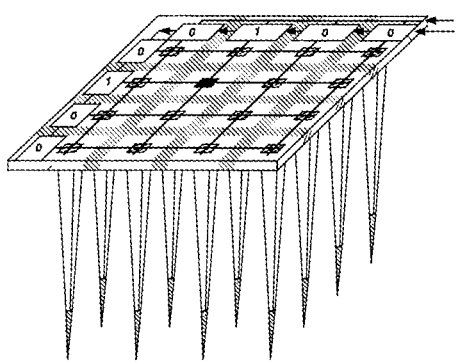
FIG. 2A and FIG. 2B depict a prior art electrode with a planar integrated circuit that is produced by silicon wafer production techniques with needles extending from the metal contacts from a planar surface, as disclosed in U.S. Pat. No. 5,215,088.
Figure 4A:
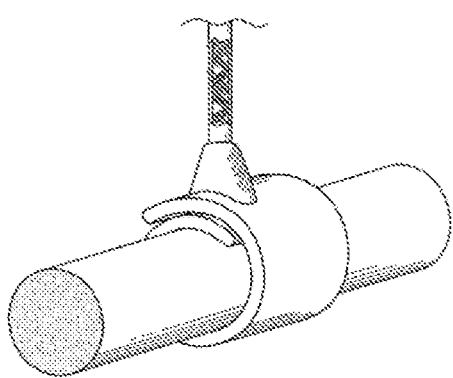
FIG. 4A is a perspective drawing of a prior art cuff electrode from US Patent Application Publication No. 20060030919 A1 and perpendicular connection to a wire, as the device is wrapped around a PNS target.
Figure 4B:
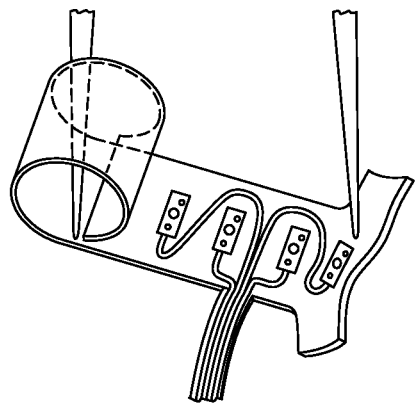
FIG. 4B is an image of a prior art cuff electrode, somewhat similar to that in FIG. 4A. The device is being held in a partially open position by an instrument, thus revealing the interior side of the device (facing the PNS target) where metal contacts are connected by wires. The lead wires to the device contact the device in the same plane of the device.

The present invention also has another distinct advantage over the prior art in its superior qualities as an electrical system for bodily tissue. A wire or needle tip FIG. 2A) or a flat or smooth metal contact (FIG. 4B) has only a small surface area to inject current capacitively. In one embodiment of the invention, a carrier material 7 such as a hydrogel that becomes porous (partially resorbed between the conductive elements) provides a greatly expanded surface area for the conductive elements. The charge injection in an implanted electrode may consist of both capacitive and resistive current transfer. In a bodily tissue, the best way to inject current is via capacitive charge injection which does not lead to irreversible chemical reactions which in turn can lead to the dissolution or corrosion of an electrode or the change in pH levels near the electrode and the nerve, thereby damaging the nerve. Cogan, S., Neural Stimulation and Recording Electrodes, Ann. Rev. Biomed. Eng. 10:275-309 (2008), Shannon, R. V. (April 1992). "A model of safe levels for electrical stimulation". IEEE Transactions on Biomedical Engineering. 39 (4): 424-426, Cogan S F, Ludwig K A, Welle C G, Takmakov P (2016). "Tissue damage thresholds during therapeutic electrical stimulation," Journal of Neural Engineering. 13 (2): 021001 (2016). In order for any electrode to provide a large charge injection capacity, two potential pathways are open: (1) increase the electrode's surface area in contact with the electrolyte and (2) use materials that offer a large charge injection capacity inherently. In one embodiment the present invention uses the ability of the body to dissolve, absorb or resorb the carrier material 7, fully or at least partially, thereby leaving the conductive elements 6 (which are not resorbed) to form pores 8 and a porous shape to which the electrolyte makes intimate contact while both, the conductive elements and the electrolyte in intimate contact are encased by encapsulation of bodily fibrous tissues. This highly increased volume of conductive charge injecting material stands in stark contrast to the generally more or less flat surface of conductive material (such as a prior art platinum disk or foil) that only provides the electrode-electrolyte interface in a more or less planar surface. The current may enter this high surface area porous shape through a wire 10 that is encased in, and in electrical contact with, the conductive elements 6, thereby permitting electron transfer as the primary means for current to travel among the conductive elements. This in turn provides a significant increase in effective electrode-to-electrolyte interface area throughout the whole volume of the conductive elements. The pores 8, filling with interstitial fluid or otherwise watery solutions inside or outside the body during or after the cured electrode placement, embody a large surface area for the charge injection process than is known in the prior art, much larger than the surface area for a smooth surface of the same volume's outer dimensions.

Calculations have been made of the surface area of the porous cured electrode surface area (S/A) assuming a 1 gram cured electrode which is approximately 0.5 cm$^3$ and these have been compared to prior art macroelectrodes reported in Cogan (2008) cited above. The surface area for the present invention cured electrodes is up to eight orders of magnitude greater than reported in Cogan, as shown in Table One.

TABLE ONE

Comparison of Surface Area to Prior Art Electrodes

| A<br>Electrode<br>Formulation | B<br>Flake<br>S/A<br>($m^2$/g) | C<br>Hydrogel<br>(g) | D<br>Powder<br>(g) | E<br>Conductive<br>Elements<br>wt % | F<br>$m^2$ | G<br>$\mu m^2$ |
|---|---|---|---|---|---|---|
| Present Invention, Low S/A Microflake | 1.0 | 0.2 | 0.8 | 80.0 | 8.00E−01 | 8.00E+13 |
| Present Invention, High S/A Microflake | 4.0 | 0.35 | 0.65 | 65.0 | 2.60E+00 | 2.60E+14 |
| Present Invention, High S/A Microflake | 7.0 | 0.5 | 0.5 | 50.0 | 3.50E+00 | 3.50E+14 |
| Cogan Macro-electrode | — | — | — | — | 1.00E−09 | 1.00E+05 |
| Cogan Macro-Electrode | — | — | — | — | 1.00E−10 | 1.00E+04 |

The surface area of the present invention cured electrodes in Columns F and G in Table One might be reduced up to 50% to allow for some surface overlap as these are only calculated values, not measured. The flakes are highly irregular in shape and therefore great compaction is not expected. Even so, the present invention enables a vast increase in surface area of the cured electrode interface over the prior art.

In another embodiment, a carrier material which is not significantly resorbable after curing (e.g., silicone, bone cement, dental resin or amalgam) may be left inside the body chronically which will enable the permeation and in-creeping of water and watery solutions along the interface of non-conductive carrier and conductive elements, thereby filling existing pores in the cured electrode or filling pores which may form over time as the mixture is subjected to forces from body movements. That is, pores may form in any cured electrode of the present invention, whether resorbable by the body or not. In another embodiment, a carrier material which is not significantly resorbable after curing (e.g., silicone, bone cement, dental resin or amalgam) may be mixed with other resorbable additives, discussed elsewhere herein, which will enable the creation of pores in the cured electrode after these additives are resorbed.

Figure 12C:
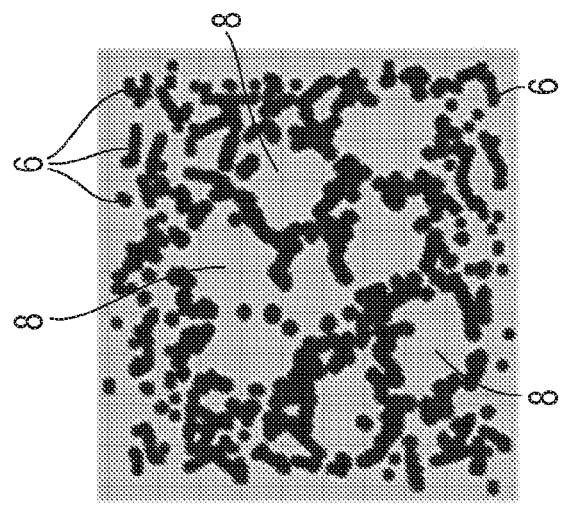
FIGS. 12A, 12B and 12C are conceptual diagrams of the liquid conductor/cured electrode. The black shapes are conductive elements and the circles represent resorbable carrier material.
Figure 12B:
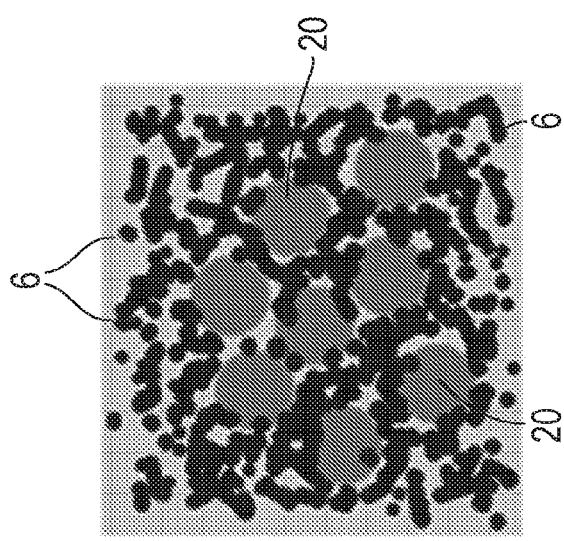
Figure 12A:
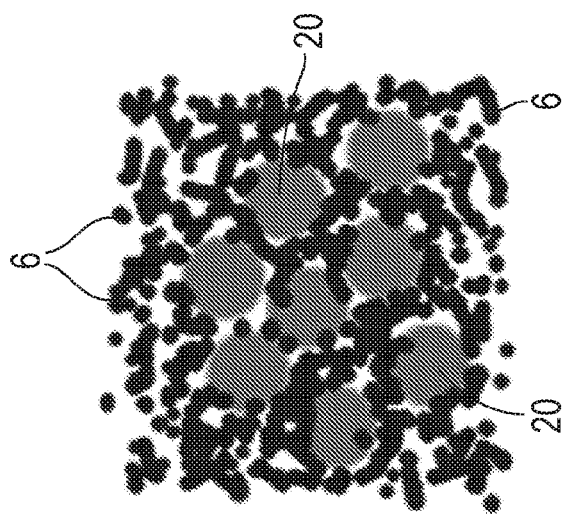

An example of pores which are enabled by a resorbable carrier material is an embodiment of the invention which comprises conductive elements and a carrier material (e.g., hydrogel) in the solid phase which is capable of being resorbed, e.g., within an approximate range of four to eight weeks. After curing and as resorption occurs during the chronic stage, the cured electrode may be somewhat compacted but comprises pores which allow for much larger charge injection capacitance values than possible with an outer-surface-only electrode. The mixture in the liquid phase is injected at the target in bodily tissue and optionally a connector blob is attached to, and then cures to, a solid interface with a wire. The cured electrode thus includes the interface molded to the target and the connector blob, the interface being integral to the connector blog. The connector blob ensures better connectivity to the wire even as the outside material gets resorbed. This is a two component system, featuring a blob of conductive elements focused to provide a stable interface (and small faradic impedance R) between a wire and the porous material that in turn has a large capacitance versus the electrolyte. FIGS. 12A-C are diagrams representing three stages with pores left after resorption creating large capacitance values. FIG. 12 represents the mixture placed on a dry surface (outside a body, not in a patient, representing composition before injection) and resorbable material (gray spheres) which can be resorbed by the body tissues, e.g., macrophages. In FIG. 12 the liquid mixture has been injected into a body and interstitial fluid immediately fills up some pores, as indicated by the gray shading, but substantial resorbable material (gray spheres) are still present. Macrophages begin digesting the resorbable material. FIG. 12C represents the cured electrode four to eight weeks post-injection. Macrophages have eaten the resorbable material (gray spheres are gone) and left additional pores 8 for interstitial fluid. The cured electrode's material to electrolyte interface has changed from two dimensional to highly three dimensional. The same process of digestion applies to a cured electrode formed outside the body on a form and then implanted in the body.

The present invention, comprises a variety of material specific physical parameters including, without limitation, curing inside the body, from flexible to stiff and/or rigid post cure, with different conductivities and the ability to mechanically interface with nearby locations within the body next to the target organ to have additional stress and/or strain relief on both, an organ and on a cured electrode post placement.

As disclosed herein, the needle-based and laparoscopic approach to placing liquid mixture resulting in a cured electrode allows for a dorsal surgical approach to connect to organs in novel ways, similar to the ability of connecting to intercostal nerves and ganglia of the autonomic nervous system, as further described herein.

Porous electrodes disclosed herein are highly advantageous for kilohertz frequency alternating current ("KHFAC") and non-destructive DC nerve block, i.e., charge-balanced direct current ("CBDC") nerve block. Recent preclinical studies with focus on reversible electric nerve block have shown that KHFAC nerve block causes DC contamination which may be more of a problem if an electrode's charge injection capacitance $Q_{inj}$ is small. Other recent preclinical studies with focus on reversible electric DC nerve block have shown that a short-term nerve block using DC waveforms of several seconds in length is possible as long as the DC is injected as capacitive displacement current of the Helmholtz double layer at the electrode-to-electrolyte interface. Materials of large surface roughness such as Platinum Black have a larger charge injections capacitance Qini and thus allow a DC-nerve block to be applied for longer than with a material that has a smaller Qini (such as Platinum).

Advantages of porous metal electrodes vs. planar metal electrodes include (1) larger charge injection capacitance Qini allowing longer duration DC injection without incurring nerve damage, (2) relatively easy to manufacture via laser patterning, sputtering or chemical plating of conductive particles that are then mixed with a non-conductive carrier (plus potential additional additives) and thereby allow the forming of an electrode as described herein, (3) a volume effect vs. a surface effect may provide a large increase in charge injection capacitance. Using the entire electrode's volume as interface to the electrolyte in the body provides a huge charge injection capacitance.

In addition to forming a large electrode-to-electrolyte contact area throughout much of the volume of the liquid mixture with the approaches described herein, the surface area of the electrode on the outside of the volume may be made porous as well by lightly modifying the approaches described (using a variety of sizes for components that may be resorbed by macrophages) with the goal to create a surface porosity that promotes adhesion of advantageous cell types and minimizes the adherence of non-advantageous cells. This improves the modification of the encapsulation response to create either thicker or thinner layers of connective tissue around the cured electrode.

In contrast to prior art electrodes, whose microscopic surface structure and macroscopic shape is formed ex-vivo, the electrode disclosed herein receives both its microscopic surface structure and macroscopic shape in-vivo: by forming a "negative impression" of the target similar to how a cast forms as a mold around an arm or leg. This is achieved by one or more processes of manufacturing the electrode in-vivo either inside a living organism or on the outside of a living organism. Although the electrode may be formed inside the body fully or in part, it may also be formed on the outside without touching

TENS

Figure 13:
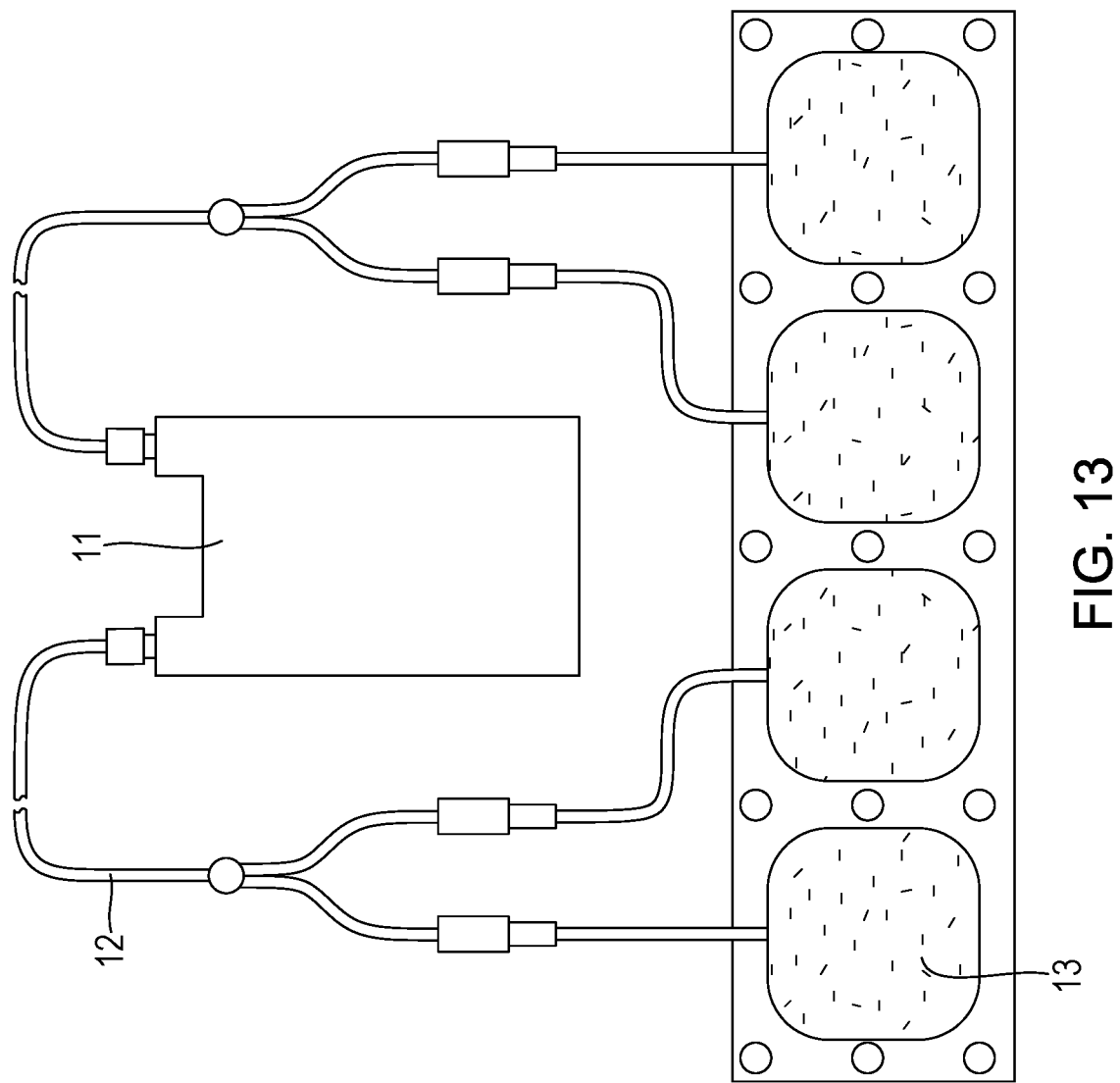
FIG. 13 is an image of a Transcutaneous Electrical Neural Stimulation (TENS) system including a signal generator, a least one cable and a TENS pad electrode.

A Transcutaneous Electrical Neural Stimulation (TENS) system includes an signal generator 11, a least one cable 12 and a TENS pad electrode 13, as shown in FIG. 13. TENS is often used for rehabilitation purposes or to provide non-invasive neuromodulation. TENS electrodes 13 are placed onto the skin and attempt to push enough current through the skin to a subcutaneous nerve that is close enough to the electrode to be depolarized, leading to an action potential. Unfortunately, densities of the current passing through the skin are dependent on the contact area (thus increasing when the electrode partially detaches) and it is often observed that stimulating a subcutaneous nerve requires current densities at the nerve which evoke action potentials in nerves and other sensory cells inside the skin between the electrode and the subcutaneous nerve which is the target 5, sometimes generating unpleasant sensations. Advantages of TENS include the ability to electrically stimulate subcutaneous nerves that are within the proximity of the TENS electrodes placed onto the skin. There is no need for surgery to electrically stimulate these nerves in close proximity to the skin. Disadvantages include paresthesia and pain felt in the skin as side effects of the neural stimulation. Primarily, the current density in the skin underneath the TENS electrodes, especially in the skin at the edge of the electrodes placed on the skin, are significantly larger than the current densities near a targeted nerve, even at a depth of 0.5 to 1 cm for a target, and even more so 1 to 2 cm in depth away from the electrodes placed on the skin (distance measured perpendicular to the TENS electrode placed on the skin). The problem is that current densities at the level of the skin need to be increased to a level that causes the sensation of paresthesia or even pain in order to have large enough current densities (or voltage differentials) at a location deeper inside the body (i.e. 0.5 to 2 cm away from the electrode on the skin).

A low-impedance path for the TENS current to pass just below the skin while potentially not or only partially passing through the cells that sense paresthesia or pain in the vicinity of the outer layers of the skin avoids this problem, by means of the liquid mixture/cured electrode disclosed herein. One embodiment of the present invention comprises an contact pad 14 (just below the last layer of live skin as disclosed herein) to make a good connection to the TENS electrodes which is then connected through channels to a lower deposit of liquid mixture (uniting all the channels) which then is connected to a wire or another line of liquid mixture to reach a nerve with high current densities right away. This embodiment may further comprise an outside layer of liquid non-mixture/nonconductive layer around the deposit deep inside the skin.

Furthermore, placing an electrode via injection around a neural target and stimulating said electrode with electrical fields applied from the outside of the body to evoke action potentials (or even to cause a temporary temperature increase interrupting nerve conduction) near a cured electrode offers advantages over the prior art. The present invention's minimally invasive delivery, combined with other abilities like providing electric field shaping towards a target, provide an advance over the prior art. The ability to be close to the target nerve offers the advantage of being able to activate or block or generally modulate said structure with small current amplitudes or voltage thresholds. Being able to guide the electrical energy from an contact pad 14 in subcutaneous tissue to the target location at e.g. 0.5 to 2 cm deep, or even deeper, by offering the current a path of <10Ω (or even <1Ω) means that current densities passing through the skin can be so small to cause no or only minor perceptions of paresthesia or pain during their passage through the outer layers of the skin. The present invention has the advantage of being able to more reliably activate neural tissue in close or far proximity to the outer skin of a person without intense or completely without the side effects of unwanted perceptions of paresthesia or pain in the skin near the TENS electrode.

"TENS electrode" includes, without limitation, an electrode with a wire embedded in a hydrogel that separates the wire mechanically from the skin but provides an electrical connection to the skin. The electrical connection may further be emphasized by smaller sized TENS electrodes (size modification), change of materials (graphene, metals, or metal composites), different optimizations of the geometry of the subcutaneously placed contact pad 14 (one line wire, plus sign, double cross #, C-shapes, O-shapes, circles, ovals, partially or fully filled, entire networks or mashes formed from liquid mixture to ensure good contact to an outside TENS electrode.

For example, a patient suffering from phantom limb pain after a traumatic injury (e.g., amputation) to the median nerve in the forearm is offered TENS stimulation to treat the pain. See FIGS. 14A-F, which are cross-section diagrams of the forearm. In order for the TENS signals to reach a PNS target 5 (here, median nerve) located in the deep tissue of the forearm, the present invention is injected around the median nerve and terminated just below the skin of the patient's arm to form a conductive pad. The procedure is conducted as outpatient procedure with localized anesthesia and in a 10 minute injection time frame. In one embodiment, the liquid mixture cures within 30-900 seconds of injection to form a mechanically compliant material with high electric conductivity. By placing a TENS electrode on the skin at the location of the contact pad 14, and using a TENS electrode 13 connected to a stimulator 15, the patient is able to achieve pain relief by stimulating this deep tissue nerve with a surface stimulation technique.

Figure 14A:
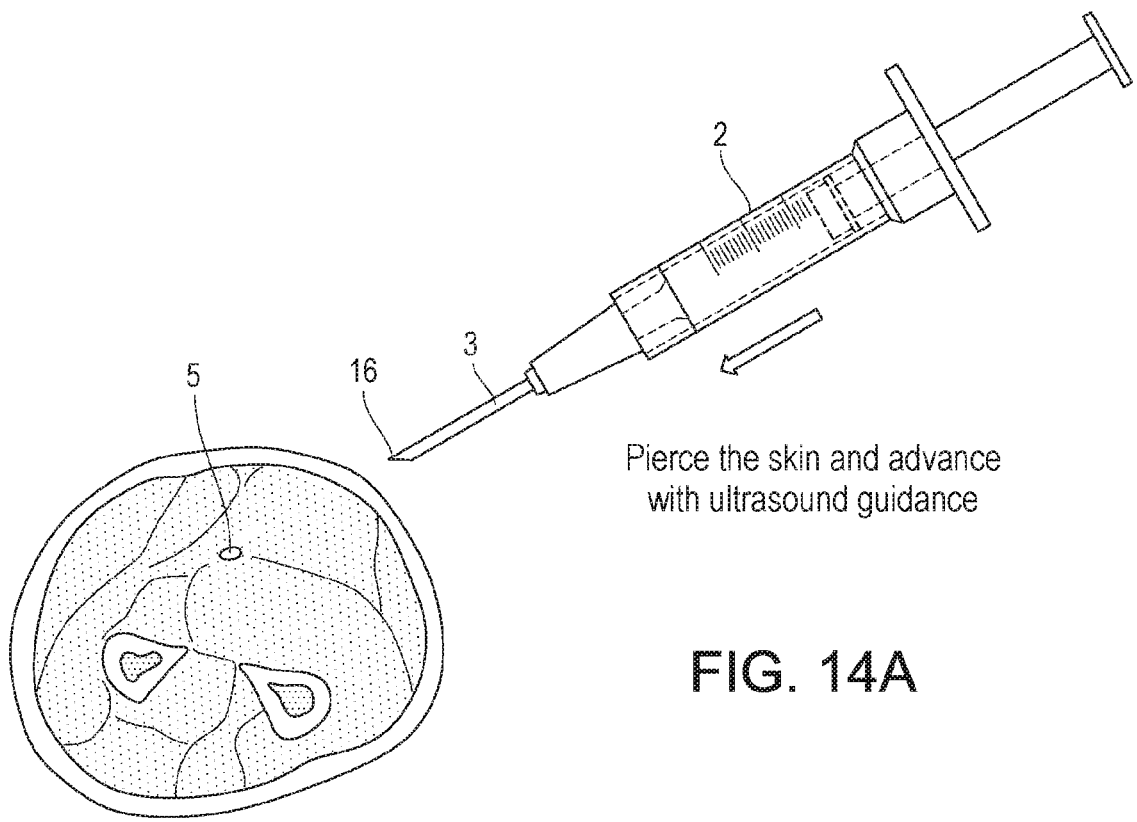
FIGS. 14A-14F are cross-section diagrams of a human forearm depicting steps in the injection of the liquid conductor around the medial nerve, and connecting it to a subcutaneous contact pad, which in turn is in electrical communication with a TENS electrode. The bar arrows represent a general direction of movement of the dispenser tip.
Figure 14B:
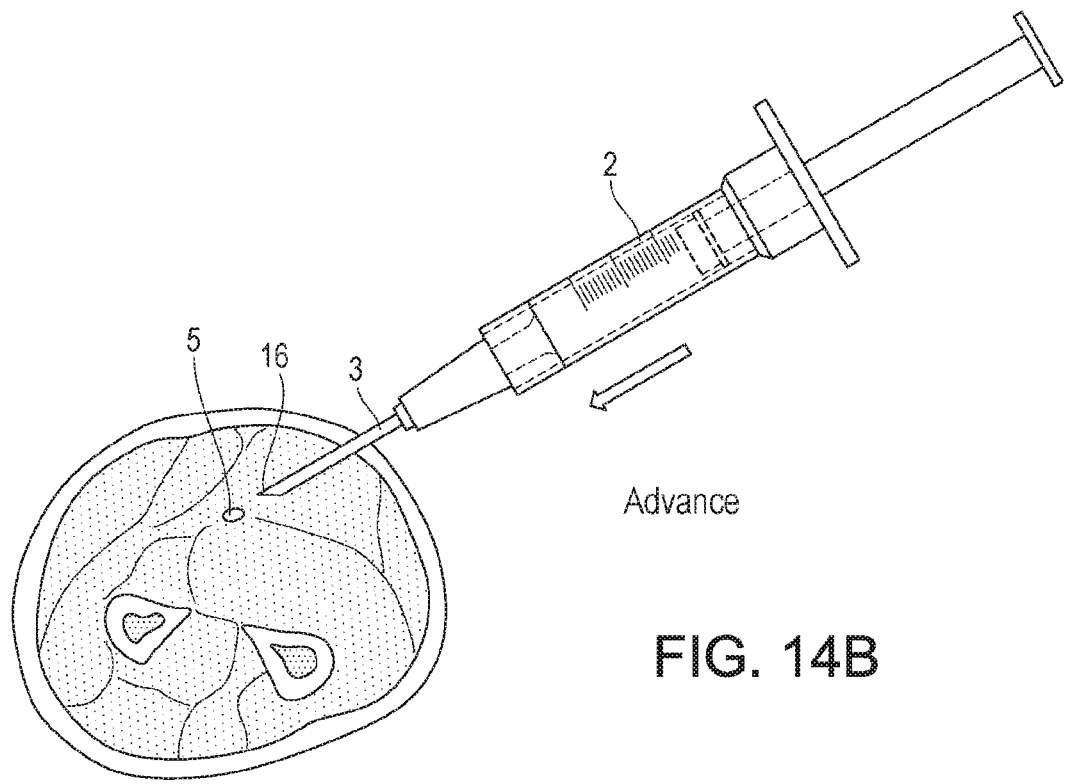
Figure 14C:
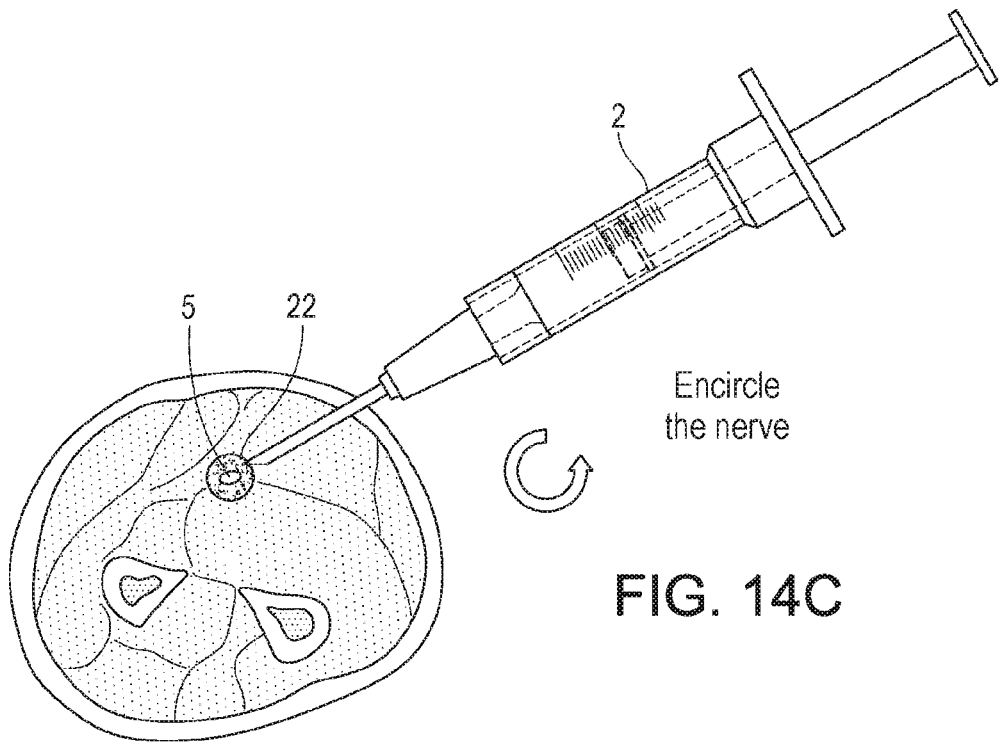
Figure 14D:
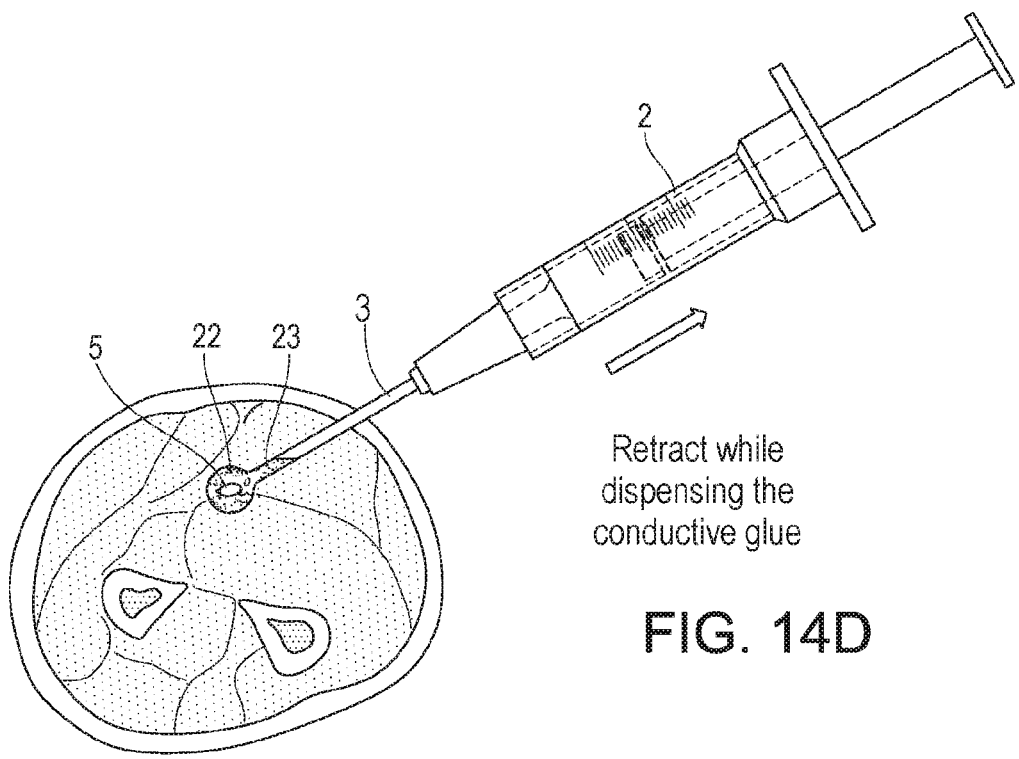
Figure 14E:
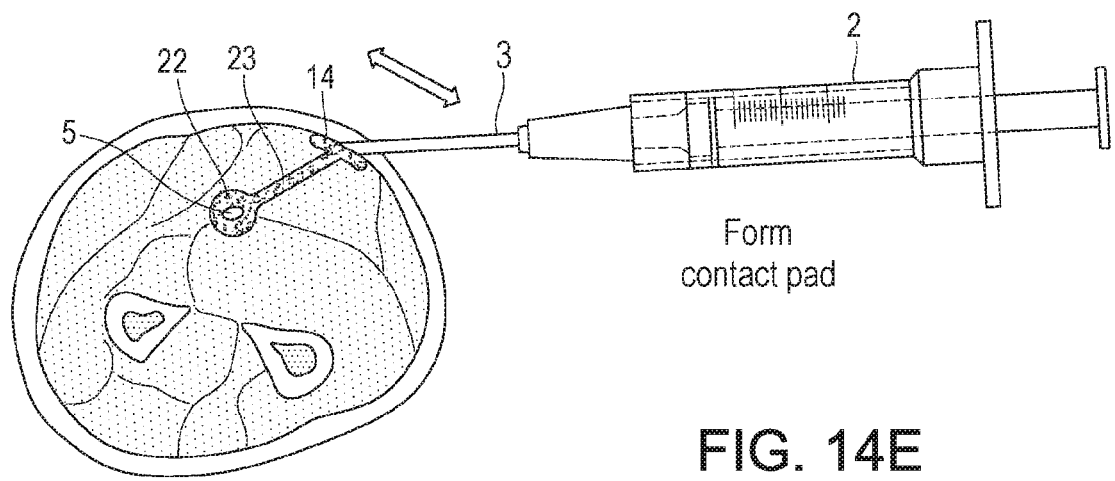
Figure 14F:
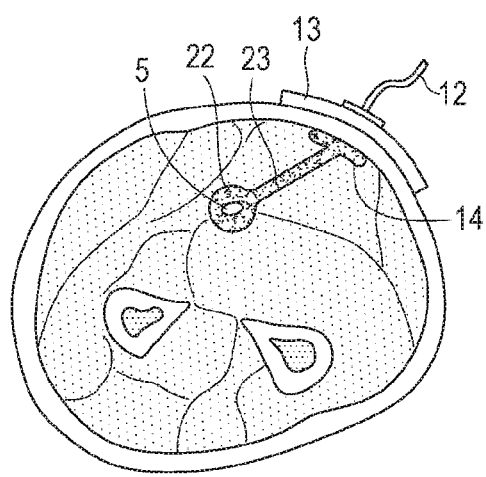

More specifically, the liquid mixture is injected all around the median nerve to form the neural interface as well as a conductive path similar to a metal wire. FIG. 14A is a diagram of a cross-section through the middle of the forearm with a dispenser 2 (here, a syringe with a needle 3) containing liquid mixture prior to injection targeting the median nerve. FIG. 14B shows the dispenser advancing to the target. Following the application of localized anesthesia, the dispenser is advanced (optionally under ultrasound, angiography or other visual guidance) to the target 5 median nerve buried deep inside the tissue. The proximity to the nerve may be verified by applying electrical pulses from an electrical stimulator 15 the dispenser's tip 16, as discussed herein, which is the only de-insulated part of the dispenser) in the range of standard neurostimulation pulses (if the connection target is a nerve but larger or stronger reactions of organs, such as muscle tissue), connected distally to the nerve are to be seen as the dispenser tip 16 comes into closer proximity with the target. If the electrical stimulator activates the nerve target, then the physician has confirmed electrical contact has been effected with the nerve. Electrical connection to the target can be further confirmed by visualization such as ultrasound, x-ray, angiography or MRI where applicable. FIG. 14C is a diagram showing dispensing of a ring-like portion 22 of the liquid mixture/cured electrode around the target. The dispensing can bluntly separate the target 5 from the connecting tissue or the liquid mixture may be dispensed in a cavity formerly formed around the nerve by blunt dissection. FIG. 14D shows dispensing the liquid mixture/cured electrode 1 forming a wire-like portion 23 of the cured electrode from the target 5 to the skin that provides an electrically conductive path from the neural target to the skin surface. FIG. 14E depicts dispensing the liquid mixture to form a contact pad 14 in the subcutaneous area which, in one embodiment, is formed by crisscrossing several lines of liquid mixture just below the skin. In this embodiment of the cured electrode, the ring-like portion 22 is electrically connected to the wire-like portion 23 which is also connected electrically to the contact pad 14, such that the cured electrode may receive electrical current from a TENS electrode on the surface of the skin. Alternatively, the liquid mixture/cured electrode may be connected to neural signal generator 17 ("signal generator") such as an implantable pulseform generator ("IPG") also implanted in the forearm located for example just below or in close proximity to the skin. FIG. 14F depicts utilization of a TENS electrode 13 applied to the skin at the approximately location of the contact pad 14 to drive electrical current to a deep tissue target 5 such as the median nerve.

In one embodiment, the present invention undergoes a phase change inside the body at body temperature, with or without the presence of air, water, and optionally may be cured by exposure to forms of energy such as ultrasound, UV or visible light, and radio frequency waves to form a partially solid, flexible or inflexible, or hard material. The carrier material 7 itself may solidify with or without the addition of air, water, energy, and it may release energy during the solidification process of forming a full or partially solid material. Conductive elements 6 to enable electrical conduction, and nonconductive particles to add to dielectric strength, are added. Hemostatic agents may be added in another embodiment. The present invention optionally may have a property to provide visualization inter-operatively via fluorescence, ultrasound or radio-/angiography, either as an inherent property of the liquid mixture, or through the addition of specific audio-, video-, mechano- or radio-opaque agents. Radio-opaque materials include, without limitation, platinum micro- or nano-particles.

In one embodiment the invention is a eutectic system comprising a liquid phase prior to injection and cures to a solid phase at or below body temperature, even under anaerobic conditions, the entire mixture forming a cured electrode upon solidification that provides impedance levels below 1 k$\Omega$ per cm of length and 1 mm$^2$ in diameter.

The present invention also comprises dispensers and systems that support the injection process by assisting a physician in finding the target (e.g., ability to electrically stimulate a nerve or sense neural responses) as well as by dispensing the liquid mixture or nonmixture.

The injection of the present invention enables formation of an insulated or uninsulated wire-like structure in one embodiment, having some similarities to (1) a bare wire in that a cured electrode 1 may not comprise a nonconductive layer 9 or (2) an insulated wire by the cured electrode optionally comprising and being at least partially surrounded by a nonconductive layer. Such a cured electrode comprising a nonconductive layer may be injected in its first liquid phase optionally through a multi-chamber dispenser 2, e.g., a first chamber 18 containing liquid mixture and the second chamber 19 containing liquid nonmixture. Or, in another embodiment, liquid mixture may be injected through one or more dispensers and the liquid nonmixture may be dispensed through at least one dispenser separate from the dispenser containing the liquid mixture.

Disclosed herein also are dispensers for pellets or capsules which are filled with liquid mixture or nonmixture, allowing the delivery of materials of different types at the same time, or to achieve curing which is delayed compared to liquid mixture or nonmixture not contained in pellets or capsules.

In one embodiment, a liquid mixture (and the resulting cured electrode) comprises resorbable materials 20 (e.g., FIGS. 12A-C) interspersed in a nonresorbable carrier material including, without limitation, sugars, amino acids, proteins and biodegradable materials which macrophages are able to consume any time after injection and within a period of 100 days, while leaving the external dimensions of the cured electrode intact, thereby creating pores 8 that the body is able to fill with interstitial fluid, connective tissue and other cells. These pores increase the electrode-to-electrolyte surface area as compared to a smooth surface of, for example, a traditional wire or metal contact, providing means to increase a cured electrode's charge injection capacity as the cured electrode "ages." The cured electrode 1 may further comprise pre-cured components that are manufactured outside the body with materials in an already pre-cured component that facilitate partial resorption. An implementation may be an already porous structure, itself electrically conductive, that may be seeded with cells, nutrients or other eutroph factors that attract the in-growth of connective and/or neural tissue (as well as neural support tissue such as glia cells and the like), that is electrically connected with the cured electrode.

In one embodiment, the invention is capable of supplying an anodic current during the insertion of the dispenser (e.g. needle) into the tissue and/or during the extraction of the dispenser from the tissue in order to achieve electrically mediated vasoconstriction. Anodic (positive) current activates a process leading to the constriction of blood vessels, reduces the probability of small vessels being ruptured during insertion and reduces bleeding time from small diameter vessels. Anodic current contracts blood vessels via the release of nitric oxide.

In contrast to using anodic current alone, higher-level (10V to 50V amplitude voltage controlled cathodic first, symmetrical charge balanced pulse trains at approximately 10 Hz) are capable of stimulating the muscle tissue of blood vessels directly and causing blood vessel contraction. This approach may be utilized to reduce bleeding not only during the placement process but also, in one embodiment, restricts blood flow to an organ.

Achieving a lower access resistance to a nerve in comparison to a traditional electrode put next to, adjacent or around a nerve. The access resistance to a nerve is directly related to the amount of charge that may be wasted while a nerve is to be stimulated: The closer an electrode is to a nerve, and especially the more tightly it wraps the nerve in the form of a cuff, the smaller a nerve activation threshold may be. See Plonsey/Barr discussed herein.

The cured electrode may be placed into, near, or around a blood vessel to be able to electrically stimulate, or block signal transmission in the blood vessel's cell wall. The liquid mixture may be injected around the outside of a blood vessel to stimulate arterial constriction or relaxation and thereby help to regulate blood flow into an organ a cell mass, the skin (to improve blood flow or reduce it to conserve body heat). The present invention may, in another embodiment, be placed around blood vessels to a tumor to prevent or reduce blood flow to a cancerous or unnecessarily growing or self-replicating site inside the body, thereby occluding blood supply and thus reducing the availability of nutrients and oxygen, leading to a reduction of the unwanted growth. Organ growth may be reduced or reversed (facilitating an intended cell/organ atrophy as medical treatment). For that, the liquid mixture may be injected by a dispenser comprising a catheter 21 from the inside of a blood vessel towards the outside of the blood vessel, either injecting it into the wall of the blood vessel or outside to the blood vessel so as to electrically contact the blood vessel's outside to an implanted wire 10. Alternatively, another component of the cured electrode may be injected to the outside of the blood vessel with an approach that comes from further away from the blood vessel and comes closer to the blood vessel. The liquid mixture may be injected as a ring around a blood vessel by injecting it through at least one needle that pierce the blood vessel wall from inside to outside and create either an interrupted or continuous ring around the blood vessel outside. Such a ring-like shape portion 22 of the cured electrode may then be contacted by a wire-like portion 23 of the cured electrode to facilitate the electrical connection to a blood vessel to a specific location inside the body or just below the skin of a patient. The wire-like portion 23 is located from outside the blood vessel from a separate injection.

Utilizing different activation thresholds for nerves and blood vessels helps to separate the two when closely aligned or nearby: While nerves will likely be depolarized at stimulation current amplitudes of 1 mA stimulation current applied for a 200 μsec pulse width, in a symmetrical, cathodic first waveform, blood vessels will more likely not react until about 10 mA++ are applied based on the fact that blood vessel walls are lined with smooth muscle cells whose activation thresholds are at least about an order of magnitude higher than that of axons in nerves. It is feasible without a nonconductive layer being placed to stimulate and activate a nerve next to an artery, but enables stimulation of only the blood vessel (e.g., to contract) but not depolarization of a nearby nerve through combinations of various stim and block waveforms.

The present invention, in some embodiments, may be placed into, near, or around an organ, especially specific structures of an organ such as internal blood vessels or neurons, or an inside or outside wall of the organ to be capable of electrical stimulation, or blockage of signal transmission, in the organ, the innervation or the blood supply of the organ, for example, the bladder. Organ activity can be changed by increasing or decreasing neural communication into and out of the organ, and some organ growth and activity can be up- or down-regulated by allowing more or less blood enter the organ, such in the case of the gut, the liver, the lungs or the kidney which are exchange systems for the body, utilizing a fine mesh of blood vessels intertwined with other vessels who either add or extract chemicals in the form of dissolved gasses or liquids. The present invention allows for an efficient way to contact an organ, such as by injecting the liquid mixture to the outside wall of an organ near an innervation point. The conductive elements may in such case comprise a mesh 24 attached via a liquid mixture and/or sutures to the organ, the electrical conduction between mesh and the organ being accomplished or improved by the liquid mixture.

Carrier Material

The carrier material 7 provides the capability of being injected because it comprises first a liquid phase and then it cures to a solid phase and, as such, the liquid phase carrier material allows injection of the conductive elements 6 which are interspersed in the carrier material 7. Although curing may begin outside of the body, at least some of the curing process is capable of occurring inside the body, distinguishing the invention from prior art electrodes which are pre-configured prior to implantation. The carrier materials include hydrogels, elastomers, tissue glues, tissue adhesives other than glues, tissue sealants, coagulants, cyanoacrylates, bone cements, dental resins, and dental amalgams. If powders are part of an embodiment, then the powder's dispenser allows the formation of a mechanical structure (with or without the addition of other materials) that becomes a less pliable structure after curing. Powders akin to some of the powders used as coagulants can form the non-conductive mechanical support structure by first coagulating bodily fluids and tissues in place co-located with the conductive carriers, while limiting the production or aiding with the transmission of excess heat away from sensitive tissues such as the neural target tissue.

Fast curing is often optimal, for example, a range of 1 to 5 seconds as the body is constantly moving with heart beats, breathing, pulse even in distal arteries, moving muscles; in other embodiments it is preferred for the curing to take no longer than 900 s. Although the curing time for a specific implementation may exceed 15 minutes (900 s) of time to reach the solid phase, a curing duration of less than 15 minutes is better in a surgical implementation than a duration of longer than 15 minutes. This curing duration does not include the encapsulation by the body or the partial dissolution and/or resorption of components or materials included as part of the embodiment of the invention in its liquid phase. Slow curing also has specific application for better long term integration to the surrounding tissue. Forming a good mechanical bond to the biological tissue is optimal. In the liquid phase the carrier material is dispensed via injection. The carrier material may have gel-like property as long as it is capable of curing further into a more stable form retaining the shape of contours of the target around which it is injected and molded against the contours of the target. The carrier material may be a putty-like, amorphous material (similar to "Sugru Mouldable Glue" in its mechanical behavior but, in contrast to Sugru, biocompatible; and curing fully without the release of toxic or partially toxic gases and other substances) that may cure inside the body, retaining some mechanical flexibility post curing or not. The carrier material may comprise a eutectic paste. The carrier material may be doped with the body's own cells to better integrate. The carrier material may also be doped with stem cells from the patient or other living organisms. It may be doped/mixed with radio-opaque particles or dyes (for example to allow the verification of the placement of the carrier material in its liquid phase around the nerve or through tissues as well as the ability to detect breaks in the cured electrode after years of wear and tear). It may be doped with sugars or other resorbable materials 20 which the body's macrophages resorb in order to change the injected liquid mixture into a porous structure (FIGS. 12A-C) as time passes and the body partially digests the blob, thereby increasing the active surface area to the embedded conductive elements. The carrier material also may comprise fluorescent particles or dyes that allow the verification of placement around the nerve or through tissues intra-operatively by shining a UV light onto it that does not cure the carrier material but instead makes it glow in the dark of the cavity and around the nerve or, if injected into the nerve, makes it glow from inside the nerve. The carrier material may also comprise pharmacological agents to produce short-term or sustained drug-delivery that have complementary action to the cured electrode (e.g. lidocaine to reduce pain from operation and/or produce local anesthesia, or other nerve-block agents or other pain-alleviating agents that may ordinarily be injected near a neural target).

The viscosity of the liquid mixture affects how readily it will flow and distribute itself within a created body cavity. Lower viscosity liquid mixtures will flow more easily than higher viscosities, but higher viscosities have greater ability to stick to a specific placement location and to hold a specific space filled without flowing to unintended spaces.

A low viscosity liquid mixture has an advantage in its greater capability to be injected behind or below a nerve but in some embodiments may be used with a pre-formed mold (described elsewhere herein) to be inserted at the target to hold this space open during the injection or other placement process. Higher viscosity affords a greater capability for the liquid mixture to resist forces from the surrounding biological tissue to be pushed out of the cavity, thereby retaining a minimum ring-like portion 22 around a nerve when injected without a pre-formed mold.

Among other advantages discussed elsewhere, higher viscosity carrier materials have the following advantages in aiding: (1) with combatting separation of conductive elements from the carrier material as the liquid mixture passes from the larger inner diameter of a dispenser to a smaller diameter needle; (2) with dispensing as the thicker material sticks in place; and (3) with surgical integration as the more viscous liquid mixture may be shaped in place, holding its form and shape to a certain degree before curing. Differences in viscosity are primarily achieved by changing the ratio of conductive elements vs. silicone carrier material. A secondary way of changing the viscosity is by adding surfactants, thickening or thinning agents. Thinning agents may be selected from a group including water, PEG solutions, glycerine, and other inactive excipients commonly utilized in the pharmaceutical industry found at www.accessdata.fda.gov/scripsts/cder/lig/index.cfm. Thickening agents may be selected from a group including inactive polymer powders such as polyethylene glycol ("PEG") powder, peptide powders, starches, sugars, silica powder, and additional metallic and non-metallic fillers that may or may not add further elements of high conductivity (graphene being one of them).

A comparison of the hydrogel PEG, fibrin glue and cyanoacrylate as a carrier material is useful. PEG becomes mechanically flexible in the solid phase after curing with medium to high water content. When PEG is hydrolyzed it dissolves, and its stability depends on crosslinking, and dendritic structures create higher cross linking. It may be polymerized or crosslinked to the solid phase by different mechanisms. Fibrin glue is also mechanically flexible as a solid having a medium water content. It can degrade enzymatically in vivo and its stability depends on crosslinking. Fibrin requires frozen storage and it may be stored up to two years, and it requires thawing before use. Cyanoacrylates have low water content and variable rigidity. Cyanoacrylates are very stable and hydrolyze over time, though the average time for a cyanoacrylate to hydrolyze is to be expected longer than the time needed for the body to take over the mechanical stabilization before the cyanoacrylate has substantially weakened. If the intended location in the body is anticipated to be under significant physical stress/strain, e.g. near contracting muscles or joints, longer hydrolysis times, at least greater than the time it takes to form a stable fibrous capsule around the implant, are desirable. The rate of fibrous capsule formation itself may be variable depending on location in the body, and is likely a function of tissue vascularity. Higher vascularization means a higher mobility of fibroblasts and macrophages to the site of implantation and thus a higher rate of scar formation.

Hydrogel

A hydrogel is a network of hygroscopic (water-absorbent) polymer chains. A form of hydrogel, cross-linked gelatin forms a cohesive matrix with tunable post-curing viscosities. Gelatin easily flows at temperatures exceeding 50 degrees C. and undergoes a reversible transition from solid to gel under specific conditions. Gelatin is a naturally occurring, and generally well-tolerated biomaterial. Gelatin is an irreversibly hydrolyzed form of collagen. It is an animal collagen thermally denatured with a very dilute acid, with many glysine residues (almost one in three), proline and 4-hydroxyproline residues. A typical structure is -Ala-Gly-Pro-Arg-Gly-Glu-4Hyp-Gly-Pro. While the basic building blocks of gelatin and collagen are the same, collagen retains more of its tertiary fibril structure. Conductive elements may be mixed with gelatin above its gelation temperature (temperature threshold for the formation of a thermoreversible gel), injected into the body, and allowed to cool. The resulting cured gel containing conductive elements will be electrically conductive. Furthermore, gelatin comprises the processed form of collagen. Gelatin can be ground up, mixed with conductive elements (and optionally a surfactant and other additives) and then added to the carrier material to form a paste that undergoes the phase change in the body, and immediately after curing begins a process by which the body's inflammatory response starts to exchange, digest, or replace the gelatin based particles with the body's own cells, thereby growing into the cured electrode or partially digesting the cured electrode, which leaves pores inside the remaining cured electrode bulk, thereby creating a porous interface of much larger surface area compared to a smooth surface of the same outer dimension.

PEG is a hydrogel, and it has many advantages as a carrier material for the liquid mixture and the cured electrode. Hydrolysis of 20 kDa cross-linked PEG is approximately 4-8 weeks. Higher molecular weight or higher cross-linking density may achieve longer hydrolysis times. PEG is hydrophilic and will therefore adsorb proteins during and after implantation to the surface, without greatly denaturing them. This increases biocompatibility and adherence to surrounding tissues compared to silicone and other hydrophobic surfaces. PEG has much greater replacement by the body than silicone. PEG provides a regenerative growth substrate for repairing damaged neurons/axons. PEG's repeating ethylene glycol units provide ample opportunity for hydrogen bonding, particularly with carboxylic acids in microenvironments above their pK (~4.5). Importantly, PEG can act as a chelator or buffer for bicarbonate, which can locally decrease the pH or presence of carbonic acid in the microenvironment which has demonstrated benefits for wound healing. A PEG based liquid mixture/cured electrode may be manufactured with an intentionally higher impedance than other carrier materials, by adding non-conductive materials, particles or elements to the mixture. The resulting insulating PEG cured electrode may be used to restrict electrical current flow from certain areas, or as a liquid nonmixture it may be used to achieve an insulation around the liquid mixture/cured electrode. In some embodiments PEG may be made more nonconductive by adding elements that make the final cured PEG more attractive to in-growth of fibrous tissue thus increasing insulation with the body's own fibrous tissue, in comparison to the PEG based cured electrode that is intended to remain conductive (with conductive elements) as the PEG is replaced by the organism.

In yet another embodiment, the addition of gelatin to carrier materials such as PEG hydrogels or silicones, is used to intensify the body's inflammatory response, on a continuous scale according to the concentration of gelatin added, thereby increasing the amount of encapsulation 52 that is formed by the body around the cured electrode. The cured electrode may also comprise gelatin to thicken encapsulation, for example, to keep the cured electrode in place and prevent conductive elements 6 from flaking off, or it may be applied as a second layer on the outer aspect of the electrode formed next to, or around, a nerve, to ensure a thicker encapsulation to increase the electric impedance towards the outside of the cured electrode with the goal to have a low impedance (i.e. thin layer) encapsulation on the inside of the ring-like portion 22 that touches the nerve and a large impedance (i.e., thick layer) encapsulation 52 on the outside of the cured electrode against the surrounding tissue. This approach may be used to interface selectively with various nerves running in parallel or it may be used to minimize muscle fiber activation or simply reduce current outflow out of the cured electrode wherever it does not do any work stimulating the target. The control of the encapsulation, and thereby the electrical interface impedance between the cured electrode and the surrounding tissue aids in constructing a lower side-effect and more energy-efficient neural interface that saves on battery lifetime for signal generators.

PEG is a carrier material which comprises a liquid phase to which conductive elements may be added or attached. PEG hydrogels are biodegradable and are resorbed by the body after injection and after curing to the solid phase of a cured electrode, thus allowing the formation of pores.

PEG is a polyether compound and is also called polyethylene oxide (PEO) or polyoxyethylene (POE), depending on its molecular weight. The structure of PEG is commonly expressed as H—(O—CH2-CH2)n-OH. PEG, PEO, and POE refer to an oligomer or polymer of ethylene oxide. The three names refer to the same compound, but historically the term PEG is preferred in the biomedical field, whereas the term PEO is more prevalent in the field of polymer chemistry. As used herein, PEG or polyethylene glycol means any compound comprising the general structure X—(O—CH2-CH2)n-Y where n is a variable number of repeat units and X and Y are functional groups at the terminal ends. If X=Y, then the PEG is called a "homo-bi-functional PEG." If X does not equal Y, then the PEG is called a "hetero-bi-functional PEG." If X or Y=—OH and is therefore unmodified, then the PEG compound is a "monofunctional PEG." Because different applications require different polymer chain lengths, PEG has tended to refer to oligomers and polymers with a molecular mass below 20,000 g/mol, PEO to polymers with a molecular mass above 20,000 g/mol, and POE to a polymer of any molecular mass. PEGs are prepared by polymerization of ethylene oxide and are commercially available over a wide range of molecular weights from 300 g/mol to 10,000,000 g/mol. In one embodiment, the PEG suitable for the carrier material is within a range of 1000 g/mol-50,000 g/mol.

While PEG and PEO with different molecular weights have different physical properties (e.g. viscosity) due to chain length effects, their chemical properties are nearly identical. PEGs/PEOs come in a variety of molecular weights, with varying degrees of polydispersity. Furthermore linear PEG chains may be initiated and terminated by different functional groups, e.g., —CH3, —OH, —COOH, —SH, depending on the initiator, capping agents, and polymerization process used.

PEGs are also available with different geometries. In order to facilitate efficient crosslinking, a branched structure is desirable for a carrier material herein. The two market leaders for PEG products, Coseal and Duraseal, use 4-arm PEG which are suitable as carrier materials CoSeal has a MW of 10 kDa and DuraSeal has a MW of 20 kDa. Hyperbranch also provides a dendritic PEG adhesive with much higher branch numbers which are suitable. Branched PEGs have three to ten PEG chains emanating from a central core group. Star PEGs have 10 to 100 PEG chains emanating from a central core group. Comb PEGs have multiple PEG chains normally grafted onto a polymer backbone. The numbers that are often included in the names of PEGs indicate their average molecular weights (e.g. a PEG with n=9 would have an average molecular weight of approximately 400 daltons, and would be labeled PEG 400.) Most PEGs include molecules with a distribution of molecular weights (i.e. they are polydisperse). The size distribution may be characterized statistically by its weight average molecular weight (Mw) and its number average molecular weight (Mn), the ratio of which is called the polydispersity index (Mw/Mn). MW and Mn may be measured by mass spectrometry or by gel permeation chromatography. All the above configurations of PEG are suitable as the carrier material for the present invention.

PEG is soluble in water, methanol, ethanol, acetonitrile, benzene, and dichloromethane, and is insoluble in diethyl ether and hexane. It is coupled to hydrophobic molecules to produce non-ionic surfactants. If inadequately purified or characterized after synthesis, PEGs may potentially contain toxic impurities, such as ethylene oxide and 1, 4-dioxane. Ethylene Glycol and its ethers are nephrotoxic if applied to damaged skin. It is therefore important that the source of PEG materials be rigorously quality controlled, as has been accomplished by a number of other manufacturers having FDA-approved PEG adhesive formulations on the market.

PEG and related polymers (PEG phospholipid constructs) are often sonicated when used in biomedical applications. However PEG is very sensitive to sonolytic degradation and PEG degradation products may be toxic to mammalian cells. It is, thus, imperative to assess potential PEG degradation to ensure that the final material does not contain undocumented contaminants that may introduce artifacts into experimental results.

Figure 15:
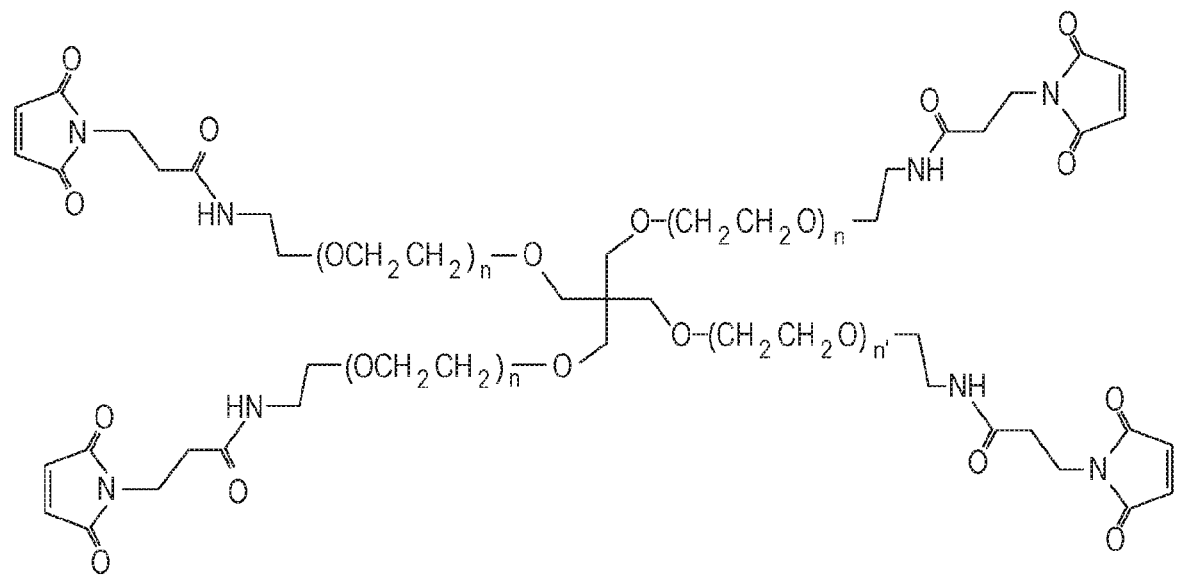
FIG. 15 is a diagram of the chemical structure of PEG in DuraSeal.
Figure 16:
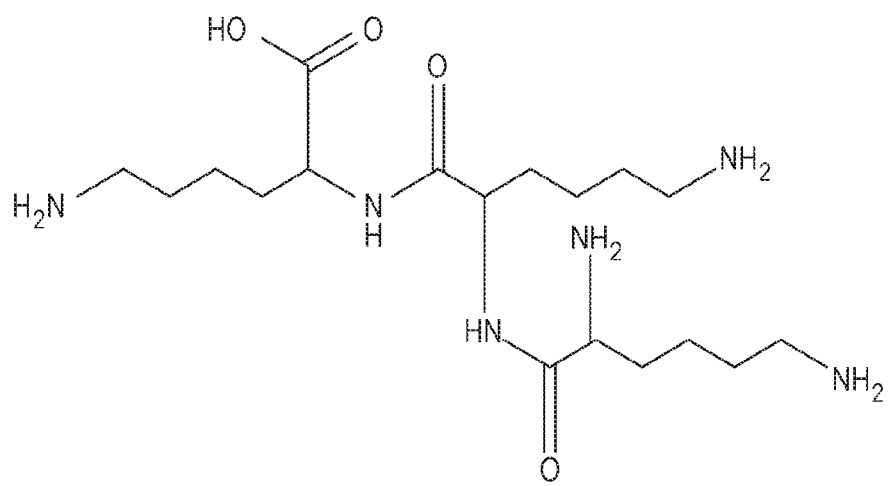
FIG. 16 is a diagram of the chemical structure of Trilysine in Duraseal.

An example of a hydrogel which can be used as a carrier material in the mixture is a PEG tissue sealant commercially available called DuraSeal. It comprises a 2-part solution system that when mixed forms a synthetic hydrogel coating that is biocompatible and degraded in the body over 4-8 weeks. More specifically, it comprises (1) a 20 kDa, 4-arm Branched PEG, terminated with NHS-ester-activated functional groups, (2) a trilysine crosslinker, and additives including (4) a preservative: BHT (butylated hydroxytoluene), (5) Dyes—help to ensure mixing is complete, FD&C Blue, (6) Buffers-sodium phosphate for PEG, and (7) Buffers—sodium borate for trilysine. The PEG is dissolved at a concentration of 0.5 g in 2.5 ml of sodium phosphate buffered saline (20% w/v or 10.0 mM). The tri(L-lysine) acetate is dissolved at a concentration of 10.5 mM in 2.5 ml 75 mM sodium borate decahydrate. FIG. 15 is a diagram of the chemical structure of PEG in DuraSeal. FIG. 16 is a diagram of the chemical structure of Trilysine in Duraseal, (showing 4 primary amines, as well as 2 secondary amines that are not reactive with NHS, which is an abbreviation for N-hydroxysuccinimide).

TABLE TWO

Total and relative amount of ingredient per single dosage of Duraseal (~5 g).

| Per Dosage Delivery | g | mg/kg |
|---|---|---|
| 4-arm PEG-NHS | 0.5000 | 7.143 |
| Trilysine | 0.0106 | 0.151 |
| SodiumBorate 75 mM | 0.0640 | 0.914 |
| Sodium Phosphate | 0.0027 | 0.038 |
| FD&C Blue | 0.0005 | 0.007 |
| BHT Preservative | 0.0001 | 0.001 |

TABLE 2

Crosslinking ratios of Trilysine:PEG

| PEG | | Trilysine | | Ratios Trilysine:PEG |
|---|---|---|---|---|
| 0.5 | g PEG | 0.01057 | g Trilysine | 0.021 |
| 20000 | MW PEG | 402.53 | MW Trilysine | 0.020 |
| 0.000025 | mol PEG | 0.0000263 | mol Trilysine | 1.050 *** |
| 0.0025 | L Buffer | 0.0025 | L Buffer | 1.000 |
| 0.010 | MPEG | 0.0105 | M Trilysine | 1.050 *** |
| 4 | NHS/PEG | 4 | Primary $NH_2$ | 1.000 |

Note:
*** 5% Excess of Trilysine: in order to ensure full consumption of NHS sites during reaction.

The above formulation of the PEG sealant is an example of a carrier material for use in the liquid mixture, with the addition of conductive elements at high enough concentration to create a continuous distributed network of separate conductive elements (described herein) such that the impedance measures below 100 ohm/cm for the purpose of curing to a solid electrode in vivo.

The PEG branching structure may be varied by changing the polymerization conditions during preparation of the PEG precursor in order to change the reaction kinetics and the ultimate hydrogel mechanical properties. The prototypical PEG used in commercially available PEG sealants is a 4-arm branched structure. The PEG structure of the present invention's carrier material may include, without limitation, any of the following structures:

(a) Linear—homo-bifunctionalized PEG provides two reaction groups and is the minimum required to form a continuous interconnected polymer hydrogel network. However, given the competing hydrolysis rate of NHS or other activated end groups, there will be some terminal PEG molecules, such that the network is likely to have some discontinuities in its structure. This may yield a low degree of crosslinking, and hence a less stiff or cohesive gel. For temporary cured electrodes or for anatomies that are particularly sensitive to stiff materials this may be a particular benefit.

(b) Branched multi-arm—The most common single-order branching structures of PEG are 3-arm, 4-arm (pentaerythritol core), 6-arm (dipentaerythritol core) and 8-arm (hexaglycerol or tripentaerythritol core). Due to multiple binding sites, the multi-arms are more likely to form an interconnected network upon curing than linear PEG, and the multi-arm structure is highly suitable as the carrier material. The increased number of binding sites will decrease polymer network mobility and increase stiffness and strength.

(c) Multi-level branched (stellate/star)—the most common PEG dendrimers are generation 1, 2, 3, and 4, and yield 2^(1+generation) potential functional —OH groups available for reactions. Certain dendrimers with particularly high cationic surface charge yield toxic side effects upon degradation, disrupting biological membranes and resulting in hemolytic toxicity.

(d) Random hierarchy-randomly branched PEG or "hyperbranched" PEGs are synthesized by random anionic ring-opening multibranching copolymerization of ethylene oxide with glycidol as a branching agent, leading to poly(ethylene glycol) structure with glycerol branching points. The benefit is a higher degree of branching and easier rate of manufacture. However, the downside is a stochastically formed polymer, which may lead to inconsistencies in polymer viscosities in batch-to-batch processing.

Ingredient concentrations in precursor PEG solutions may be varied by increasing or decreasing the molarity of the solutions and these variations will change the reaction rate and system viscosity. For example, increasing the concentration of PEG will increase precursor solution viscosity. Increasing crosslinker concentration relative to PEG will yield faster curing rates. It will also affect swelling characteristics. Swelling of Duraseal is ~98% by volume. Increasing or decreasing the viscosity of the precursor solutions has advantages in getting selective or consistent suspension of conductive elements. Viscosity also largely determines the pressure required to deliver the solutions through syringe/needle devices. Lower viscosity solutions (lower concentrations) will mix more easily than higher viscosity solutions. Lower concentrations will also cure slower compared to higher ones according to a molecule-molecule interaction (collision theory).

The PEG molecular weight may be varied by changing the polymerization conditions, (e.g., the use of varying monomer feed-rates, feed-ratios, catalyst choice, catalyst ratio, duration of polymerization as well as the use of capping agents to quench the reaction) during preparation of the PEG precursor changes the reaction kinetics and the ultimate hydrogel mechanical properties as well as the viscosity of the precursor PEG solution to enable selective suspension or precipitation of conductive filler particles. Suitable PEGs for the present invention are in the range 5 kDa, 10 kDa, 20 kDa 4-arm branched structure. Higher molecular weight PEG will take longer to degrade and therefore have longer time for clearance in renal system. A hydrogel carrier material of 30-50 kDa is suitable for the present invention. At some point >50 kDa, the rate of dissolution of the lyophilized PEG powder with the diluent will be a limiting factor. E.g., 100 kDa PEG is likely to take over 15 minutes to reconstitute in aqueous diluent buffer without applying additional heat or solvents. This would make clinical implementation challenging.

Figure 17:
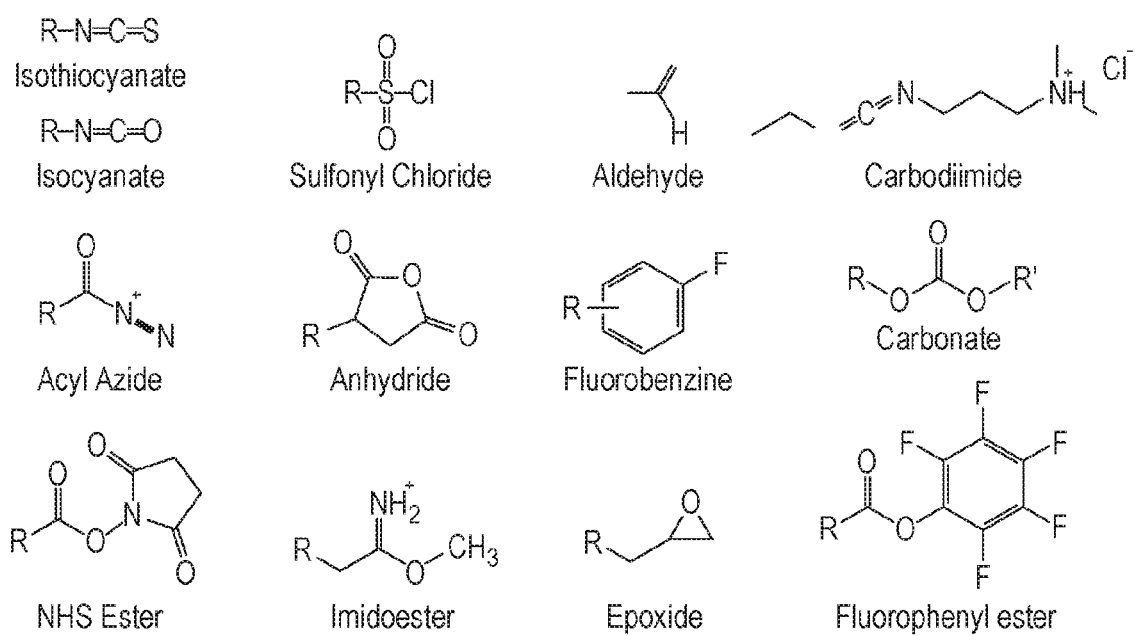
FIG. 17 includes examples of amine-reactive functional groups which can be substituted for NHS-ester as the active leaving group.

The amine-reactive functionalization chemistry may be varied by changing the active leaving group, for example from NHS to others listed in FIG. 17 in order to optimize reaction kinetics to allow for slower/faster curing times and/or lower toxicity of reaction byproducts. The change may also resolve compatibility issues in the presence of the conductive elements if the conductive elements negatively interact with the crosslinking chemistry (e.g. catalyzes undesired reactions)

The amine-containing crosslinker may be varied from trilysine to other multi-amine containing molecules selected from a group containing higher order poly-lysines (quadlysine, pentalysine) polyamines selected from the group containing putresceine, spermindine, or spermine, and other branched polyamines selected from a group containing Tris(3-aminopropyl)amine and tetrakis(3-aminopropyl)ammonium. These crosslinkers may optimize the reaction kinetics to allow for slower/faster curing times and/or better mechanical properties of the final cured system. Furthermore selection of a different amine-containing crosslinker may enable different viscosities, allowing for better or more stable suspension of the conductive elements. The crosslinker itself may become a surface-modified conductive element. See herein re covalently bonded agents.

Additives for the PEG hydrogel may also be varied. Other preservatives, such as BHT, sucrose, trehalose, glycerin, sodium citrate, poloxamer, CTAB may be added to help stabilize the conductive element suspension or resuspension. Dyes may be added to allow ultrasound, MRI, or CT imaging, as well as buffers to change the reaction kinetics, e.g., high or low pH phosphate or boron buffers (e.g., 50-100 mM) as well as other ionic buffers (e.g. hypotonic, isotonic, or hypertonic saline, depending on desired swelling properties).

Conductive elements may be surface-modified by covalently conjugating (or otherwise associating chemically) moieties on the surface or in order to improve chemical or mechanical integration with the carrier matrix material.

A liquid nonmixture which cures in vivo to a nonconductive layer is also disclosed, using the same PEG hydrogel as used in the liquid mixture, described herein. As described herein regarding the carrier material for the liquid mixture, the PEG branching structure may be varied by changing the polymerization conditions during preparation of the PEG precursor in order to change the reaction kinetics and the ultimate hydrogel mechanical properties in different configurations: (a) Linear, (b) Branched multi-arm, (c) Multilevel branched (stellate/star), and (d) Random hierarchy.

The liquid nonmixture may also vary the ingredient concentrations in precursor solutions by increasing or decreasing the molarity of the solutions so that it will change the reaction rate and system viscosity. Higher molarity means more viscous. Different ingredient concentrations will also affect swelling characteristics. Swelling of "Example Commercial PEG Sealant" is 98% by volume. A higher initial ingredient molarity (e.g., hypertonic with respect to physiological conditions), will encourage more water ingress to attempt to balance the ionic and solute gradients, increasing the post-cure swelling.

Figure 21:
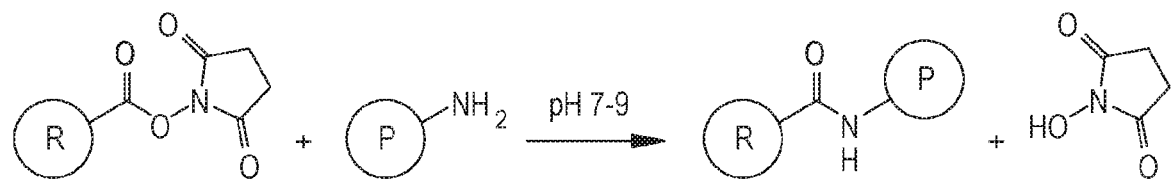
FIG. 21 contains diagrams showing steps of amine reactive crosslinker chemistry delivering stable conjugates and NHS.
Figure 22:
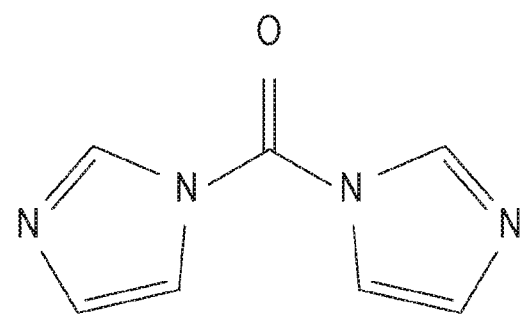
FIG. 22 depicts the chemical structure of carbonyldiimidazole zero-order cross linker.

Varying the PEG molecular weight of the carrier material by changing the polymerization conditions during preparation of the PEG precursor in order to change the reaction kinetics and the ultimate hydrogel mechanical properties as well as change the viscosity of the precursor PEG solution to enable selective suspension or precipitation of conductive elements. As shown in FIG. 21-0, the selective suspension or precipitation of conductive elements may be used to create a phase-separated electrode, in which conductive elements sink to the bottom of the electrode solution confined in a volume, creating a conductive interface at the bottom, leaving a non- or less-conductive interface at the top. A lower viscosity suspension that would take longer to cure allows for conductive elements to sink to the bottom due to gravity if surgery/injection is done such that the nerve is lower or against a specific location then one can have a higher density filler against the nerve and lower density filler region away from the nerve—thereby creating an insulating layer on the top.

As with the liquid mixture described herein, it is possible to vary the amine-reactive functionalization chemistry by changing the active leaving group in order to optimize reaction kinetics to allow for slower/faster curing times and/or lower toxicity of reaction byproducts, for example from NHS to other compounds in FIG. 17. The change may also resolve compatibility issues in the presence of the conductive elements if the conductive elements (e.g. hypotonic, isotonic, or hypertonic saline, depending on desired swelling properties) negatively interact with the crosslinking chemistry (e.g. catalyzes undesired reactions).

To store a dry PEG carrier material mixture, mix dry PEG powder with conductive elements, then mix it with solvent when ready for use/injection. Mixing may include rapid shaking by a machine akin to a dental amalgam shaker.

Likewise, the PEG carrier material for the liquid nonmixture may vary the amine-containing crosslinker from trilysine to other multi-amine containing molecules, in order to optimize the reaction kinetics to allow for slower/faster curing times and/or better mechanical properties of the final cured system. Furthermore selection of a different amine-containing crosslinker may enable different viscosities, allowing for better or more stable suspension of the conductive elements.

Changes in additives may be made such as preservatives (listed herein) for better stability, dyes—allowing Ultrasound, MRI, or CT imaging to change the reaction kinetics. Glycerine/glycerol slow down the reaction kinetics and lengthen the curing time, as shown herein.

Another hydrogel suitable for the carrier material herein are hyaluronic acid gels which comprise hyaluronic acid, comprising a chemical formula of $C_{28}H_{44}N_{20}O_{23}$ and a molecular weight of 776.651 g/mol. It is a natural high-viscosity mucopolysaccharide with alternating beta (1-3) glucorinide and beta (1-4) glucosaminidic bonds. It is found in the umbilical cord, in vitreous body and in synovial fluid. Hyaluronic Acid is a glucosaminoglycan consisting of D-glucuronic acid and N-acetyl-D-glucosamine disaccharide units that is a component of connective tissue, skin, vitreous humour, umbilical cord, synovial fluid and the capsule of certain microorganisms contributing to adhesion, elasticity, and viscosity of extracellular substances. (pubchem.ncbi.nlm.nih.gov/compound/3084050#section=Top)

Variation of the PEG branching structure alters the rate of curing of the PEG hydrogel carrier material. "Example Commercial PEG Sealant" is a 4-arm PEG, but a 2-arm, 3-arm, 5-arm, etc. are suitable structures for the PEG carrier material by synthesizing or obtaining PEGs generated with varying core structures with the advantage being an increase or decrease in the number of potential cross-linking sites. This allows a change in the reaction rate and the strength of the polymer, the approach being focused especially on slowing curing and thereby allowing the physician to modify the liquid mixture for optimal fit in the body while or before curing in part or completely. FIG. 19 is a diagram of the chemical structure of a PEG with a Hexaglycerol core (8-arm). FIG. 20 is a diagram of the chemical structure of a PEG with a Tripentaerythritol core (8-arm).

Dendrimers are a versatile polymer structure that have been utilized in the field of drug delivery, in particular, used for improving solubility and bioavailability of poorly soluble drugs. Dendrimers have potential downsides resulting from biological toxicity related to their degradation byproducts or their cationic surface charge. Several strategies to counteract this toxicity have been employed including selection of biodegradable cores and other easily metabolized branching units, as well as by masking the surface charge by appending a neutrally charged group (e.g., PEG, acetals, carbohydrate or peptide conjugation). Such modified dendrimers do not exhibit the same degree of biological toxicity as their unmodified counterparts.

An example of variation of the ingredient concentrations in precursor solutions is a PEG concentration of 20% w/v or 10 mM and a Trilysine concentration is 10.5 mM. Examples of variation of the PEG molecular weight are disclosed as follows. Higher and lower viscosity mixtures are possible to enable homogeneous or heterogenous suspensions of conductive particles. For example a 10 kDa PEG (20% w/v) may have an optimal viscosity to homogeneously suspend gold nanowires, however, gold microparticles may sink to the bottom of the solution. On the other hand, a 100-300 kDa PEG solution (20% w/v concentration) may be optimal for fully suspending gold microparticle and short microwire segments. "Example Commercial PEG Sealant" is a 20 kDa PEG. Two other PEG-based hydrogels that are legally marketed surgical sealants are suitable hydrogels: FocalSeal by Genzyme and CoSeal by Cohesion Technologies. FocalSeal has a molecular weight of 31,500 Da.

The amine-reactive functionalization chemistry may be varied. NHS-Ester activation chemistry converts hydroxyl (—OH) or carboxylic acid (—COOH) groups that normally terminate linear or branched PEGs into NHS-ester leaving groups that may react with amine (—NH2) functional groups. In the case of "Example Commercial PEG Sealant", the PEG molecules are first modified to —COOH terminal groups using succinic anhydride, the intermediate is then reacted with sulfo-NHS, EDC, or DCC activators.

FIG. 21 contains diagrams showing steps of amine reactive crosslinker chemistry delivering stable conjugates and NHS. (Source: www.thermofisher.com/us/en/home/life-science/protein-biology/protein-biology-learning-center/protein-biology-resource-library/pierce-protein-methods/amine-reactive-crosslinker-chemistry.html) Hydrolysis of the NHS ester competes with the primary amine reaction. The rate of hydrolysis increases with buffer pH and contributes to less-efficient crosslinking in less-concentrated protein solutions. The half-life of hydrolysis for NHS-ester compounds is 4 to 5 hours at pH 7.0 and 0° C. This half-life decreases to 10 mins at pH 8.6 and 4° C. The extent of NHS-ester hydrolysis in aqueous solutions free of primary amines may be measured at 260 to 280 nm, because the NHS byproduct absorbs in that range. NHS-ester crosslinking reactions are most commonly performed in phosphate, carbonate-bicarbonate, HEPES or borate buffers at pH 7.2 to 8.5 for 0.5 to 4 h at room temperature or 4° C. Primary amine buffers such as Tris (TBS) are not compatible, because they compete for reaction; however, in some procedures, it is useful to add Tris or glycine buffer at the end of a conjugation procedure to quench (stop) the reaction.

Other amine-reactive functional groups may be substituted for NHS-ester chemistry. A table of several examples is provided in FIG. 17. Furthermore, other chemistry linkage types may be substituted, including thiol-based (e.g. maleimide —SH), click-chemistry, or other common bioconjugation techniques known in the art. FIG. 17 depicts the chemical structures of examples of other chemistry linkage types. Carbonyldiimidazole (CDI) chemistry is another strategy for linking a carboxylic acid or hydroxyl group to a primary amine. The byproduct of the conjugation reaction is a urea, which possesses relatively low toxicity and readily cleared by the body. FIG. 22 is a diagram of the chemical structure of carbonyldiimidazole zero-order cross linker. An additional advantage of CDI is that the hydroxyls of the PEG may be directly activated as opposed to requiring prior conversion to carboxylic acid as with NHS chemistry. The coupling reaction of CDI-PEG proceeds much slower than that of NHS-PEG, such that the curing time of the electrode may be increased. At low temperature (4-deg-C), reaction rate may be extended up to 48 hours. CDI activation must be carried out in organic solvents, and the coupling reaction is most efficient in alkaline environments (or ~1 pH above the pK value of the amine to be coupled). CDI-PEG remains active for years if stored in a properly desiccated environment. Imidazole carbamates (the reactive intermediate formed with CDI to PEG) have longer half-lives in water. Whereas the half-life of NHS-PEG in water is on the order of minutes due to hydrolysis. The half-life of the imidazole carbamate is on the order of hours. The rate of hydrolysis must be balanced with the rate of the reaction. If hydrolysis occurs too rapidly once reconstituted, it may be impractical for use. If hydrolysis is too slow, it may increase the risk of toxicity side effects.

Figure 23:
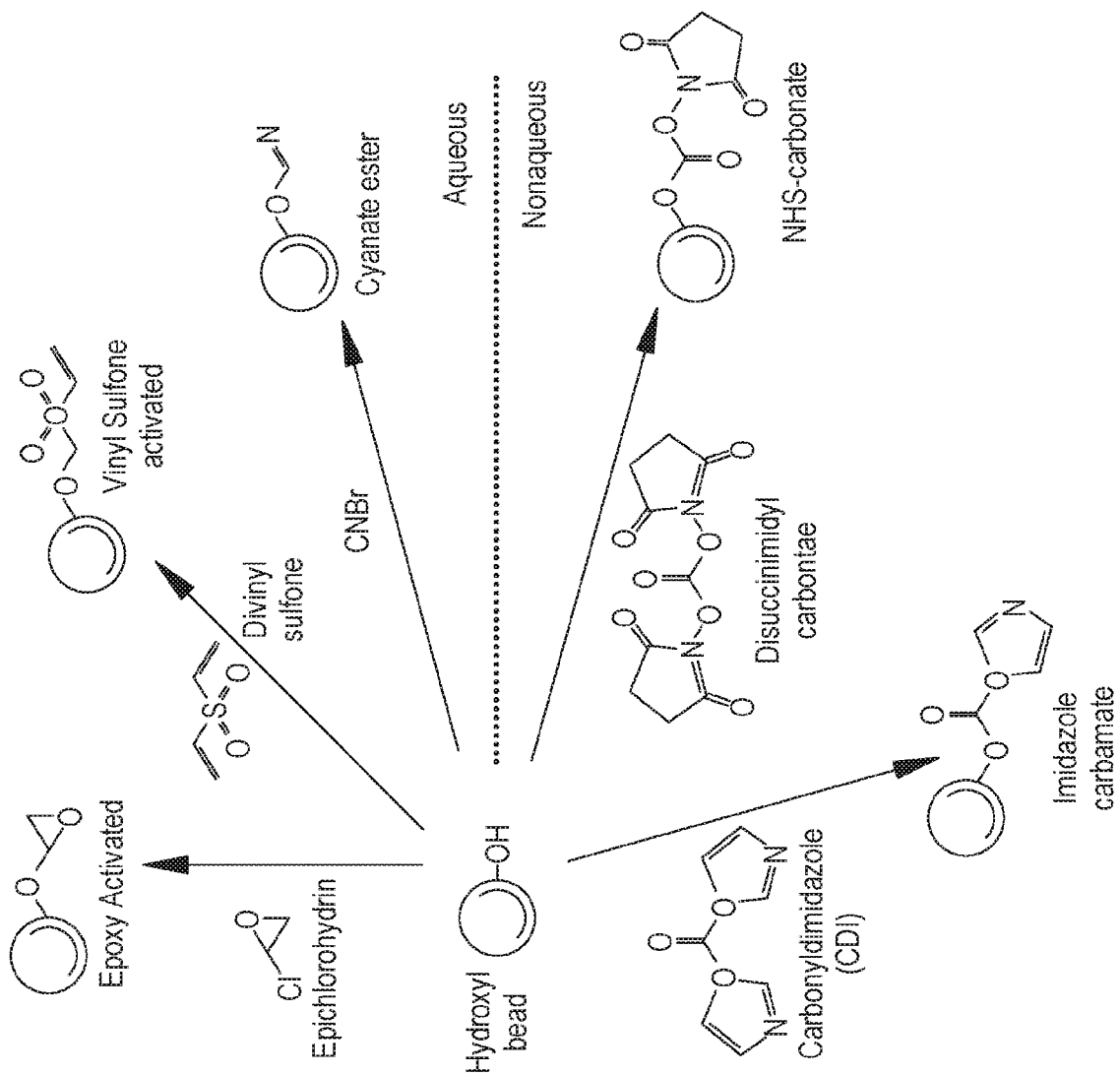
FIGS. 23-24 are diagrams showing how the hydroxyl moiety can be activated for coupling ligands.
Figure 24:
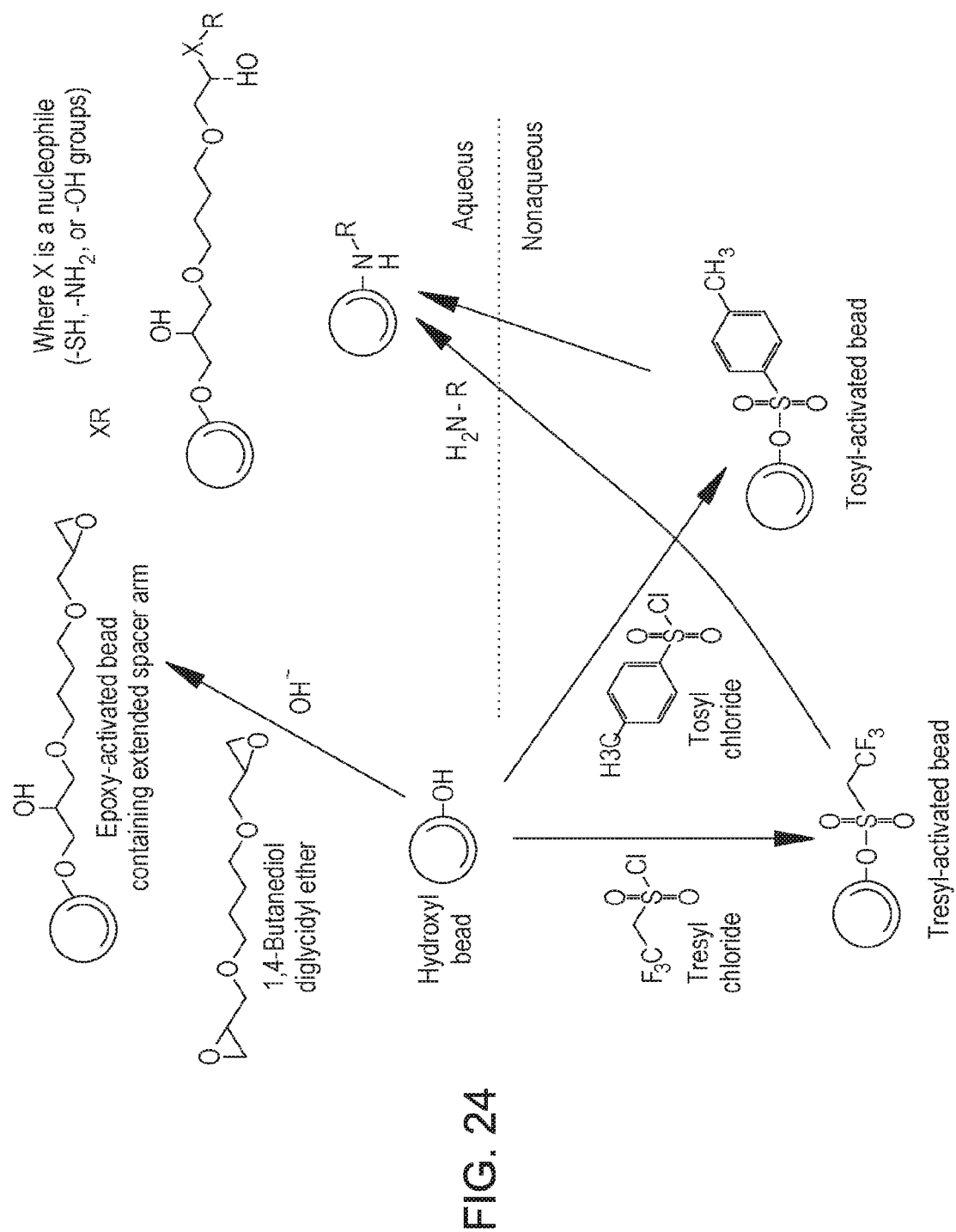
Figure 25:
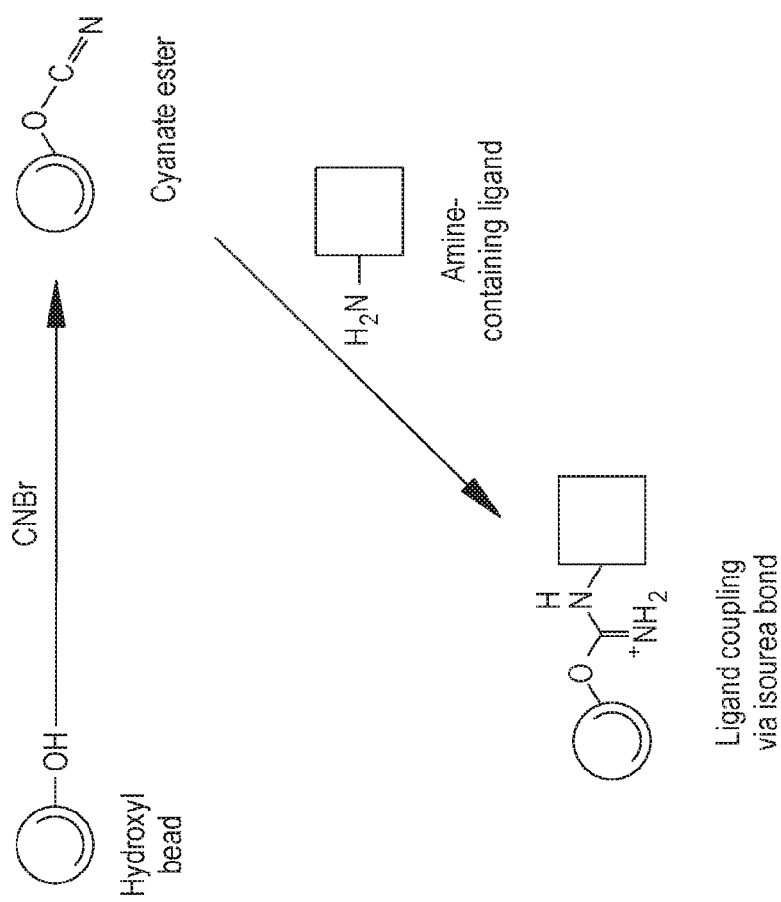
FIG. 25 illustrates the use of cyanogen bromide to couple an amine ligand.

Hydroxyl-containing particles can be activated for coupling ligands using a number of strategies, which involve either aqueous or nonaqueous reactions. Epoxy and vinyl sulfone activation procedures provide reactive groups able to couple with amine-, thiol-, or hydroxyl-containing ligands. Cyanogen bromide activation and the CDI and DSC methods provide reactive groups for coupling amines. FIG. 23 is a diagram showing hydroxyl-containing particles use. (Source: Hermanson et al Bioconjugate Techniques). Additional hydroxyl particle activation methods include bis-epoxide modification, tosyl activation and tresyl activation methods. The tosyl chloride and tresyl chloride activation procedures must be carried out in dry organic solvent, but the coupling of an amine-containing ligand can be performed either in organic solvent or aqueous buffer. FIG. 24 shows these additional hydroxyl particle activation methods. (Source: Hermanson et al Bioconjugate Techniques). Cyanogen bromide can be used to activate a hydroxyl particle to a reactive cyanate ester, which can then be used to couple amine-containing ligands. FIG. 25 illustrates cyanogen bromide use. (Source: Hermanson et al Bioconjugate Techniques)

It is possible to change the amine-containing crosslinker from lysine by selecting a molecule from the group consisting of quadlysine, pentalysine, Lys-tryp-lys, Polylysine, and Polyarginine. These poly-amine containing molecules may be used as a crosslinking agent. Other poly-lysines may be used as a substitute for tri-lysine (e.g. poly(lysine)n where n maybe be any number greater than. Other multi-amine valent peptides may also be substituted including poly (arginine)n. Poly peptides with primary amine functional groups (e.g. lysine or arginine) may also include patterned or randomly distributed spacer peptides (e.g. glycine, tryptophan, etc.) so as to reduce stereotactic hindrance of amine-crosslinking. Besides polypeptides, other polyamines may be used, including multi-arm or branched PEGs terminated with amine groups, micro- or nano-particles with surface modified amine presenting groups, or other polyamine molecules where the presentation of amines make them available for crosslinking.

Figure 18:
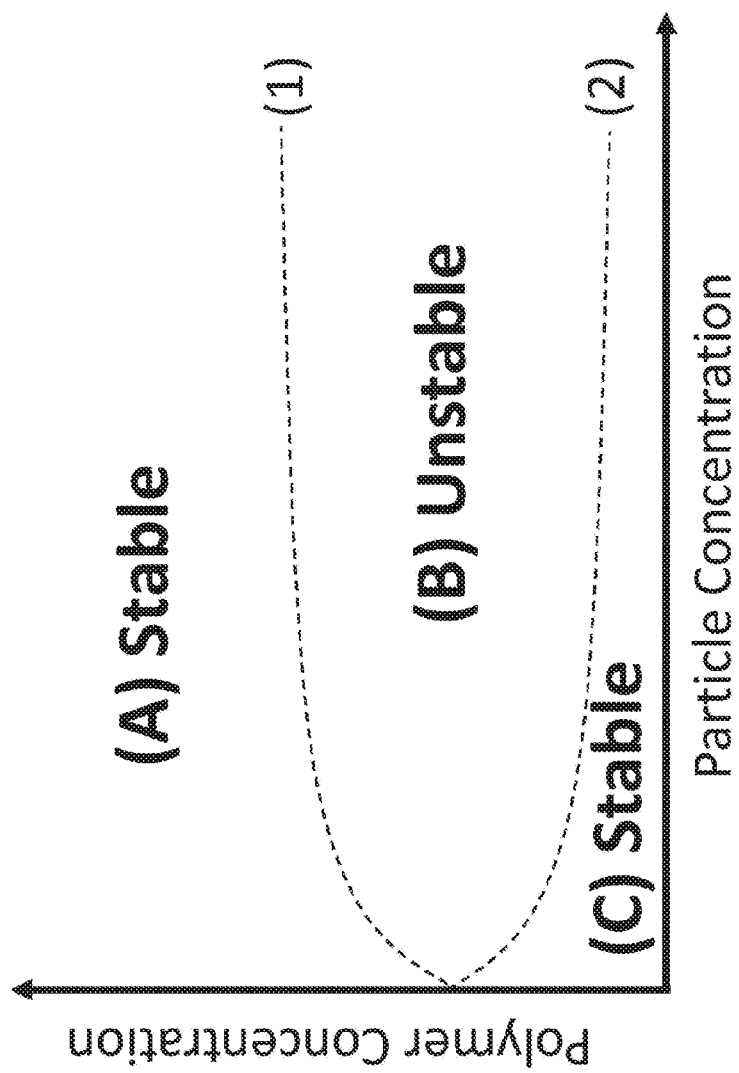
FIG. 18 is a chart of a function depicting the stability of PEG gels based on the concentration of elements, i.e., conductive elements.
Figure 19:
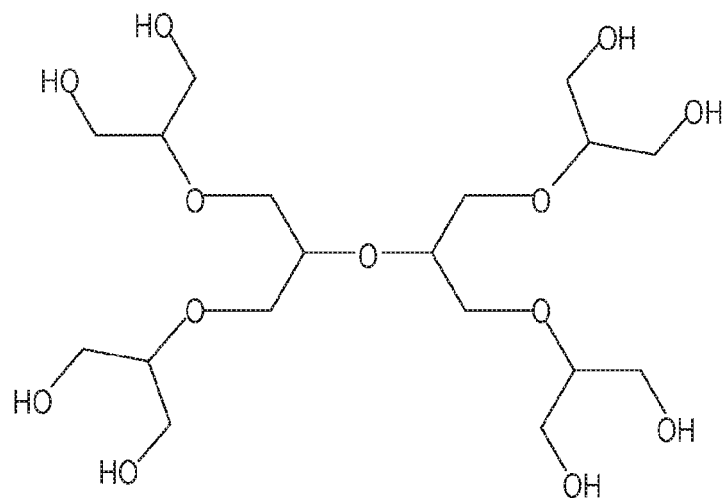
FIG. 19 is the chemical structure of a PEG with a Hexaglycerol core (8-arm).
Figure 20:
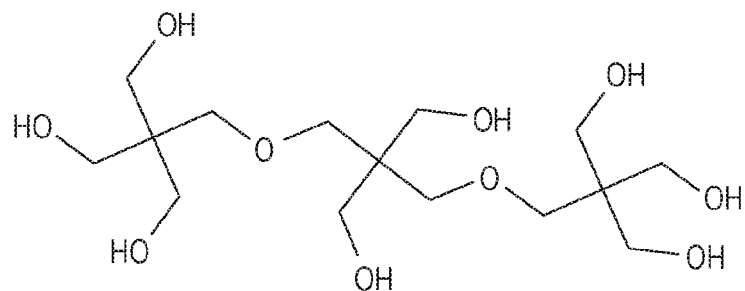
FIG. 20 is the chemical structure of a PEG with a Tripentaerythritol core (8-arm).

Preservatives may be added to PEG carrier material to achieve better solution stability, particularly surfactants for colloidal (re)suspension. FIG. 18 depicts the stability of PEG gels based on the concentration of preservative used. Hydrophobic particles have a higher propensity for aggregation in aqueous solutions and will shift the threshold (1) upward. Threshold (1) shifts downward on the y-axis with polymers of higher inherent viscosities, or with the use of surfactants that stabilize the particles in suspension. Threshold (2) shifts downward with larger or more hydrophobic particles. It shifts upward with the use of surfactants. At a greater polymer concentration (A) the suspension of particles is stable due to high viscosity of polymer (e.g., PEG solution). At a decreased polymer concentration (B) the suspension of particles is unstable as the polymer solution is not viscous enough to prevent particle aggregation and/or settling; particles settle on bottom of container. At a concentration of polymer even further decreased, Suspension of particles is stable due to low concentration of particles, thereby limiting chances for particle aggregation to occur; this region is only of considerable relevance when particles are small (e.g., less than 100 microns). Macro-sized metallic particles (e.g. greater than 100 microns are unlikely to exhibit much stability in this region without the use of surfactants or other viscous stabilizers.

Buffers may be modified in PEG carrier materials, particularly increasing or decreasing the acidity or ionic concentrations of the buffers to change the reaction rate kinetics. Phosphate buffers and borate buffers, among others, in the range of pH 6-8 could may be used.

DuraSeal (Confluent Surgical, Waltham, MA; Covidien), is a 4-arm 20-kDa polyethylene glycol crosslinked with trilysine, used to prevent leakage of cerebrospinal fluid from dural sutures during spinal surgery; it is hydrolyzed and absorbed over a 4-8 week period. A newer formulation using a lower molecular weight polyethylene glycol, DuraSeal® Exact, has been reported to provide a tighter hydrogel matrix with less swelling than the original formulation. It is degraded by hydrolysis and reabsorbed over a 9-12 week period. In both cases, the hydrogel is believed to adhere to tissue by mechanical means.

CoSeal (Angiotech Pharmaceuticals, Vancouver, BC; Baxter), is a mixture of a 4-arm PEG tetra-hydroxysuccinimide ester and a 4-arm PEG tetra thiol, each of approximate MW 10 kDa, used for arterial and vascular reconstruction. The resulting gel comprises thioester linkages that are hydrolytically labile, resulting in eventual gel degradation and resorption. Tissue adherence is provided by reaction of some of the reactive hydroxysuccinimide esters, and possibly some of the thioester groups, with protein amine groups in the tissue. CoSeal is reported to remain effective at the application site for 7 days, and is fully degraded after 30 days. It is a synthetic, translucent gel for cardiovascular and peripheral vascular surgery applications. It consists of two PEGs that rapidly crosslink with proteins in the tissues, forming a covalent bond. Also mechanically adheres to synthetic graft materials. Intended for adjunctive use to seal areas of leakage.

Progel (Neomend, Irvine, CA), is a hydrogel which is human serum albumin crosslinked with a bifunctional hydroxysuccinimidyl-polyethylene glycol (U.S. Pat. No. 6,899,889 B1), used for intraoperative sealing of pleural air leaks. It is a hydrogel sealant made of human serum albumin and PEG. A formulation using a recombinant albumin, Progel Platinum Surgical Sealant, has been developed. Progel AB is a hydrogel adhesion barrier sealant that may be sprayed onto general visceral organs during surgery to help prevent postoperative adhesions. Approximately 60% of Progel is degraded after 1 day, and complete degradation is observed after 2 weeks FocalSeal-L (Genzyme, Cambridge, MA) is a mixture of a polyethylene glycol capped with short segments of acrylate-capped poly(L-lactide) and poly(trimethylene carbonate) with a photoinitiator, eosin Y, and has been used to limit air leak after pulmonary resection. The solution polymerizes upon exposure to blue-green light to form a thin film hydrogel. The sealant does not bond covalently with tissue, and expands upon contact with bodily fluids over approximately 24 hours. Hydrolysis of the lactide and carbonate linkages allows for gel degradation and resorption. FocalSeal has been used as a tissue adhesive.

Adherus Dural Sealant and Spinal Sealant (HyperBranch Medical Technology, Durham, NC), a mixture of poly (ethylene-imine) crosslinked with a bifunctional PEG-hydroxy-succinimidyl ester, used in cranial and spinal surgery to prevent cerebrospinal fluid leakage and dural adhesions. Polyethyenimine can take different structures including linear or branched, with the general formula X—($CH_2$—$CH_2$—NH)$_n$—Y, where X and Y may be primary amines, methyl or hydroxyl groups, and where branching may occur off the nitrogen groups, forming a tertiary amine structure. Molecular weights that may be used in such applications may range from 1,000 Da to 50,000 Da.

OcuSeal Liquid Ocular Bandage (HyperBranch Medical Technology, Durham, NC), a synthetic hydrogel that is applied directly to the ocular surface as a liquid, using a brush applicator.

There are synthetic hydrogels, some PEG based, that are approved for use in the clinic. A combination with electrically conductive particles, wires, strands, meshes, fibers, one or more of them being optionally surface modified, and or optimized for a heightened mechanical integration with the synthetic hydrogel provides the electrical conductivity needed for them to be applicable in the field of neuromodulation.

The modifications described herein focus on ease of use for the physician user who places the liquid mixture with an emphasis on work time (may be as short as seconds or may be as long as tens of minutes), viscosity to allow optimal access around or into various target structures of interest, mechanical strength and ability to integrate with the surrounding tissue, degradability optimized for the specific tissues the liquid mixture is placed (i.e. injected) into or around or next to, as well as other factors of interest.

Other modifications of the synthetic hydrogel focus on achieving and retaining a homogeneous suspension of the electrically conductive particles in the PEG base by optimizing the viscosity of the PEG solution prior to (and/or during a beginning) curing process. This further facilitates reproducibly homogeneous conduction of energy, especially electrical energy, across the liquid mixture or the cured electrode and ensures an optimal connection between an active implantable device and a target in bodily tissue.

Another aspect is the modification of the synthetic hydrogel to be resorbed at a rate that is most optimal for the specific placement location. While a nerve in a location that is not subjecting the injectable electrode to shear forces may allow for a faster resorption time, most applications will require an injected electrode to be mechanically stable (cohesive) for a period of at least two weeks, and most applications for at least four to six weeks until the tensile strength of the encapsulating tissue is able to provide structural support. Faster resorption can be accomplished by using a lower molecular weight PEG. For example the 10 kDa, 4-arm PEG used in tissue adhesive/sealant applications degrades over 4-8 weeks. A reduction in molecular weight to 5 kDa can reduce resorption time to 2-4 weeks, whereas an increase in molecular weight to 20 kDa can increase the resorption time to 8-12 weeks. A liquid mixture may be injected at locations where shear forces are present or may be expected. By providing a cured electrode with higher tensile strength, these shear forces may be resisted better while the body absorbs and/or remodels the PEG/hydrogel by replacing it with connective tissue, fibrous tissue and or other tissues that may take up the forces.

Combinations of PEGs and Cyanoacrylates may be used to allow for a porous structure that i.e. binds temporarily to bony tissue or other tissues of higher tensile strength in the body, while providing the means for the body to grow into the structure and replace an overwhelming amount of the total volume of the porous structure with its own cells, or the porous structure is filled by interstitial fluid, thus adding to the surface area of the conductive elements, as described elsewhere herein.

An example of a PEG based cured electrode is as follows. A ~1 mL volume nanowire-based liquid mixture has the nanowires suspended non-covalently in a PEG hydrogel matrix. Part A and Part B are mixed in a 1:1 ratio, and allowed to cure to form a PEG hydrogel-based cured electrode.

Part A:
  A. Carrier Material Part A: 0.1 g 20 kDa 4-arm PEG-NHS at 20% w/v (0.5 ml total solution) in sodium phosphate buffer, pH 7.4
  B. Conductive elements mixed with Carrier Material Part A: Gold conductive elements (~2 nm diameter, ~5 μm length) at 25-50% weight % (with respect to PEG+carrier solution, e.g., 50% would be ~0.5 g gold nanowires to ~0.5 g PEG solution).

Part B
  A. Carrier Material Part B: 10 mM trilysine (0.5 ml total solution) in 75 mM borate buffer
  B. Conductive elements mixed with Carrier Material Part B: Gold conductive elements (~2 nm diameter, ~5 μm length) at 25-50% weight % (with respect to trilysine+carrier solution, e.g., 50% would be ~0.5 g gold nanowires to ~0.5 g trilysine solution).

The resulting mixture of Part A and Part B will form a cured electrode in 1-5 minutes. The conductive elements provide additional mechanical strength.

An example of a liquid mixture, comprising micrometer size particles+PEG based is described herein. A ~1 mL volume gold powder-based liquid mixture that has gold powder/grains covalently bound in a PEG hydrogel matrix. Part A and Part B are mixed in a 1:1 ratio, and allowed to cure to form a PEG hydrogel-based cured electrode.

Part A: 0.1 g 100 kDa 4-arm PEG-NHS at 20% w/v (0.5 ml total solution) in sodium phosphate buffer, pH 7.4
  Part B: 10 mM trilysine (0.5 ml total solution) in 75 mM borate buffer, or Modified Conductive filler Mixed with Carrier Part B: Gold conductive elements (~100-500 μm major axis width, with aspect ratio 1-5) at 85-99% weight % (with respect to trilysine+carrier solution, e.g., 99% would be ~0.99 g modified gold particles to 0.01 g trilysine solution). The particles will be themselves modified on the surface with a 5 kDa linear PEG terminated at one end with a thiol (—SH) and at the other end an amine functional group (—NH2). The thiol binds and forms a stable bond to the surface of gold, exposing a free primary amine that may itself react with the PEG-NHS carrier in Part A.

The resulting mixture of Part A and Part B will form a cured electrode in 1-5 minutes. The particle covalent bonding provides additional mechanical strength. The higher molecular weight PEG provides additional viscosity allowing the particles to become fully suspended to form a homogeneous mixture during the curing process. The conductive particles, having free amines are initially only suspended in Part B, which has the potential additional benefit of preventing unwanted reaction of the NHS with the metal surface which may or may not act as a catalyst for hydrolysis during storage.

Another example of a cured electrode comprises PEG and gold conductive elements, at least a portion of which form covalent bonds with one another when mixed, forming a higher degree of crosslinking between polymer and conductive elements, improving the mechanical/chemical interface characteristics.

Part A comprises PEG-NHS+Gold-NHS
Part B comprises Trilysine or PEG-NH$_2$+Gold-NH$_2$ Another PEG matrix cures rapidly and suspends gold conductive elements in solution—pre-cured. This allows gold conductive elements to coalesce and covalently or ionically interact during hydrolysis of hydrogel matrix. During hydrolysis, the gold conductive elements coalesce and cross-link Part A comprises PEG-NHS+gold conductive elements with short (di)sulfide bridges that will react with the gold wires from Part B to form stable bonds.

Part B comprises trilysine+gold conductive elements

The impedance of several PEG-silver carrier materials using CoSeal were tested, with the silver conductive elements comprising aspect ratios of approximately 2:1 to 3:1 on average, with major axis as high as 6 microns, and the data is in Table Three.

TABLE THREE

Impedance of PEG-Silver Liquid Mixture/Cured Electrode

| Mix | Ag (mg) | PEG (µL) | Glycerol (µL) | Ag-PEG % | Impedance (ohms, 1 kHz) Pre- and Post Cure |
|---|---|---|---|---|---|
| One | 800 | 200 | — | 80.0% | <1 |
| Two | 800 | 200 | 200 | 66.6% | 10-50 |
| Three | 800 | 200 | 100 | 80% | <1 |

Mix one was 80% silver, 800 mg silver and 100 µL each of part A and part B. Mix two was 66% silver with 16.6% glycerol, 800 mg silver, 200 µL glycerol and 100 µL each of part A and part B. Mix three was 73% silver with 9% glycerol, 800 mg silver, 100 µL glycerol, and 100 µL each of part A and part B. The curing times were: Mix one cured almost instantaneously, with in 3 to 5 seconds; Mix two cured over a long period of time, getting tacky within 30 to 45, and fully curing within 10 to 15 minutes; and Mix three became tacky within 10 to 15 seconds and fully cured within 45 seconds to one minute. The mechanical properties observed were: Mix one was brittle, chalky and had the most flaking of the three; Mix two was sticky/slimy, very flexible and Jell-O like once cured. There was some but not a large amount of flaking; Mix three was similar to mix two, being flexible, sticky and Jell-O like in consistency. Similar to mix two, there was not as much flicking in this formulation compared to silicone. Tearing force was relatively strong for a gel, breaking around approximately 3 to 5 g force. Mixes two and three were both still electrically conductive after stretching twisting and bending. Mix three was placed in water after cured. Its initial weight was 710 mg. After three hours of soaking, it had swollen to a mass of 1.2 g. A small amount of flaking was observed at the bottom of the beaker, but not a huge amount. The gel was removed from water and it was still conductive and mechanically cohesive.

Silicone

By combining vinyl terminated siloxane and a polyfunctional silicon hydride with a catalyst, silicones may be achieved that do not require moisture to cure, as follows:

$Si-H+CH_2=CHSi \rightarrow SiCH_2CH_2Si$

The typical by-products of the condensation of such a silicone curing process is a small amount of hydrogen gas that may easily dissipate and not cause acute or chronic inflammatory responses in stark contrast to industrial silicones that create either alcohol or acetic acid as by product of curing. FDA has approved food grade silicones for chronic contact with food, and these cure around food and are known to not leach significant amounts of toxic by-products into the food before, during or after curing near or around food items intended for human consumption. The curing time may depend on the utilized catalyst and platinum has been shown to provide advantageous curing times (<5 minutes) while not causing a heightened chronic inflammatory reaction.

Figure 26:
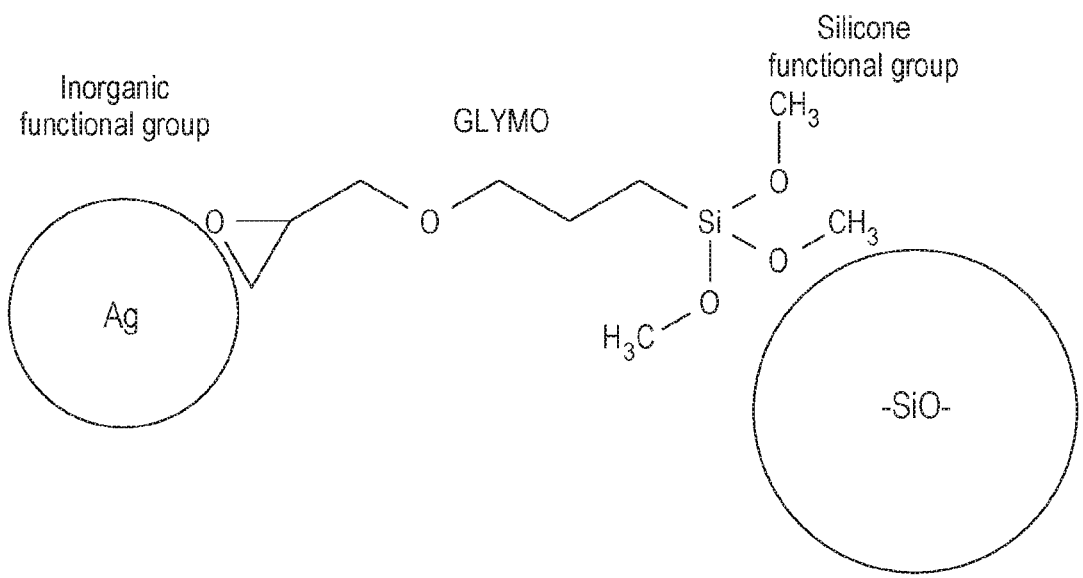
FIG. 26 is a diagram of the chemical structure showing the interaction between GLYMO and a silicone as the carrier material and, on the other hand, GLYMO and silver as the conductive element.

Silicone is also used in implanted medical devices, including breast implants, wire leads, and device components. It is tough, flexible, soft, and highly elastic. By itself it is an electric insulator, but it can be mixed with conductive elements as described herein to form a liquid mixture which cures upon injection into a bodily tissue. During polymerization it is very self-cohesive and tends to encapsulate conductive elements leading to non-percolation of the bulk composite. Addition of a surfactant (e.g., 3-Glycidyloxypropyltrimethoxysilane, herein "GLYMO") helps to interface the metallic (inorganic) mixture with the polymer (organic) phase as shown in the diagram which is FIG. 26 which is a diagram of the chemical structure of bonds between, on one hand, GLYMO and a silicone as the carrier material and, on the other hand, GLYMO and silver as the conductive element. Thus, GLYMO as surfactant prevents the silicone from completely engulfing the conductive element, thereby preserving the liquid mixture/cured electrode's low impedance.

With two part curing silicone systems, it is possible to incubate the GLYMO with conductive elements first, ensuring a full and homogenous coating of the conductive elements. With silver (e.g., grains sized 50-200 um), the weight % (GLYMO/silver) in one embodiment is approximately 5-15% weight % of final electrode (e.g., 5% GLYMO, 75% silver, 20% silicone) to achieve uniform coating of the conductive elements with GLYMO. Beyond a level of approximately 50% weight % of the weight of the entire mixture (silicone-silver-GLYMO) the final silicone-GLYMO-silver particle mixture was no longer electrically conductive, thereby suggesting an upper boundary of approximately 50% weight over which the GLYMO fully coats and electrically isolates the conductive elements.

The GLYMO-silver mix may then be mixed separately with part A and part B silicones. In one embodiment the silver-GLYMO-silicone mix required to achieve electrical percolation was measured to be at least 65% (silver/silicone) to achieve impedance values below 10Ω for the overall mix. Longer whisker metal particles (aspect ratio at least 5:1, or within a range of 5:1 to 10:1) allowed lower volume/weight percentages of silver to be present (such as 50-60%) to still provide sufficient conductivity (Z<100Ω) for a liquid mixture/cured electrode to be able to connect to a nerve at lower impedance values than the surrounding tissues. One embodiment achieving suitable conductivity comprises 200 mg silver, 50 mg GLYMO, and 100 mg silicone (50 mg part A, 50 mg part B). The precursor materials are mixed as such, where the mixing operations within the parentheses are performed first.

Step 1: (100 mg silver+25 mg GLYMO)+50 mg Part A silicone

Step 2: (100 mg silver+25 mg GLYMO)+50 mg Part B silicone

Step 3: mixture from Step 1 is combined and homogenously mixed with mixture from Step 2

Different colored dyes are added to Part A and Part B silicones to allow for visual confirmation of mix homogeneity. In another embodiment, the silicone used may be a one-part room temperature vulcanization ("RTV") curing system, although for biomedical applications, there are typically concerns over acetic acid buildup as a result of the condensation reaction during curing but with small amounts injected (e.g., 10-50 µL), the amount of acetic acid is low.

Table Four is a comparison of Silicone based cured electrodes outside the body utilizing gold and silver as conductive elements in various concentrations. All impedances were measured with sinusoidal waveforms at 1 kHz.

TABLE FOUR

| Silver-Silicone Impedance | | | | |
|---|---|---|---|---|
| Ag (mg) | GLYMO (µL) | Silicone (µL) | Ag-Silicone % | Impedance (ohms, 1 kHz) |
| 100 | 50 | 100 | 50.0% | — |
| 150 | 50 | 100 | 60.0% | — |
| 200 | 50 | 100 | 66.7% | 2.4 |
| 250 | 50 | 100 | 71.4% | 2.0 |
| 300 | 50 | 100 | 75.0% | 1.9 |

| Silicone-Gold Impedance | | | | |
|---|---|---|---|---|
| Au (mg) | GLYMO (µL) | Silicone (µL) | Au-Silicone % | Impedance (ohms, 1 kHz) |
| 200 | 50 | 100 | 66.7% | <1 |
| 150 | 50 | 100 | 60.0% | 2.5 |

Figure 27:
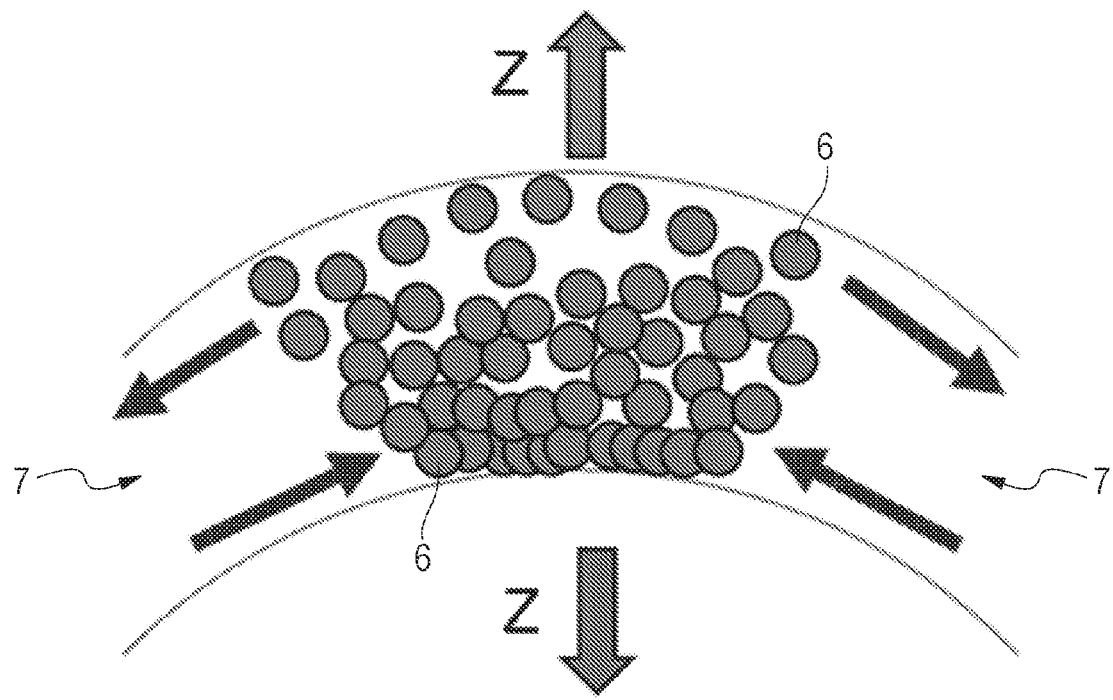
FIG. 27 is a diagram of the mechanism of a cured electrode with low aspect ratio conductive elements during bending: as the convex top is bent and conductive elements move apart slightly and reduce conductivity in the area of the bend, but conductive elements at the concave bottom are pressed together and increase conductivity.

Silicone has an advantage of high flexibility, and it can withstand elastic strains up to 50-100%. Due to this flexibility and bendability, the cured silicone may bend at very low radii. While cured silicone can withstand this bending strain, the cured electrode will undergo compression and tension at the inner and outer aspects of the bend, respectively. If the conductive elements comprise a low concentration or have a low aspect ratio, the resulting bend may yield a non-conductive surface on the outer aspect (Z increases), while the inner aspect may decrease in impedance. FIG. 27 is a diagram of the mechanism of a cured electrode with low aspect ratio conductive elements retaining similar impedance during bending: as the convex top is bent and particles move apart slightly, particles at the concave bottom are pressed together. While locally the impedance at the top or bottom aspect may change during bending, the bulk conductivity along the axis remains relatively consistent.

Figure 28:
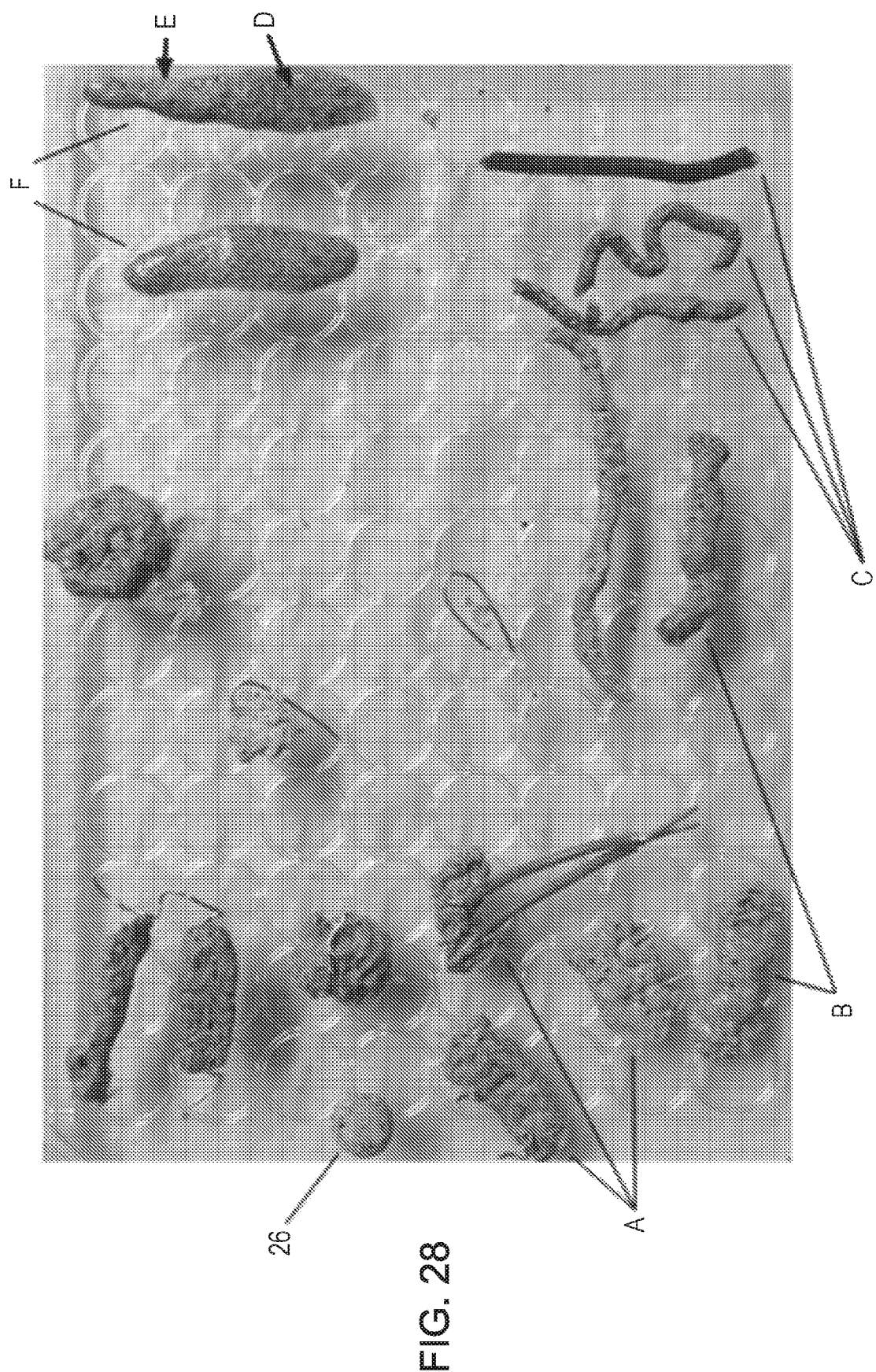
FIG. 28 is an image of a collection of different shapes for a silicone carrier material.

FIG. 28 is an image of a collection of different curing capabilities based on varying viscosities of a silicone carrier material. Pictured is blob portion 26 of a cured electrode. Reference A shows cured electrodes with embedded wires. Reference B shows cured electrodes of high viscosity of 4-6 mm in diameter. Reference C shows cured electrode of high viscosity of 2 mm diameter. References D and E are for one cured electrode with a conductive element % weight which are low and high respectively. F also shows a low viscosity cured electrode. Differences in viscosity are primarily achieved by changing the ratio of conductive elements vs. silicone carrier material. A secondary way of changing the viscosity is by adding surfactants, thickening or thinning agents. Cured materials in FIG. 28 are all silicone based and retain their flexibility post cure.

Cyanoacrylate Section

Cyanoacrylate based materials are also a carrier material for inclusion in a liquid mixture. Although offering less flexibility in comparison to silicone based mixtures, cyanoacrylates as a carrier material have a variety of advantages, such as more ability to resist stress and strain, and excellent integration with bone and other tissues. They offer the ability for immediate coagulation and control of bleeding under surgical conditions. There are surgical cyanoacrylate variations available as FDA approved surgical glue that function as more viscous and less viscous carriers in gel form. The gel variety has advantages for delivery via small diameter needles where the gel may help with keeping the liquid mixture with e.g. metal particles more uniform when subjected to the stress due to passing from large inner diameter syringe into small inner diameter needle. Once the cyanoacrylate-surfactant-conductive element mixture has been injected as a gel mixture and is allowed to cure inside the body, the carrier portion gel polymerizes and forms a solid that is able to provide structural stability to the cured injected electrode Certain cyanoacrylates are safe for biomedical application, including injection into the body as blood-contacting implants. These comprise a first liquid phase which is fast-curing within several seconds of application, in particular on contact with water. As cured in a second solid phase, it is significantly stiffer than soft tissues. It bonds mechanically strongly with biological tissues, including nerves, skin, muscle, fat and bone. By itself it has a high impedance and acts as an insulating material. When combined with conductive elements at high concentrations, the resulting liquid mixture/cured electrode is conductive.

Figure 29:
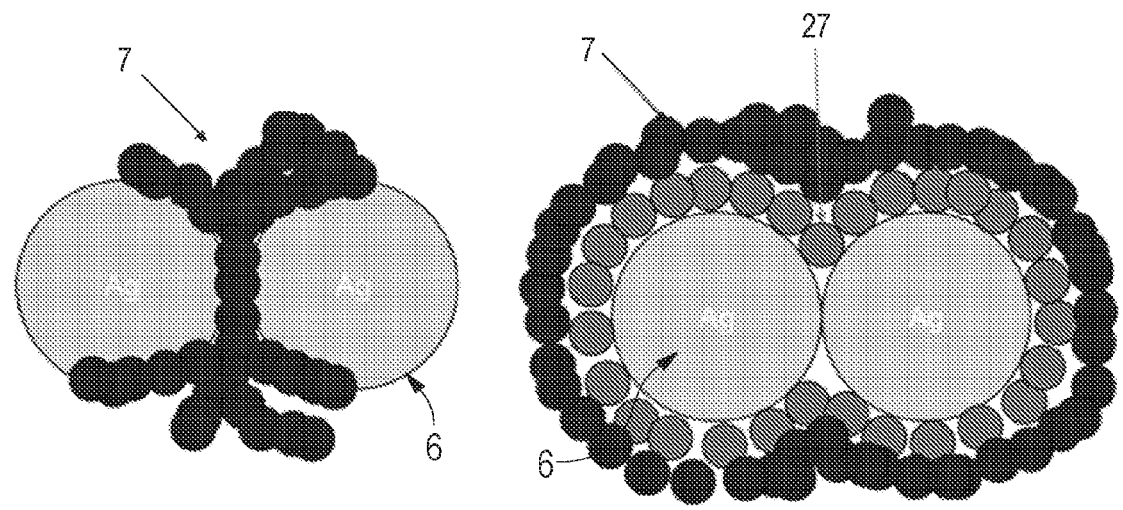
FIG. 29 is a representation of the function of surfactant to promote conductivity in a cyanoacrylate based cured electrode with silver conductive elements.

The conductive elements must be mixed with the cyanoacrylate solution in an ultra-dry environment. The conductive elements may be pre-treated with inert gases (e.g. Argon, Nitrogen), or dry solvents (e.g. isopropyl alcohol) to dry it fully. The cyanoacrylate may be mixed homogenously with the conductive elements. However, the conductive elements may also be intentionally separated into distinct high and low concentration regions by use of a thin (low viscosity) cyanoacrylate solution, in which the heavy conductive elements selectively sink to the bottom. This may be used to achieve low electrical impedance at the bottom interface, while achieving high impedance at the top surface after curing, and this process applies to all carrier materials and especially for those that are insulative: silicone, cyanoacrylate and dental resin. Furthermore, since cyanoacrylate has a high cohesive property while curing, it may cure all around the conductive elements 6 leading to complete isolation from one another. To overcome this, a surfactant 27 may be added, such as water and/or ethanol. Alternatively a 95% ethanol solution mixed with the conductive filler material appears to be sufficient to allow for electrical percolation. Ethanol is mixed with the conductive elements, and then immediately mixed with cyanoacrylate to prevent significant evaporation of ethanol. The mechanism of enabling electrical percolation is by coating the conductive elements with an ethanol/water layer, leading to condensation/polymerization of the cyanoacrylate at the water interface coating the conductive element rather than at the metallic interface itself, thereby allowing metal-metal contacts to persist throughout the curing process. Water alone initiates polymerization of the cyanoacrylate and is not as effective as alcohol to yield this effect. Ethanol dissolves the cyanoacrylate and reduces the rate of polymerization. FIG. 29 is a representation of the function of the water/ethanol surfactant 27 in a cyanoacrylate based cured electrode with silver conductive elements. Without any surfactant present, cyanoacrylate creeps between the conductive elements. If the conductive elements have been pre-wetted with surfactant, then the strong bonds between cyanoacrylate are not able to pull the conductive elements apart and isolate them. As a result, the overall liquid mixture/cured electrode that includes the surfactant remains conductive.

The most commonly used forms of cyanoacrylate for medical applications include n-butyl cyanoacrylate and 2-octyl cyanoacrylate, each of which has some flexibility after curing. Both are suitable for the liquid mixture herein. In some embodiments, cyanoacrylates may be functionalized with chemical sub-groups that allow the carrier medium itself to become conductive, for example PEDOT:PSS. In that case a placement of the liquid mixture may be accomplished by spray-on technique similarly as liquid band aid is dispensed on an open wound, this time the liquid mixture being sprayed laparoscopically on a nerve, with spray channels both, a functionalized, electrically conductive cyanoacrylate as channel 1 and an electrically non-conductive cyanoacrylate as channel 2.

To achieve electrical percolation with silver conductive elements (in one embodiment, ~50-200 micron size distribution) and n-butyl cyanoacrylate, over 85% weight % (silver/cyanoacrylate) was required, with the silver particles produced by a dremel. Lower silver weight % may be attainable with the use of additional surfactants or the ethanol (and resulting water phase separation) method discussed herein. Furthermore, the use of other high aspect ratio conductive elements, such as microwire rods or whiskers, allow electrical percolation to occur at lower conductive element weight % concentrations.

Omnex (Ethicon, Somerville, NJ) produces a mixture of 2-octyl cyanoacrylate and butyl lactoyl cyanoacrylate which is used in vascular reconstructions, and which is suitable for the liquid mixture/cured electrode herein. Omnex degrades by hydrolysis over approximately 36 months. While cyanoacrylates have also been used as tissue adhesives, for example DermaBond (Omnex), their use is limited by toxicity, such as tissue necrosis at the site of application.

Fibrin Glue

Fibrin glue (also called Fibrin sealant) is a formulation used to create a fibrin clot. It comprises fibrinogen (lyophilised pooled human concentrate) and thrombin (bovine, which is reconstituted with calcium chloride) that are applied to the tissue sites to glue them together. Thrombin is an enzyme and converts fibrinogen into fibrin monomers within 10 and 60 seconds giving rise to a three-dimensional gel. In some embodiments, fibrin glue may also contain aprotinin, fibronectin and plasminogen. Factors that influence dimensional structure of fibrin gel giving rise to fine or coarse gel: (1) changing concentration of fibrinogen, (2) changing concentration of thrombin increasing concentration increases ultimate tensile strength and Young's Modulus of gel, (3) changing concentration of calcium, (4) ph, and (5) temperature.

Fibrin glue is a human-derived tissue adhesive used for hemostasis and sealing of tissues. This biological glue can be manufactured from clotting factors taken from donor plasma (fibrinogen, cryoprecipitate and thrombin) or made intraoperatively out of fibrinogen coming from the patient's own blood. A mixture of thrombin and fibrinogen to enhance local surgical hemostasis (arrest of bleeding) and to provide effective tissue adherence has long been explored, in 1998 a commercial product (Tisseel) was approved by FDA. Later, a number of other fibrin glue products have been developed commercially. (i.e. FloSeal). Also, many fibrin pads, bandages and patches have become available that help arrest bleeding.

Intraoperatively, making fibrin glue, has become state-of-the-art with the development of devices for the harvesting of platelet-rich plasma (PRP). Medtronic's Magellan, Cell Factor Technologies's GPS System, Interpore Cross's AGF Processor and Harvest's SmartPReP are some examples of new technologies available intraoperatively to process PRP for tissue adhesives, which can be employed to prepare an autologous fibrin glue for incorporation as a carrier material into the liquid mixture/cured electrode of the present invention.

Fibrin glue is derived from two components. The first component contains human fibrinogen and coagulation factor XIII and varying amounts of other plasma proteins such as fibronectin and plasminogen. The second component contains thrombin (of either bovine or human origin). In Europe, both components are human derived and supplied in commercial fibrin glue "kits". In the United States, only the bovine thrombin component is commercially available, but commercially manufactured human thrombin and fibrinogen preparations are currently under development.

The elastic property, tensile strength, and tissue adhesiveness of plasma fibrin glue or sealant has made it an important adjunct in microsurgical techniques, conventional hemostasis, cardiopulmonary bypass surgery, colostomy closure and splenic injury repair. On cosmetic surgery, tissue fibrin adhesives have been used in lieu of sutures to reduce scar formation and in aiding skin graft fixation in burn patients. In various microsurgical techniques, fibrin sealants have been used not only to achieve adequate hemostasis but also to attain a fluid or air barrier, to maintain tissue adhesiveness and as adjunct in bone and cartilage repair.

When human tissue is injured, bleeding ensues and then ceases due to formation of a blood clot. This is the initial mechanism of natural wound closure. A clot is formed as a product of the final common pathway of blood coagulation. Fibrin glue mimics this coagulation cascade resulting in its adhesive capability.

Once the coagulation cascade is triggered, activated factor X selectively hydrolyses prothrombin to thrombin. In the presence of thrombin, fibrinogen is converted to fibrin. Thrombin also activates factor XIII (present in the fibrinogen component of the glue), which stabilizes the clot, by promoting polymerization and cross-gluing of the fibrin chains to form long fibrin strands in the presence of calcium ions. This is the final common pathway for both the extrinsic and intrinsic pathways of coagulation in vivo, which is mimicked by fibrin glue to induce tissue adhesion.

There is subsequent proliferation of fibroblasts and formation of granulation tissue within hours of clot polymerization. Clot organization is complete two weeks after application. The resultant fibrin clot degrades physiologically.

The two components of fibrin glue can either be applied simultaneously or sequentially, depending on the surgeon's preference.

Generally, the two components of the fibrin glue may be mixed with the conductive elements right before injection/placement into the patient; or one of the two components may be pre-mixed by the manufacturer, thereby providing a situation for the physician where to mix two components together ("component A," by way of example only, being a 15% fibrinogen, 70% gold particle mix; "component B" being the remaining 15% thrombin of the weight of the total volume of 100% liquid mixture). In another embodiment, "component A" may contain a 15% thrombin, 70% gold particle mix; "component B" being the remaining 15% fibrinogen of the weight of the total volume of 100% liquid mixture. These ratios may be skewed more towards a 25% fibrinogen, 25% thrombin, 50% gold (or other metals) liquid mixture ratio or other ratios as needed to be thin enough to be dispensed by the means applicable and able to provide sufficient levels of conductivity inside the body once cured.

Figure 30:
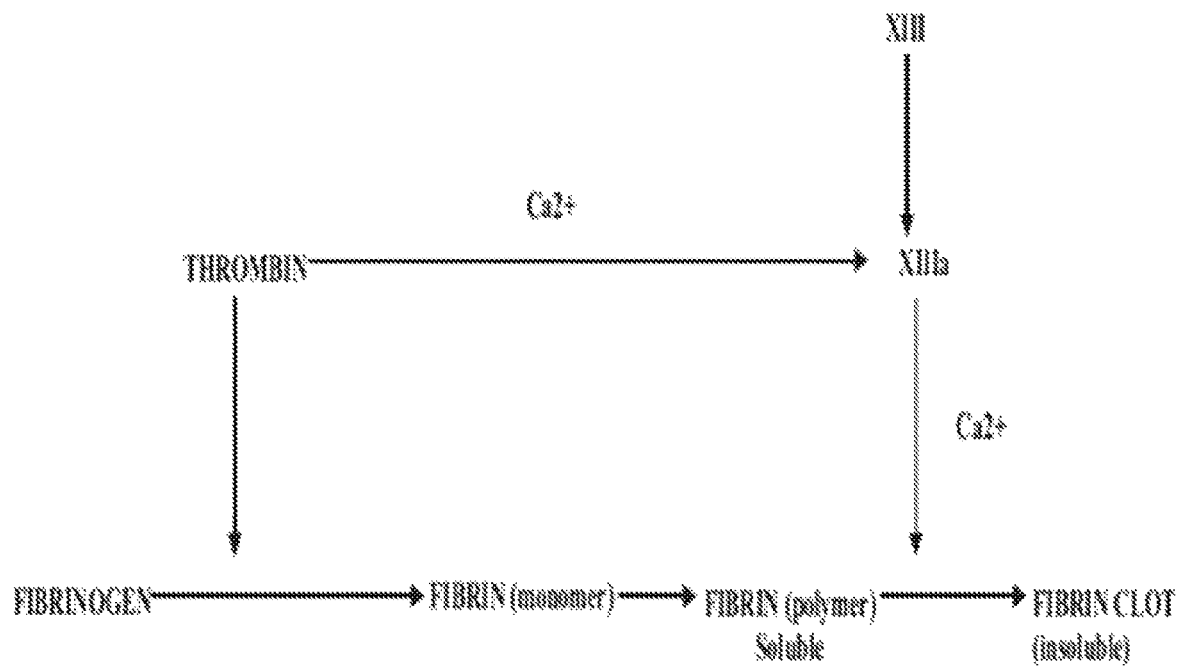
FIG. 30 shows the final common pathway of coagulation cascade for fibrin glue.
Figure 31A:
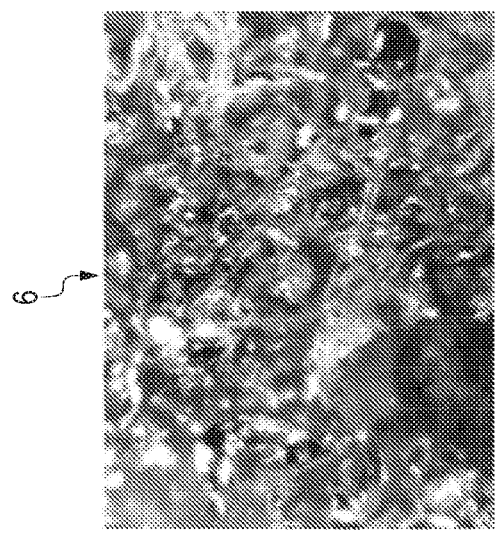
FIGS. 31A-31D are images of high-aspect silver flakes manufactured with various grain size sand paper wheels using a Dremel tool.
Figure 31B:
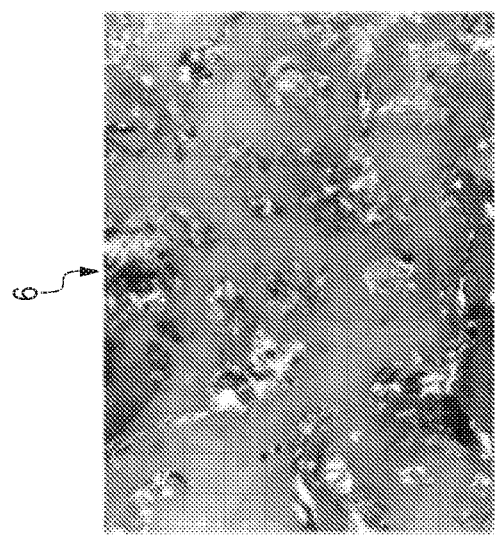
Figure 31C:
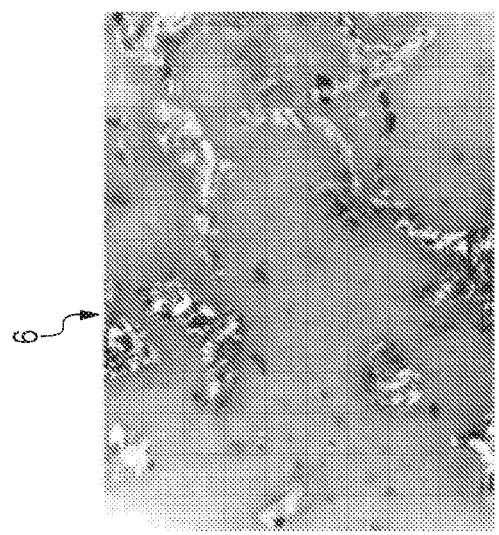
Figure 31D:

When simultaneous application is preferred, both the components are loaded into two syringes with tips forming a common port (e.g., Duploject syringe). When injected, the two components meet in equal volumes at the point of delivery. The thrombin converts the fibrinogen to fibrin by enzymatic action at a rate determined by the concentration of thrombin. The more concentrated thrombin solution, thrombin 500, produces a fibrin clot in about 10 seconds and the more dilute thrombin solution, thrombin 4, results in a clot in about 60 seconds after glue application to the surgical field. As mentioned earlier, both the extrinsic and the intrinsic mechanisms of blood coagulation are bypassed but the physiological final common pathway of coagulation is replicated. Factor XIII (present in the fibrinogen component of the glue) cross-glues and stabilizes the clot's fibrin monomers while aprotinin inhibits fibrinolytic enzymes, consequently resulting in a stable clot. The final common pathway of coagulation cascade is represented by the diagram in FIG. 30.

For sequential application, thrombin is first applied to the area of interest, followed by a thin layer of fibrinogen. In a minute or two, coagulation starts and by two or three minutes, polymerization is complete.

Alternatively, when apposition is required between opposing surfaces, thrombin solution may be applied to one and fibrinogen to the other surface.

In all of these cases, prior to application of the glue, the surgical field must be dried meticulously. After application, the tissue is pressed gently over the glue for 3 minutes for firm adhesion. At the end of the procedure, pad and bandage is applied after instillation of antibiotic drops.

Fibrin glue prepared from a donor is as safe as other tested blood products. Most but not all viruses can be inactivated by solvent or detergent treatment.

The alternative approach to ensure that fibrin glue is virus free is by preparing it from homologous fresh frozen plasma from donors in whom current tests for viral markers are negative for at least six months after the donation. This simple accreditation measure excludes the theoretical possibility of the donors having been in the "window period" when they donated blood or plasma. To further ensure its safety, most of the proteinaceous products are sterilized by gamma irradiation.

If autologous serum is utilized to produce the liquid mixture, then manufacturer provided conductive elements may be mixed in pre-determined ratios by weight to provide e.g. gold-based conductive elements with the patient's blood to form the conductive fibrin glue. Such autologous serum based may be very well tolerated by patients and, not utilizing ingredients such as grass-fed beef, it is vegan and thus applicable to a larger patient population.

Fibrin glue reduces the total surgical time because time required to place sutures is saved. The use of glue has been found to lower the risk of post-operative wound infection, contrary to conventional suturing. This can be attributed to accumulation of mucous and debris in sutures which may act as a nidus for infection. However, there is no data available to substantiate the low incidence of post-operative reaction and infection.

Mixtures of fibrin glue and antibiotics are being used for local delivery of antimicrobial activity. It is well tolerated, non-toxic to the tissue wherever it is applied and has some antimicrobial activity. The smooth seal along the entire length of the wound edge results in a higher tensile strength, with the bond being resistant to greater shearing stress. Fibrin glue is also a useful adjunct to control bleeding in selected surgical patients. It has a low incidence of allergic reactions. However, anaphylactic reactions following its application have been reported. This reaction has been attributed to the presence of aprotinin in fibrin glue.

Fibrin glue encourages the formation of adhesions when applied to contaminated tissues. Its use in infected wounds has been reported by two authors. This may be possible due to presence of aprotinin which possesses some antimicrobial activity. Chen et al. Curr Pharm Des. 2002; 8(9):671-93, however, reported that fibrin glue failed to demonstrate any bacteriostatic effects to either Gram−ve or Gram+ve bacteria by verifying the size of the bacterial growth inhibition. They also detected minimal cytotoxic activity but this was not found to be significant clinically.

Collagen, proteins and other patient-provided, animal-sourced, other-patient-sourced or synthetically gathered components may further be part of the mixture to advance with tissue integration and wound healing.

Biodegradable (mesh/suture) strips that have a glue (dispensed) on them to be able to attach to themselves in the wound and be filled or coated on the other side with conductive, biocompatible mix (fibrin glue and other carrier materials with conductive elements).

Hemaseel (Haemacure Corporation, Montreal, CA), is a fibrin-based sealant used between skin grafts and wound sites, and is suitable for use as the carrier material in a liquid mixture. As used currently, the use of the fibrin sealant between the skin graft and the wound bed interface provides adhesive qualities allowing fixation of the graft without the use of staples or sutures and seals the tissue bed layer, thereby inhibiting seroma or hematoma formation without compromising the healing process, resulting in a higher percentage of graft take with a more acceptable cosmetic outcome than using mechanical fixation.

As with two part silicones, each part of the fibrin glue (e.g., thrombin-containing crosslinker and fibrin) may be separately mixed with conductive elements and then mixed via a dispenser at the time of application. To improve the chemical and mechanical characteristics of the conductive element integration within the fibrin matrix, the conductive elements may be surface modified with a tri-amino acid sequence, arginine-glycine-aspartate ("RGD") peptide or other functional group that improves the interface between the two materials. With conductive elements consisting of gold, the surface may be modified through disulfide chemistry with the gold surface.

The process of injecting a liquid mixture from autologous ingredients includes the following steps (1) blood is drawn to extract serum; (2) the serum is processed to extract the ingredients to form fibrin glue or a likewise structure to form the carrier medium of the liquid mixture, and (3) the carrier medium is then mixed with conductive elements to form the liquid mixture to form a cured electrode.

Protein Glues, Amino Acids, Arginine, Polyamine, and Other Ionic Conducting Polymers Protein glues are suitable carrier materials. One example of a protein glue suitable as a carrier material is transglutaminase, also called meat glue that provides a carrier medium for the liquid mixture. Transglutaminase is an enzyme that stimulates a bonding process at the cellular level with the amino acids lysine and glutamine in proteins. It is a protein present naturally in both plant and animal systems. The product used in kitchens is created from natural enzymes using a fermentation process. The preparation of the liquid mixture may require further processing to ensure proper human biocompatibility.

Generally, transglutaminase may be any of various enzymes that form strong bonds between glutamine and lysine residues in proteins including one that is the active form of clotting factor XIII promoting the formation of cross-glues between strands of fibrin.

By doping the protein glue with conductive (biocompatible) materials before or during the curing process, electrically conductive tissues may be built inside the body to form a liquid mixture.

Conductive elements may be selected from a group consisting of Metal particles (Silver, Gold, Platinum, and other conductive metals); Graphene, graphite and other forms of carbon-based mixtures; N or P Doped silicon particles (wafers doped to become highly conductive semi-mixtures) were then ground up; Other mixtures; Carbon nanotubes; Ionic ends added to the protein structures [add these to earlier section on conductive elements—but delete the rest of this paragraph after doing so, providing fully- or semi-conducting proteins, amino acid complexes etc.

Dental Resins, Cement and Amalgam

Dental resins are nonmixtures by nature, biocompatible, malleable when placed and may be cured with the application of UV or blue light in-vitro. While many applications for the liquid mixture/cured electrode may require a flexible electrode, there may be situations where an inflexible cured electrode is advantageous. For these applications, resins that are mixed with a conductive particle in appropriate mixture ratio (e.g., 70% mixture, 30% resin; or 50% mixture, 50% resin; etc.).

Dental composite resins are types of synthetic resins which are used in dentistry as restorative material or adhesives. Synthetic resins evolved as restorative materials since they were insoluble, aesthetic, insensitive to dehydration, easy to manipulate and reasonably inexpensive. Composite resins are most commonly composed of Bis-GMA and other dimethacrylate monomers (TEGMA, UDMA, HDDMA), a filler material such as silica and in most current applications, a photo-initiator. Dimethylglyoxime is also commonly added to achieve certain physical properties such as flow ability. Further tailoring of physical properties is achieved by formulating unique concentrations of each constituent.

Many studies have compared the longevity of composite restorations to the longevity of silver-mercury amalgam restorations. Depending on the skill of the dentist, patient characteristics and the type and location of damage, composite restorations can have similar longevity to amalgam restorations.

As with other composite materials, a dental composite typically consists of a resin-based oligomer matrix, such as a bisphenol A-glycidyl methacrylate (BISGMA), urethane dimethacrylate (UDMA) or (semi-crystalline polyceram) (PEX), and an inorganic filler such as silicon dioxide (silica). Compositions vary widely [this is a problem—we need to say more than this], with proprietary mixes of resins forming the matrix, as well as engineered filler glasses and glass ceramics. The filler gives the composite wear resistance and translucency. A coupling agent such as silane is used to enhance the bond between these two components. An initiator package (such as: camphorquinone (CQ), phenylpropanedione (PPD) or lucirin (TPO)) begins the polymerization reaction of the resins when external energy (light/heat, etc.) is applied. A catalyst package can control its speed.

A hand-held wand that emits primary blue light ($\lambda$max=450-470 nm) is used to cure the resin within a dental patient's mouth and may be used similarly near neural structures in the patient's or proband's body without risk to the neural structure during light application. An example of a dental resin liquid mixture comprises (1) Bis-GMA or other dimethacrylate monomers (TEGMA, UDMA, HDDMA), and (2) Ag or Au [how much?]. It is injected in its liquid form and then cured in the body with blue light in the way that it is dispensed around a target, then cured, then dispensing continues, then curing continues. This process continues alternating the dispensing of the liquid mixture and the curing as needed to mold the desired shape of the electrode around or near the nerve.

A range of resins and cements exists, providing different levels of mechanical hardness and stability.

Glass ionomer cement ("GIC")—composite resin spectrum of restorative materials used in dentistry. Towards the GIC end of the spectrum, there is increasing fluoride release and increasing acid-base content; towards the composite resin end of the spectrum, there is increasing light cure percentage and increased flexural strength.

Resin electrodes might allow an integration of the liquid mixture which then cures into a bone, mechanical fixation around, near or into a bone, as well as the formation of mechanically stiff cured electrode able to resist muscle forces where needed.

GICs are hybrids of glass ionomers and another dental material, for example Resin-Modified Glass Ionomer Cements (RMGICs) and compomers (or modified composites). These materials are based on the reaction of silicate glass powder (calciumaluminofluorosilicate glass) and polyalkenoic acid, an ionomer. Occasionally water is used instead of an acid, altering the properties of the material and its uses. This reaction produces a powdered cement of glass particles surrounded by matrix of fluoride elements and is known chemically as Glass Polyalkenoate. There are other forms of similar reactions which can take place, for example, when using an aqueous solution of acrylic/itaconic copolymer with Tartaric acid, this results in a glass-ionomer in liquid form. An aqueous solution of Maleic acid polymer or maleic/acrylic copolymer with Tartaric acid can also be used to form a glass-ionomer in liquid form. Tartaric acid plays a significant part in controlling the setting characteristics of the material.

Fissure sealants, which involve the use of glass ionomers as the materials can be mixed to achieve a certain fluid consistency and viscosity that allows the cement to glue into fissures and pits located in posterior teeth and fill these spaces which pose as a site for caries risk, thereby reducing the risk of caries manifesting.

Cermets are metal reinforced, glass ionomer cements and they improve the mechanical properties of glass ionomers, particularly brittleness and abrasion resistance by incorporating metals such as silver, tin, gold and titanium. The use of these materials with GIC increases compressive strength and fatigue limit as compared to conventional GIC, however there is no marked difference in the flexural strength and resistance to abrasive wear as compared to glass ionomers. This means that there are some processes of mixing the dental cements with metal particles in place and a substitution of the currently used metals (aimed at mechanical stability) for a metal aimed to increase conductivity is desirable (Ag, Au, etc. as well as non-metal mixtures such as graphene, carbon nanotubes etc.)

Eutectic systems, for example dental amalgams, are metal compositions that are composed of metals in powder form and at least one metal in liquid form at the time of formation. Dental amalgam is one example of such an eutectic system, where mercury provides the flux (ability to flow and react)

for the said metals to form a eutectic structure in an exothermic reaction that creates a hard, durable and electrically conductive medium. A cured electrode formed as a eutectic system does not necessarily need another carrier medium, as the metallic components of the eutectic system provide high levels of electric conductivity.

As amalgam assumes the mechanical properties of a paste prior to curing, so a simple syringe/needle system may not be sufficient for delivery/injection, especially a small gauge needle. In these cases, the needle/syringe and the amalgam column inside is vibrated at frequencies of 600 to 60,000 Hz. Vibrating the dental amalgam can allow more viscous material to achieve a lower effective viscosity (similar to how sand can flow similar to a liquid when vibrated). Vibration may be used to assist in delivery of amalgam and also any other liquid mixture.

Dental amalgam is a liquid mercury and metal alloy mixture. Low-copper amalgam commonly consists of mercury (50%), silver (~22-32%), tin (~14%), copper (~8%) and other trace metals.

Basic constituents include (1) Silver, to increase strength and expansion, (2) Tin—to decrease expansion and strength, and to increases material setting time, (3) Copper—to bond to tin, reduce tarnish, corrosion, creep and marginal deterioration and increase strength; (4) Mercury—to activate reaction of the material; (5) Zinc—to decrease oxidation of other elements, increase clinical performance, and produce less marginal breakdown; (6) Indium—to decrease surface tension, reduce amount of mercury necessary, and reduce emitted mercury vapor; and (7) Palladium—to reduce corrosion. Being electrically conductive, amalgam does not need conductive elements to increase its conductivity.

Amalgam may not be applicable for all potential applications, though there are locations where high tensile strength, shear strength, or mechanical stiffness may be advantageous or not considered a problem. Examples of such implant locations are the leg stump of an amputee where there is no muscle activity or where a nerve is running very close to a bone and there is little or no lateral motion between the nerve and the bone. Placing the amalgam partially into the bone (optionally, after creating a hole in the bone) allows for a stable attachment of the amalgam in one location. A dispenser may employ a small drill to provide an anchor point for the cured electrode in which the carrier material is dental amalgam.

A variation is a cured electrode of dental amalgam which is both soft and hard. One part is hard and e.g. anchored into a bony tissue near the nerve to be stimulation to eloquently hold it in place, while the contact to the nerve is established though a soft portion which is glued (electrically conductive or non-conductive) to the hard portion, allowing for mechanical stability of the entire system and increased flexibility of the connection to the nerve.

An amalgam cured electrode, when encased in a nonconductive carrier material during or post curing/setting of the amalgam may further provide a variety of applications to conduct electrical current inside the body without unintentionally stimulating nearby tissue or losing currents to crosstalk and parallel pathways.

In yet another embodiment, a cured electrode of amalgam may be placed without anchoring it into a bone to be able to move with the surrounding tissue. As long as the relative motion between a nerve and an amalgam cured electrode is minimal, such as not more than 0.5 mm co-axially and not more than 0.2 mm radially to the nerve, then such a cured electrode may be applicable in a location where there is very little or no muscle and/or skin movement near the cured electrode.

Bone Cement

In another embodiment bone cement, or poly(methyl methacylate) ("PMMA") based materials, may be used as the liquid carrier material. PMMA bone cement has been used extensively as an implantable biomedical material. It is a rapidly curing polymer and may be mixed with conductive elements to yield a liquid mixture. A cold-cure system typically consists of a powder, a cross-linking agent, and an accelerator that is typically integrated with the solvent (e.g. N,N-Dimethyl-p-toluidine). A conductive filler may be combined homogenously throughout the powder (PMMA+ crosslinking agent) which is then combined with the solvent and accelerant solution to initiate polymerization.

Conductive Elements

Very high intrinsic electrical conductivity is the primary property for the conductive elements, although intermediate conductivity levels are useful when resistivity is to be exploited to form electrodes of varying impedance levels. [Please elaborate on this] In one embodiment particle sizes tested are in the m range (in a preferred embodiment approximately 10 to 300 μm) as produced by filing metal with a conventional metal file and most filings had a diameter of approximately 100 to 200 um. The nanometer range shall be avoided for conductive elements as metals in the nanometer range have been reported to show characteristics (such as toxicity) which are not observed in micron and macroscopic levels. Considering that the conductive elements are applied as a device to conduct electricity and not as a "drug" to kill cancer cells which can be observed with gold particles in the nanometer range, conductive elements have at least one dimension which is one micron or more, and in some preferred embodiments the conductive elements are in the range between approximately 10 and 300 μm. Different conductivities are desirable to enable resistive as well as well conducting lines in parallel. This partially-conductive material may comprise a conductivity between the most conductive and the most insulating material. Innate biocompatibility of the conductive elements mixed with the carrier medium is advantageous, but not absolutely necessary.

The conductive elements herein may comprise dental amalgam (comprises Ag, Ni, Cu, Hg). Although dental amalgam includes elemental mercury (approximately 50% of the material content as measured by weight in dental amalgam is Hg), the Hg is bound so well in the eutectic structure of the amalgam, that the amount of Hg leached even when mechanical forces (biting) and chemical solvents (in saliva as well as acids in fruit and other food) are applied in combination, the contamination of the human eating with a Hg-containing tooth filling in their mouth is considered safe. Innate biocompatible materials are gold in pure and in alloyed form, titanium (pure or alloy), platinum (pure or alloy) and others. The conductive elements comprise a metal with appropriate properties selected from a group consisting of gold, vanadium, niobium, iron, rhodium, titanium, tantalum, gallium, arsenic, antimony, bismuth and platinum. While some of the alloys and pure forms of these metals possess innate toxic properties, limiting the metal's bioavailability is key to its use as implanted materials. The conductive elements also may comprise a carbon-based conductive material from a group consisting of graphite, graphene, diamond and carbon nanotubes. While diamond is an insulator, graphite and graphene show highly conductive properties for electrical current. Another metal with high conductivity is aluminum (Aluminium internationally). Carbon Nanotubes, nanometers in diameter but micrometers in length, are highly conductive for electricity and are very biocompatible, biotolerable or bioinert in chronic implantation in both, preclinical and clinical studies and applications. Stainless steel is used widely in medical implants and is electrically conductive. Alloys such as nitinol (51% nickel, 49% titanium) are being used in heart valves, ocular applications and other implant locations of the body. While a patient may have an allergic (or otherwise unwanted medical) reaction to a compound (e.g. nickel) of an alloy, patient tolerance to the alloy as a whole is significantly improved. While toxic to bacteria and living tissue (such as cells of animals or humans), copper and silver (in pure form as well as their alloys) are highly electrically conductive and can be implanted when bioavailability is limited. Copper (II) ions are toxic for biological systems and it is important to shield copper metal from dissolving and its ions being able to diffuse or otherwise travel away from the implant location, thereby becoming bioavailable. If on the other hand copper (and copper alloys, as well as similar metals considered harmful to biological tissue) are coated with another metal that does not dissolve in the biological environment under chronic conditions, then copper can be used. Corrosion resistance to the chronic implant location is important, not necessarily for the pure metal as such, but for the implanted system as a whole: While aluminum itself is highly reactive with oxygen, it is the oxides of the metal that allow aluminum to be practically inert in nature, making it attractive for many industrial applications. Furthermore, many metals are present in the human body in bound form (referred to as "biometals"), meaning that the human body is able to process metals in solution to a certain extent, especially when they are present in chemical compounds inside the body. One example of a metal alloy is bronze.

TABLE FOUR

Conductance for metals and carbon based substances, in ohms:

| Material | Conductivity (1/(Ωm)) |
|---|---|
| Au (gold) | $6 \times 10^7$ |
| Ag (Silver) | $6.29 \times 10^7$ |
| Ti (Titanium) | $2.4 \times 10^6$ |
| Ni (Nickel) | $1.43 \times 10^7$ |
| Pt (Platinum) | $5.5 \times 10^7$ |
| Cu (Copper) | $5.95 \times 10^7$ |
| Al (Aluminum) | $3.77 \times 10^7$ |
| Fe (Iron) | $1.03 \times 10^7$ |
| Carbon nano-tubes | $106$ to $10^7$ |
| Graphene | $2.9 \times 10^7$ |
| Conductive polymers | $104 \times$ to $10^7$ |

The conductive elements may comprise high aspect ratio materials, although all conductive elements need not have a high aspect ratio. As used herein, aspect ratio of the conductive elements refers to the ratio of the maximum dimension of the particle compared to the minimum dimension. A sphere, by definition has an aspect ratio of 1, where as a rod with diameter 1 micron and length 10 microns has an aspect ratio of 10. High aspect ratio conductive elements have the advantage that they may achieve electrical percolation throughout a composite matrix at a lower weight percentage than lower aspect ratios.

Figure 32:
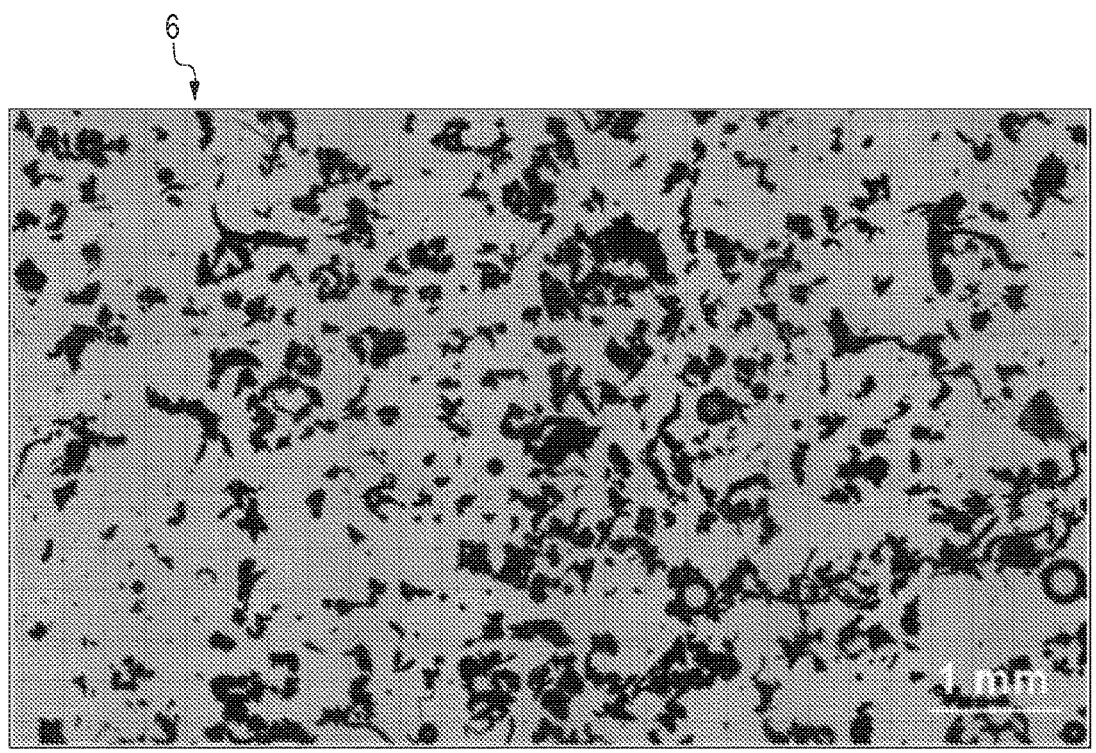
FIG. 32 is another image showing the same high-aspect ratio silver filings as in FIGS. 31A-31D.
Figure 33:
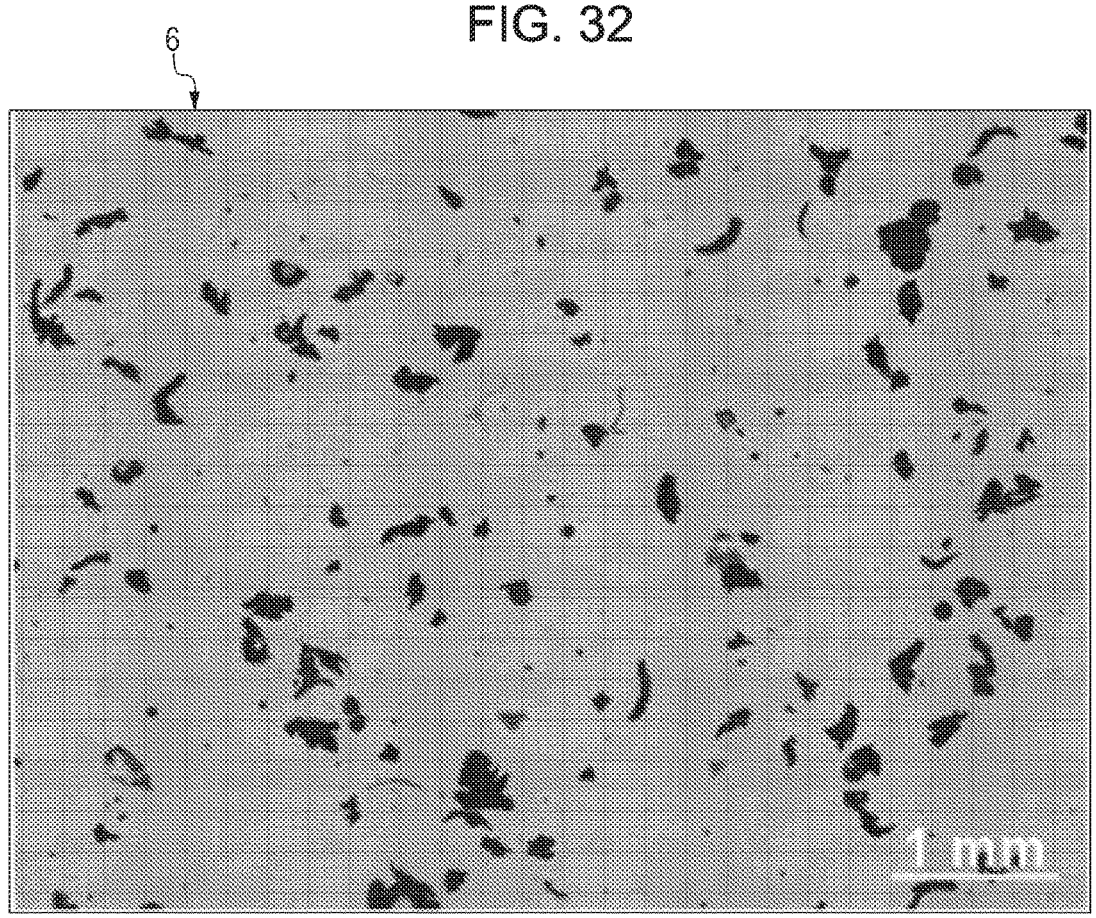
FIG. 33 is an image of gold flakes of various aspect ratios produced with a Dremel tool.

FIGS. 31A-D are images of silver flakes manufactured with various grain size sand paper wheels using a Dremel tool. FIG. 32 is another image showing the same high-aspect ratio silver filings as shown in 31A-D. FIG. 33 is an image of gold flakes of various aspect ratios produced with a Dremel tool.

A portion of the metal flakes produced by grinding in this fashion comprise shapes that may interlink as a hook and loop fastener holds on and bonds through many small connections for both electrical conductivity as well as mechanical stability of the cured mixture. Thus, the production of flakes through grinding via dremel produces inherently non-uniform, high aspect ratio, bent and pointy metal particles. Another method of producing conductive elements is use of wet and dry sand paper of 600 pitch grain, which produces conductive elements affording significantly increased [reduced?] impedance values for liquid mixture/cured electrodes of the same weight percent as compared to the non-sandpaper-post-processed material. In addition to the interlinking properties of metal flakes described herein, the conductive elements, metal or otherwise, may be manufactured with specific features selected from a group consisting of hooks, loops and coils, so that these features can interlink with one another, thus improving the connectivity and durability of the network of conductive elements. In one embodiment the conductive elements are small bits cut from a conductive material comprising fibers of a shape found in a steel wool.

For metal flakes and other conductive elements an aspect ratio of 5:1 and up to 1000:1 is desirable, although an aspect ratio as low as 2:1 is acceptable depending on the application. Conductive elements of less than 2:1 are capable of conducting current, but the percent weight of the conductive elements within the mixture (comprising the carrier and the conductive elements) would increase. The aspect ratios stated herein may be, but are not necessarily, uniform throughout a liquid mixture/cured electrode. The conductive elements, as described herein, maintain connectivity even under mechanical deformation that a flexible carrier material can withstand.

In one embodiment, gold bonding wire, as used in the semimixture industry, is used to manufacture conductive elements is a suitable source for the conductive elements. Gold bonding wire—describe diameter/width and any other relevant information such as a product or manufacturer name. In one embodiment, the gold bonding wire may be cut into bits comprising lengths of 10 μm to 900 μm, three images of which are shown in FIG. 34. The shorter wire bits (approximately 10-60 μm) are better for fitting through a tight needle, with a maximum of 20 gauge, and preferentially 22-26 with <10 micron conductive elements, improve conductivity even when the cured electrode is stretched or bent. FIGS. 35A-B are idealized section views of a cured electrode in its original shape and a subsequent bent position showing how, after bending, the high aspect conductive elements FIG. 35B maintains connectivity compared to lower aspect ratio FIG. 31A. The mechanism of action of longer bits providing better conductivity at lower weight percentages, especially when non-uniform, bent and with the ability to interconnect is shown in low aspect ratio FIG. 35A conductive elements are more likely to lose connection to neighboring conductive particles when the cured electrode is bent, not so high aspect (FIG. 31B) versions.

When connective elements of high aspect ratio are used, such as fibers, whiskers, bonding wire bits, flakes, then these elements can shift in two dimensions within the cured electrode without the loss of connectivity. Using the example of two bits of bonding wires, these may slide along their axes, twist against each other, and slide along each other's axis so that connectivity (by continuing to touch) is never lost. In contrast, if low aspect ratio (e.g., a sphere) is shifted against another sphere then connectivity is lost virtually immediately. In one embodiment, advantageous results are achieved with at least a portion of the conductive elements comprising an aspect ratio 2:1 to 20:1, comprising a diameter of 15-50 µm, and length 15 to 300 µm, maintaining a high likelihood of maintaining contact with movement in two of three dimensions.

Methods of manufacturing conductive elements include: (1) Laser cut: (plain cutting or with the goal to round off the cutting edges, essentially forming a small ball at each end of the wire; if the ball is larger in diameter than the wire and a mini barbell is formed, then these too may interconnect and interlock with each other, providing added mechanical strength, while minimizing the risk of puncturing the nerve with sharp edges as well as minimizing the electrical field density at the tip of the wire on the edge of the liquid mixture/cured electrode at the interface to the electrolyte). (2) Electrical cut: burning through the wire at specific points with high current; similar results to Laser cut are possible. (3) Scissor cut. (4) Cryo-Cut approach: encase gold bonding wires (or the like) into a matrix, then freeze, and use a sharp blade to cut the matrix, which increases the ability to mass-produce similar length wire bits. Microwires, such as gold bonding wire, may be incorporated in a cutting matrix such as an OCT (optimal cutting temperature) compound used for cyro-histology. The wires may then be cut using a precise microtome (or vibratome, cryostat) such that a reproducible length of conductive elements is produced, which are collected from the collection pan below the blade, and rinsed on a filter to remove the cutting matrix compound. (5) Shaving from a spool: using a file, a knife, an angle grinder—because of shaving from a spool, mass production is possible by essentially cutting through the spool.

Gold bonding wire, cut into various lengths as conductive elements, may be (1) uniform or varying length within limits (2 sigma within L=100 µm long, rest 50<L<200 µm), (3) with bending (intentionally) or without bending (intentionally), and/or (4) with or without tips rounded via electric zap.

Conductive elements of nitinol wire (or other shape memory electrical mixtures) may be processed with aspect ratio, in one embodiment, 10:1 to 30:1. When processed from an oblong spool, in one embodiment they can be programmed to be curved at the edges (hooks at both ends), and flattened during cold processing, then they may be injected (easily flow) at room temperature, and then heated above their return "shape memory" threshold such that they return to a "hook" shape and are more likely to cross and form interlocking features 28, such as coils and hook-and-loop-like structures, for conductive elements 6. In another embodiment, they may be extruded as a straight wire and coiled afterward with cold-processing, and then cut into small segments such that they can be injected with low aspect ratio (coils that flow easier through a needle) and later be uncoiled into straight rods with high aspect ratio (better electrical percolation through the matrix, more mechanically encapsulated in the material.

Figure 36:
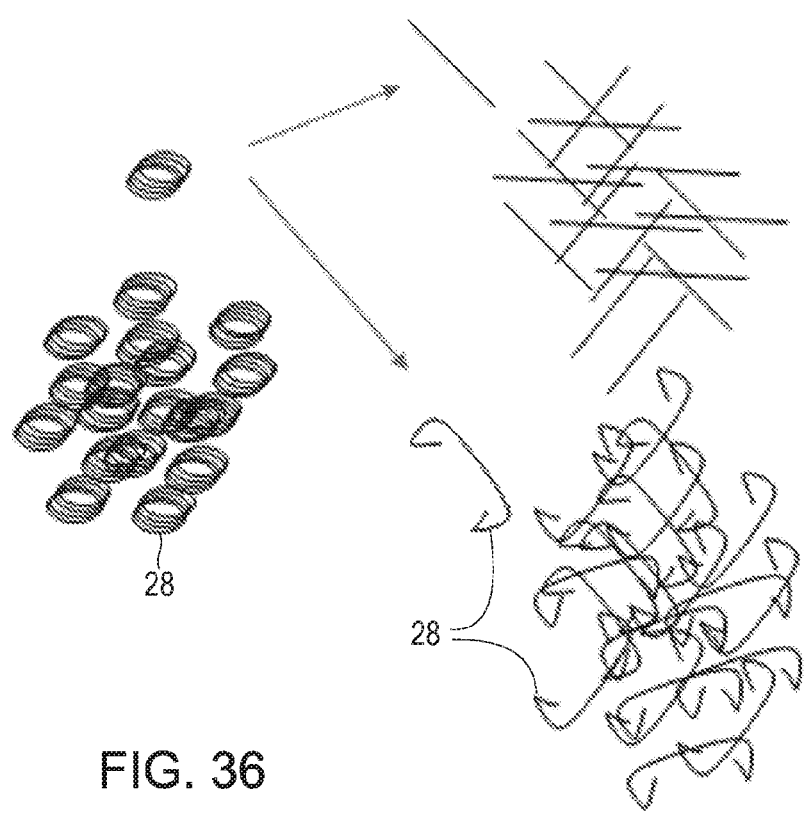
FIG. 36 is a diagram of a change of shape for NiTi wire conductive elements.

FIG. 36 is a diagram of a mechanism of action for NiTi wire conductive elements added to the liquid carrier material to provide a decrease in impedance. NiTi wires may come pre-coiled to a small diameter with the drive to straighten once subjected to body temperature (transition temperature about 35 degrees C.). The pre-coiled assembly facilitates the delivery of the small NiTi wire coils 28 through a smaller diameter bore needle or other dispenser, while the straightening of the wires (with or without ends remaining hooks) themselves interconnect within the carrier material once inside the body and heated to body temperature but before the carrier material of the carrier has cured. Once the liquid mixture has fully cured, a matrix of interconnected NiTi wires retains a low impedance value.

In yet another implementation, the wires are partially un-coiled for delivery through a small bore needle or other dispenser. At a transition temperature just below body temperature, the wires coil slightly. As the partially coiled wires link together more post-delivery (after injection) but pre-curing of the liquid carrier, the small coils 28 interconnect across the bulk of the mixture, forming an interconnected network from small formerly disconnected elements.

In another embodiment, high aspect ratio conductive elements with sharp tips have these advantages: (1) ability to penetrate the epineurium over time and provide a better SNR, (2) ability to make electrical contact with the entire nerve, (3) may be added with a liquid carrier material as "glue" to existing electrodes just prior to implantation to achieve better electric coupling to the nerves, and (4) may be used to integrate better into bone and other rough surfaces.

In another embodiment, low aspect conductive elements may be interspersed with those of high-aspect, so as to reduce irritation to tissue in some applications.

Figure 37:
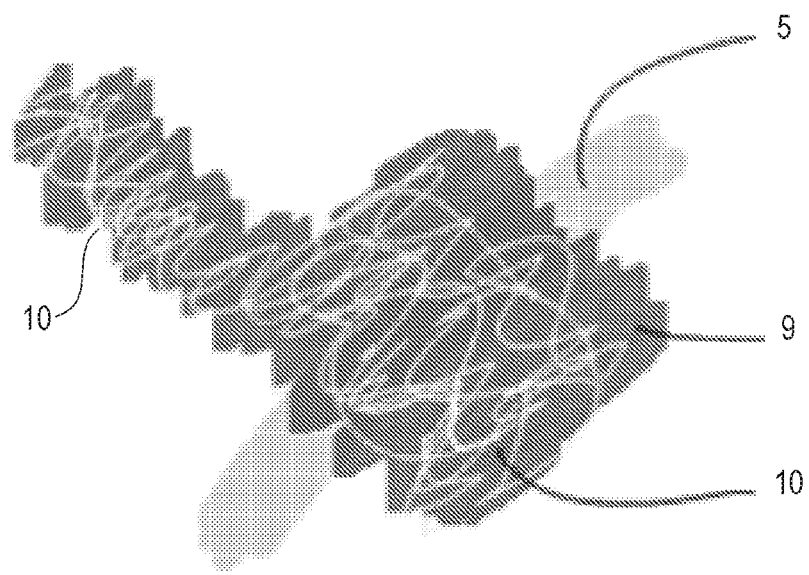
FIG. 37 is a diagram of a mesh of a cured electrode comprising gold bonding wire continuous loops that interconnect with each other, in place around a target.

In another embodiment, the conductive elements may comprise a network of conductive mesh 24, forms or filaments of electrically conductive surgical suture; and mesh, forms or filaments of other conductive elements; the filaments may be made from materials/fibers such as conductive metals or carbon-based materials or biocompatible polymers with functionalized groups for conductivity. Alternatively, carbon nanotubes (of at least a micron in one dimension) may be used to create the mesh, or may comprise individual elements. One embodiment of such a mesh structure is to form it from one wire instead of dispensing a net of conductive elements. A dispenser 2 dispenses a thin (e.g. 15 µm diameter) bonding wire covered with surfactant. This wire 10, in one embodiment, may be dispensed as a continuous string through a dispenser comprising multiple chambers and controls on the dispenser: one dispenses carrier material alone, another dispenses wire alone and yet another dispenses carrier material 7 and wire at the same time. The wire may be dispensed through a multi-chamber dispenser, each chamber having its own exit point 29 near the dispenser tip 16, and the wire is pushed by rollers toward the exit point 29 of one of the chambers. FIG. 33-0 FIG. 37 is a diagram of a mesh of gold bonding wire continuous loops that interconnect with each other. Even though the wire is one continuous wire, the meshing and interweaving of the surfactant-covered bonding wire allows for many physical connections between gold wire loops. In case one of the wire loops breaks or loses connection to a neighboring loop, there are still many others conducting electricity to the target.

Another material which can be used as a conductive element is poly(3,4-ethylenedioxythiophene) polystyrene sulfonate ("PEDOT:PSS") which is a conductive polymer. It can be solidified and ground into particles and dispersed through a liquid carrier material.

In another embodiment the conductive elements comprise surface-covered Si2O grains using chemical vapor deposition (CVD) or physical vapor deposition (PVD) to deposit diamond. This conductive diamond covered sand is electrically conductive and may be used as conductive elements.

In another embodiment, the surface of conductive elements such as gold may be functionalized with a sulfo-PEG-X or disulfide-PEG-X where X is a —OH, —COOH, —NH2 or —SH group. Surface functionalization may covalently interact during cross-linking, e.g. amine functionalized with NHS-PEG, and it may act as a surfactant or allow chain-chain interactions with the carrier material (e.g. PEG-PEG or PEG-PAA hydrogen bonding)

Visualization and Other Placement Considerations

A significant advantage of the present invention electrode is that the entire procedure of finding the connection target (i.e., nerve, blood vessel, organ or alike), placing the electrode into, next to, around or nearby the connection target, laying the connection (similar to a "lead wire") to the connection target and connecting to another target (biological or non-biological such as a signal generator)) can be done minimally invasively.

This means that the entire procedure may be done through one small "key hole" incision of <1 cm in length, or even without an incision if a dispenser comprising a needle is used in conjunction with a non-invasive visualization: ultrasound is able to visualize both, organ walls, blood vessels and often nerves that generally run alongside an artery. Furthermore, ultrasound is able to visualize tissue plains to some degree and separated tissue plains easily, and it can visualize a metallic needle or other dispenser for the mixture in the first (liquid) phase placed into bodily tissue. Ultrasound is furthermore able to visualize live, without the need for additional contrast agents and it may visualize the dispensed liquid mixture material around, inside and near a target, especially metallic conductive elements.

In addition to ultrasound, angiography (radiography, video- and still X-ray) may be used to visualize the target, a dispenser advancing to the target, injection of the liquid mixture at the target, as well as any other structure in the area such as a previously implanted electrode or lead wire. Furthermore, visualization after post-chronic encapsulation by fibrous tissue may easily be achieved months and years post-implantation especially when metals are used as the conductive elements, such as silver and platinum. If desired, visualization may be improved by adding some platinum or silver powder in sufficient quantity (i.e. 5 to 20% by weight) as both are very radio-opaque. A continuous insulation of a cured electrode may be visualized post-operatively if the mixture uses platinum particles on a nano-scale level as long as these do not become bio-available. Although these kind of nano-particles may not intrinsically provide an improvement of conductive properties, they may not significantly increase impedance either. Even elements that are naturally electrically conductive on the micrometer scale, tend to be completely surrounded by the carrier material in such a way that the carrier medium interrupts continuous electrical connections. Surfactants may be used to aid with the assurance that sufficient direct mechanical connections between the conductive elements exist in order to facilitate for the whole network of conductive elements to possess an overall low mixture impedance as described above. Platinum powder on the nanoscale level provides visualization because of its radio-opaque character, while providing sufficient insulation through the carrier and absent electrical connections between the nanoscale particles. Visualization may be further improved by utilizing contrast agents that are injected into blood vessels near the target (i.e. an artery next to a nerve of interest; an artery providing oxygenated blood to the bladder for electrode placements near or on the bladder wall) as angiography is used in cardiac and neurosurgery.

Furthermore, in one embodiment the dispenser itself has the ability to electrically stimulate when an insulated wire is included in the dispenser which is capable of providing current through a de-insulated tip in contact with the injected liquid carrier material around, at, inside or near the connection target. Finding a nerve is achieved by providing a repetitive (or intermittent) neurostimulation pulse (200 μs pulse width, 1 mA current amplitude, cathodic first vs. distal return, symmetrical charge balanced for nerves being the connection target; other, likely larger current and time values for muscle stimulation, blood vessel stimulation or organ/muscle stimulation). As the dispenser's tip 16 (e.g., needle tip or exit point 29) comes in close proximity with the target, a response may be visible (e.g., muscle movement), measured (e.g., muscle EMG, change in blood flow distal or proximal to the stimulation location measured with Ultrasound-doppler) or otherwise verified. In one embodiment the invention has the capability to immediately visualize a functional response following the electrical stimulation of the liquid mixture/cured electrode placed at, into, near, or around the target allows for immediate documentation of a successful placement. Furthermore, as the dispenser is retracted to form a wire-like portion 23 of a cured electrode, a successful continuous connection through the wire-like portion 23 can be verified by continued intermittent stimulation as only the intact connection placed by the electrode will provide conduction. A pressure sensor inside the delivery device measuring the pressure during injection/extrusion of the uncured material mixture may aid with the assessment of line continuity. Furthermore, by adding accelerometers or other types of positioning sensors to the delivery device with or without monitoring of or restraining of the target tissue, the relative position of the delivery device inside the body/tissue can be calculated by a processing system. This allows for relative motion between delivery device and various bodily tissues be used to drive the injection/extrusion of the uncured material mixture in relative manner to the motion of the delivery device. Such a computer aided delivery may utilize location information, pressure data, conductivity data and other information to assess the injection/extrusion speed, pressure and if pulsatile delivery is used, define the specific pressures and timing of injection/extrusion pulses. The automated injection/extrusion may be further correlated with expected blood vessel density in a specific tissue with the intent to seal off, glue or coagulate any blood vessels that may have been partially or completely severed during the insertion or manipulation of the delivery device into the body by injecting/extruding slightly more volume (5-15%) from the needle than the needle took up, thereby utilizing the aid of some residual pressure caused by the material left in the location the needle (or delivery device tip) took up when present in the body.

The combination of electrical functional testing, ultrasound or x-ray visualization and a general understanding of the anatomy allows a skilled physician to place a cured electrode at or around a target within five minutes or less measured from beginning of the injection to having the dispenser removed from the body of the patient.

The placement/injection of the electrode as herein may be accomplished under local anesthesia, disabling sensation in only one limb or even only a part of a limb. Avoiding general anesthesia means saving lives (local anesthesia has a much reduced risk profile in comparison to general anesthesia), cost, operating room time and personnel, and reducing recovery times. Conducting the placement of the electrode under localized anesthesia allows many interventions in bioelectronics that have previously required general surgery to become outpatient procedures.

The ability to place the entire electrode through a needle and without a large incision for surgical instruments to place a prior art cuff or electrode such with further need to secure it by sutures or encase the indwelling electrode with further reduces surgical risk of complications and reduces OR time.

An example of a patient-physician interaction for placing a neural connection would include: Office visit 1: finding the neurostimulation target 5, applying local anesthesia and verifying the best placement location via electrical stimulation through the dispenser 2. Placement of the liquid mixture/cured electrode 1 through a needle and verification of good connection from, e.g., a pad formed just below the skin to allow an interface for TENS electrodes later. Entire placement procedure done in <5 minutes. Office visit 2: One day to one week later, providing the patient with the TENS unit, verifying activation thresholds and best stimulation parameters. Patient takes TENS unit home; this TENS unit comprises very specific minimum and maximum parameters programmed into it to ensure that the TENS unit does not accidentally over-stimulate the nerve. Office visit 3: One month post implant: Verification of efficacy and safety, collecting patient feedback, verifying neural activation thresholds and adjusting waveforms as needed.

Visualization may be created or further improved by adding imaging contrast agents for use with MRI, CT/x-ray/angiography, and ultrasound, unless radio-opaque particles are added to form the PEG based liquid mixture, in which circumstance the metal component alone may be sufficient to increase visibility on MRI, CT/x-ray/angiography, ultrasound.

Visualization and other properties (stability of the suspension during the injection process, ease of injection, ease of placement, improved stickiness, ability to coagulate blood vessels and add the element of facilitating hemostasis during the injection process) may also be effected and improved by adding other polymers to the mixture. These may be in form of soluble materials or as insoluble suspensions. Soluble materials may be such as hyaluronic acid, PVA, PVP or other hydrophilic biomaterials. The insoluble suspensions may be particles of degradable and non-degradable biomaterials, including esterified HA, ceramics, polymeric suture materials and the like.

More than one of the cured electrodes of the present invention may be placed near one another for selectivity and specificity, to yield different nerve activations. If one cured electrode herein is placed near but not touching the other, then stimulating either one of these leads to an activation of a different set of nerve fibers. This is because the fibers within a fascicle as well as the fascicles within a nerve trunk as well as the nerves within a set of nerves are not stationary with their location relative to the epineurium, the outermost layer of dense irregular connective tissue surrounding a peripheral nerve. Fascicles change their relative position within a nerve trunk in relation to the others down the length of the nerve trunk. As the probability function for a nerve fiber to be activated is described by the second spatial derivative of electric field potential over time, and the electric field itself decays as function of the squared distance from its source, the probability of axon depolarization is especially correlated with the distance of a given nerve fiber to a depolarizing electrode. Secondly, as nerve fibers are primarily activated at the nodes of Ranvier, and the fact that the nodes of Ranvier for various fiber diameters do no not necessarily line up the same way within the distance of a few (e.g., 5 to 10) millimeters, essentially the width of a given electrode placed around a nerve, it may be assumed that any single electrode's interface with a nerve might not line up with the same nodes of Ranvier each time.

Figure 38:
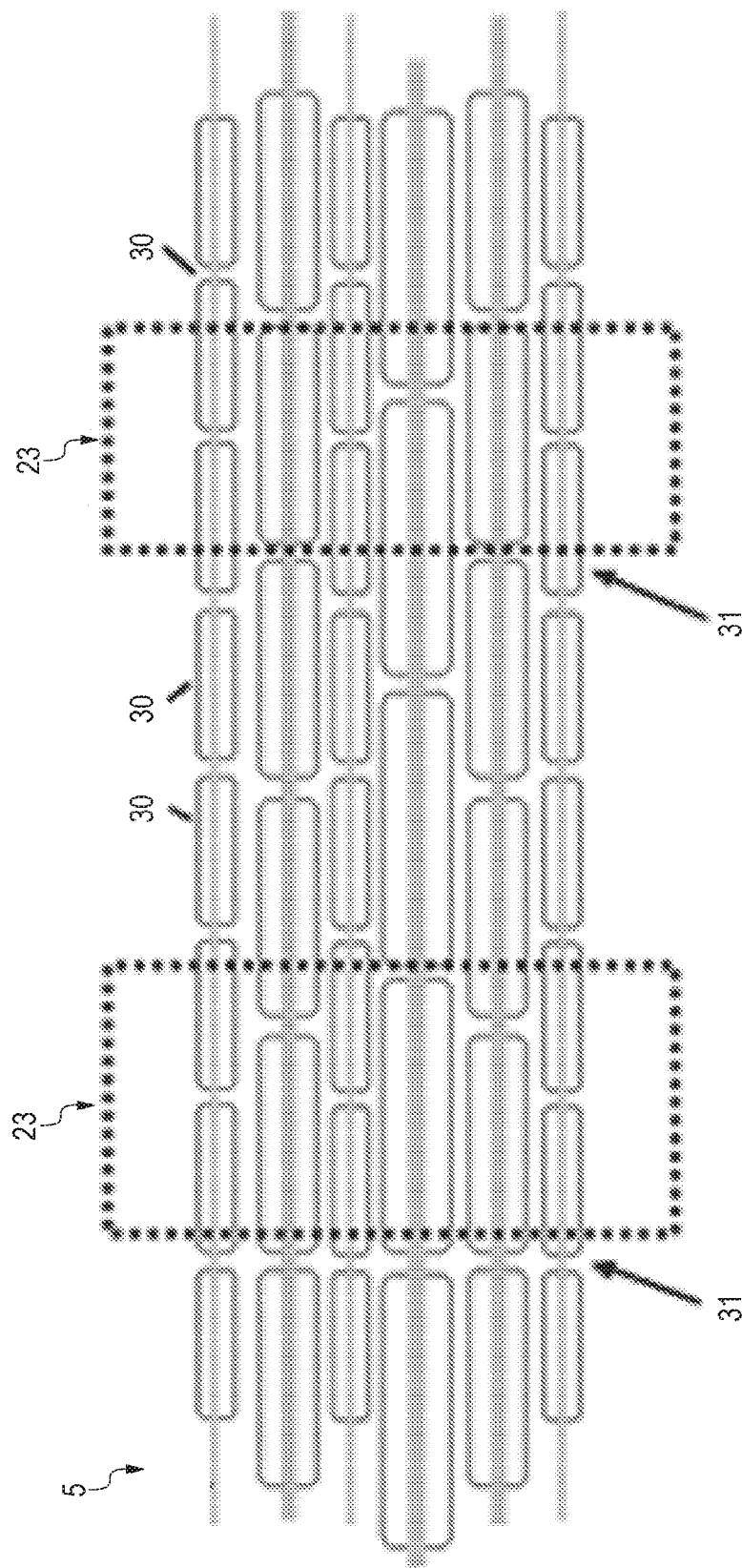
FIG. 38 is a depiction of two cured electrodes on the same nerve fiber with different activation thresholds as a result of proximity to nodes of Ranvier.

FIG. 38 is a depiction of two cured electrodes on the same nerve fiber. While the interface of electrode one lines up well with all the nodes of Ranvier of all fibers, this is not the case with for electrode two. As the change in electrical field density is the highest at the edges of an electrode, which is equally true for a cured electrode, it is the physical location of the cured electrode that defines which nodes of Ranvier will be depolarized at a given electrical field strength (i.e., stimulation amplitude in voltage or current). This causes a different activation threshold for the fibers of the whole nerve for electrode one in comparison to electrode two. Specifically, the activation thresholds for all nerve fibers, thin and thick alike, at once for this nerve will be the lowest for electrode one, while the expected stimulation thresholds for electrode two will be larger. This may be true for all fibers of this nerve and equally true for a subset of nerve fibers of a given diameter. Furthermore, not every cured electrode placed around a nerve is alike. Some might form a ring around the nerve with a ring width of 2 mm (not the diameter, but the width of the ring formed by a 2 mm diameter injection needle). Some might form a 1 mm ring width. Some might form an oval shaped object. Some cured electrodes might be a thicker ring on one side of the nerve than on the other. Either way, placing several electrodes along one nerve and connecting them to different signal generators will likely lead to different nerve activation thresholds for each of the electrodes and thereby the option for selective neural stimulation by placing a multitude of electrodes on the nerve. Related concepts are presented herein.

Figure 39:
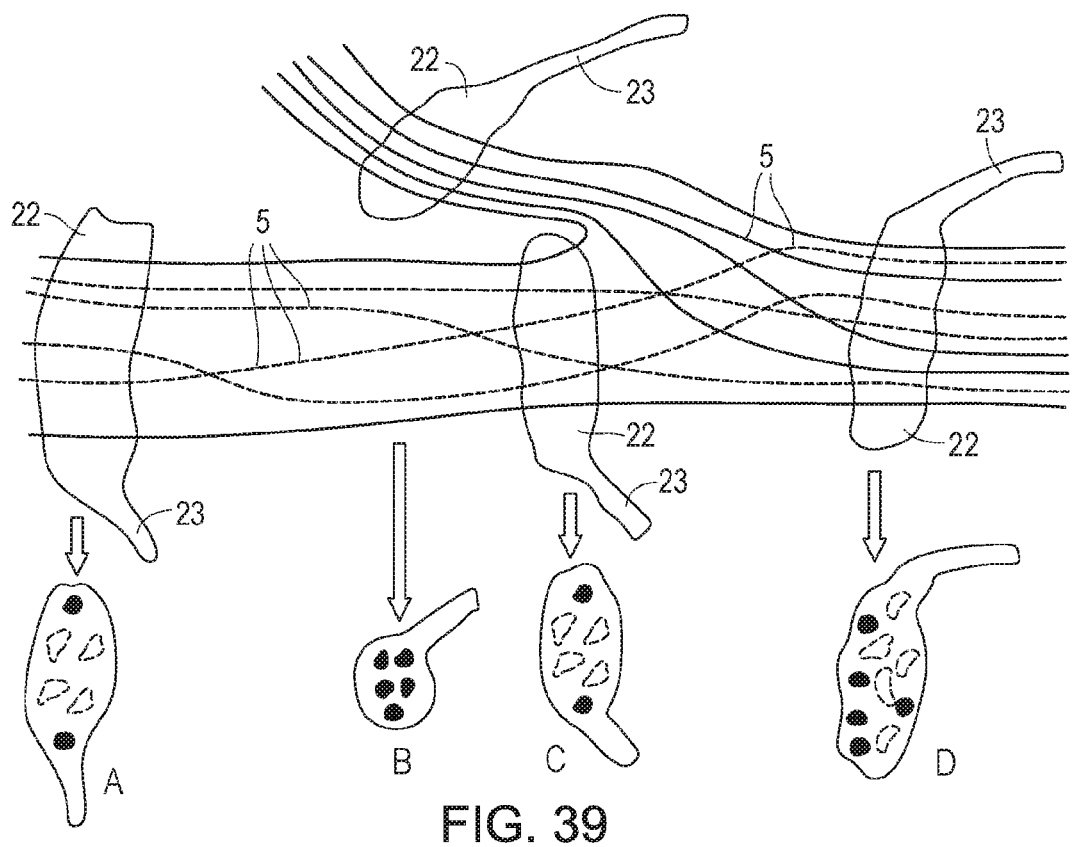
FIG. 39 depicts four cured electrodes which have been injected along a nerve with a Y-junction, enabling the possibility of selective fascicle stimulation. Section views of the cured electrodes at the location of the bar arrows are shown in A-D.

In one embodiment, a nerve fascicle may be selectively activated with a cured electrode injected along a nerve and at a nerve Y-junction, i.e., where a nerve branches. Fascicles inside a nerve do not retain their position along a nerve for an extended period of time. In fact, especially when nerves branch into two or more sub sections, a reorganization of fascicles inside a nerve takes place. This biological phenomenon can be utilized to interface with several cured electrodes, placed around the whole nerve at specific intervals, in order to achieve fascicle selective activation. This allows the specific activation of some fascicle with one electrode at one location placed more proximal along a nerve with respect to another electrode placed more distally, that cannot activate that fascicle within the same nerve at the same stimulation amplitude as the more proximally placed cured electrode did. This is especially apparent in cases where significant reorganization of fascicle locations occur such as around a Y-junction. FIG. 39 is a diagram showing four different electrodes placed at different locations provide means of fascicle selective interfacing with the present invention.

FIG. 39 depicts four cured electrodes which have been injected along a nerve with a Y-junction. The longitudinal view illustrates the location of the four electrodes along the nerve while the transversal (cut through each electrode across the nerve) illustrates the location of each specific fascicle in relation to the electrode. Each distinct fascicle shape illustrates how the relative position of fascicles shifts throughout the nerve over distance. Similar shaped fascicles from one cross-section to the next are used to show how one fascicle may be right next to the outer rim of the nerve, meaning next to the epineurium of the nerve, while being more in the middle of the nerve in another location along the nerve that is surrounded by an electrode of the present invention. Proximity of a fascicle to the electrode may determine activation thresholds for that specific fascicle, providing a different fascicle selective activation for cured electrode "A" from that achieved with cured electrode "C." As cured electrode "B" only surrounds the smaller nerve sub section, it will provide a different activation of fascicles too. The cured electrode, "D", surrounding all fascicles of both nerve sub sections forming the Y-junction, has the ability to drive all fascicles.

Figure 40:
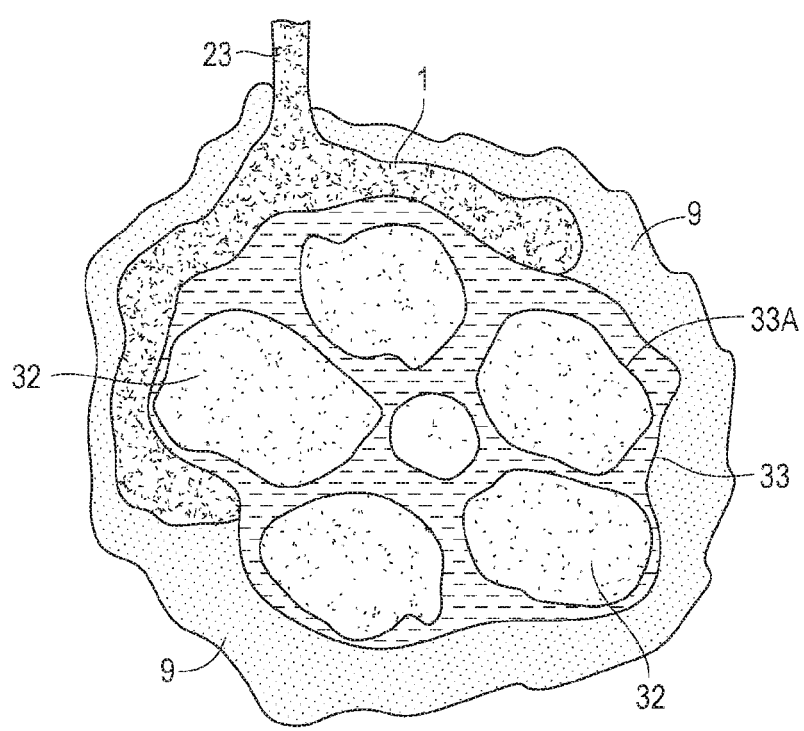
FIG. 40 depicts a selective interface by positioning a cured electrode to specific fascicles A and B of a nerve.

In one embodiment a fascicle selective electrode may be constructed by using liquid mixture and liquid nonmixture carrier materials to surround the whole nerve or only parts of a nerve. By surrounding only a part of a nerve with the mixture, fascicles with closer proximity to the liquid mixture will be activated preferentially to fascicles more distant to the liquid mixture. The remainder of the nerve may be surrounded with liquid nonmixture or may be left uncovered. For example, using a two-chamber dispenser to deliver two separate carrier materials, one with conductive elements and the other without, the physician may selectively surround the nerve with either liquid mixture or nonmixture, while still providing a structure that encases the entire nerve and provides the mechanical stability and anchoring of the cured electrode around the nerve. FIG. 40 depicts a selective interface to two specific fascicles. FIG. 40 depicts a liquid mixture/cured electrode and liquid nonmixture/nonconductive layer surrounding a nerve with six fascicles. Only the two fascicles (A) and (B) are preferentially stimulated with this configuration. The depicted optional surrounding of the liquid mixture with a layer of non-conductive carrier material provides additional electrical shielding against the environmental biological tissue such as adjacent nerves, connective tissue, blood vessels or muscle fibers.

In one embodiment, a nonconductive layer may be added to a cured electrode of the present invention after the cured electrode has cured in place at or around a target in bodily tissue. First, a liquid mixture is provided and mixed and loaded in a dispenser. Then the surgeon injects the liquid mixture in the first phase at or near a target in bodily tissue, and then withdraws the dispenser (needle) for at least 5-10 minutes to allow the liquid mixture to undergo a phase change. In one embodiment, a wire is embedded in the first injection. Then the surgeon opens the wound again and bluntly separates the cured electrode by vibration, pulsed air or a blunt needle tip from the surrounding tissue on the outside of the cured electrode (muscle, fascia, etc.) Next, the physician injects the liquid nonmixture of the same type as contained in the just-cured cured electrode. If a wire was encased earlier, the liquid nonmixture is placed around that wire, adding to the anchoring of the wire with the surrounding tissue. Optionally, the physician may make a loop or knot in the wire and embed that loop/knot near some structure such as a bone in the nonconductive layer. Next, the surgeon withdraws the needle and allows the nonconductive layer to cure around the cured electrode.

An example of the above paragraph is a liquid mixture comprising silicone as a carrier material and silver as the conductive elements, which is placed either by a needle or in a laparoscopic procedure around a peripheral nerve under ultrasound or angiogram visualization.

Figure 41:
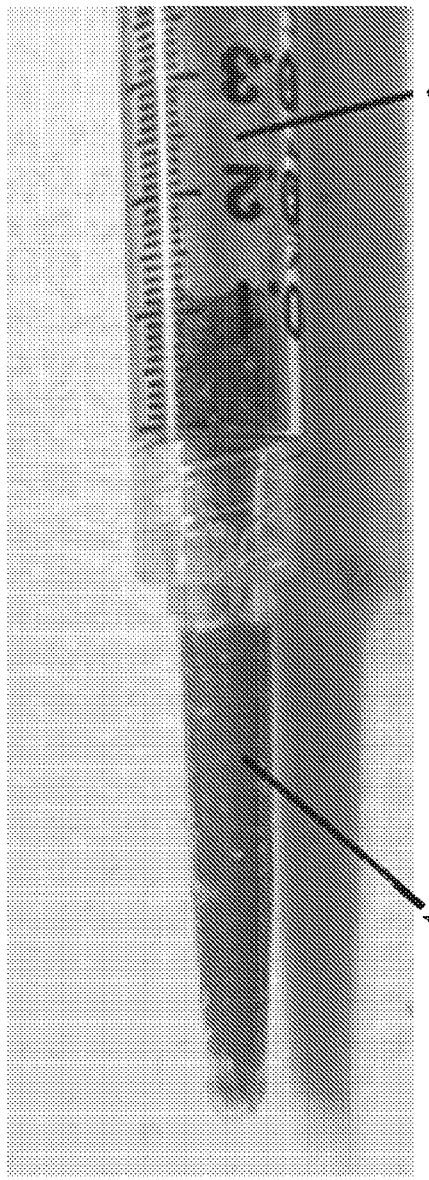
FIG. 41 depicts a method of loading the liquid mixture and liquid nonconductor in a single chamber dispenser, with the liquid mixture in front (1st) portion nearest the tip and the liquid nonconductor in back (2nd) portion.
Figure 42:
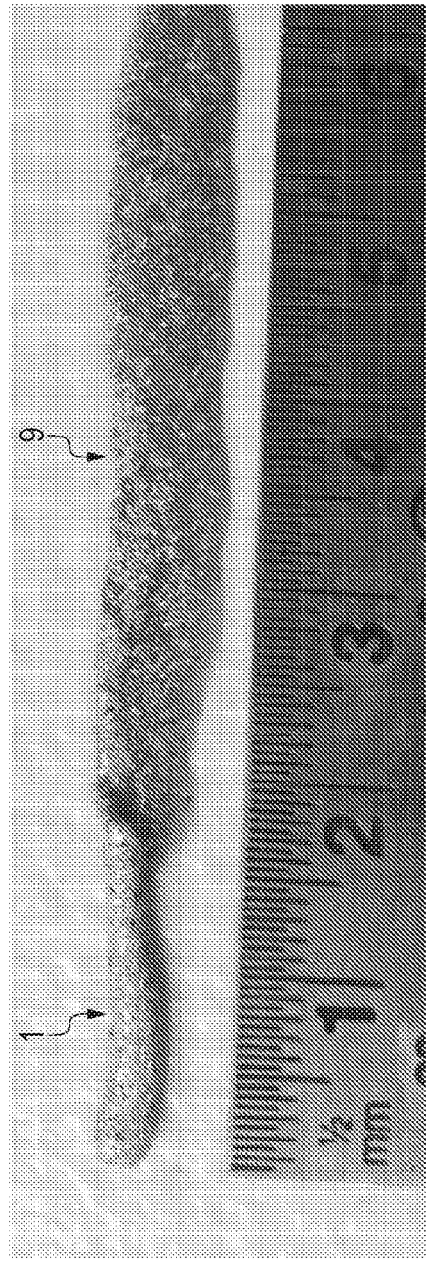
FIG. 42 is an image of an embodiment of a low viscosity silicone and silver based cured electrode dispensed through the dispenser in FIG. 41.

FIG. 41 depicts a method of loading the liquid mixture and nonmixture in the same syringe, with the mixture in front (1st) portion and the nonmixture in back (2nd) portion. During the placement, the physician may choose to place the 1st portion at the neural interface, encasing the nerve and connecting a lead wire with the mixture as it cures, or just after curing. Immediately or after a short wait the physician may encase the cured electrode with the liquid nonmixture to add insulation as well as further improve mechanical attachment to the surrounding tissue in the formerly created cavity, but without the risk of introducing new connective points that are in any way connected to the cured electrode. This configuration allows dispensing liquid mixture and/or nonmixture around a target and wire, then after a brief pause (10 sec to 10 minutes) continue to inject from same syringe the back 0.5 cc to insulate the placed liquid mixture against the other bodily tissue and improve the mechanical attachment of the overall cured electrode at the injection location. FIG. 42 is an image of an embodiment of a low viscosity silicone and silver based cured electrode injected through the arrangement depicted in FIG. 41. The first portion, shown on the left side of the image, is highly conductive due to the high Ag content. The second portion has only sparse amounts of Ag and is inherently insulating.

Figure 43:
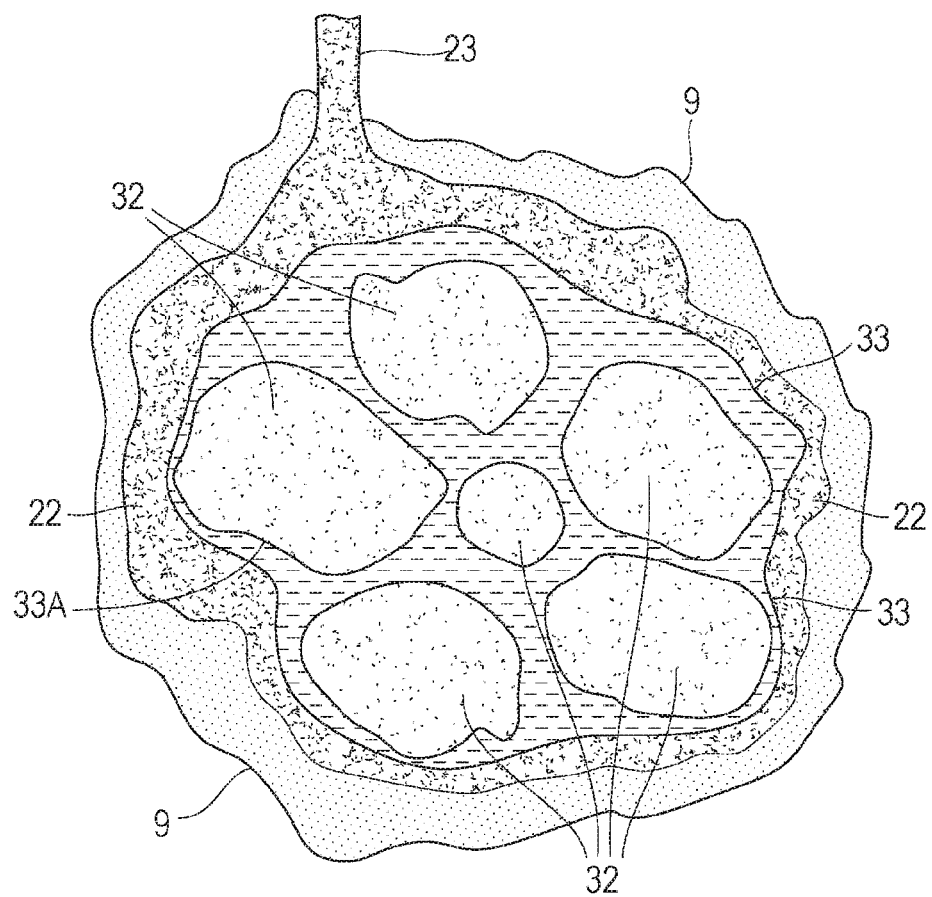
FIG. 43 depicts a cross section of a nerve fascicle surrounded by the cured electrode herein in turn surrounded by the nonconductive layer.

The present invention includes a method for minimizing "flaking" of the conductive elements from a cured electrode, and preventing mobilization of any flakes from the cured electrode over a period of chronic use in the body, by using chemical bonds to increase the cohesion of the bulk of the cured electrode. Such chemical bonds include, without limitation, valence bonds, Van der Waals bonds, hydrogen bonds, covalent bonds, and ionic bonds (between the conductive elements added to the liquid carrier material and specific functional side groups added to the carrier molecules or chains). Surface tension and/or the use of surfactants to cause the aqueous environment to drive the conductive elements toward a hydrophobic bulk material like silicone (i.e., drive toward lowest energy conformation) may be used (FIG. 43). Another method or configuration to minimize any mobilization of conductive elements that may have formed flakes and became mechanically detached from the bulk of the cured electrode, a nonconductive layer may be dispensed to keep any flakes in place.

FIG. 38-0 depicts covering the liquid mixture/cured electrode 1 with nonconductive layer 9, an additional layer of mechanical stability may be provided to the cured electrode as a whole as well as any conductive elements. In some embodiments, the nonconductive layer 9 may be seeded with cells, other biological or non-biological components to produce a thicker encapsulation of the cured electrode on the outside, while the inside cured electrode (the mixture in contact with the nerve) remains encapsulated by a thin layer of fibrous tissue. The fibrous connective tissue formed by the body as it encapsulates any foreign object such as the cured electrode will add yet another layer of mechanical stabilization and reduce the probability of conductive element mobilization. The thickness of the fibrous connective tissue may be modified intentionally by seeding the mixture or nonconductive material with particles, cells, other biological and a-biotic components to enhance the inflammatory response of the body temporarily and cause a thicker outside encapsulation. Reduction of flaking may also be encouraged by the shape of the conductive elements themselves. Other embodiments for reducing flaking include, without limitation, conductive elements with a high aspect ratio, interlocking features 28 at either end (e.g., hook, loop or coil), or a coiled or similar structure throughout the length of the conductive elements to improve mechanical stability within the cured electrode. More solutions are described elsewhere herein.

In one embodiment a signal generator 17, an IPG such as a miniaturized BION (e.g., Alfred Mann Foundation, Bioness, Advanced Bionics) may be connected to a target in bodily tissue with a cured electrode at or surrounding the target. Some of these signal generators may be injected via a large bore needle and thus may relatively easily be placed into a patient's body without the need for a major surgery. The shortcoming of these very small signal generators is that they are not able to depolarize, address, stimulate, or block the whole nerve without the use of a cuff-like structure that encases the nerve. Any prior art small metal contact placed next to a nerve will not achieve a uniform field or an electrical field that is more or less of the same field strength all around the nerve, but the present invention may incorporate an IPG or other signal generator 17 to address these issues. (FIGS. 44 & 45). FIG. 45 is a diagram showing an embodiment of the present invention with each of two cured electrodes, at a first end of each cured electrode, connected with a signal generator 17, and at the other ends connected to a nerve to provide a uniform electrical field for the whole nerve, not just a strong depolarization signal to the nerve fibers inside the nerve that are closest to the signal generator's contacts. Two cured electrodes may be placed, one on each contact of the signal generator to utilize two active cured electrodes, one cathode and one anode.

FIG. 45 shows how a cured electrode may also be placed on only one side to connect the signal generator to the nerve (active cathode), or may be placed at another location to provide a better electrical interface to the surrounding tissue at the location of the distal anode.

In another embodiment, the present invention has the ability to bluntly separate tissue plains. That is, it has the ability to be injected into spaces and crevices created by blunt dissection. This blunt dissection may be accomplished by traditional surgical means with forceps and scissors or it may be achieved by directing pressurized air, liquid, or a liquid mixture or nonmixture at an interface between two tissue plains to separate these two plains. A simple way to encase a nerve using the liquid mixture or nonmixture is to inject the material directly around the nerve at a 10 to 90 degree angle to cover (1) more nerve tissue longitudinally (using the 10 degree angle measured vs. the longitudinal axis of the nerve) or (2) a shorter distance along the nerve and place more of a thin ring around or at least a C-shape liquid mixture/cured electrode behind/next to the nerve (using an angle closer to 90 degrees as measured vs. the longitudinal axis of the nerve). In one embodiment of the present invention, there is a method of blunt dissection may be aided by vibrating the liquid column inside the dispenser or by vibrating the tip of the dispenser or by vibrating both, the tip and the liquid column, using the vibration as a means to have short moments of higher and lower pressure gently move the tissue plains apart for the injection. The vibrating pressure may be applied in bursts or continuously, it may be directed in the same direction as the longitudinal axis of the dispenser or it may be directed orthogonally to the longitudinal axis of the dispenser. The vibration may be along one axis or it may be circular to cover a two-directional movement of the dispenser and or dispensed liquid material next to the two tissue plains intended to be bluntly separated.

The present invention also has the ability to form an electrode-to-nerve interface in stages, in seconds to hours. Uncured liquid mixture, as long as it has not been contaminated with bodily fluids or tissue, may be added to a previously injected cured electrode of the same carrier material or, in some combinations, of a different carrier material of compatible chemical and mechanical properties. Cured electrodes, especially when fully or partially covered by biological tissue, may first require an optimized cleaning procedure (including mechanical cleaning and a chemical deep-clean or even roughening of the cured electrode surface) prior to continued electrode placement/molding/sculpturing in the patient.

A cured electrode in a cuff-like embodiment around a target may be injected as a continuous stream of liquid mixture, or in steps, to cover first the volume behind or underneath a nerve, before placing liquid mixture next to the nerve and on top of that nerve to close the ring-like portion 22 of a cured electrode.

A cured electrode also gives the physician the ability to go in a second time later and fix a sub-optimal prior art electrode or other device, or even a prior implanted cured electrode, without the requirement of explantation of the previously implanted device. In so doing, the cured electrode provides an opportunity to restore or supplement the function of a previously implanted electronic device.

Figure 46A:
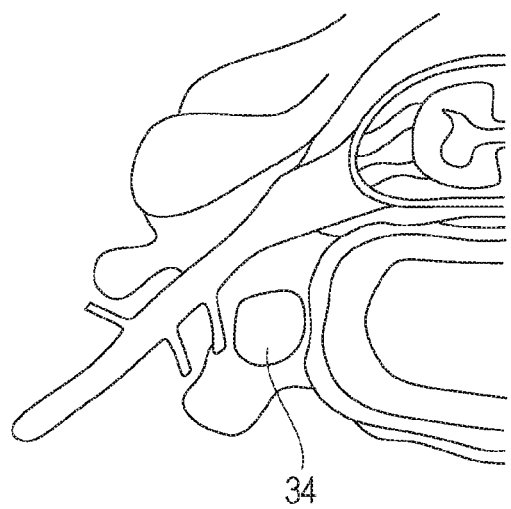
FIGS. 46A and 46B are the same cross section of a single vertebra, 46A before injection of a cured electrode, and 46B, after injection, depicting a foramen transversium as location of the anchor of a cured electrode, here a ring like portion around a nerve target.
Figure 46B:
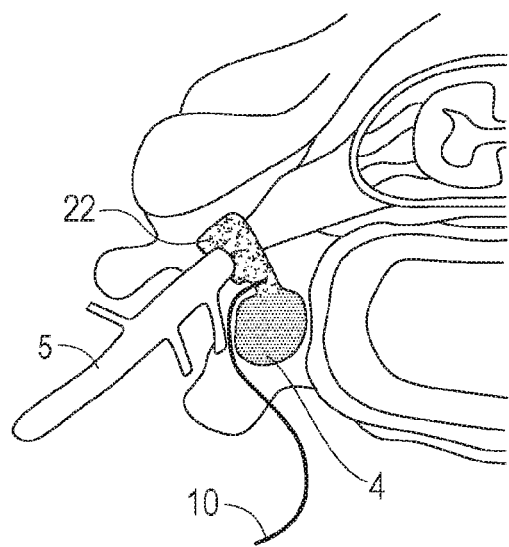

The present invention also has the capability to integrate with boney tissue. Nerves of the PNS often run close to bones and generally do not move significantly relative to these bones, and liquid nonmixture may be used to anchor a cured electrode used to stimulate a nerve in close proximity near a bone. For that, the bone itself may be encased in part, or completely with liquid material; or the bone skin (periosteum) may be lifted away from the bone at a location close to the cured electrode-to-nerve interface to allow the injection of liquid carrier material into a pocket between bone skin and bone; or the bone itself may be punctured or drilled to form an anchor point for a placement of liquid mixture; all of which may be done through a minimally invasive, laparoscopic approach (FIGS. 46A and 46B). FIG. 46A-0 is a section diagram of a vertebra, and 46B is the same view after placement of liquid mixture to encase a nerve 5 and attach a lead wire to, then anchor the liquid mixture with liquid nonmixture/non-conductive layer in the foramen transversium 34. The anchor 4 for a cured electrode may be done in a hole drilled specifically for the purpose of providing space for an anchor 4, or a naturally occurring bony structure that may take up mechanical force may be used. An example of an anchoring point is a foramen.

Another embodiment of the present invention further comprises integration of a current-limiter within the cured electrode-nerve-interface. A significant danger to the nerve in the vicinity of the neural interface is current overstimulation that may lead to temporary nerve damage or permanent nerve damage and scarring. The lead wire itself may comprise a fuse component included that may be glued back in place using the present invention if the fuse is blown by, e.g., a static shock, applied currents of unintentionally high levels, or a shorting caused by improper electrode injection/placement during surgery.

A pre-formed mold 35 may be used to hold the shape of the liquid mixture/liquid nonmixture temporarily or permanently during or after it is applied and cured in the body. The advantage of a pre-formed temporary mold: a specific shape for a cured electrode covering a specific volume may be created. The removal (including removal by biodegradation if the pre-formed material consists of a labile material such as), would then fully expose the cured electrode to the body tissues. A permanent pre-formed mold 35 may be used, in one embodiment, which is porous to allow free passage of ionic currents. This has the advantage of fully containing the liquid mixture or nonmixture during and even after curing. A permanent pre-formed mold 35 that still allows for proper functioning of the invention, has the advantage that it would ensure flakes of the conductive elements 6 do not migrate into tissues, and complete removal of the pre-formed mold-encapsulated device could be accomplished.

Figure 47:
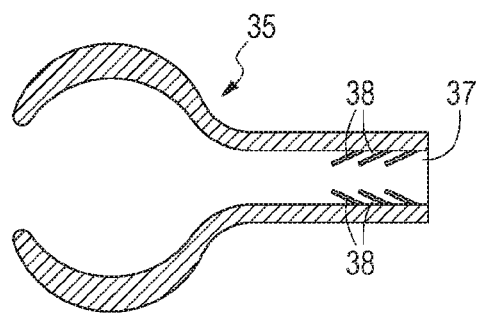
FIG. 47 contains cross-sections depicting embodiments of a mold for placing around a nerve target, comprising an opening through which a wire can be placed and secured by crimp hooks, and the wire being in electrical communication with a cured electrode dispensed into the space between the hook and the nerve target. The two diagrams on the left side depict the mold before insertion, and the two right side diagrams depict the hooks after placement. The two lower diagrams depict a mold comprising a movable slider capable of sliding out to cover all or a portion of the gap in the mold.
Figure 47:
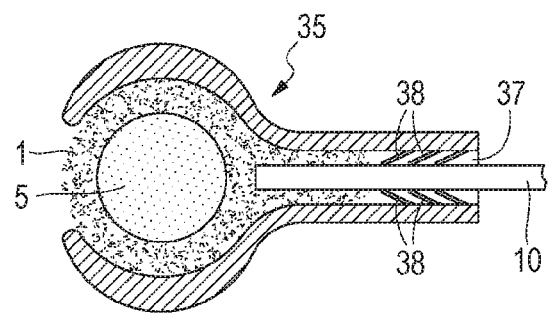
Figure 47:
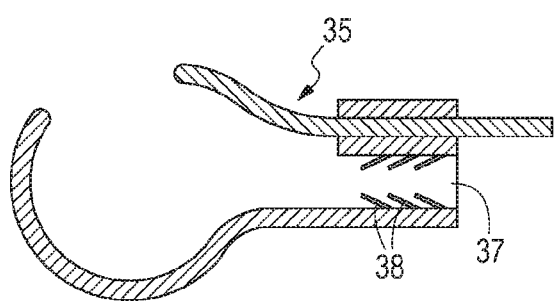
Figure 47:
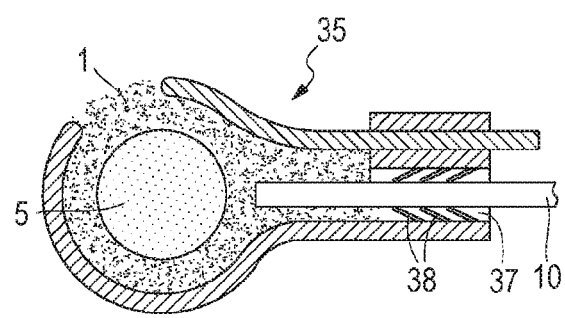

In one embodiment, a pre-formed mold 35 comprises the shape of hook 36 which may be fit loosely around a nerve with liquid mixture. Once the nerve is freed up from surrounding tissue (e.g., in a laparoscopic procedure), a mold in the form of a C- (as in FIG. 47) or O-shaped hook may be placed around a nerve. In another embodiment, an injectable hook (not pre-formed) may be injected in liquid form to surround the nerve by 180, 210, 240, 270, 300, 330 or even 360 degrees. The pre-formed mold 35 may be in the form of a cuff that is sliced open. It may be in the embodiment of a hook comprising a slider to close the hook. These pre-formed molds, in different embodiments, are electrically conductive, but the injection of liquid mixture makes them conductive. The hook, in another embodiment, may also comprise a valley running inside the opening around the hook which is filled with liquid mixture to ensure a minimum thickness of liquid mixture around the nerve. In one embodiment the hook 36 comprises an opening 37 on the opposite side away from the nerve with means for securing the end of a wire, such as crimp hooks 38 to which a lead wire may be connected by just sliding it into the hook. The hook, in one embodiment, allows the inserted wire 10 to touch the liquid mixture that is injected into the opening between nerve and hook (either prior to putting the hook on the nerve or after the hook has been placed on the nerve), but the wire 10 is prevented from touching the nerve by having designed minimum separation distances between the nerve and the distal end of the hook, which will correspond with a measure on the lead wire that prevents an insertion which is too far from the cured electrode material. FIG. 42-0 is a diagram depicting two embodiments of the hook 36 which enable a complete covering of the nerve with liquid mixture. Liquid mixture 1 may be placed onto or into the hook prior to placing the hook on/around the nerve in a laparoscopy or other surgical procedure, or it may be injected into an opening 37 on the hook or in a gap between a loosely fitted hook and the nerve. The hook further ensures that the lead wire does not touch the nerve and that the lead is integrated with the liquid mixture. The hooks may be manufactured from a flexible or a more rigid material. The pre-formed mold may be left in place around the liquid mixture/cured electrode or, in another embodiment, it may be removed prior to the end of the procedure, once the cured electrode is complete. One means for removal comprises the pre-formed mold being made in multiple pieces which may be disassembled by the physician near the end of the procedure.

In another embodiment, the present invention provides a method for repairing broken electrode leads for targets, i.e., the wire connections between an implanted signal generator and an electrode which is placed on a target. Sometimes these electrode lead wires break. This is a problem for neural and cardiac applications alike. In fact, one of the reasons for revision surgeries in cardiology is to replace broken cardiac pacemaker leads that do not deliver the signal from the signal generator to the stimulation location inside the heart. The liquid mixture material has the ability to "weld" or "glue" cardiac leads with a minimally invasive procedure. The main advantage of repairing instead of replacing a broken electrode lead is that the interface between the electrode at the end of the lead and the body's tissue does not need to be disturbed as is usually the case when a broken electrode lead is being removed: A typical technique used in the cardiac space is to simply pull out the electrode lead, which may lead to tearing and other unintended damaging of the heart muscle, the cardiac valves and other surrounding tissues. In contrast, by leaving the electrode lead in place and only fixing the break, the lead is allowed to stay in place and the electrode/tissue interface is not injured.

Figure 48:
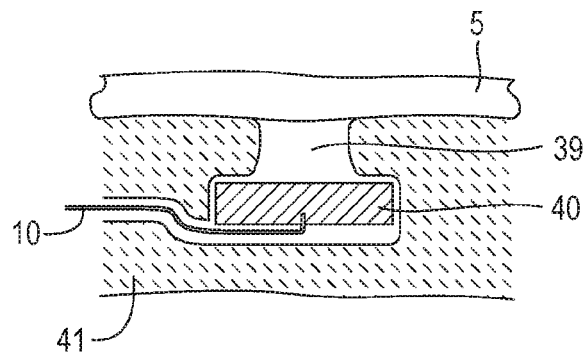
FIG. 48 is a diagram showing a section view of a portion of a prior art cuff electrode around a nerve, showing a void between the metal contact of the prior art electrode 40 (e.g., platinum) and the nerve 5.

Another capability of the liquid mixture is to increase the contact area for prior art electrodes which have a limited contact area to the electrolyte as well as the target in bodily tissue: most prior electrodes provide a planar interface which is not perfectly suited to interface with a 3D-object such as neural tissue in the body. In fact, most pre-configured cuff electrodes implanted in the body have a pre-formed carrier 41 such as a strip of silicone (manufactured outside the body which holds the metal contacts (providing the electrode-electrolyte-interface) in place, but also causes the electrode contacts to be recessed into the carrier 41 (FIG. 48). FIG. 48 is a diagram showing a section view of a prior art electrode around a nerve, showing a void 39 between the metal contact of the prior art electrode 40 (e.g., platinum) and the nerve 5. This void 39 creates additional distance for the electrical current to pass (thus reducing stimulation capability) and also fills with fibrous tissue that causes a significant change (often 2-5× increase) in stimulation impedance. As a result of chronic encapsulation over the time of a month or more inside the body, this void fills with connective tissue, increasing the electrode-to-nerve impedance significantly and causing a (sometimes large) portion of the current used to stimulate the nerve actually shunt around the nerve as the impedance in the interstitial fluid between electrode and encapsulation may be significantly smaller than the impedance electrode-encapsulation-nerve-encapsualtion-back-to-return-electrode. In contrast, the injectable liquid mixture 1 allows for a direct interface of the conductive elements 6 of the liquid mixture material to the electrolyte near the target nerve without leaving a void for encapsulation to build up. This results in a smaller electrode-to-nerve impedance for chronically implanted cured electrodes in comparison to prior art cuff electrodes.

Figure 49A:
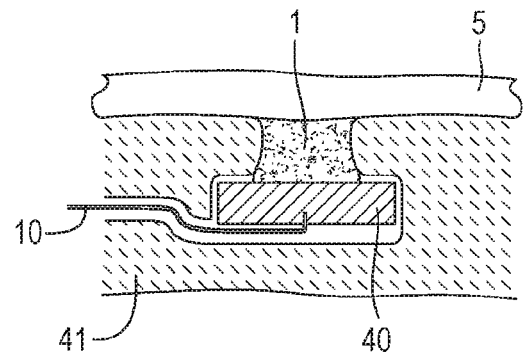
FIG. 49A is the same view as in FIG. 48, also showing that a cured electrode may function as a bridge between a prior art metallic electrode contact and the nerve if liquid mixture is placed onto the contact prior to implantation of the cuff.
Figure 49B:
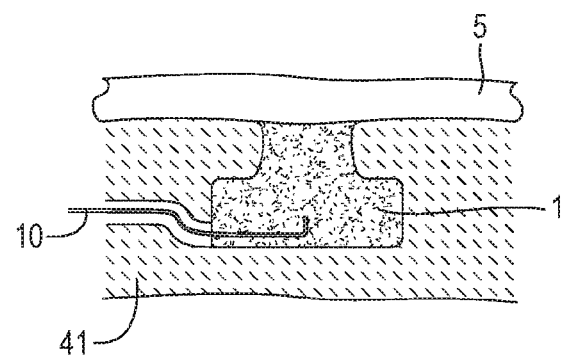
FIG. 49B is similar to the view in FIGS. 48 and 49A, except that the metallic electrode contact is not present, and the space has been filled completely by a cured electrode.

It is advantageous to cover prior cuff electrodes with liquid mixture at their respective electrode contact locations to fill the void marked in FIG. 43. By using liquid mixture to fill this void prior to implantation, long term electrode-to-nerve interfaces may be provided that have smaller impedances, advantageous for both stimulation and sensing (FIG. 49A). FIG. 49A depicts filling the void in FIG. 48 with liquid mixture prior to implantation, only a thin film or fibrous may form between the cured mixture material and the nerve, providing a better long term chronic interface. The liquid mixture may be injected/extruded into the void 39 above the original metal contact (FIG. 44A-0) or may replace the metal contact entirely, providing the connection from the lead wire directly to the nerve, as in FIG. 49B.

Figure 50:
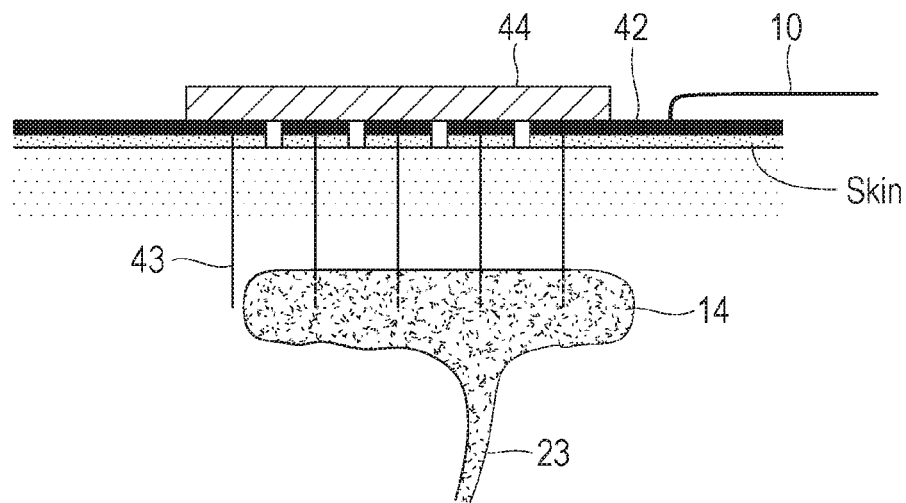
FIG. 50 depicts a cross section of a needled skin patch electrode with test electronics connected to a subcutaneous contact pad. All but one of the needles is in contact with the contact pad.

In another embodiment, the liquid mixture or nonmixture may be seeded with stem cells, including the patient's own stem cells, or neurons, glia, astrocytes, red or white blood cells, tendon or muscle cells. The resulting cured electrode may chronically form a thinner encapsulating layer as well as a spongy bulk form, allowing for better integration with the surrounding biology of the cured electrode recipient. Thicker encapsulation between the cured electrode and the non-target bodily tissue is desirable, whereas thinner (preferably, none) encapsulation between the target and the cured electrode is desirable In another embodiment needled skin patch electrodes 42 may be placed on the skin outside the body. In order for a skin patch electrode to make a continuous contact to a deep tissue nerve 5, a continuous electrical connection of low impedance throughout is advantageous. The skin provides an impedance of about 500 to 1000Ω transcutaneously (depending on thickness, sweating) produces a large voltage drop if not compensated appropriately. Although the approach of placing a pad of liquid mixture/cured electrode subcutaneously in electrical communication with a TENS unit (e.g. FIGS. 14A- to 14F) may overcome the skin impedance, other embodiments of the present invention provide additional solutions to the problem of skin impedance. One embodiment is a needled skin patch electrode 42 comprising small needles 43 which form a direct electrical connection to the contact pad 14 and thereby are able to reduce the transcutaneous impedance to levels below 10Ω. The needles 43 may connect to electronics 44 to test and report impedance, in order to determine the sufficiency of the electrical connection of the needles 43. The needled skin patch electrode 42 itself may or may not be conductive any more as the primary means of conducting the electrical energy is to pierce the skin with the needles to connect to the subcutaneous cured electrode. If the patch electrode is not conductive, then it is a sticky patch without any electrical hydrogel replaced with glue similar to that on band aids. For example, electrodes without hydrogel may serve as band aids with needles, or, a TENS electrode 13 with micro needles 43 to connect electrically to an electrical field connector 15. This allows the test between needles to verify successful integration into the contact pad 14, allowing the physician to confirm successful contact has been established. FIG. 50 is a diagram of a cross section of a needled skin patch electrode with test electronics 44 connected to a contact pad 14.

Figure 2B:
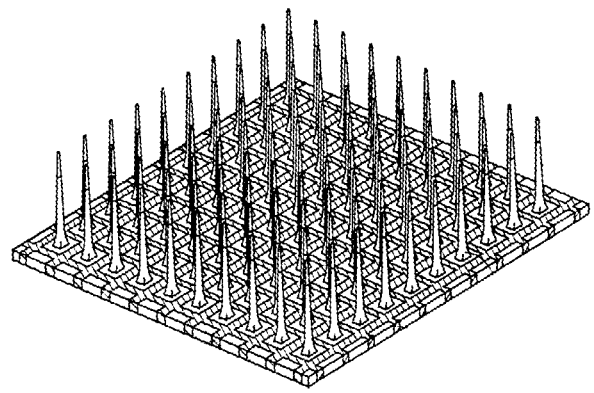
Figure 3A:
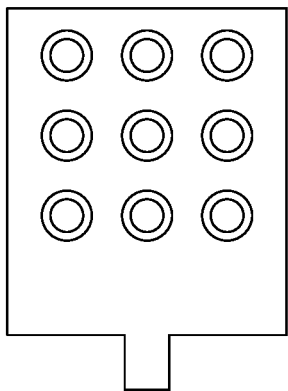
FIG. 3A is an image of a prior art planar electrode from US Patent Application Publication No. 20150367124
Figure 3B:
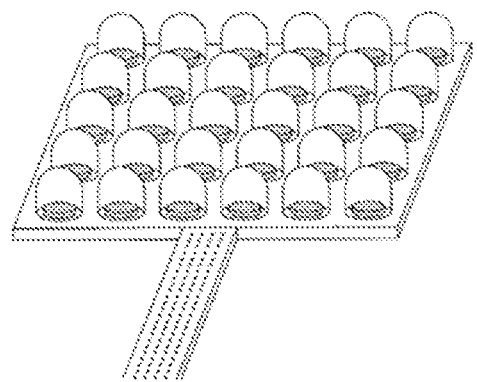
FIG. 3B is a perspective drawing of the same.

Disclosed is a method of testing the needled skin patch electrode 42 embodiment of the present invention to verify successful connection through the skin. If needles 43 penetrates the skin to connect either to a cured electrode in the shape of a pad or to a fixture such as a needle matrix 45 (FIG. 51) embedded in a contact pad 14 in the subcutaneous tissue, then an impedance measurement may be used to determine the connectivity of the microelectrodes to the cured electrode. This enables the physician to ensure that only needles 43 which are in direct connection to the contact pad 14 or to a needle matrix 45 in one embodiment) will receive electrical energy. FIG. 46-0 is a representation of a cross-section of the needled skin patch electrode 42 with an implantable needle matrix 45 embedded in the contact pad 14, and the needle matrix 45 and the needles 43 from the outside electrode 42 are configured to make electrical connection with one another. The implantable needle matrix may take 1,000,000 needle injections and not bend, as in the Utah electrode array (FIGS. 2A-0, 2B-0) turned towards the skin and using spring action.

Figure 51:
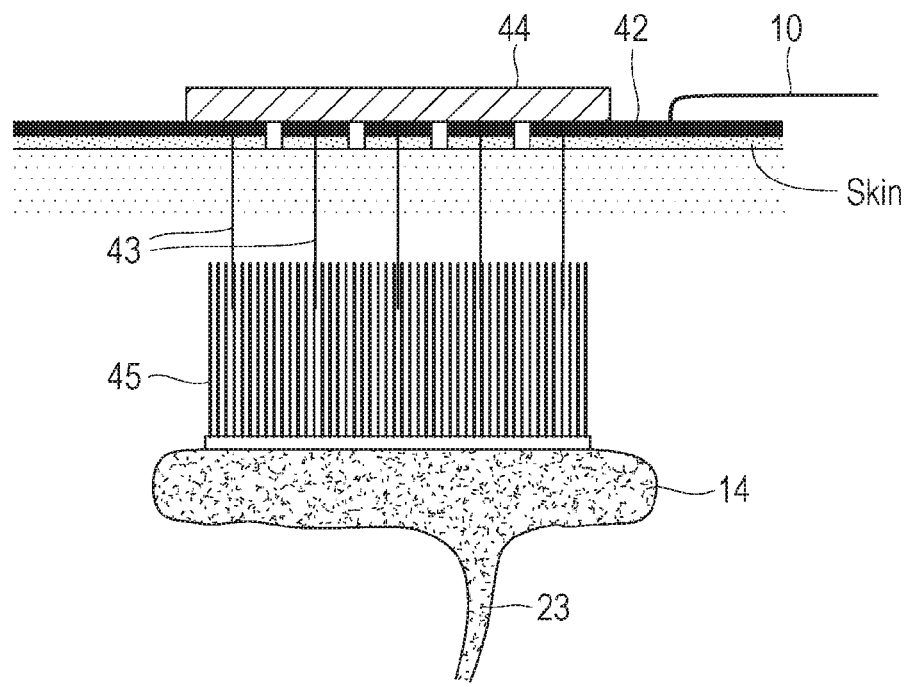
FIG. 51 is a representation of a cross-section of the needled skin patch electrode connected electrically to an implantable needle matrix embedded in the contact pad, and the needle matrix and the needles from the exterior electrode are configured to make electrical connection with one another.

In FIGS. 50 and 51, a subcutaneous contact pad 14 of a cured electrode 1 may contact needles 43 inserted from the skin and this connection transfers current across the skin. If a set of needles 43 penetrates the skin to connect to either an contact pad portion 14 of a cured electrode 1 or a fixture such as a needle matrix 45 in the subcutaneous tissue, then an impedance measurement may be used to determine the connectivity of said needles 43 to the contact pad 14 or needle matrix 45. This ensures that only microelectrodes who are in direct connection to the cured electrode (or fixture) will receive electrical stimulation energy. A needled skin patch electrode 42 with hydrogel or with band aid glue and needled electrodes 43 will achieve good direct (continuous) electrical contact by, for example, the needles 43 (conductive core, partially insulated to pass through sensitive area of the skin) piercing the subcutaneously buried cured electrode pad inside the deep tissue. Needles 43 may come with or without insulation in different embodiments.

The cured electrodes disclosed herein may be used with a current limiter to avoid neural over-stimulation from static shocks or applied currents of unintentionally high levels. A current-limiter is embedded in the wire-like portion 23 of the cured electrode, or one current-limiter is added to each of the needles 43 to provide a safety feature for the nerve. That is, a current limiter is seated between two sections of the wire like portion 23, or at the beginning or end of each of the needles 43. The applications for the current limiter include post-surgical or post-operative pain treatment with self-dissolving cured electrodes that allow TENS treatment for a deep tissue nerve. The current-limiter is in the needle or in the wire leading to the electrode.

Figure 52:
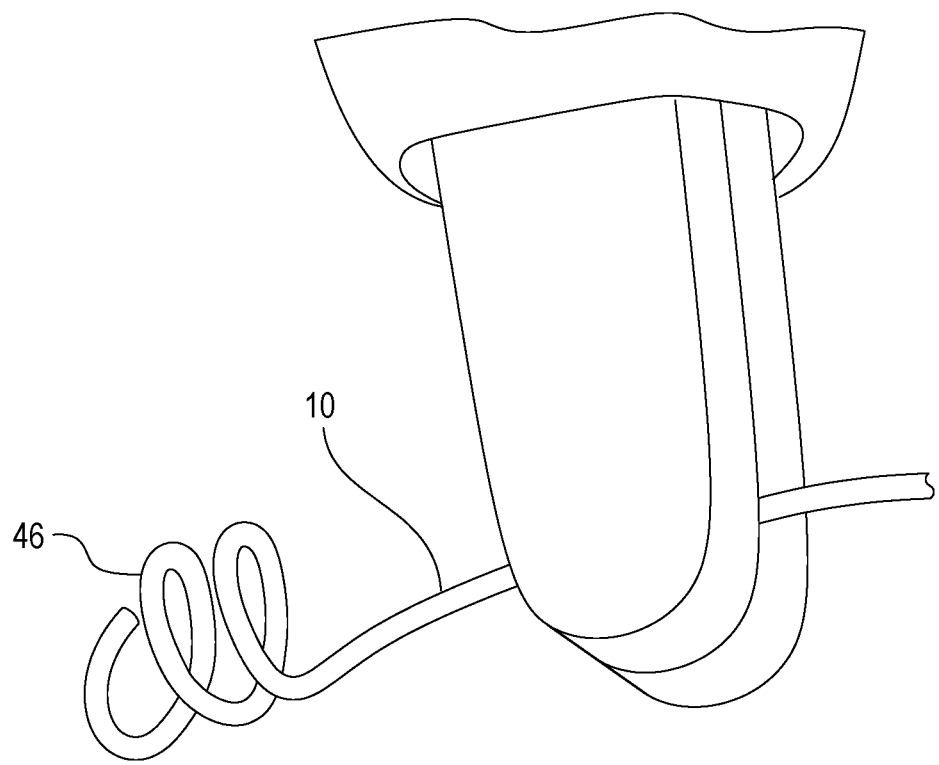
FIG. 52 is an image of a connecting feature for a lead wire to a cured electrode, here a helix screw (or, cork screw), held for display by an alligator clip.
Figure 53:
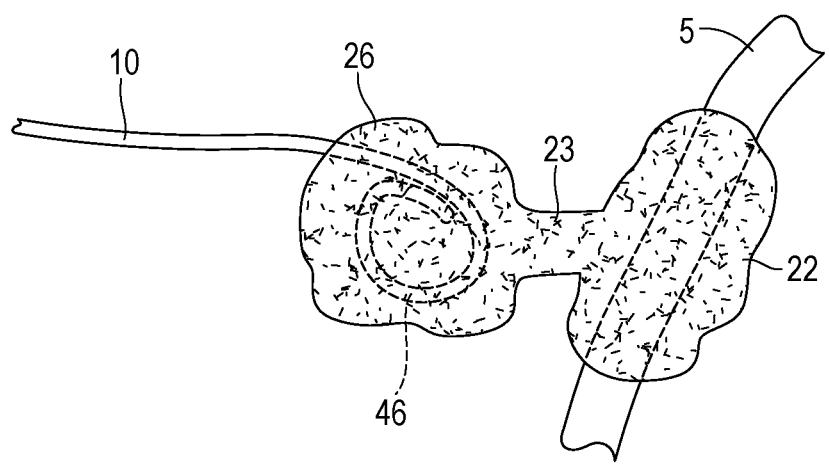
FIG. 53 is a representation of a wire loop which is embedded in one portion of a cured electrode which also comprises an interface molded and cured around a nerve target.

Leads, cables, or connecting wires are continuous metal connections, generally insulated for most of their length, which allow a direct metal connection between, for example, a signal generator 17 and a signal applicator. A typical signal applicator in the prior art is an electrode, or a metal connection to a target 5 with insulating components. In the present invention the wire 10 (i.e., cable or connecting wire) may form a direct (i.e. continuous or pure metal connection between, for example, a signal generator and the liquid mixture/cured electrode 1, which in turn connects to the target 5. A lead wire 10 may be a helical or double helical metal wire encased in silicone to provide insulation against the surrounding biological tissue. The function of the lead is to connect the electricity from, e.g., a signal generator to a nerve. In the case of the present invention, a prior art cuff electrode may be replaced by the liquid mixture/cured electrode. To achieve an optimal mechanical and electrical contact between the lead and the cured electrode, specific interfaces are described herein. One type of lead comprises a connecting feature 46 such as a helix, screw or other type of barb at the end (terminal) as interface to the cured electrode as shown in FIG. 52 which is an image of a helix screw (or, cork screw) interface with a cured electrode, held for display by an alligator clip. Another embodiment of a connecting feature resembles the shape of a bird's nest, or a mesh, to interface with the cured electrode. In one variation, the connecting feature 46 at the lead terminal(s) may be a crumbled up wire, similar to a bird's nest. This may be formed by continuously (or on button push) dispensing a gold bonding wire (that is optionally covered by a surfactant for good electrical conductivity that is not impeded by having the entire outside of the wire be covered by the carrier such as silicone, cyanoacrylate, fibrin etc. FIG. 37 is a representation of the "bird's nest" or mesh of gold bonding wire loops that interconnect with each other. Even though it is one continuous wire, it is the meshing and interweaving of the surfactant-covered bonding wire that allows for many physical connections between the gold wire loops. In case one of the wire loops breaks or loses connection to a neighboring loop, there are still many others conducting electricity to the nerve. Another connecting feature 46 for a lead wire 10 is a loop or a similar shape to increase mechanical adhesion, as compared to a linear shape of a wire, to connect to the cured electrode. In some cases, a loop may be the most advantageous connection as shown in FIG. 53, a representation of a wire loop 46 which is embedded in one portion of a cured electrode which also comprises an interface molded and cured around a nerve target.

Figure 54:
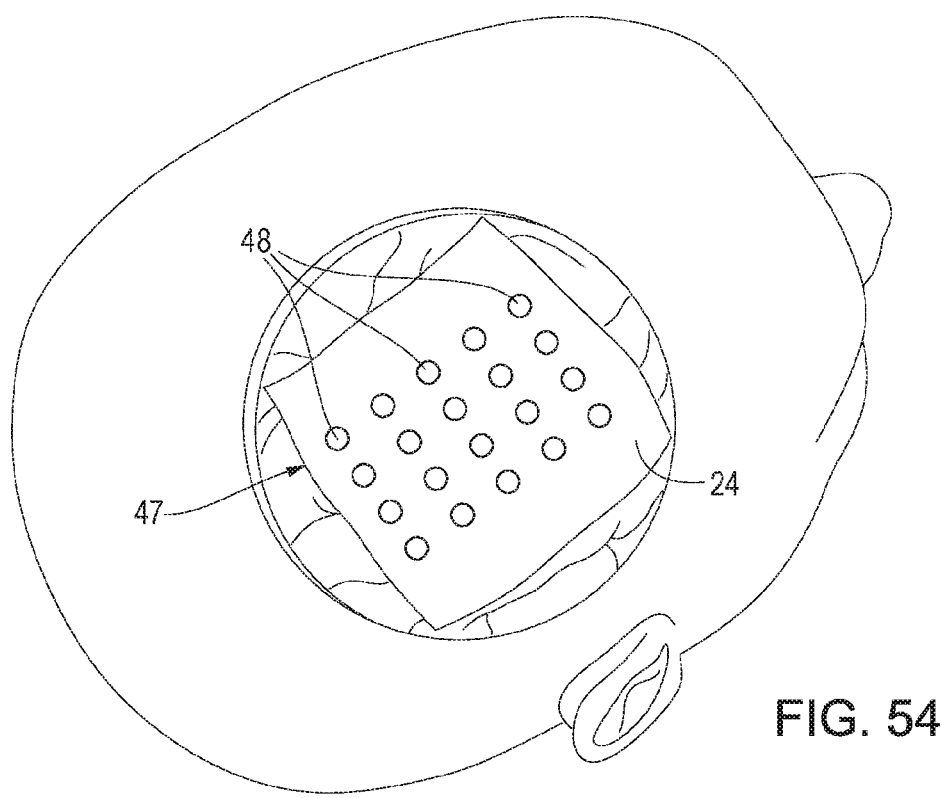
FIG. 54 depicts an electrocorticography ("ECoG"] electrode matrix of the present invention in position on human neocortex.
Figure 55A:
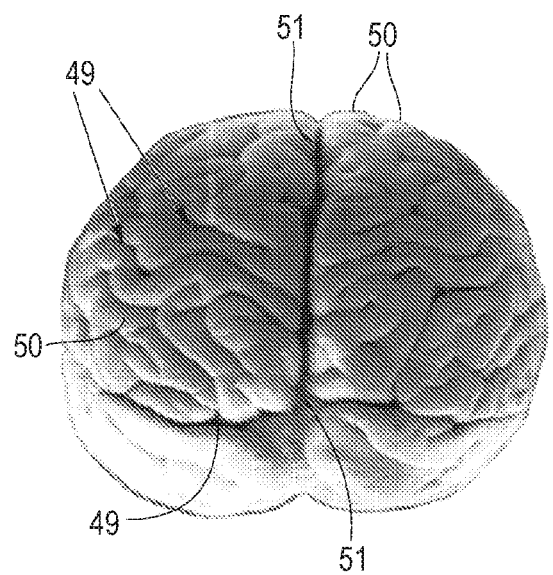
FIG. 55A is an image of a human brain, depicting the sulci and gyri of the neocortex and the midline between the two hemispheres.
Figure 55B:
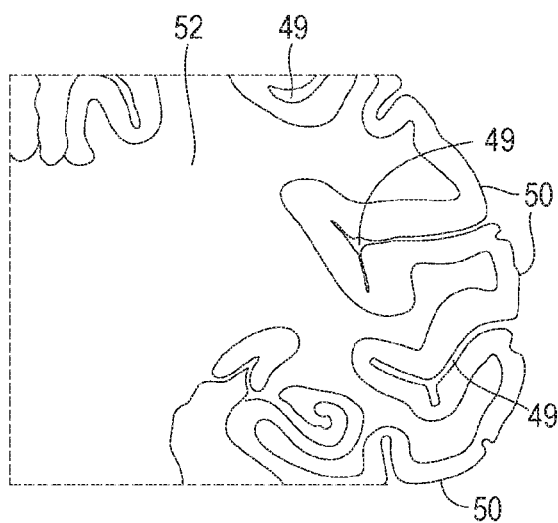
FIG. 55B is a representation of a section of neocortex and the underlying white matter showing the depth (and relative inaccessibility) of the areas within the sulci.

The cured electrode also has embodiments for cortical applications, connecting to sulcus and gyrus alike, as in FIG. 54 in an electrocorticography ("ECoG"] electrode matrix 47 where the liquid mixture 1 is pushed through at specific ECoG points such as holes 48, some embodiments of the holes comprising structures (e.g., the hole being in the shape of a frustum open at the smaller end nearest the brain, as in FIG. 56B) with the connecting wire 10 of the lead exposed and the hole in the shape of a frustum 48 allowing for mechanical attachment and integration of cured electrodes in each of the holes. De-insulated tips of wires 10 (optionally with the connecting feature 46) are incorporated into the electrode matrix 47 and extend into the middle of each of the holes 48, for the liquid mixture to be injected into through, thereby making an electrical connection to the liquid mixture 1 injected to the gyrus 50 or sulcus 49 underneath. A prior art ECoG electrode as placed subdurally and on top of the arachnoid mater is depicted in the perspective drawing which is FIG. 54. Prior art matrices are able to contact only the gyri 50 (hills) of the brain's cortex but are not able to penetrate into the sulci 49 (trench/valley) between two gyri. FIG. 55A is an image of a brain, of interest here more specifically the sulci of the cortex and the midline 51 which is the deep trench between the two hemispheres. The gyri and sulci enable the cortex to have a large surface area. FIG. 55B is a representation of a section of neocortex and the underlying white matter 52 showing the depth (and relative inaccessibility) of the areas within the sulci and midline, and how stimulation of gyri only through prior art electrodes is inadequate for any area of the neocortex not specifically on a gyrus. Prior art ECoG electrodes do not reach into the depths of the sulci, but the liquid mixture 1 of the present invention can be injected into the sulci as shown in FIG. 56B, and without the risk of injuring the blood brain barrier as the liquid mixture, the liquid mixture 1 in one embodiment formulated to be molded and cured as flexible and pliable against the soft neocortex. Injecting liquid mixture (deep) into the midline 51 allows mid and deep brain stimulation without injuring the blood brain barrier. FIG. 56B is a representation of a portion of an ECoG electrode matrix 47 from the top showing the matrix and holes with wires terminating in the holes where the wires make electrical contact with the liquid mixture which has been injected into the hole to make close with, and to mold and cure against, the neocortex underneath. The holes 10 (e.g. frustum with the shorter end open) allow the surgeon to place the liquid mixture material deep into the sulci (FIG. 56B). On one end the wires 10 at each hole 48 terminate in the open area of the holes and, on the other end, terminate at a signal generator 17 and, optionally, each wire may be activated separately from each of the other wires, by means of a controller inserted at the time of the procedure. In contrast to the traditional ECoG electrodes that only touch the tip of the cortex, thereby only getting a high SNR signal from gyri underneath the contact point of the ECoG electrode matrix, the combined liquid mixture-ECoG electrode is able to get signals from the sulci between the gyri by injecting the liquid mixture into a sulcus. The ability to interface with high SNR to both, a gyrus as well as well as a sulcus allows for better sensory and stimulating neural prosthesis. The advantage of being able to press the liquid mixture/cured electrode into the deep valleys 49, 51 and letting the liquid mixture mold against and retain the shape of the valley minimizes damage to the neocortex, assures a perfect fit, and allows for a high fidelity, low-risk neural interface into deep valleys of the brain which does not breach the blood brain barrier.

Aside from injecting the liquid mixture onto a gyrus or into a sulcus through the pre-positioned liquid mixture-ECoG matrix 47 sitting on the cortex, yet another embodiment uses a laser to display the most probable location of all (e.g., 20) contacts of a prior art ECoG electrode as they sit on the brain's cortex to allow the surgeon to place the liquid mixture on top of gyri and inject liquid mixture into sulci, followed by then placing the prior art ECoG electrode (without the holes described herein) onto the cortex. By having liquid mixture placed in contact with the cortex first at the specific locations that the ECoG matrix 47 of the present invention has its electrodes, a connection to a traditional ECoG electrode can be made with the advantage of being able to connect to the deeper structures within the sulci and a better direct interface with the gyrus directly beneath each ECoG electrode of the matrix.

These advantages put the liquid mixture-ECoG approach in a range of interface fidelity between that of a traditional ECoG placed on top of the arachnoid mater and that of a penetrating microneedle-based electrode system (e.g., FIGS. 2A and 2B) that breaches the blood-brain-barrier by injuring the arachnoid mater and the combination of neural supporting and vascular tissue beneath the arachnoid. The present invention allows a novel combination of the liquid mixture/cured electrode 1 with the ECoG electrode matrix 47 to provide the safety level of the traditional subdurally placed ECoG, while achieving a much higher SNR than the traditional ECoG array placed as a planar interface on top of a 3D-object such as neocortex. Additionally, as the liquid mixture-ECoG is mechanically adapted and to a certain degree mechanically integrated within each sulcus, SNR stays high even with brain movements present due to heart beat, breathing, and inertia moving cortical tissue during walking or other causes of (even abrupt) accelerations and decelerations of the brain or the skull. The liquid mixture/cured electrode makes not only a good electrical connection to the neocortex, but also a strong mechanical connection as the cured electrode in a sulcus acts to fasten the ECoG matrix electrode 47 in place. The liquid mixture which cures to a solid electrode allows for a more flexible neural interface with the cortex and thereby allows the physician to control the expected mechanical match between cortical tissue and cured electrode. Specific liquid mixture mixtures comprising hemostatic agents (described herein) further offer the ability to immediately stop any bleeding, making the liquid mixture an excellent choice for brain surgery with an open cortical wound where the blood brain barrier is already breached or, similar to a DBS electrode, the liquid mixture may be injected into the cortical (or deeper brain) tissue to connect to said structures while being able to stop bleeding at the source of the injury by using the liquid mixture as a blob 26 to glue any bleeding vessels and then, in so embodiments, supply current. Such a cured mass may be chosen as a liquid mixture/cured electrode or a liquid nonmixture in order to later connect to e.g. an electrical wire, allowing the liquid mixture 1 (initially used to stop a bleeding) to be used as electrode for neural stimulation, block or sensing applications.

In another embodiment the liquid mixture 1 may also be placed through a small skull bur hole in the skull through which a dispenser, e.g. a flexible tube, may dispense the liquid mixture, under ultrasound or angiographic visualization with the goal to form an contact pad 14 of liquid mixture 1 epidurally or subdurally. Such an contact pad 14, when stimulated by a signal generator 17, may be used to arrest seizure activity in patients. In contrast to other electrode technologies, the liquid mixture may be placed through a very small bur hole.

In another embodiment, the present invention comprises a connector 51 (e.g., clip, hole, matrix, mesh, sponge) for attachment to the output(s) of a signal generator 17 to connect mechanically and electrically with the liquid mixture, a wire, signal amplifier or any other signal applicator.

FIG. 57 is a representation of two types of connectors 51 to enable an excellent mechanical and electrical connection to the cured electrode.

Figure 58:
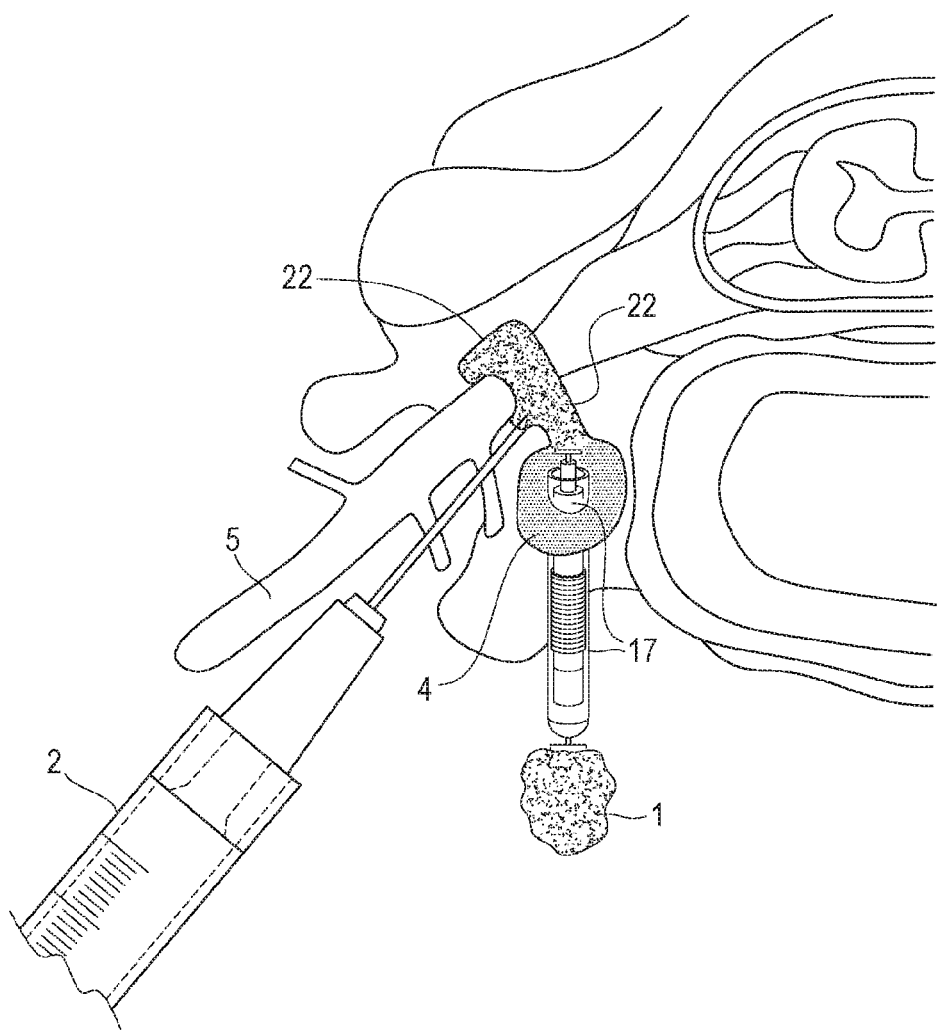
FIG. 58 is a representation of a neural signal generator encased with a ring-like portion of a cured electrode around a target and an anchor in a foramen (shown in FIG. 46A) for securing the neural signal generator in place. An additional cured electrode is connected to the neural signal generator at the end opposite the target.

Another embodiment of the present invention's ability to encase other electrical components achieves a mechanically and electrically stable interface to a signal generator 17 in liquid mixture 1 and nonmixture 9 as depicted in FIG. 58. FIG. 46A shows the anatomical structure including a foramen 34 before insertion of the signal generator and the liquid mixture and nonmixture. FIG. 58 is a representation of a signal generator 17 encased with liquid mixture 1 comprising a ring-like portion 22 and a nonmixture 9 as an anchor 4 in the foramen 34 (shown in FIG. 46A) for electrical and mechanical integration with the underlying neural tissue.

Incorporating signal generators as described herein provides yet another embodiment of a neural interface system, the signal generator providing the signal, and the cured electrode providing the mechanical and electrical integration with the anatomy and biology optimized during implantation for each specific patient. The present invention thus provides the capability of connection of a signal generator 17 to internal organs with highly flexible surfaces selected from the group consisting of bladder, stomach, gut, heart and liver as well as the ability to connect to neural plexi in the abdominal cavity and other locations of the body.

In another embodiment, the present invention comprises an electrically conductive mesh 24 wrapped around or covering a target. The mesh 24 is configured and shaped outside the body and does not require curing inside the body and the present invention also comprises an electrical and mechanical connection to a wire 10, allowing for an electrical interface to the target 5 encased in liquid mixture 1 insulated by the nonmixture 9.

Disclosed here are further advantages of the present invention comprising a liquid mixture injected into the body by optimizing electric lead-cell communication. The electrode-electrolyte-cell interface is established primarily between a liquid mixture and cured in the close vicinity of a bodily target. The electric signal of interest travels as an input or output in relation to a signal application This input or output, an electronic lead, is commonly made of metal or another highly conductive material, that passes through an opening in a perimeter which is the enclosure of a synthetic device capable of either generating an electric output waveform or capable of sensing an electric input waveform. As used herein, "waveform" means the change of voltage potentials of the lead vs. another lead or the outer shell or another distantly placed electrode (distant being a relative term, encompassing electrically the concept to be a location that is far enough to provide a common reference point to which an electronic signal may be measured against).

There is a difference in the environment in the body between an acutely and a chronically placed electrode lead (or other implanted synthetic material), and the environment changes over time to become more hostile the implanted object. Whenever an object is implanted into a living organism that the organism recognizes as a foreign object, the living organism will begin a process of attacking, concealing and expelling said foreign object. This process is a foreign body (object) rejection reaction and it incorporates an acute and a chronic inflammatory reaction of the living organism against the foreign object. As the foreign object is first attacked with macrophages and encased in fibrous tissue, the electrical interface impedance between the foreign object (i.e. an electrode, a lead, or the outside wall of a signal generator) and a stimulation target in the vicinity of the foreign object may increase.

As used herein, the electrode or the lead connected to a signal generator, other signal applicator or implant shall be sometimes referred to herein as an "electronic interface object" and sometimes as a prior art electrode, both being referenced as feature 40 herein. An increase in electrical impedance may result from (1) Encapsulation of the electrical stimulation (or sensing) sites on the electronic interface object with cells that form an added impedance between the e.g. metallic surface of the electronic interface object and the target; (2) "Walling off" of the electronic interface object by the body through growth of fibrous tissue, which in addition to the formation of cells, is further dried out by the body, further increasing the mechanical strength of the encapsulation while increasing the electric impedance between the cured electrode and the target interface cells of interest, or (3) Physically moving the electronic interface object by thickening the encapsulation, similar to the process of walling off, but with an active movement in one preferred direction and potentially away from the target interface cells of interest.

In one embodiment, the present invention enables extending an electronic interface object towards a cell (electrically and otherwise). As described herein, the cured electrode possesses the ability to change the path a neurostimulation current takes after an electrode has been in the body and the process of walling off has begun. The present invention allows the ability to correct bad electrode placement (such as in DBS or other rod-shaped electrodes for the PNS) by creating a better current path later on through the injection of the liquid mixture herein, for example, by placing a trace of liquid mixture on the opposite side of a stimulation site to re-route current to that site. Such an extension may be accomplished during the implantation procedure of the electronic interface object. Such an extension may be accomplished a day after the implantation procedure of the electronic interface object and thereby during the acute phase of the living organism's rejection (i.e. inflammatory) reaction. Such an extension may also be accomplished a few days to weeks after the implantation procedure of the electronic interface object and thereby during the beginning chronic phase of the living organism's rejection (i.e. inflammatory) reaction. Or, an extension may be accomplished at least three weeks after the implantation procedure of the electronic interface object and thereby during the stable chronic phase of the living organism's rejection (i.e. inflammatory) reaction. In fact, the extension may be accomplished even before the implantation procedure of the electronic interface object and thereby in preparation of the implantation of the electronic interface object.

In yet another embodiment, the present invention enables extending a chronically implanted electronic interface object towards a target 5. For this embodiment, the implanted electronic interface object shall be understood as having been placed several days to a few weeks prior with a stable inflammatory response having at least to some degree been walled off the implant from the surrounding environment. As a result of the beginning (or stable) chronic stage encapsulation, electric communication between the electronic interface object and the target is impeded or distorted in its communicated frequency components or otherwise changed from the level of communication quality that was present on the implantation day or potentially shortly thereafter. This loss in signal or communication quality may impact the amount of voltage a signal generator needs to provide in order to achieve a consistent or a predictable or a preferential response by the electrically interfaced target. This loss in communication quality may render the implanted electronic interface object useless or merely unreliable for its intended task. To address this problem, liquid mixture/cured electrode may be placed to extend the chronically placed electronic interface object electrically, mechanically (or otherwise) towards the target, either (1) by pushing the tissue formed by encapsulation closer to target, or (2) by breaching the tissue formed by encapsulation between the electronic interface object and the target, (3) by forming a bridge through (or across) the encapsulation between the electronic interface object and the target, (4) by pushing the target closer to the encapsulation formed around the electronic interface object, or (5) by two or more of the above combined.

In another embodiment, the invention enables reproducible stimulation, especially reproducible selective stimulation (i.e. by fiber type, fiber size or with effects of unidirectional activation) as well as partial and/or full nerve block by establishing a stable electrical interface between the electronic interface object and the target intended to be modulated with stimulation and/or block waveforms. In order to achieve an optimal electrical interface, a cured electrode may be placed by surrounding the nerves (axons, or nerve fibers as a whole) with liquid mixture in the PNS prior to placing a conventional lead (or conventional lead with conventional electrodes) next to said nerves, or it may be placed shortly thereafter. In order to achieve an optimal electrical interface, the liquid mixture may be placed to surround the target (axons, or nerve fibers as a whole) in the PNS after a conventional lead (or conventional lead with conventional electrodes) had been placed days or weeks, or months, or even years before next to said nerves. The liquid mixture may be placed in an open cut-down procedure, in a laparoscopic procedure, in an injection via syringe and needle or similar setup utilization based procedure, or otherwise facilitated by the liquid mixture.

Figure 59A:
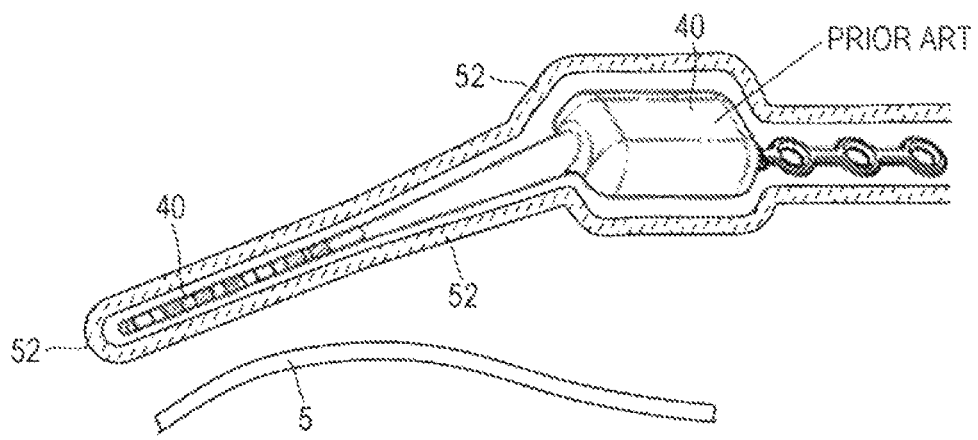
FIG. 59A, FIG. 59B and FIG. 59C are representations of how a cured electrode can reestablish successful electrical connection between a chronically implanted electronic prior art electrode and a target, where the prior art electrode has been walled off by the body's encapsulation by the body's fibrous tissue. 59A shows encapsulation of, and blocking signal from, the prior art electrode, 59B shows reestablishment of an electrical connection between the prior art electrode and the target by means of a cured electrode, and 59C shows encapsulation of the arrangement in 59B wherein electrical communication between the prior art electrode and target is maintained.
Figure 59B:
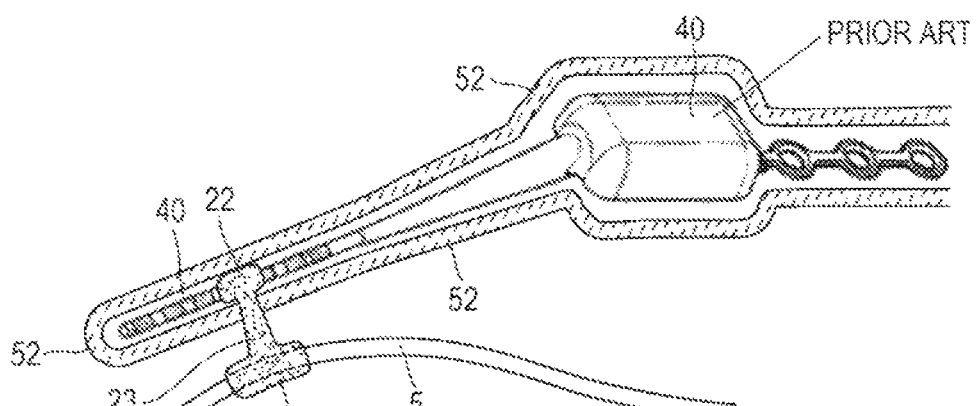
Figure 59C:
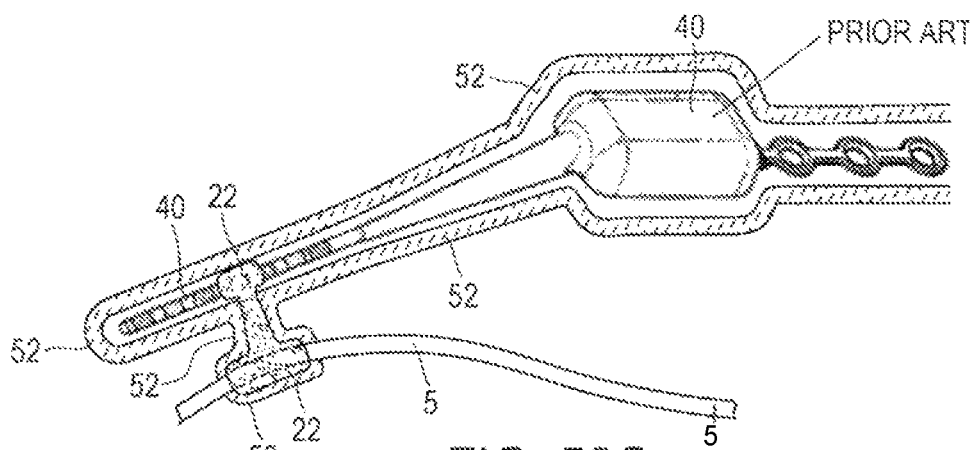
Figure 61:
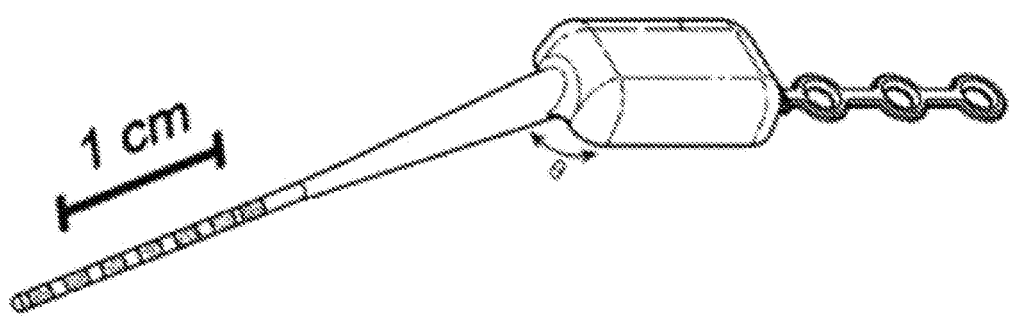
FIG. 61 shows a prior art electrode from U.S. Pat. No. 8,494,641 B2.

FIGS. 59A-C are representations of how a cured electrode can re-establish successful electrical connection between a chronically implanted electronic interface object 40 and a target 5, where the electronic interface object has been walled off by the body's encapsulation 52 by the body's fibrous tissue. FIG. 59 is a representation of an electronic interface object 40, here a prior art electrode from U.S. Pat. No. 8,494,641 B2 as shown in FIG. 61, surrounded by encapsulation 52. FIG. 61 is another example of a prior art rod-shaped electrode carrier/lead with disk electrodes as shown in U.S. Pat. No. 8,565,894 B2, which could also be encapsulated.

FIG. 59B represents a step in which a physician, in a revision procedure, has cut away the encapsulation 53, encircled each of the electronic interface object 40 and the target with ring-like portions 22 of a cured electrode and connected them with a wire-like portion 23, thus establishing a good electrical connection between the electronic interface object 40 and the target 5. FIG. 59C is the same as 59B, except that encapsulation 52 has now surrounded all the portions 22, 23 of the cured electrode and therefore the encapsulation 52 by the body's fibrous tissue has now provided insulation. The solution of placing the liquid mixture/cured electrode provides a means for the waveform energy to travel from the SIGNAL GENERATOR to the target nerve again using the path that the cured electrode provides.

Reproducible stimulation, especially reproducible selective stimulation (i.e. by fiber type, fiber size or with effects of unidirectional activation) as well as partial and/or full nerve block may require a stable electrical interface between the electronic interface object and the neural cells intended to be interfaced/modulated with stimulation and/or block waveforms.

The present invention has beneficial effects of increasing signal integrity and preservation. Based on the activating function developed by Frank Rattay, the further away an electrode (or open/uninsulated end on a lead) is from a target, the larger the voltage must be in order to electrically interface with the voltage gated channels of that cell. The activating function is a mathematical formalism that is used to approximate the influence of an extracellular field on an axon or neurons and is a useful tool to approximate the influence of functional electrical stimulation (FES) or neuromodulation techniques on a target. It predicts locations of high hyperpolarization and depolarization caused by the electrical field acting upon the nerve fiber. As a rule of thumb, the activating function is proportional to the second-order spatial derivative of the extracellular potential along the axon. By reducing the distance between an electrode (electrode contact/lead contact/exposed electrode) intended to electrically interface with a target, various advantages arise:

(1) Signal Preservation
   (a) Electrical signals traveling to and from the target are received with a reduction of distortion, at a higher SNR and likely of higher signal quality and integrity. This may be achieved with the aid of an additionally placed cured electrode.
   (b) Signal strength may be preserved better with the aid of an additionally placed cured electrode.
(2) Lower Current Densities
   (a) Lower current densities at the electrode-electrolyte interface may be achieved with the aid of an additionally placed cured electrode which allows a reduction in voltage needed to convey the neuromodulation effect reliably, thus requiring lower voltages to be applied when the electrode is used as an output medium to transmit signals to a target.
   (b) Lower current densities passing through tissue in the vicinity of the (conventional) electrode in order to reach the specific target.
   (c) Lower compliance voltages may be needed by an output unit in order to drive the lower currents needed to achieve the reproducible neuromodulation effect, thereby further reducing the probability of high current densities either through tissue or at the electrode-electrolyte interface.
   (d) Lower levels of charge per phase and lower levels of charge density per phase may be required if the cured electrode is placed to overcome a distance and/or encapsulation issue with chronically placed conventional electrodes/electrode-lead combinations etc.
(3) Smaller Battery Requirements, and Less Issues with Battery Life
   (a) With a reduction in voltage requirements thanks to decreased electrode-cell (as well as variations thereof such as electrode-neuron, electrode-axon, lead-axon, or lead-neuron) distance, meaning thanks to an increase in proximity and/or thanks to a cured electrode bridging through (or across) one or more layers of encapsulating tissue that may have been in place between the electrode and the target (as well as variations thereof), there may be a reduced need for stored charge in a battery.
   (b) This reduction in stored charge may enable the use of smaller batteries, it may enable longer discharging intervals and time spent before a battery may need to be re-charged and it may enable longer battery life before a battery reaches its end of life due to the overall number of charging/discharging cycles or due to the depth that a battery was discharged to (optimal charging levels for typical batteries used in implantable devices such as lithium ion batteries are often in the range of 70% to 30%, whereas charging them up to maximum capacity (95+%) or discharging them to being almost empty (down to i.e. 15% of capacity or less) may be damaging to the long term lifetime of the battery).

(4) Smaller Coil Size Needed to Provide the Inductive Charge of a Transcutaneously Powered Device
  (a) With a reduction in voltage requirements thanks to decreased electrode-cell (as well as variations thereof such as electrode-neuron, electrode-axon, lead-axon, or lead-neuron) distance, meaning thanks to an increase in proximity and/or thanks to a cured electrode bridging through (or across) one or more layers of encapsulating tissue that may have been in place between the electrode and the cell (as well as variations thereof), there may be a reduced need for electrical energy to be transmitted via coil.
  (b) The reduction in electrical energy required to operate an implantable device (with or without the additional presence of a charge storage device on board such as a battery or a capacitor) may enable the use of smaller receiver (and/or transmitter) coils.
  (c) With smaller coils being used to transmit the energy, smaller form factors may be possible for implantable devices. The key is a more efficient electrode-cell transmission.

(5) Possibility to Retain Enough Power in a Capacitor to Drive Stimulation or Block
  (a) With a reduction in voltage requirements thanks to decreased electrode-cell (as well as variations thereof such as electrode-neuron, electrode-axon, lead-axon, or lead-neuron) distance, meaning thanks to an increase in proximity and/or thanks to a cured electrode bridging through (or across) one or more layers of encapsulating tissue that may have been in place between the electrode and the cell (as well as variations thereof), there may be a reduced need for stored charge in a capacitor.
  (b) Capacitors may be used instead of batteries to store the charge in an implantable device while retaining a long enough application of the device without the drawback of degradation of the charge storage over time to the same tune as is known from batteries.

Figure 60:
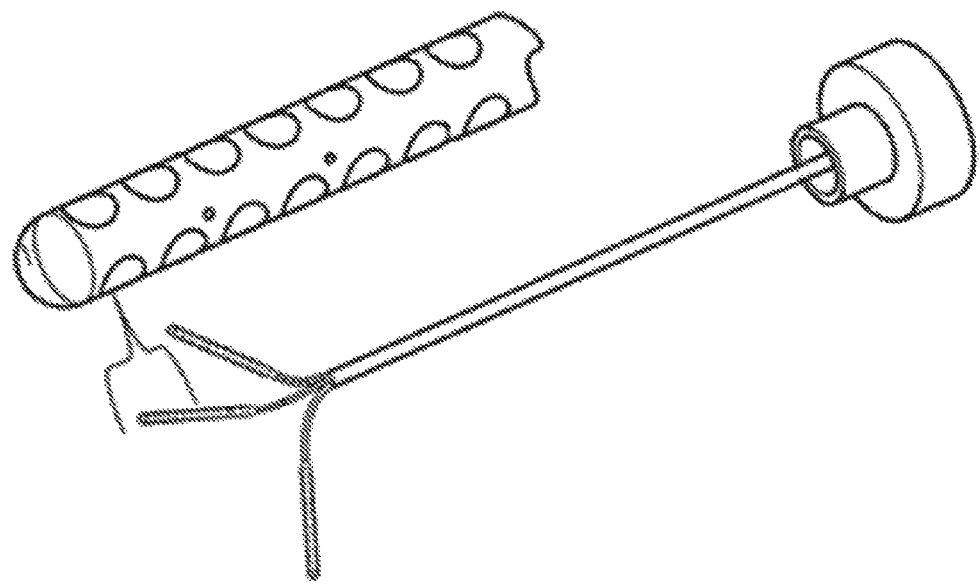
FIG. 60 is another example of a prior art rod-shaped electrode carrier/lead with disk electrodes as shown in U.S. Pat. No. 8,565,894 B2.

(6) Transforming a Wire into a Cuff
  (a) Some implanted neuromodulation devices may utilize electrodes placed on the outside of a lead, showing the appearance of DBS-style electrodes with electrodes placed either as circumferential ring or as disk-shaped electrode next to other non-disk or non-ring shaped electrodes, e.g. faceted lead technology (FIG. 60-61).
  (b) All of these electrodes still only sit on the outside of a rod-shaped structure.
  (c) None of these electrodes are encasing, enclosing, cuffing, or otherwise surrounding a nerve (such as a cuff would around the vagal nerve for example).
  (d) As these rod-shaped structures become encapsulated by the body's fibrous tissue, they may be physically moved, as the body first encases a foreign object and then contracts the cells while drying them out, thereby being able to mechanically express (expel) a foreign object from the body over time.
  (e) All these encapsulation reactions have a high likelihood of decreasing the SNR, increasing the voltage requirements for a stimulation to occur reliably and potentially making it impossible for a successful neuromodulation to occur if the rod-shaped lead with electrodes on-board has been walled off sufficiently or moved away from the target (neural) cell or both in conjunction.
  (f) Furthermore, the rod-shaped (lead with integrated electrodes) structure itself may have been placed sub-optimally with respect to the target (nerve) cells. It may have been originally too far away, it may be at an unfortunate angle, or it may be that movement of the body (of the implanted person) may impact the impedance between the electrodes and the target cells.
  (g) In either way, the cured electrode herein may be placed via injection, open cut-down, via a laparoscopic procedure or otherwise to facilitate a low-impedance bridge between the electrodes and the target cells of interest. This cured electrode may be placed through encapsulating tissue and surround either the nerve, or the rod-shaped structure, or both, like a cuff.

(7) Achieve KHFAC or Neuromuscular Junction ("NMJ") Nerve Block with Help of the Cured Electrode
  (a) While a rod-shaped electrode (FIGS. 60 and 61) is able to achieve a stimulation effect on a neural cell, it is not very likely to achieve a nerve block effect as the emitted electric field is neither homogeneous nor stable over time.
  (b) By surrounding a nerve that is intended to be blocked with a cured electrode (i.e. via placing the cured electrode around said nerve), one is able to ensure that the electric field applied to the nerve is either uniform, or homogeneous, or relatively stable over time (less affected by the effects of encapsulation than a non-cuff approach), or two or all of these three in combination.

(8) Interface Means for Neuromuscular Junctions (NMJs)
  (a) NMJs generally require a wire to be interwoven (threaded) into the muscle in close proximity to where the nerve enters the muscle. By placing liquid mixture, which cures to an electrode, at that interface (with or without the threading of the wire being utilized) a better energy transfer may be achieved at lower amplitudes required to achieve neuromodulation. When the body's encapsulation has insulated a prior art implant's interface with the bodily target so much that electric stimulation waveforms generated by the implant do not achieve the desired response by the target, placing a cured electrode around or on the contact(s) of the signal generator (or generator's lead) and placing the same cured electrode around the target nerve, or just in the close proximity of the target nerve (a cuff may not always be needed) now allows for the electric stimulation waveforms generated by the implant do not achieve the desired response by the target nerve nearby. The newly forming encapsulation encases the cured electrode around the nerve and around the prior art electrode(s) of the signal generator without again adding so much insulation that communication were hindered sufficiently.

Immunoreactive Section

The body is constantly remodeling and therefore presents the unique challenge as well as opportunity for implanted materials to have differing properties over a specified time course to achieve different goals. Furthermore, with local release or modification of materials, it may be possible to achieve localized regional effects at different locations of the same cured electrode.

For a cured electrode in one embodiment, it is possible to accelerate and increase remodeling of the local environment to produce or accelerate a fibrous encapsulation 52 around the cured electrode 1, thereby forming a naturally occurring insulating layer around the cured electrode to isolate it from surrounding tissues that may be activated as collateral during stimulation. It should be noted that the encapsulation of an electronic interface object from fibrous tissue does not inherently produce a high impedance, but rather it acts to physically separate the tissue from the electrode by a given distance, thereby decreasing the electric field by a factor of the inverse square of the distance. Thus, the present invention can produce a controlled inflammatory response ("CIR"), which term means an increase of inflammation leading to a predictable thickness of encapsulation.

The goal of mediating the inflammatory response may vary but can be used to 1) achieve encapsulation 52 for the cured electrode serving as a wire lead, 2) achieve encapsulation 52 for a cured electrode serving as an contact pad 14 so as to prevent collateral activation of nearby subcutaneous c-fibers during transmission from the electrical stimulus from an external stimulator, through the contact pad 14, 3) downregulate the inflammatory response at the intended nerve interface to prevent fibrous encapsulation between the nerve and the electrode, 4) for use with a biodegradable carrier system so as to cause a progressive "tightening" of the conductive elements 6 as the cured carrier material (e.g., hydrogel) degrades. The encapsulation 52 (i.e, scar tissue) thus squeezes the conductive elements of the cured electrode together.

Modulation of encapsulation may be achieved through the addition of cells and other inflammatory mediators selected from a group consisting of: (1) cells (e.g. mesenchymal stem cells that are known to secrete anti-inflammatory molecules), (2) inflammatory mediators (e.g., minocycline or dexamethasone, having precedence in the demonstration of lowering the glial scar formation with CNS implanted devices, (3) NSAIDs (non-steroidal anti-inflammatory drugs) and the like.

Nonconductive materials may be coupled to conductive materials, as described herein. Disclosed is a method of dispensing liquid mixture 1 around a target, followed by the dispensing of liquid nonmixture/nonconductive layer 9 with and without deploying anchors 4 is described, comprising: (1) Connecting the liquid mixture (which cures to an electrode) to a target, (2) insulating the liquid mixture or cured electrode, using similar material (silicone based liquid mixture is covered with silicone based liquid nonmixture; and the same is true for fibrin glue mixtures, cyanoacrylate glue mixtures and the like), and (3) optionally, the nonconductive layer may be used to further anchor the cured electrode to the target or to surrounding structures or just the local anatomy nearby the cured electrode.

The present invention, in one embodiment, may use current to change the carrier material of the liquid mixture/cured electrode, or the neighboring environment, as follows:
(1) Driving currents to cause partial dissolution of the material by means of:
   (a) Material changes chemical composition, or
   (b) Fast cycling with kHz frequency to not cause nerve activation but cause partial dissolution of the carrier
(2) Changing the thickness of the encapsulation with currents
   (a) increasing or decreasing encapsulation with application of kHz frequency, or
   (b) increasing or decreasing encapsulation with application of MHz frequency

Powder Mixtures and Hemostasis

Combining a hydrophilic polymer and potassium ferrate can provide a mixture that is able to form a stable scab when applied into a wound first under pressure. When this mixture is combined with conductive elements a powder mixture results. These powders are available as prescription-free, over the counter solutions for small external cuts and bruises. Upon contact with blood (as well as chicken meat), the powder forms a sticky compound that keeps mechanically fused biological tissues mended as well as blood vessels coagulated. A mixture of hydrophilic polymer and potassium ferrate can also be added to another carrier material as a hemostatic agent.

Styptics cause hemostasis by contracting blood vessels. Anhydrous aluminum sulfate is the main ingredient and acts as a vasoconstrictor in order to disable blood flow. The high ionic strength promotes flocculation of the blood, and the astringent chemical causes local vasoconstriction. Anhydrous aluminum sulfate powder mixed with a conductive metal powder may be seen as yet another embodiment.

Chitosan hemostats are topical agents composed of chitosan and its salts. Chitosan bonds with platelets and red blood cells to form a gel-like clot which seals a bleeding vessel. Unlike other hemostat technologies its action does not require the normal hemostatic pathway and therefore continues to function even when anticoagulants like heparin are present. Chitosan is used in some emergency hemostats which are designed to stop traumatic life-threatening bleeding. Their use is well established in many military and trauma units.

Kaolin and zeolite are minerals which activate the coagulation cascade, and have been used as the active component of hemostatic dressings (for example, in QuikClot).

All of the above may be provided in solution or suspension or as powder and mixed with conductive elements.

As powders may express the mechanical behavior of a high-viscosity paste prior to curing, a simple syringe/needle system may not be sufficient for delivery/injection, especially when a small gauge needle is utilized. In these cases, the needle, the syringe, the powder column inside the syringe or needle may be vibrated at frequencies of 600 to 60,000 Hz. Vibrating the structure or the mixture can allow more viscous material to achieve a lower effective viscosity (similar to how sand can flow similar to a liquid when vibrated). This approach may be utilized for both, pure particle mixture approaches as well as low-viscosity powder mixtures.

The dispenser may not be a basic syringe and needle system for such a powder based mixture, but the conductive material may instead come in small capsules that are opened at the target for connection or a vibration (similar to the one explained for the amalgam) may be utilized in a syringe based dispenser.

Dispensers

Figure 62:
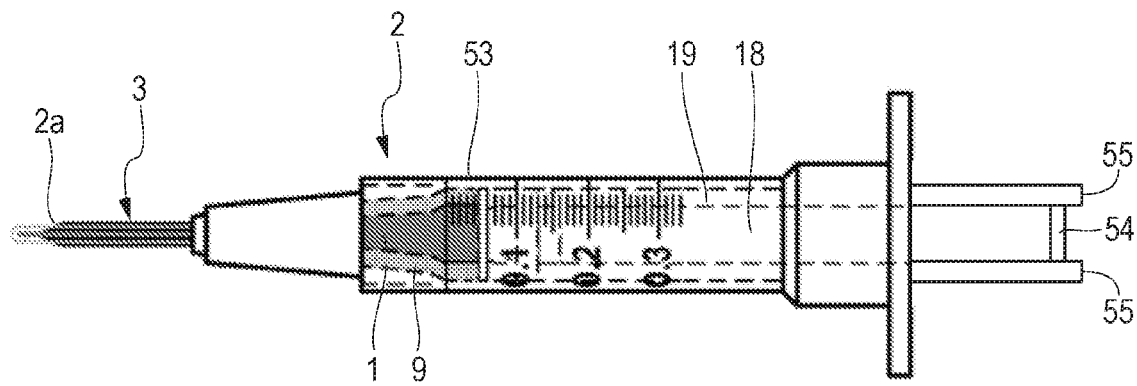
FIG. 62 is a side view of a two-chamber dispenser comprising a syringe body comprising two coaxial chambers, a first chamber containing liquid conductor and a second chamber containing liquid nonconductor, said second chamber encircling said first chamber, a first plunger fitted for the first chamber, and a second plunger fitted for the second chamber, a coaxial needle with an exit point for both chambers.
Figure 62A:
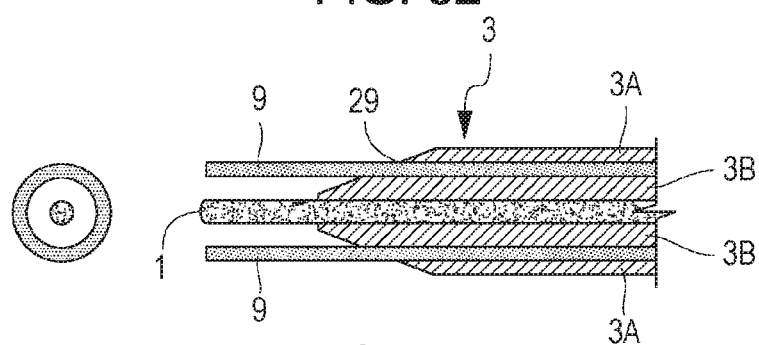
FIG. 62A is an enlargement of a coaxial needle tip in cross section, showing the outer wall of the needle enclosing an outer needle lumen containing liquid nonconductor and extruding it beyond the exit point, the wall of the inner needle lumen extruding liquid conductor also beyond the exit point. Additionally, a pattern of extrusion is shown.

Placing an insulated wire-like structure is feasible with a multi-chamber dispenser 2 which can simultaneously or sequentially, or alternating between the two, injects liquid mixture and/or nonconductive carrier material and/or a continuous wire. FIG. 62 is a diagram of a two-chamber dispenser 2 comprising a syringe body 53 comprising two coaxial chambers, a first chamber 18 containing liquid mixture 1 and a second chamber 19 containing liquid nonmixture 9, said second chamber encircling said first chamber, a first plunger 54 fitted for the first chamber, and a second plunger 55 fitted for the second chamber, a coaxial needle 3 with an exit point 29 for both chambers. FIG. 62 is an enlargement of the coaxial needle 3 in cross section, showing the outer wall of the needle 3A enclosing an outer needle lumen containing liquid nonmixture and extruding it beyond the exit point 29, the wall 3B of the inner needle lumen extruding liquid mixture beyond the exit point 29. To the immediate left of the exit point in FIG. 62 is the pattern of extrusion of liquid mixture (inner circle) surrounded by liquid nonmixture (outer circle). 62B is the same as 62A, except that wire 10 is being extruded from the inner lumen. In one embodiment the inner chamber for the liquid mixture is surrounded by the chamber for the nonconductive carrier material, i.e., they are coaxial. In one embodiment, the dispensing needle comprises two channels which are coaxial, the inner lumen being for dispensing the liquid mixture and the outer lumen for dispensing the nonconductive carrier material, and the inner channel of the needle communicating fluidly with the inner chamber and the outer channel of the needle communicating fluidly with the outer chamber. Each plunger may be activated separately or they may be activated simultaneously. When the first chamber's plunger is activated separately, only the liquid mixture is injected into a bodily tissue and, upon curing, this material will be a cured electrode without exterior insulation. When the second chamber's plunger is activated separately, only the nonconductive carrier material will be injected and will cure as a nonconductive structure, such as for anchoring. If both plungers are activated simultaneously, then both chambers will dispense material and the liquid nonmixture will surround the liquid mixture and, when cured, will take the form of an insulated wire-like structure, having a conductive middle and a nonconductive outer covering.

In another embodiment, the present invention comprises a dispenser 2 comprising two separate chambers, each chamber fitted for a plunger 54, 55 to dispense from one chamber a liquid mixture comprising a carrier material and conductive elements and, from the other chamber, a nonconductive carrier material which is an insulator. The two chambers can next to one another in any configuration or relation to one another.

Figure 62B:
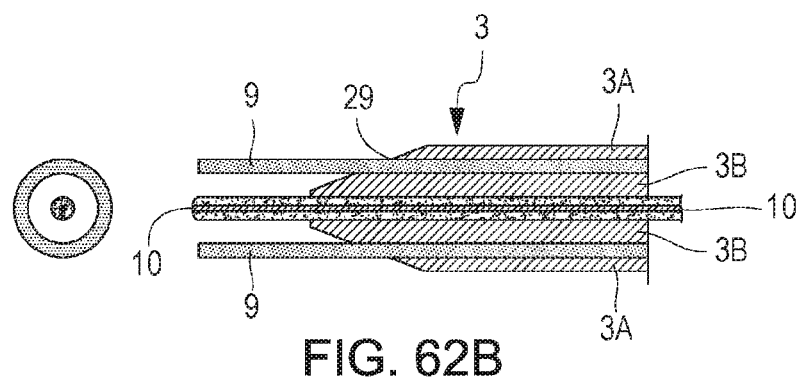
FIG. 62B is similar to FIG. 62A, except that a wire is also being extruded from the inner lumen.

In another embodiment, two separate syringes can be filled with different materials which can be extruded into a single lumen needle or into a separate coaxial needle like the one in FIG. 62-62B.

In one embodiment, the dispenser further comprises the attachment of a fiber that conducts light to the injection site to provide illumination for the surgeon (during laparoscopy) or with a different light using e.g. blue or UV to cure the just dispensed liquid mixture or nonconductive carrier material.

Mixing fluorescent or radio-opaque dyes into the insulator enables the surgeon to verify that there is no breakage in the insulation around the mixture. Utilizing such fluorescent or radio-opaque dye in the liquid mixture can help the physician to verify proper application of the glue interoperatively, and even years post-op when radio-opaque dye or particles are part of the liquid mixture.

In one embodiment the dispenser is a device that holds the target in place or that is held against the nerve. The dispenser can inject the liquid mixture at predetermined angles and to predetermined depths into or near the nerve. The dispenser is further able to dispense from both the inner and outer chambers while the dispenser is being extracted from the bodily tissue, thereby sealing or coagulating any potentially formerly nicked blood vessels, and also creating a linear structure from the target to the subcutaneous region.

Needle sizes may vary based on the exact composition of the liquid mixture, e.g., viscosity and other physical properties of the liquid mixture such as the size and shape of the conductive elements, as well as the anatomical environment of placement. The needle may be designed to have a sharp edge to pierce the encapsulation that is present around a chronically implanted electrode, or electrode/lead combination, or electrode/stimulator, or electrode/lead/stimulator combination. Or, the needle may be designed to have a blunt edge to minimize risk of damaging vital anatomical structures. The needle may also have a retractable or otherwise moveable blade to pierce the encapsulation that is present around a chronically implanted electrode, or electrode/lead combination, or electrode/stimulator, or electrode/lead/stimulator combination. The needle may have an opening on the side to facilitate the placement of liquid mixture or nonmixture at an angle to the insertion tract of the needle. The needle may be formed as a continuation of the syringe, of the same material or of a different material and be or not be detachable. The needle may have elements of these points described above in combination.

Figure 63:
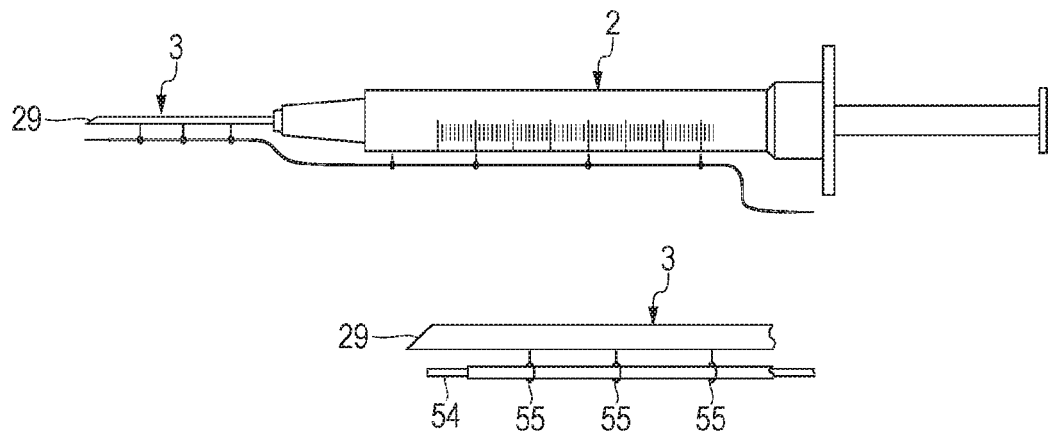
FIG. 63 is a side view of an embodiment of the dispenser comprising an insulated stimulator wire with an uninsulated electrical stimulator which is near the exit point of the dispenser.
Figure 64:
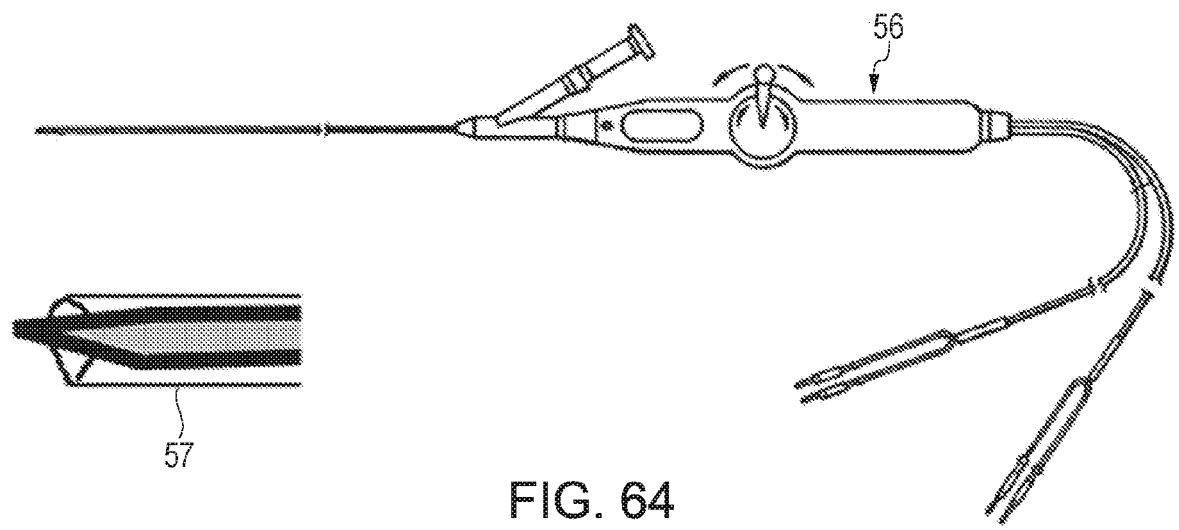
FIG. 64 is a diagram of one embodiment of a dispenser as a catheter for dispensing liquid conductor or nonconductor.

In another embodiment, the dispenser comprises an insulated stimulator wire 54 with an uninsulated electrical stimulator 15 which is near the exit point 29 of the dispenser as shown in FIG. 63. The stimulator wire's other terminal is connected to a power source. The liquid mixture and nonconductive carrier material are injected and the electrical stimulator 15 can provide electrical current to the liquid mixture or to the target 5, to determine if current flows to a target. The feeding of the wire 10 may be similar to a fishing rod feed the fishing line to the hook from a spool (FIG. 63). In this embodiment the electrical stimulator 15 may contact the blob 26 of liquid mixture or nonconductive carrier material which has been injected, formed and molded at or around the contours of the target. The liquid mixture establishes the connection of the wire to the target with a large surface are and good mechanical coupling. Using the dispenser, the liquid mixture and the stimulator wire can both be guided to the connection site at the nerve.

FIG. 63 depicts one embodiment of the dispenser with a stimulator wire, i.e., a syringe filled with liquid mixture with wire guides 55 attached. Wire is threaded through wire guides to be able to contact the target directly or an electrode placed around or near the nerve that the wire is being contacted to. This provides the ability to test the electrical connection of the injected material with the target. The stimulator wire may then be similar to the traditional electrode lead.

Mechanical stability is provided by extruded wire (not the stimulator wire described above) while interface to the body is provided by the blobs 26 of liquid mixture or nonmixture (similar to how a spider dispenses a web) and then places liquid mixture on key points onto the web). Extruded wire with blobs is placed at various points, so that it approximates "blobs on a string." Extruded wire can be fed external to the needle or through the exit point 29, thus part of the dispenser. Wire can be extruded through the same needle tip and only when the liquid mixture or nonmixture is dispensed, a blob is formed along the wire. Wire can be extruded through the needle of the dispenser, only pulling liquid mixture or nonmixture along when pushed out in parallel to the extruded wire. When the wire is pushed out alone then no liquid mixture or nonmixture is placed around the wire. Liquid mixture or nonmixture is then only placed on locations were the wire is to be connected to the tissue electrically and mechanically.

The dispenser's electrical stimulator 15 is able to provide current in order to verify proper liquid mixture or nonmixture flow or placement either before dispensing, during dispensing or after dispensing. The needle itself may be conductive and be connected directly to a power source (FIG. 63). The liquid mixture itself may have a connection through the syringe/dispenser to verify that the dispensed liquid mixture is indeed connected and in electrical communication with the target. This allows the physician to prevent bad connections during the dispensing process. In one embodiment, the dispenser has the ability to verify correct placement location near or inside the target before and during injection. The dispenser in one embodiment thus has the ability to both sense as well as stimulate a target by connection to an amplifier, a display, and a signal generator. Optionally, a secondary electrode may be placed distally or proximally to the injection site to be able to listen to compound action potentials or single fiber activity at the injection site prior and during inject. In another embodiment the dispenser can deliver anodic current to contract blood vessels such as arteries and arterioles that respond to anodic current with contraction, thereby aiding in hemostasis during the needle (or other dispenser) injection and extraction process.

In another embodiment the dispenser automatically dispenses during retraction from the target. If the dispenser retracts in an automated fashion from the tissue into which it is injecting liquid mixture then the thickness of the blobs or strings (wires) of liquid mixture may be varied based on the retraction speed of the needle (or other dispenser tip) in proportion to the ejection speed of the liquid mixture. The retraction may be achieved by the following steps and configurations:

(1) The dispenser comprises a sensor for acceleration (e.g., accelerometer) and uses this information to predict extraction speed.

(2) The dispenser comprises a pressure sensor for measuring pressure applied during the injection of the liquid mixture while the dispenser is being extracted. The pressure information is used to predict extraction speed.

(3) The dispenser comprises a sensor (mechanical or via laser) to determine a distance to skin measurement to acquire the information to predict extraction speed.

(4) All or some of the above combined.

(5) A visualization system from the outside is capable of displaying an image of the liquid mixture comprising radio-opaque particles. This display may be used to determine injection speed to allow a sufficiently thick line. The display information may be fed to an analysis device running visual signal analysis (e.g. via ImageJ) able to determine the thickness of the injected liquid mixture. This information may be fed back into the dispenser automatically and control the injection speed.

If liquid mixture is being placed as the dispenser is being retracted a specific path the dispenser may be anchored at or near the location of dispensing to ensure that there is no relative motion due to pulsing tissue, heartbeat, breathing or any other movement. The physician may select the desired thickness of the blobs or strings of liquid mixture. The surgeon may provide the information about the tissue into which the liquid mixture is being injected. This matters because fatty tissue for example possess significantly less resistance than do tight connective tissue or various muscle tissues. In another embodiment, a component providing pressure measurement during injection is able to help with a heightened accuracy during the injection. Injecting liquid mixture into more dense tissue will give different pressure results during injection than will more soft tissues. The liquid mixture may be visualized via ultrasound, angiography, or MRI as applicable.

In another embodiment, the dispenser comprises a catheter 56 to inject the liquid mixture to a target. This embodiment of the invention comprises:

(1) A catheter with control rods (or other means) inside.

(2) Exit point 29 holds a retractable needle 57 (retractable; may be retracted into the shaft when not in use to dispense liquid mixture into target) to dispense the liquid mixture.

(3) An electrical stimulator 15 is located near the exit point 29 for verification of proper injection location as well as verification of successful modification of injection.

(4) Retractable needle 57 must be electrically conductive to verify correct injection location with the application of stimulation during the injection process and needle communicates with a power source and sensor in the body of the catheter.

(5) Catheter optionally has the ability to electrically stimulate the tissue prior to and during placement, (6) Catheter optionally has means to inject liquid mixture or nonmixture and other additives such as resorbable materials, immunoreactive and hemostatic materials and the like.

(8) Catheter optionally has the ability to dispense a fluorescent or radio-opaque dye to improve visualization of correct injection location prior to, during and post injection.

FIG. A59-0 is a diagram of one embodiment of a dispenser as a catheter for dispensing liquid mixture or nonmixture herein.

In another embodiment the dispenser 2 uses vibration to aid with the dispensing process. Vibration is applied to the column of liquid mixture and/or nonmixture which allows the injection of higher density mixtures of liquid mixture. Vibration further helps to keep the liquid mixture more uniform provides finer or less fine particles during injection. The vibration can be applied throughout the entire dispenser, or just the needle, or just to the column of the liquid mixture (e.g. from the side or the back of a syringe). The vibration can be tuned to specific liquid mixture properties. The vibration, depending on the chosen frequency, can make the liquid mixture appear stiffer or more pliable during dispensing. Vibration allows a very fine needle to dispense rather highly viscous liquid mixture having large conductive elements. Vibration applied at the tip of the dispenser helps to achieve blunt separation of tissue plains.

One embodiment of the dispenser enables injection of liquid mixture or nonmixture into a nerve. An example of this embodiment uses a smaller diameter needle, e.g., 27 gauge (outer diam. ~0.4 mm), to insert into and place material inside a nerve. In one embodiment, the dispenser comprises elements such as e.g. a rounded tip or a source for pressurized air for blunt separation of tissue. Another capability in one embodiment is a pressure sensor to measure the pressure applied during injection to ensure that the blood supply inside the nerve is not being obstructed as the injected material increases the pressure inside the nerve and any intra-neural pressure in the PNS above 60 mm Hg quenches off blood supply to the structures of the nerve that may be distally to the injection site.

In another embodiment the dispenser is enabled for the injection around a nerve, as in a larger diameter needle (see FIG. 14A-F) 12 gauge (outer diameter 2 mm), to inject liquid mixture around a nerve, especially for higher viscosity material. The dispenser also comprises elements for blunt separation of tissue. Such elements may be spreaders, blunted scissor tips that can be opened and closed with a by-wire mechanism (similar to elongated alligator slips)

An embodiment of the cured electrode is produced by dispensing and securing the liquid mixture/cured electrode to a target by covering the target in a crisscross fashion similar to how a spider attaches a web to a twig. Spiders need their webs to be attached to surrounding structures in a mechanically very stable way in order for the web to withstand forces resulting from wind on the web and the surroundings (twigs of a tree the web is attached to) as well as the force when an insect is caught and decelerated by the web. Spiders crisscross the twigs with their web. The present invention may be dispensed in vivo to cure in the shape of a mesh, as in FIG. 37. The liquid mixture also may comprise a substance which "etches" an insulator off the wire so that the system itself becomes one fully insulated wire that then is only de-insulated where the blobs are placed.

In one embodiment the dispenser can dispense pellets or capsules of liquid mixture mixed on or near the target inside the body to have the ability to use materials that require very little time to solidify (or otherwise transform to form a mechanically more stable structure). One embodiment of the present invention provides a system that utilizes capsules or pellets that can be applied laparoscopically very close to the connection site. Pellets are loaded into a dispenser and then placed where needed. Capsules may comprise either one or two components, in the case of the latter having a separating wall in-between them and the wall may be crushed or pierced to initiate mixing. The pellets or capsules have application, for example, in the CNS, e.g., connecting to a DBS electrode sitting next to the stimulation target and is able to stimulate the target correctly when the pellets of liquid mixture connect the DBS electrode to the stimulation targets. They also have applications in the PNS (e.g. to form a cuff-like conductive structure around the nerve and behind the nerve or inside a nerve), or for placement in the abdomen in or near an organ by placing pellets or capsules next to each other that then form a conductive path to a wire, a signal generator or similar.

The dispenser also, in another embodiment, possesses the ability to provide UV or blue light for curing at the target in bodily tissue. If the material is a UV/blue light cured compound (like dental acrylic) then the dispenser may comprise a syringe with a UV/blue light LED on the top of the needle, and this can be coupled with visualization through an endoscope.

FIG. 63 depicts the dispenser 2 in one embodiment comprising a light 58 such as an LED attached to the needle 3. The light is positioned near the exit point 29 and can be connected to a power source by means of a wire attached with wire guides 55 (similar to the manner as described regarding FIG. 63).

In another embodiment, the dispenser has the ability to provide blunt dissection, using either arms that can spread tissue or pressurized water or pressurized air to bluntly separate tissue near the tip of the dispenser and hold the tissue separated may be an advantage. The dispenser can comprise an element (e.g., rounded tip) which can provide blunt dissection (thereby opening the path around the nerve) and an element that can keep a cavity open for the material to fill around a nerve (i.e., holds open a channel for the material to flow in around the nerve); the blunt dissection being provided by blunt tips like on blunt scissors. In another embodiment, instead of arms that spread tissue along tissue plains, blunt dissection may be achieved with pressurized saline or pressurized air. Once the dissection through muscle plains and other tissue plains reaches the nerve, the nerve can be freed from its surrounding tissues with such a technique without injuring the nerve. Another embodiment can create an air filled cavity near the target by pumping air out near the target and blocking the escape path out the keyhole incision with approaches such as a balloon catheter. Such a catheter comprises a balloon a few (~10 to 15) centimeters recessed from the tip of the catheter to be expanded and thereby block the artery or vein that it is passed inside. If the balloon inflates wide enough in a small keyhole incision that was created laparoscopically then it can hold air or saline inside the cavity injected from the tip of said catheter. Such a cavity created around the nerve the nerve to be freely suspended once freed from surrounding tissues and thereby provide an easy way to form a molded cuff from injectable material around the nerve.

Figure 66:
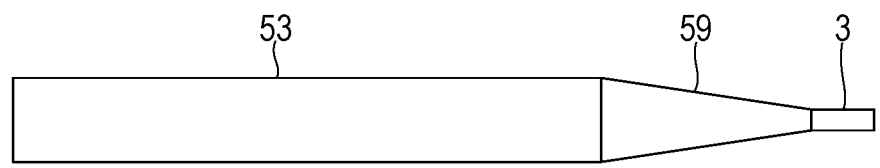
FIG. 66 is a diagram of a conical frustum for graduated diameter decrease for a dispenser.

Another dispenser embodiment comprises a syringe-needle-system with a conical frustum 59 near the end of the chamber of the dispenser transitioning to the needle 3. As the liquid mixture or nonmixture is being pressed out of a large diameter syringe into a smaller diameter needle, pressure points can arise at each location where the diameter of the dispensing column decreases. Such high pressure points may lead to a separation of the liquid carrier material and the conductive elements. Therefore, the ideal flow for most liquid mixtures and nonmixtures involves plug flow, or uniform flow rate, across the entire cross-sectional area of fluid being delivered (i.e., flow rate at the wall is the same as that in the center). By gradually decreasing the diameter of the dispensing column from the syringe, or another version of the primary container during storage and/or dispensing, diameter to the needle diameter, steps between the various diameters are avoided. FIG. 66 is a diagram of a conical frustum for graduated diameter decrease for a syringe. The result is a typical decrease in diameter tested successfully at a decrease from 5 mm inner syringe diameter to 1.5 mm inner needle diameter over the distance of 1.5 cm, and other geometries are also available. The gradual decrease in diameter avoids the step function and dispensing of more grainy and thicker liquid mixtures is more easily accomplished. This method is further improved when ultrasound or mechanical vibration are added to the syringe, either to the column of liquid mixture on nonmixture inside or to the syringe itself. Vibration makes the conductive elements behave more as elements of a liquid, allowing the entire composite to advance without separation from the large inner diameter needle to the smaller inner diameter tip of the needle and eventually the syringe.

In other embodiments the dispenser comprises means for vibration. Vibration has been tested and shown to aid in mixing the carrier material with conductive elements and keeping the carrier material mixed thoroughly with the conductive elements while the liquid mixture is in a liquid phase. Such mechanical vibrations may come from a sound transducer, an ultrasound transducer or a mass out of midline (balance) able to slightly move the carrier material or conductive elements at a relatively high frequency (more than 20 times per second, in one embodiment 50 to 100 Hz). This vibrating column is able to pass through smaller diameter needles and overcome larger changes in inner diameter over travel distance inside dispenser and has even been shown to overcome small step function changes in the dispenser chamber.

Controlling viscosity of the liquid mixture also has been shown to minimize separation of the conductive elements from the carrier material. As the liquid mixture is being pressed out of the larger diameter syringe into the smaller diameter needle, pressure points may build up at each location where the diameter of the dispensing column decreases. Such high pressure points may lead to a separation of the less-conductive carrier medium and the more conductive particles added to the carrier to increase conductivity of the overall mixture and increasing the viscosity of the carrier medium and/or other components of the liquid mixture.

Figure 67:
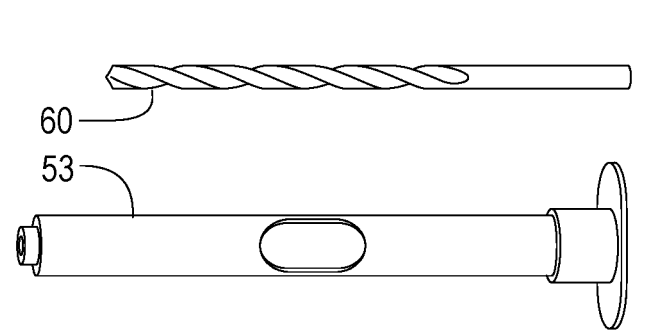
FIG. 67 are images of an auger embedded in a dispenser to provide a predictable forward motion of liquid conductor through the dispenser.
Figure 67:
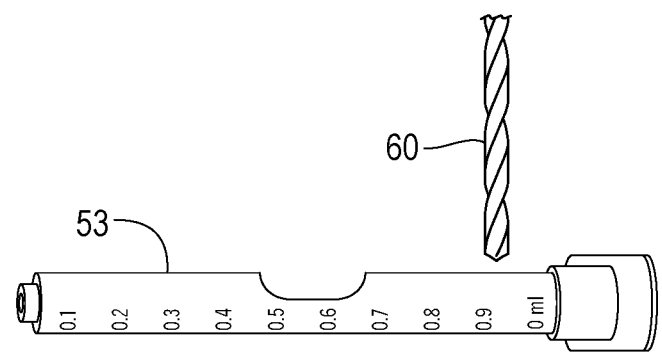
Figure 67:
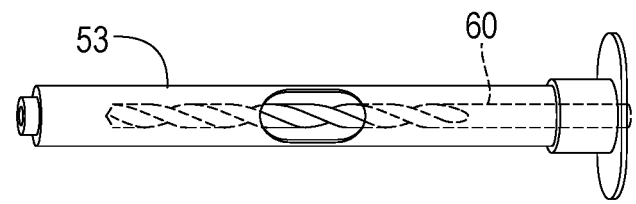
Figure 67:
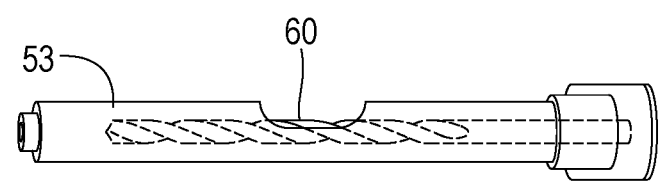

In one embodiment, augers 60 (also called extruders) selected from a group consisting of a screw conveyor, screw feeder and auger drive. All of these systems use a screw inside a hollow tube (e.g., pipe, syringe or needle) that transports material along the axis of the hollow tube by turning inside the tube around the same axis, pushing materials with its threads. Auger based systems utilize any of: (1) A screw on the inside of a hollow tube. (2) A system of a guiding rod placed centrally inside a tube and a coil on the outside of the width of an outside tube providing the driving motion forward. (3) Two screws on inside of an oval shaped or somewhat eight-shaped hollow tube. Additionally, and optionally a forward-backward (or random directional) vibrating motion that may be employed to further avoid clog-up with the target to partially transform the transported material into behaving more like a liquid than a mixture of solids. FIG. 67 are images of an auger embedded in a dispenser to provide a predictable forward motion of liquid mixture through the syringe and reduce the separation of large-grain particles from low-viscosity carrier media at the transition point between syringe and needle. By turning the auger, liquid mixture is transported from the entry-hole, located at the 0.5 ml mark, to the front end of the syringe. A liquid mixture based on silicone as well as metal and coagulant were dispensed from the syringe. The rotational speed determined the amount of material transported over time.

Figure 68:
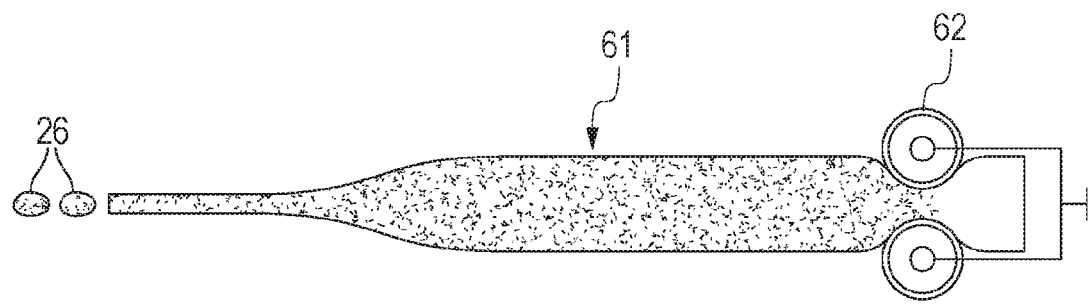
FIG. 68 depicts a rollable tube embodiment of the dispenser comprising a nozzle on the front end and optional apparatus at the rear to facilitate the rolling of the tube to force the liquid conductor to the needle.

In another embodiment the dispenser comprises a tube 61 which may be rolled up from the rear to dispense liquid mixture from the nozzle 62, and note how the lumen of the tube narrows to the nozzle in a manner consistent with, and for the same purposes as, the conical frustum 59 of FIG. 66. In one variation, the dispenser 2 relies on a tube filled with liquid mixture which is then compressed by rollers 63 that are applying pressure onto the tube starting from the back and moving forward. FIG. 68 depicts a rollable tube 61 embodiment of the dispenser comprising a nozzle on the front end and optional apparatus at the rear to facilitate the rolling of the tube to force the liquid mixture to the needle. In one embodiment, the tube is in the shape of a pipette, approximately 0.5 mm in inner diameter for the length of 10 cm, followed by a graduated tip of the length of 2 cm that ends at an inner diameter of 2 mm. In another embodiment, the tube is in the shape of a pipette, approximately 0.5 mm in inner diameter for the length of 10 cm, followed by a graduated tip of the length of 2 cm that ends at an inner diameter of 1 mm. The pipette-shaped tube is sealed at the back end and may be cut open before dispensing of the liquid mixture, causing any pressure that builds up on the inside of the tube by applying rolls perpendicular to the axis of the tube to force out liquid mixture at the front of the tube.

As the rollers 63 are compressing the back end of the pipette-shaped tube and move forward along the axis of the tube at a linear speed, contents of the tube are expressed at a speed which is linear correlated at the tip of the tube: the speed of liquid mixture dispensing is proportional to the speed of the rolls advancing forward (FIG. 68). In yet another implementation, a plunger is provided at the back of the tube instead of the rollers, utilizing more of a syringe approach to dispense the liquid mixture or nonmixture.

In another embodiment a dispenser comprises means for oscillating pressures and vibration that are at a continuous or variable rate. A continuously oscillating pressure has been investigated as a method of mixing and retaining liquid mixture mixed within the delivery. Furthermore, modulated amplitude vibrations have been investigated as a method of mixing and retaining material mixed within the delivery. Both methods allowed the liquid mixture to behave more similarly to a liquid than to a composite of dry particles, noted as effects equally for silicone and cyanoacrylate based carriers with silver and/or aluminum flakes, as well as dry silver flakes with coagulating powder mixtures. The oscillating pressure as well as the vibration by itself did not necessarily allow for a reliable dispensing of the liquid mixture by itself, but instead helped with a more uniform and linear flow from the syringe tip with the added benefit of a need for smaller pressures to be needed at the back end of the syringe to be applied at the plunger to drive liquid mixture from the dispenser.

Figure 65:
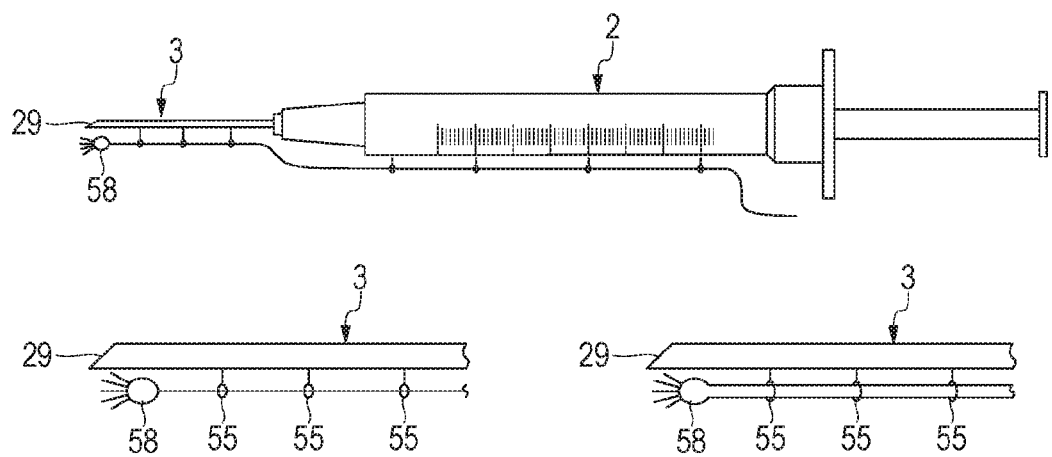
FIG. 65 depicts the dispenser in one embodiment comprising a light such as an LED attached to the needle.
Figures 69A, 69B:
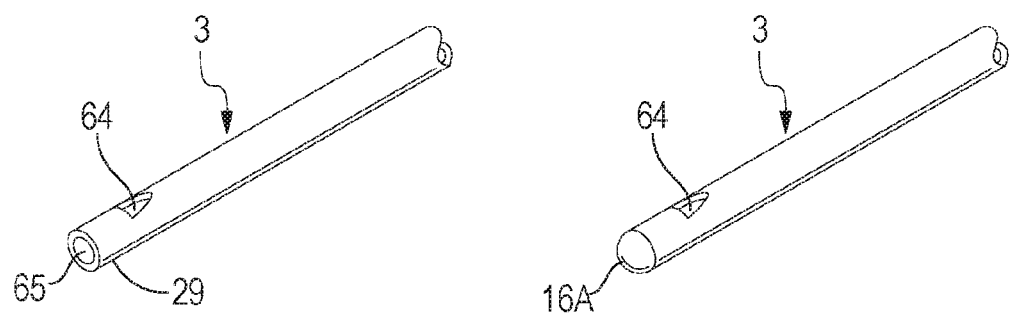
FIG. 69A shows a needle system that utilizes an open tip as well as an open side port.
FIG. 69B shows a needle system that utilizes a closed and rounded needle tip and a side port near the tip.
Figure 72A:
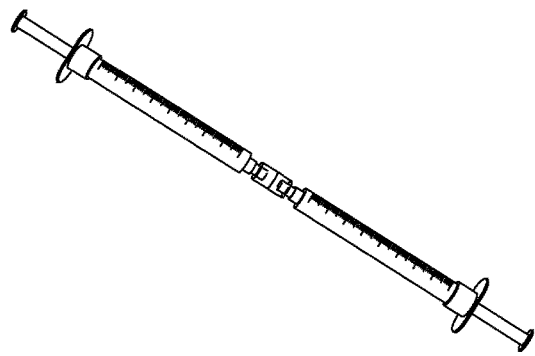
FIG. 72A, FIG. 72B, FIG. 72C and FIG. 72D contain four images of one embodiment of a manual mixer.
Figure 72B:
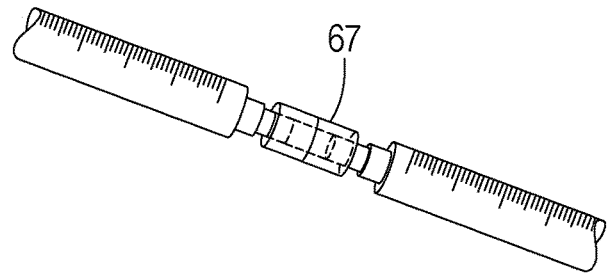
Figure 72C:
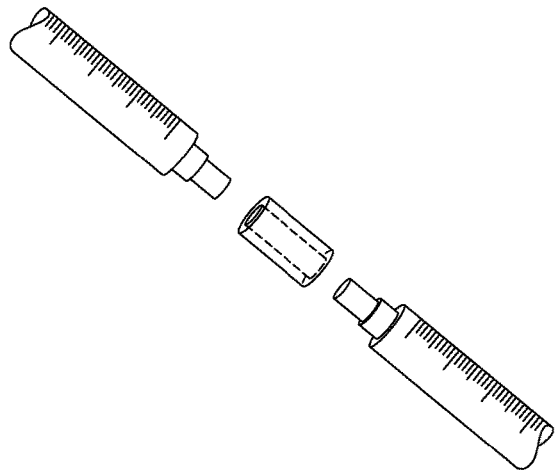
Figure 72D:
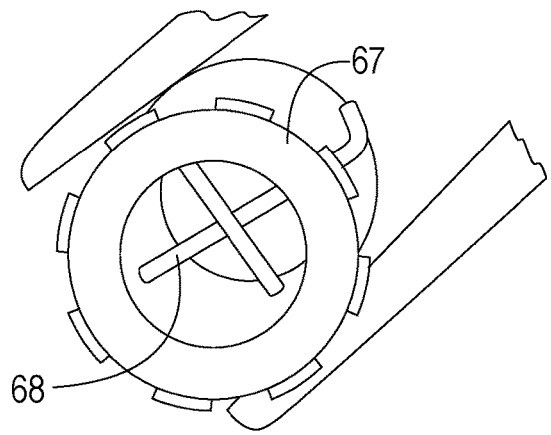

In another embodiment a needle 3 of the dispenser comprises an exit point 29 on the side instead of at the front. The opening at the exit point 29 may be of any shape. In order to combat unwanted injury to the nerve or other tissues during the dispensing, different delivery needles were developed. One of these needle systems, depicted in FIG. 65A, utilized an open tip 65 at the exit point 29 at the needle tip as well as an open side port 64, to be able to dispense liquid mixture at both, at the tip and at the side port. Another embodiment of these needle systems, shown in FIG. 69B, utilized a closed and rounded needle tip 16A and relied only on the open side port 64 to be able to dispense only at the side port 64. The open and the closed (and rounded) tip allows a blunt dissection of the nerve with the ability to verify best needle location without unnecessarily high risk for injury to the nerve. Both needles may be insulated throughout except for the electrically conductive end at the exit point 29, as an alternate way to deliver current near the exit point, the wire to the needle may travel through the walls of the syringe body 53 or through the walls of the first chamber 18 in a coaxial dispenser. To be able to verify correct liquid mixture placement, needles may be insulated everywhere except at the tip 16 in order to use electrical stimulation to determine proximity to the nerve. Alternatively, the de-insulated tip 16 in one embodiment comprises a sensor to record electroneurography ("ENG") signals as a method to locate a target nerve. When electrical stimulation was delivered with the needle placed blindly during surgery at a location assumed to be close to the target 5 then the activation thresholds for the target 5 were obtained and verified. The activation thresholds as smallest values that activate a sub-section of the nerve of interest provided the proper information about the likely best liquid mixture injection location.

For most injections of liquid mixture or nonmixture, a needle gauge smaller than 0.6 mm (>20 gauge) is desirable. The needle gauge can be modified to change the form in which it is extruded. In terms of characterizing the extruded liquid mixture or nonmixture, there is a mathematical relationship between the liquid mixture or nonmixture volume, the needle gauge, and the extruded paste length.

The smaller the needle bore, the longer the extruded material becomes, potentially making the electrode more porous too. The smaller the needle bore will also increase the force required to drive the material through.

TABLE SEVEN

Volumes of Liquid Mixture or Nonmixture per Needle Extruded Length (cm)

| Needle Ga. | Inner Diameter (mm) | Needle Vol/cm Length mL/cm | Injected Volume μL | | | | | | | |
|---|---|---|---|---|---|---|---|---|---|---|
| | | | 50 | 100 | 200 | 400 | 800 | 1,600 | 3,200 | 6,400 |
| 14 | 1.60 | 0.020 | 2 | 5 | 10 | 20 | 40 | 80 | 159 | 318 |
| 16 | 1.19 | 0.011 | 4 | 9 | 18 | 36 | 72 | 144 | 288 | 575 |
| 18 | 0.84 | 0.006 | 9 | 18 | 36 | 72 | 144 | 289 | 577 | 1,155 |
| 20 | 0.60 | 0.003 | 18 | 35 | 71 | 141 | 283 | 566 | 1,132 | 2,264 |
| 22 | 0.41 | 0.001 | 38 | 76 | 151 | 303 | 606 | 1,212 | 2,424 | 4,848 |
| 24 | 0.31 | 0.001 | 66 | 132 | 265 | 530 | 1,060 | 2,120 | 4,240 | 8,479 |
| 26 | 0.26 | 0.001 | 94 | 188 | 377 | 753 | 1,507 | 3,014 | 6,027 | 12,054 |
| 28 | 0.18 | 0.000 | 196 | 393 | 786 | 1,572 | 3,144 | 6.288 | 12,575 | 25,150 |
| 30 | 0.16 | 0.000 | 249 | 497 | 995 | 1,989 | 3,979 | 7,958 | 15,915 | 31,831 |
| 32 | 0.11 | 0.000 | 526 | 1,052 | 2,105 | 4,209 | 8,418 | 16,836 | 33,672 | 67,345 |

The diameter or width of the extruded material can be read from Table Seven under the "Inner Diameter" column. To fully form a ring-like portion 22 of a cured electrode around a large nerve in a human, approximately 400-800 microliters of material is required. For gauges 20-24, this yields extruded lengths of 141-1060 cm.

In one embodiment the dispenser is automated based on sensing neural activity: once the sensor is in proximity to the nerve, changes in impedance and electrical activity may be detected. The nerve may then be freed from surrounding tissues, with the position of the nerve being mechanically or electrically stored in memory. This embodiment may be integrated with ultrasound data as follows: the initial path of tool insertion may be predetermined from pre-operative ultrasound visualization, it may guide the tool path intraoperatively, or may be used at the tip of the tool to differentiate tissue types (e.g., nerve, muscle, fat, etc.) in proximity to the tool One sensor senses pressure during injection and extraction. Dispensing occurs at a pre-defined amount per second by actuation of a button allows a "3-D printing" of neural electrodes in vivo. Each actuation of a control may be graded: e.g., a volume of 1 mm3 is dispensed, or another kind of actuation dispenses every 0.25 seconds a volume of 1 mm$^3$, optionally comprising a dial that selects the amount per click and the amount of time between click dispenses. In one embodiment, an auger system is used to dispense discrete amount with the button push.

In another embodiment a dispenser for use in general surgery combines the ability to throw stitches or place staples into (a) surrounding tissue, (b) the nerve itself, (c) an organ wall—with the goal to anchor the liquid mixture better to the organ wall, nerve or the surrounding tissue. This embodiment provides another method for long term attachment of the liquid mixture if general surgery is needed.

Dispensers may differ according to the type of material to be delivered to the target: (1) auger 60 (screw-in-needle system) to drive higher density/viscosity material, (2) syringe for lower viscosity material, or (3) tube 61 to dispense liquid mixture of medium viscosity. Herein, "high viscosity" is 100,000-10,000,000 mPa-s (e.g., toothpaste-like) and "low viscosity" is 1-100 mPa-s (e.g., water-like). "mid viscosity" is 100-100,000 mPa-s (e.g., syrup-like).

In another embodiment, pre-formed molds 35 may be used by the surgeon as stiff or as flexible devices, and may change in one or more dimensions. One such example is a balloon 66 that may be inflated when pushed as a "U" shape behind the nerve, then inflated in order to provide a specific cured electrode thickness between the nerve and the tissue behind the nerve (FIG. 70A-C).

FIG. 70A-C is a sequence of diagrams depicting, after a nerve has been bluntly separated from the underlying tissue, dispensing a liquid mixture or nonmixture is possible but consistent thickness may not be easily guaranteed. By placing an uninflated U-shaped balloon 66 between the nerve 5 and the underlying tissue, as in FIG. 70A and then inflating the balloon 66, a uniform distance of the nerve to the underlying tissue may be guaranteed. Once this distance is established in FIG. 70B, the liquid mixture 1 may be safely injected below, behind, near and on-top of the nerve to form a ring-like portion 22 of a cured electrode of a guaranteed minimal thickness, as shown in FIG. 70C. The balloon is mechanically designed similar to a cardiac stent placement balloon: a u-shaped wire provides the mechanical stiffness and is covered with inflatable material, i.e., a balloon 66. When that material is filled with air or a liquid, it assumes a predetermined diameter. This diameter is equal to the separation distance between the nerve and the underlying tissue.

In another embodiment the dispenser comprises a magazine and the liquid mixture, already mixed, is loaded into the magazine. The dispenser is connected to a source of pressurized air, and pressurized air is used to propel small volumes of the liquid mixture from the magazine at a pressure that the physician can adjust to propel the liquid mixture. The pressurized dispenser allows an even or adjustable flow to the target site, and may also comprise a flexible hose for negotiating the tip of the dispenser into locations hard to reach by a straight device such as a needle, such locations as in the brain's midline and in cortical sulci. See FIG. 55A-B.

In another embodiment of the dispenser, an automated dispenser uses ultrasound and a Dispense-Jet, comprising (1) on the input side: (a) ultrasound to acquire a live data stream of the anatomical structure and any dispensed liquid mixture or pellets, (b) a graphical user interface that is part of input from the operator and part of output to the operator, that is, a display of the optimal placement at the target location and (c) a mouse or finger pointer to mark the optimal placement at the target; (2) on the output side: (a) a pressurized air dispenser to propel liquid mixture or pellets to a pre-calculated distance, and (b) a processor to determine the pressure and timing needed to dispense the liquid mixture or pellets at the optimal location.

In another embodiment shown in FIG. 71, an extruded wire 10 is integrated within the dispenser, e.g., a syringe, so that the wire is coaxial with the liquid mixture. This allows liquid mixture to encase a nerve first behind the nerve and then, when the last ⅓ of the liquid mixture leaves the syringe the wire with anchoring leaves the syringe too. The liquid material behind the liquid mixture may be a liquid nonmixture such as a biocompatible starch, cellulose or the like.

FIG. 71 depicts a syringe with a wire 10 with a connecting feature 46 at its forward most point embedded in the liquid mixture. The wire begins in the second half to last third of the liquid mixture and continues to the end of the syringe (where the stencil is).

Mixing

A mixer for the liquid mixture is also disclosed herein. For cases where four ingredients form the liquid mixture, an automatic mixer may be used to first mix components 1 and 2 together (such as conductive elements and a surfactant), then mixing components 3 and 4 together (such as in a 2-part silicone mix or fibrinogen mixed with thrombin to form the fibrin mix), followed by mixing the ½ with the ¾ mixtures. In different embodiments, the mixer may be part of or separate from the dispenser. The mixer may use a stirring, revolving or a shaking motion to mix components. In another embodiment the mixer uses manual action. In one embodiment the manual mixer is syringe based, with turbulence for improved mixing created in part by addition of at least one baffle 68 located within the lumen of a connector 67. Two syringes are joined with a connector 67 in the middle, with the connector comprising at least one internal baffle 68 to increase turbulence for material passing through the connector. Each syringe is filled with one or more of the components of the liquid mixture. The at least one baffle 68 causes an increase in turbulent flow and speeds up the mixing process as the liquid mixture components are being pushed from one syringe into the other and back a few times (FIGS. 68A-0 to 68D-0). For example, a first syringe holds silicone part A and silver flakes that were formerly mixed with a surfactant such as PVA, and a second syringe holds silicone part B, and silver flakes that were formerly mixed with a surfactant such as PVA. FIG. 72A-D are four images of one embodiment of a manual mixer. Images A and B show two syringes without needles joined by a connector. Image C depicts the syringes and the connector prior to being joined. Image D is an image of the manual mixer comprising a baffle in the lumen of the connector.

Figure 73:
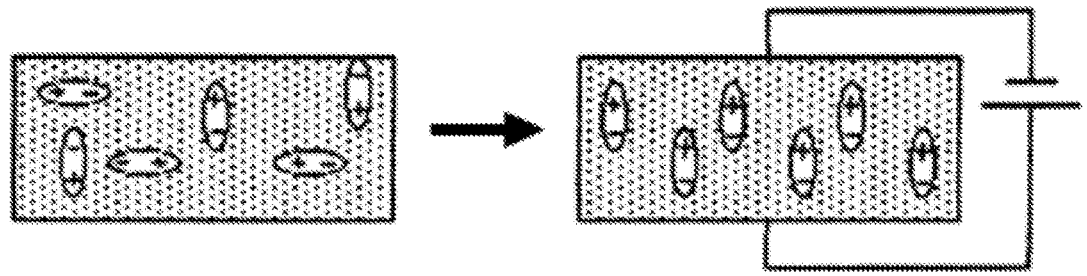
FIG. 73 is a schematic of dielectric polarization and heating brought about by RF waves.

In another embodiment, the liquid mixture or nonmixture comprises polymers curing with radio frequency ("RF") or other energy waves. The physician uses the dispenser to place this polymer (with or without conductive elements) which is subject to curing under a magnetic or RF field. Polar molecules will align themselves in the presence of an electromagnetic field. FIG. 73 is a schematic of dielectric polarization and heating brought about by RF waves.

Surgical Modifications and Anchoring

Figure 74:
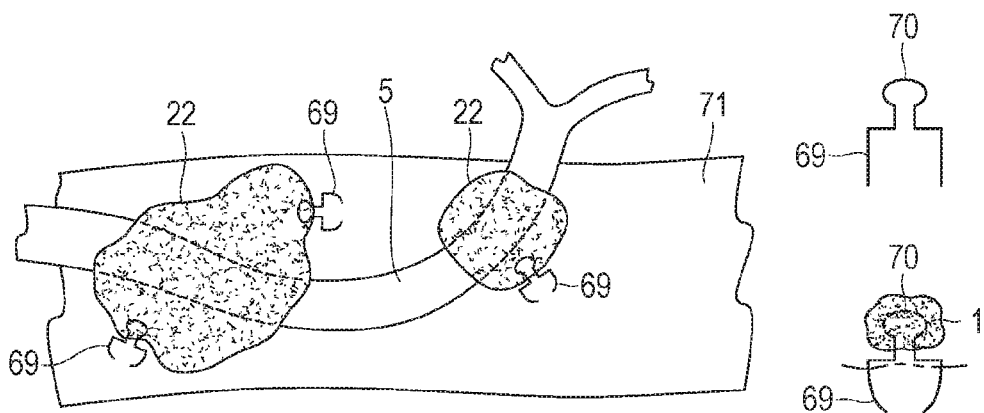
FIG. 74 contains a larger diagram of staples with prongs inserted into a connective tissue plain and the staple heads embedded in cured electrodes surrounding a nerve target. Two smaller diagrams are of a staple before insertion (top) and post insertion with head embedded in a cured electrode (bottom).
Figure 75:
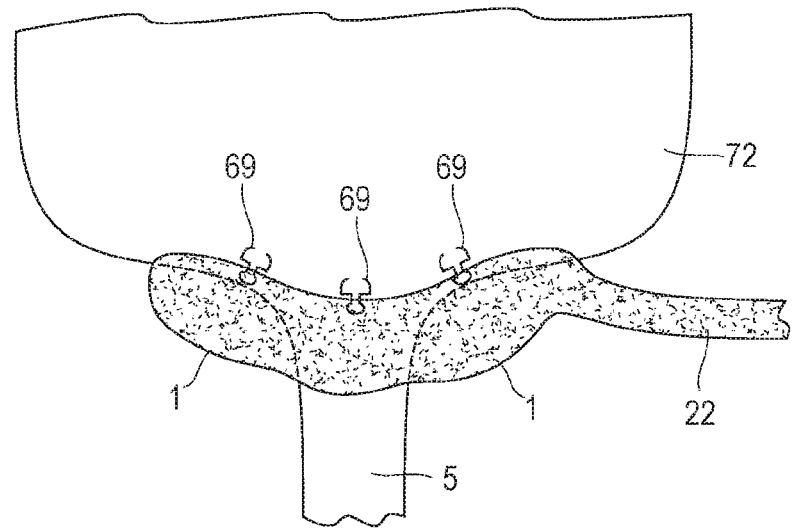
FIG. 75 depicts staples with a connecting head, the prongs of the staples crimped into a wall of an organ (e.g., bladder), and the connecting head embedded in the liquid conductor/cured electrode.

In some embodiments, additional surgical modifications and anchoring may be used with the liquid mixture and nonmixture described herein. To ensure that the cured electrode is mechanically anchored well with the surrounding tissues near the target, additional structures may be used. These structures may be quick and easy to be placed surgically through a keyhole incision, require only very little time to be placed but may provide a significant increase in mechanical integration with the surrounding tissue. In one embodiment, prongs of staples 69 may be placed into the tissue next to the target, so that the stables provide a mechanical support (FIG. 74-75). FIG. 74 is a diagram of staples 69 inserted into a connective tissue plain 71 with the nerve target 5 running next to it. The staples have a connecting head 70 (akin to connecting feature 46) here in a mushroom shape which provides a better mechanical connection after being embedded in liquid mixture which cures. The connecting head may be any shape aking to a loop which creates additional friction to prevent the pulling out of the staple. The ring-like portion 22 of the liquid mixture/cured electrode 1 is anchored with a stronger mechanical attachment to the muscle using the staples. Staples 69 with a connecting head 70 are shown on the right side of FIG. 74: the upper view having straight prongs and mushroom-shape embedded in a cured electrode 1, the lower view with its ends crimped together post placement into e.g. connective tissue 71. FIG. 75 depicts staples 69 with a connecting head 70, the prongs of the staples crimped into an wall 72 of an organ (e.g., bladder), and the connecting head 70 embedded in the liquid mixture/cured electrode to ensure optimal mechanical integration with the cured electrode that is surrounding the bladder at a location of nerves 5 entering into or connecting with the organ wall.

Suture loops provide increased mechanical integration and, in one embodiment, suture loops may be placed similar to staples into the tissue near the target to provide a better mechanical integration with said locations. These sutures may be designed to have specific loops that are open for the liquid mixture to integrate with.

Figures 76A, 76B:
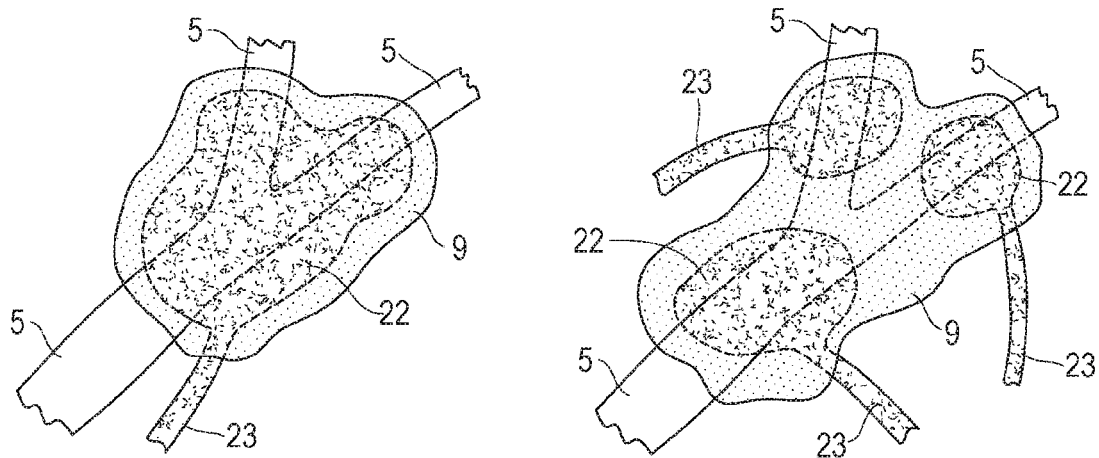
FIG. 76B depicts lacing ring-like portions of the liquid conductor around each of the smaller side arms as well as additional liquid conductor around the major remaining arm, all surrounded by a single liquid nonconductor/nonconductive layer.
Figure 77:
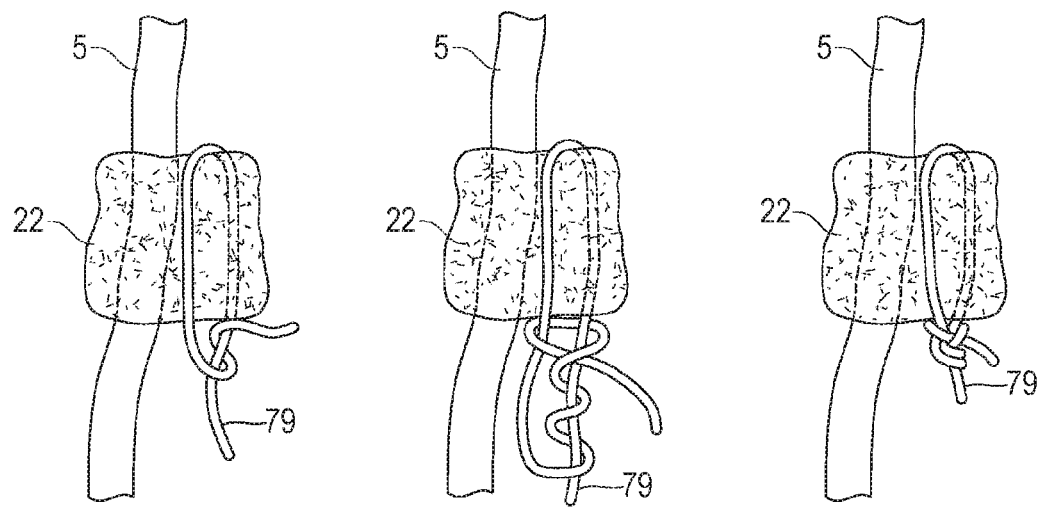
FIG. 77 contains three diagrams showing steps of tying an adjustable hitch knot integrated with the cured electrode to allow breakage of the cured electrode by pulling on the loop to enable easy removal of the cured electrode.

In another embodiment, injection around nerves at a Y-junction adds additional mechanical stability, connecting mechanically to at least one of several nerve branches as well as supporting structures nearby in the area. Placing the liquid mixture/cured electrode at a Y-junction of a nerve provides an excellent mechanical integration with the nerve, and additional advantages. There are several options. Placing the liquid mixture all around the connection point of the three side arms forming the Y provides a means to stimulate all nerve fibers entering and exiting the Y-junction as in FIG. 76A. A different option as in FIG. 76B is lacing ring-like portions 22 of the liquid mixture around each of the smaller side arms 5 as well as additional liquid mixture around the major remaining arm 5, then mechanically stabilizing these three placements with one liquid nonmixture/nonconductive layer 9 surrounding all of them allows for a selective stimulation of either one of the small side arms as well as the stimulating of all fibers by stimulating the major arm. One may further stimulate on one of the small side arms and block on one of the other two arms leaving the Y, either to block afferent or efferent activity directly or to suppress the resulting reflexive neural traffic coming from the spinal cord a few tens to hundreds of milliseconds post initial stimulation.

Blunt dissection of a nerve from surrounding tissue may be achieved by injecting the liquid mixture or nonmixture. Blunt dissection provides ways to integrate the liquid mixture with the nerve but stay movable with the surrounding tissue, such as integration around a nerve Y junction secures it around the nerve but after encapsulation is somewhat movable against the muscle or fascia tissue around it. In another method for placing the liquid mixture, blunt dissection using pulsed air or water may be used to bluntly separate a nerve from its surrounding tissue. The air pressure is to be set to a level that does not overstretch the nerve in case the nerve is subjected to the full blast. Pulsed air as well as continuously flowing air were tested and pulsed air at approximately 2 to 10 Hz, meaning 2 to 10 air bursts per second, proved to be least destructive to the surrounding tissue as well as left the nerve intact, while separating the nerve from the underlying connective tissue. Pulsed water was tested at the same frequency bandwidth and proved to be efficacious. Water in contrast to air was able to "split open" muscle cells from each other, separating the strings of muscle cells, the open space between these muscle cells or strands remaining filled with water or air for seconds to minutes following the end of the pulsed water application. These gaps between the muscle cells, separated from each other but still intact longitudinally, may be filled with liquid mixture or nonmixture injections, allowing a direct interface to muscle cells as well as the stretch receptors surrounding each of the muscle cells or cell strands. The pulsed air may be combined with the delivery of liquid mixture or nonmixture: first a strong burst of air separates the tissues along their plains, then a less intense burst of air is used to shoot a small amount of liquid material into the void. The void is then extended by a stronger burst again, which in one embodiment is followed by an air delivered "pellet" of liquid mixture or nonmixture. The process is continued until a nerve has been covered all around with liquid mixture or nonmixture.

Another aspect of the present invention is a cured electrode finder, say for example, a tool for use in revision surgery. A device may be used to find the extent to which cured electrode is spread below a tissue layer. While this may be done with an ultrasound machine or x-ray/angiography, there is the further option to use a needle-based system similar to the needled skin patch electrode 42 described herein that connect transcutaneously to the buried cured electrode and verify the existence of cured electrode in contact with two or more of the needles by measuring the impedance between the needles.

In yet another implementation, the method of measuring a change in capacitance at a distance of e.g. 2 cm may be utilized. The capacitance of biological tissue may here be understood as the background "noise" capacitance, which changes with cured electrode present within the vicinity of a capacitance reader. Such a capacitance reader may comprise an antenna connected to an output stage to send out an RF signal and connected to an input stage which is used to measure the wave reflected from the surrounding dielectric material. As a cured electrode with its relatively higher conductance will reflect RF signals differently from the lower-conductance biological tissue as well as air, the location of the cured electrode can be determined down to a sub-centimeter XYZ accuracy. When this RF based finder is combined with an accelerometer and moved across a likely cured electrode location, then a 3D-image of the cured electrode may be obtained using this device alone, without any ultrasound or X-ray use.

Removal

The present invention also comprises an integrated electrode removal system. Prior art neural electrodes do not incorporate a removal feature, so that removal requires the surgeon to cut into the connective tissue that surrounds any chronically implanted electrode followed by cutting the electrode itself. Disclosed herein is a break feature which, if activated, forces the electrode to break at a specific location. This aids with the removal of cured electrodes. A system has been developed and tested successfully to break a cured electrode, comprising a suture placed adjacent to the target before encasing both the target and the suture with liquid mixture or nonmixture which is allowed to cure. Prior to encasement, the suture is tied in a knot which may be released later by pulling. Example knots are the adjustable grip hitch, the palstek knot and the like. FIG. 74A-C are diagrams showing steps of tying an adjustable hitch knot integrated with the cured electrode to allow breakage of the cured electrode by pulling on the loop to support easy removal of the cured electrode. The adjustable grip hitch knot allows for a tightening, thereby cutting through the cured electrode at a later point in time, even after years of chronic implantation. Also, see FIGS. 99B-C.

The temporary cured electrode (e.g. for DBS, SCS, PNS stim/block) is resorbable over the course of approximately 6 weeks by the body's regular processes, and it thus loses its mechanical integrity. The injectable electrode is placed minimally invasively in a first surgery using resorbable materials such as liquid carrier materials like fibrin glue, proteins, hydrogels and polymers that the body is able to digest, and mixtures of these. Conductive elements of iron, graphene and conductive polymers such as PEDOT:PSS should be sized no larger than 20 microns to allow resorption. Post injection, the electrode is used to e.g. test a neural stimulation target deemed likely to be the best location for a therapy. Two outcomes: either inject a liquid mixture designed to be permanent in the same location, or find a new location. In one embodiment the temporary cured electrode may comprise the patient's own cells integrated as part of the carrier material. The patient's own fat cells might be used to provide a partial resorption.

Figures 78A, 78B:
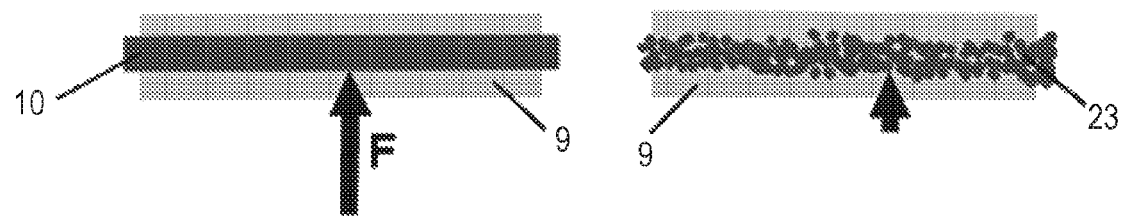
FIG. 78A and FIG. 78B. are graphics showing shear forces (arrows denoted F) required for cutting and/or removing are greater for insulated solid wire FIG. 78A than for the cured electrode, FIG. 78B.

Any cured electrode is relatively easy to remove compared to prior art devices. The ring-like portion 22 of a cured electrode around a nerve is cut and removed. The carrier material for specific embodiments may be designed such that the electrodes can be more easily removed. The properties of the tensile strength of the mixture and the insulator materials chosen can be modified easier than those of standard silicone or polyimide used in traditional electrodes. Furthermore, by applying thicker injected electrodes around a nerve, a higher total tensile strength can be achieved while a thinner application of the material allows for a smaller tensile and shear strength. This means that the physician has a direct influence on the cured electrode's final tensile and shear strength during his or her electrode injection procedure. In contrast to prior art (Case spiral or Huntington spiral) cuff electrodes in which the carrier and metal connectors may be difficult to cut once they have been around a nerve and have become fully encapsulated, the liquid mixture and nonmixture material can be one that has the mechanical tensile strength similar to silicone. Furthermore, there are continuous metal wire connections between the signal generator and the actual electrode contact in a prior art cuff. In contrast, the metal connections achieved by the cured electrode comprise many small particles requiring less force to separate than a continuous metal wire (FIG. 78A-B). The arrow labeled F in 78A and the arrow in 78B just indicate the greater force necessary to break the prior art structure. The embodiment of the cured electrode may further utilize the body's encapsulation through formation of scar tissue to achieve mechanical stability. Without a prior art wire core (as in the prior art cuff) a cured electrode may be removed more easily, and less invasively.

The cured electrode can furthermore contain additional materials that allow for a long-term modification of the encapsulation. Such materials can be, but are not limited to, e.g., metals that cause a heightened buildup of connective tissue on the outside of the cured electrode (while the inside of the cured electrode next to the nerve is designed to have only a small encapsulation tissue thickness).

FIG. 78A-B are diagrams comparing the difference in tensile shear strength that can be achieved between traditional continuous wire-based conduction of electricity (78A) and the cured electrode (75B). The cut or shear forces for a solid wire connection are much higher and thus it is generally not possible to cut an implanted cuff inside the body that has been there for some time and has thus become encapsulated fully by the body. It is advantageous to be able to have specific wire like connections to and around a nerve that can be more easily cut by a surgeon.

Additional Applications

Figure 79:
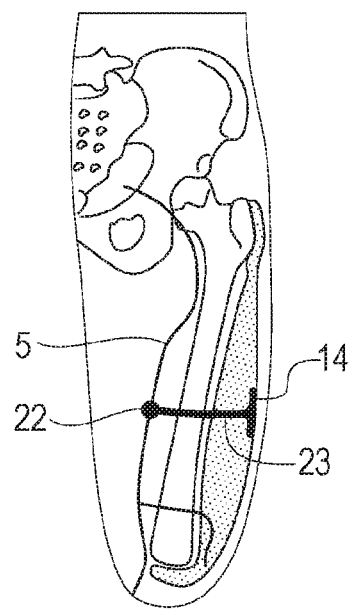
FIG. 79 is a diagram illustrating the location of the present invention in an above the knee amputation.

The present invitation may be used to relieve phantom limb pain, pressure, tickle or paresthesia after amputation. The remaining nerves can form a neuroma which can lead to phantom limb pain, the sensation that the amputated limb hurts. FIG. 79 is a diagram illustrating the location of the present invention in an above the knee amputation. An contact pad 14 under the skin surface collects signal (from a TENS electrode 11 as in FIG. 14F), and the current is transmitted on a wire-like portion 23 to a ring-like portion 22 around the nerve target 5.

In one embodiment the liquid mixture is dispensed as a rod-shaped cured electrode that may or may not be flexible post cure but will in every case be electrically significantly more conductive than the surrounding biological tissue of the limb. Instead of a portion of the cured electrode comprising a wire-like structure 23, the cured electrode may also comprise a contact pad 14 below the skin may terminate in a coil that may receive electrical energy via induction from a signal generator held against the skin from the outside, or outside the body from a TENS electrode.

Also disclosed is a method of repairing a broken electrode lead wire of a previously implanted electrode. Neural and cardiac stimulators often have the IPG in one location A and at least one of the stimulation or sensing electrodes in a remote location B. The connection between these two locations A and B is commonly achieved through a lead wire. If the lead wire breaks due to age, excessive movement, force or other causes, then the electrical conduction between point A and B is interrupted. Liquid mixture as described herein may be used to either contact the two ends of the wire directly at the location of the breakage, or it may be used in conjunction with a splitter that allows the surgeon to connect a multi-threaded wire to a connection board on one end and do the same on the other end.

Connecting to a Prior Art Electrode

Figure 5:
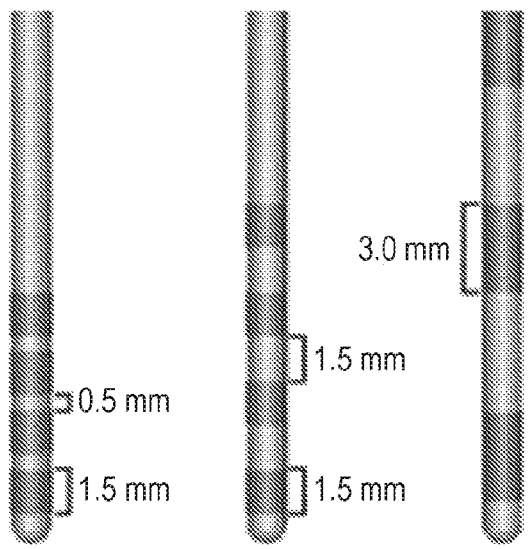
FIGS. 5 and 6 depict prior art rod-shaped electrode configurations with one or several electrode contacts aligned linearly along the rod.

The present invention also comprises a method for electric field shaping to correct improperly placed electrode configurations, or ones which have deteriorated over time. As discussed herein, rod-like electrode configurations are utilized in the CNS for deep brain stimulation or in the PNS to stimulate neural targets from branches of the trigeminal nerve (FIG. 5 from US20110191275 and FIG. 6, from U.S. Pat. No. 8,473,062 B2) to ganglia such as the sphenopalatine ganglion. They are primarily used because of their ease of implantation. They have limited ability to steer the current field lines as each electrode contact is a "point source" from a field geometry perspective. It is hard to stimulate a structure near the rod without stimulating other adjacent structures unintentionally. The present invention incorporates methods and capabilities to combine rod-shaped electrode configurations with the cured electrode, including the ability to (1) change the path a current takes after an electrode has been placed chronically, (2) revise bad electrode placement (such as in DBS) by creating a better current path later on through the injection of liquid mixture, and (3) revise bad DBS electrode implants by placing a trace of liquid mixture on the opposite side of a stimulation site to re-route current to that site. The present invention also includes the capability to achieve a better fit for previously implanted prior art cuff electrodes and thereby increase selectivity.

The present invention includes capability to selectively stimulation and block of superficial nerves and thereby control muscles with surface stim selectively or block pain selectively that may otherwise not be possible with TENS surface electrodes. Selectivity is achieved through liquid mixture being injected into the nerve near specific fascicles. This reduces or eliminates pain formerly caused by high current densities in the skin.

Figure 7:
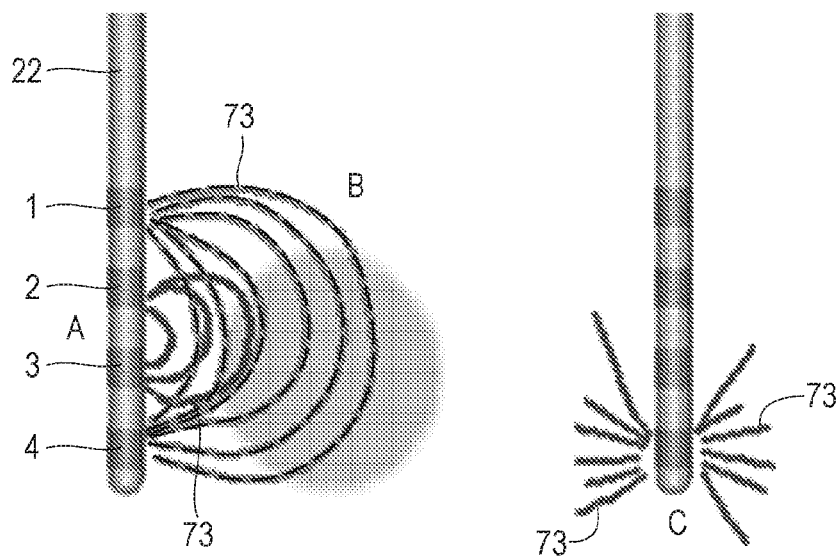
FIG. 7 contains two duplications of the prior art rod-shaped electrode in the center of FIG. 5. Near the left side rod, a shaded circular area to the right represents the neural target area, and electrical field lines between electrode contacts are shown, some of which run through the neural target area. On the right side rod, the electrical field lines near the end of the rod are depicted as scattering in almost 360 degrees from a single electrode contact.
Figure 8:
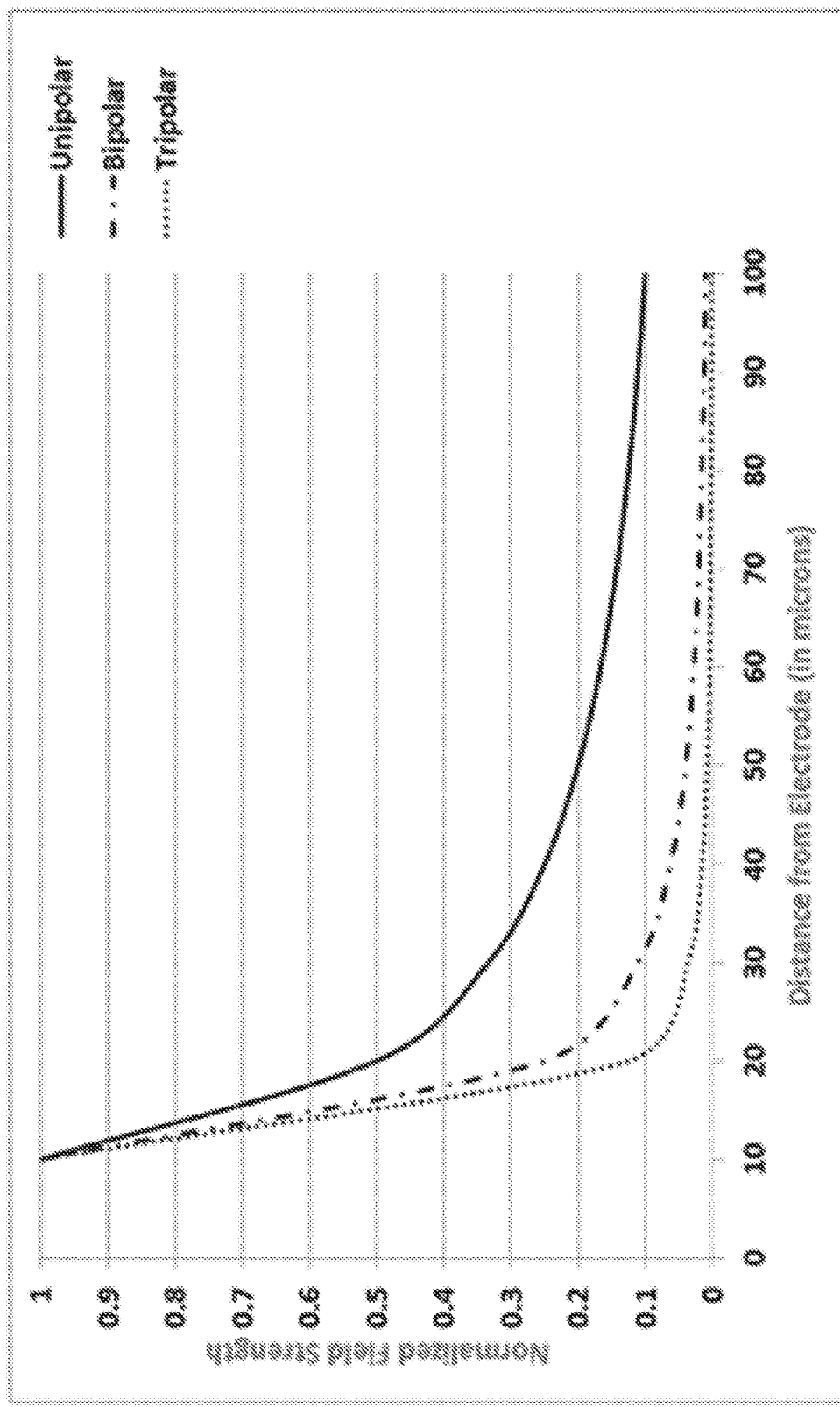
FIG. 8 is a chart depicting normalized field strength as a function of distance in microns from an electrode for unipolar, bipolar and tripolar electrodes.
Figure 80A:
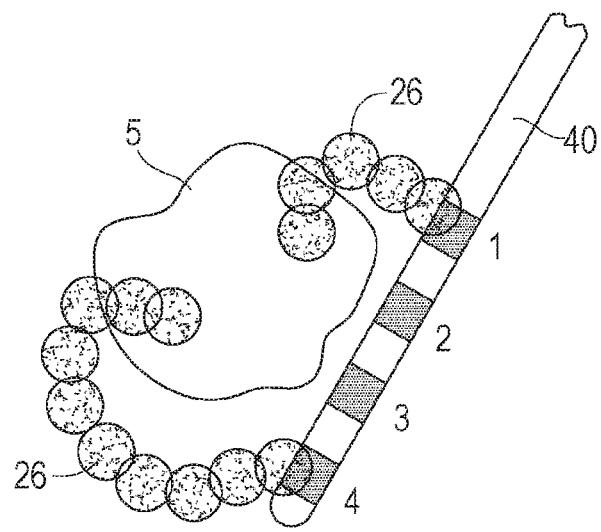
FIG. 80A and FIG. 80B are diagrams depicting examples of placement of liquid mixture "blobs" on prior art electrodes to align field lines through the target.
Figure 80B:
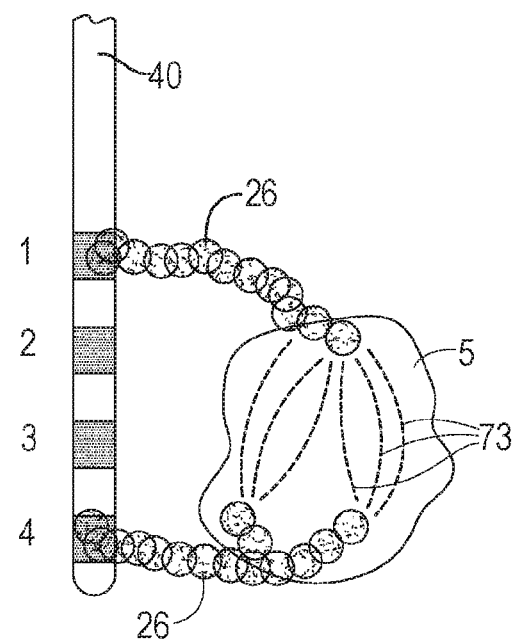

Connecting previously implanted electrode wires to a nerve with a wire (e.g., a plain Pt wire) simply being injected with a 20 gauge needle, each end of the wire being connected to a liquid mixture: one blob 26 near (around) the nerve and one blob 26 in the sub-cutis. This allows the capability to stimulate deep nerves (in legs, in abdomen, etc.) with a surface-stim approach. The implant is only a wire 10 and two blobs of the liquid mixture. Materials needed include a very fine needle (micro-needle) for both, PNS and CNS applications, a syringe filled with liquid mixture, and a syringe filled with liquid nonmixture (chosen for high impedance). This approach includes (1), if a DBS electrode is too far from a neurostimulation target (as in FIG. 7 on the left side), the present invention provides the ability to guide the electric current to the proper location without a major revision surgery that requires the ejection and re-insertion of the DBS electrode, (2) using a micro-needle (of 8 to 10 cm length), that is attached to the syringe filled with liquid mixture, a current path can be injected into the brain through a series of "blobs" 26. FIG. 80A-B0 are diagrams depicting examples of placement of liquid mixture "blobs" on prior art electrodes to align field lines through the target structure. That is, a string of blobs from contacts #1 and 4 makes contact with the target 5, and the electrical field lines 73 are centered on the target, unlike in FIG. 7, where the current fields A and B are not able to electrically stimulate the neural target structure (shaded area) with or without simultaneously activating other structures unintentionally. Thus liquid mixture may be dispensed to create a path from a prior art electrode to the neural target.

The present invention may be configured as a flexible DBS electrode. Materials needed include a long micro-needle, a syringe filled with liquid mixture (e.g. PEG carrier material mixed with silver conductive elements), and a syringe filled with liquid nonmixture (chosen for high impedance). This approach includes (1) use of a syringe, and a liquid mixture is placed into the brain from the GPI-STN as a string of conductive blobs 26 in the form of a track back out to the skull, where a contact point is made, and (2) (optionally) an insulator on the outside of the conductive track to avoid accidentally stimulating neighboring structures. An advantage is that this one cable, in form of pearls making the "cable" flexible, may stimulate the nucleus of interest in the brain. This DBS style design allows a more minimally invasive approach with the option to later correct the electrode placement by imply adding more liquid mixture at the correct location. The carrier material may be protein based with a matrix that holds the conductive elements (such as gold) in place, ensuring conductivity and keeping the flexible electrode in place. The mixture may be injected at the same or a higher rate than the injection needle may be extracted with the potential to chemically seal any bleeders that may arise from the injection of the needle into brain tissue. If the material is conductive from the point of injection onwards (meaning even before a curing period has passed), the conductive material may be used to apply an anodic potential that contracts small blood vessels in the vicinity of the injected electrode material. This approach is able to hold ruptured blood vessels shut for the first few seconds post injection and minimize bleeding into the wound channel, thereby reducing the expected neural scarring (glial scarring) at/near the injection site, thereby allowing lower neural stimulation thresholds and better SNR values for recording setups using the cured electrodes.

Electric fields 73 using the present invention may be achieved, in one embodiment, by shaping by adding conductive material into the nerve. Using induced charge transfer to activate nerve fibers using kHz waveforms to stimulate, even a normal stim pulse of 200 μs cathodic and 200 μs anodic charge balancing will effectively be a 2.5 kHz signal for the moment of stimulation. The liquid mixture may be porous for maximal capacitance effects. Electrical field lines 73 pass preferentially through materials of low impedance. At the location of the interface of a good mixture to a bad mixture field lines are most dense. By injecting the conductive material into the nerve itself and without completely connecting the liquid mixture through the nerve's membrane, electric field shaping is possible as electrical field lines 73 follow the path of least electric resistance. FIG. 81A-B are diagrams showing how placing a material of high conductivity into a medium of lower conductivity with a homogeneous field that passes through the low-conductivity medium causes a distortion of the electrical field lines 73. In 81A there are homogenous field lines 73, but 81B depicts distorted field lines due to a placement of a liquid mixture into the electric field lines which are bent towards and into the medium of high conductivity. Field lines are able to pass through the medium of high conductivity in higher density. Thus, field lines in the medium of low conductivity may be bent towards the high conductivity medium, creating hot spots in the medium of low conductivity with locally heightened field densities. These higher field densities may be utilized by placing them near a stimulation (or block) target, i.e., placing a high conductivity liquid mixture blob 26 near a fascicle 32 with the fascicle in line with the liquid mixture blob 26 will cause higher field densities through that fascicle while blobs placed near a fascicle on an axis perpendicular to the field lines will reduce the field lines through that fascicle. The placement of liquid mixture blobs can change the probability for fascicles to be stimulated based on whether the blob is placed in line or perpendicular to the field lines.

Figure 83:
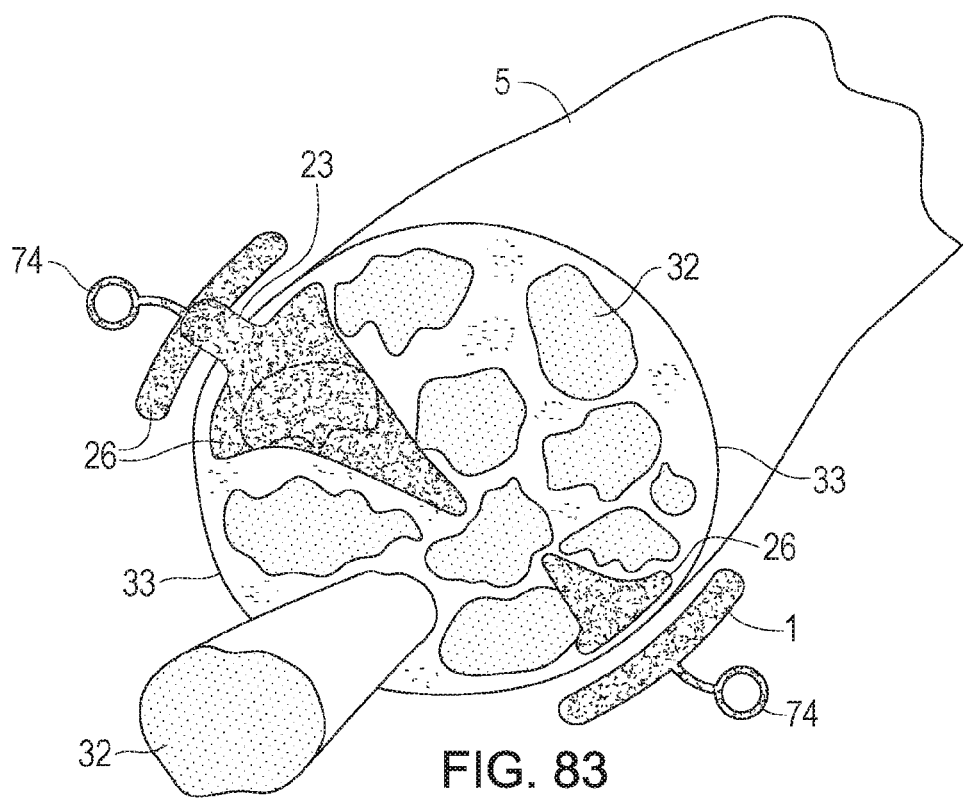
FIG. 83 depicts a liquid conductor blob injected into the nerve while leaving a wire-like portion of the cured electrode through the nerve's epineurium, here shown only on the left side.

At least two configurations result from the foregoing. First the liquid mixture 1 may be placed inside a fascicle 32 without an exit trace. FIG. 82 is a diagram showing liquid mixture blob 26 injected into the nerve 5 without leaving an exit trace through the nerve's epineurium 33, and the liquid mixture/cured electrode connects with two additional cured electrodes just outside the epineurium which in turn connect to other wires or devices at 74. Another option is to inject liquid mixture into the nerve 5 with a connection left across the epineurium. FIG. 83 depicts a liquid mixture blob 26 injected into the nerve while leaving a wire-like portion 23 of the cured electrode through the nerve's epineurium, here shown only on the left side but it is possible to do so on both sides. The liquid mixture 23 on the left side exits the epineurium to form a faradic bridge and the exit from the nerve can be at a 90 degree angle (perpendicular to the nerve) or at a very shallow angle leaving a comparably long trace inside the nerve. FIG. 83 shows the perpendicular exit of the wire-like portion 23 of the liquid mixture through epineurium. For these interventions in FIGS. 79-0 and 800-0, the materials and approach include (1) a small diameter needle; (2) measurement of pressure during injection to avoid occluding blood supply to distal structures; (3) use of ultrasound or fluorescent dyes to verify injection into the nerve is successful, and (4) depending on a variety of parameters, the liquid mixture blobs 26 may be injected into the nerve without leaving a continuous stream through the epineurium utilizing capacitive displacement current and voltage field shaping for the intended effect. In FIG. 83, electrical field lines forming inside the nerve are changed from uniform lines to more compacted lines near the injected conductive blobs making up the cured electrode.

Figure 84:
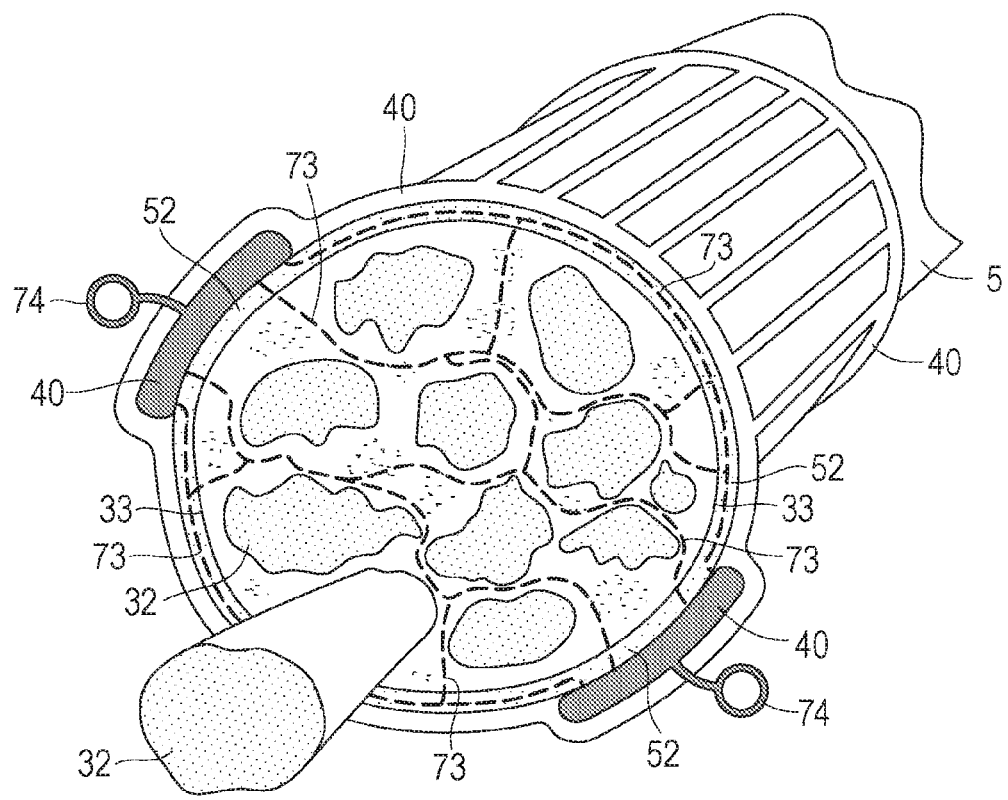
FIG. 84 depicts a nerve target with a chronically-implanted prior art cuff electrode with two solid metal contacts on opposite sides of the nerve, and the nerve encapsulated in fibrous tissue. Electrical field lines scatter through the nerve and also around the perimeter (the epineurium) and in the encapsulation.

Electric field shaping may also be achieved by adding liquid mixture around or into the nerve. The current amplitude is always inversely proportional to the impedance of a current path. As there is generally more than one current path in a biological system, controlling current flow through optimal placement of low and high impedances (resistive and capacitive) becomes very important. A prior art nerve cuff electrode 40 shown in FIG. 84 (see FIGS. 4a-b) for example will rarely conform to the contours of a nerve optimally (i.e., without space between the outer cells of the nerve's epineurium and the cuff's inner diameter) unless the cuff is intended to reshape the nerve, thereby applying an intentional pressure to the nerve from the moment of cuff placement. This open space between the nerve and the prior art cuff will generally be filled with an encapsulation 52 of connective tissue which is relatively dry and higher in impedance than the surrounding interstitial fluid as well as the neural tissue of the nerve to be stimulated. This means that some current (electrical field lines 73) will pass from one contact inside a cuff to another other within the same cuff without passing through the nerve (as shown by dotted electrical field lines 73 including those on the circumference of the nerve just inside the epineurium 33), even when two cuff electrode contacts 40 are diametrically on opposite sides of the nerve inside the cuff. FIG. 84 depicts field lines 73 through and around a nerve with two electrodes placed diametrically on opposite ends. Note how the shortest current path is through the nerve but some low impedance paths might be just outside the nerve and between the encapsulation 52 of fibrous tissue that has formed between the nerve and the cuff 40. Yet without a layer of insulation around the outside of the electrode contacts and the nerve, there is even more current spread which is why an insulating material helps to provide strong, more uniform electrical fields through a nerve instead of non-uniform fields around it.

Figure 85:
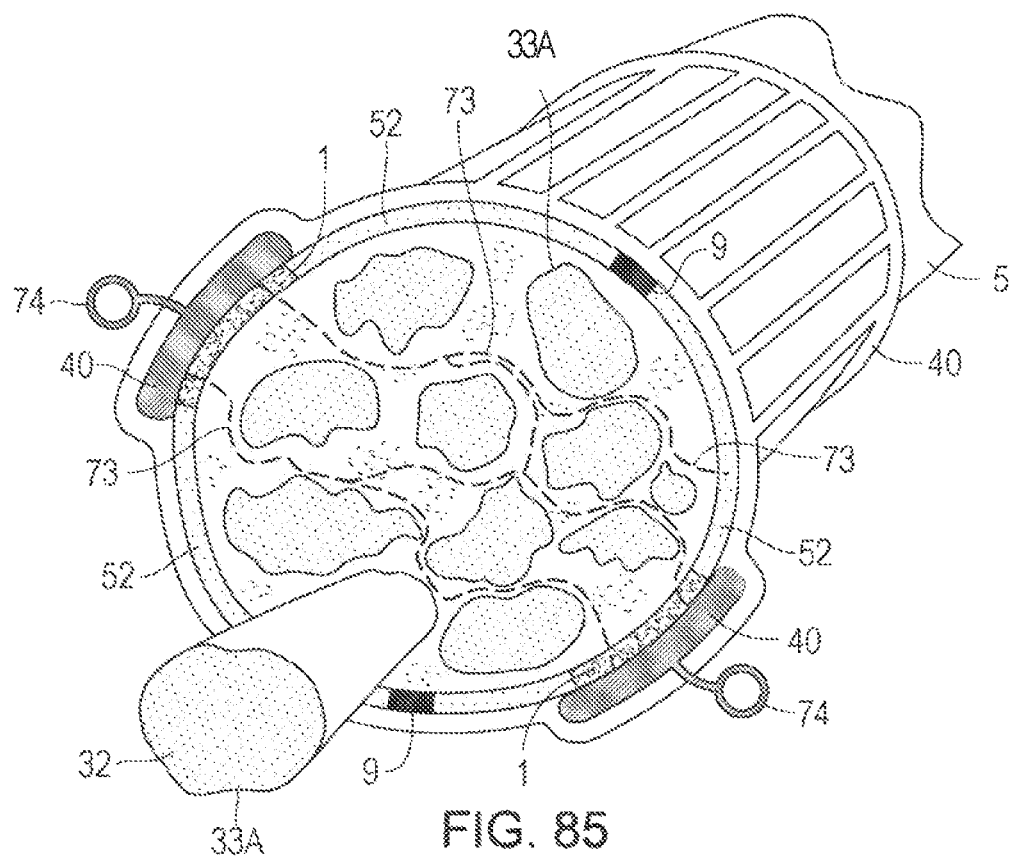
FIG. 85, like FIG. 84, contains a chronically-implanted prior art cuff electrode.

Current shunting around a fascicle is achieved in a manner similar to the method for shunting around a nerve when stimulation electrodes are outside the nerve or even when inside the nerve and the perineurium 33A around the fascicle 32 is too dense, so that injecting contacts next to the fascicle of interest can take care of that problem (FIG. 85).

FIG. 85 is a diagram showing that field lines 73 (compared to FIG. 84) can be changed even in a chronic cuff electrode placement around a nerve 5 by placing liquid mixture 1 just underneath the two cuff electrode contacts on opposite sides of the nerve just inside the cuff electrode. Also, note that two insertions of nonmixture 9 have stopped the electric field lines 73 from going circumferentially, as shown in FIG. 84, with the electrical field lines 73 concentrated in the middle of the nerve instead of scattered throughout or at the edge.

Figure 6:
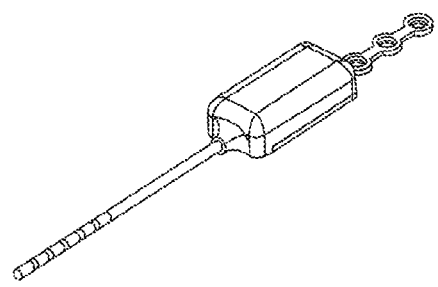
Figure 86:
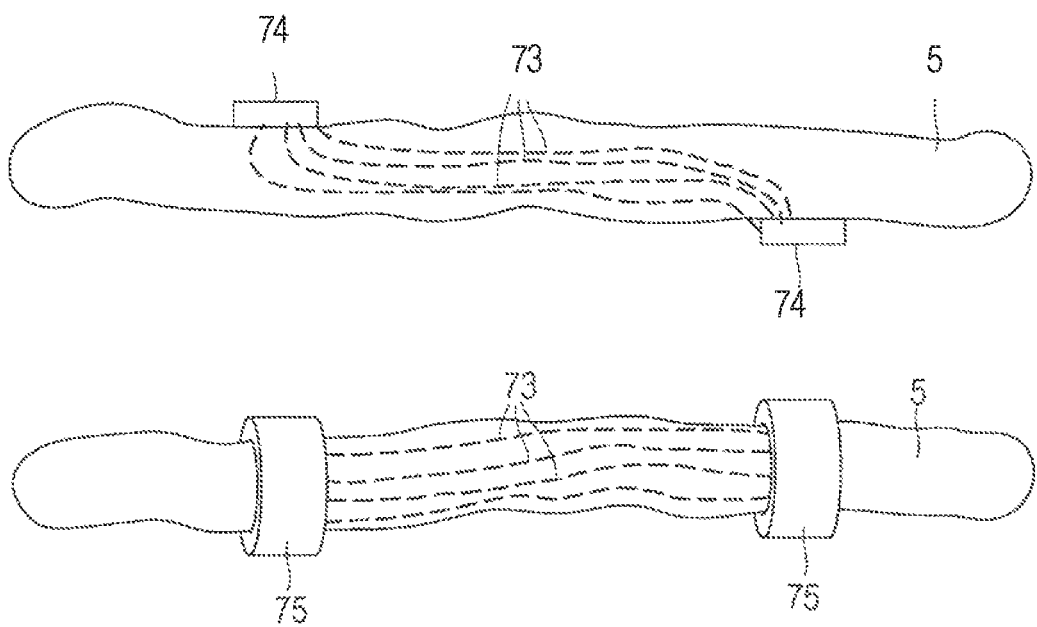
FIG. 86 shows electrical field lines through a nerve target between (top) disc electrodes, and (bottom) ring electrodes, either of which may be prior art electrodes or electrodes manufactured and cured in situ.

Another method allows shaping non-uniform electrical field lines 73 which current will follow. Another aspect of designing electrical fields 73 that depolarize all nerve fibers of a given fiber size within a nerve is to use circumferential electrode contacts instead of disc electrode contacts. Field lines 73 around ring electrodes 75 are not uniform: the closest field lines appear near the edge of the disc electrodes 74 that is facing the other electrode leading to higher current densities and thereby larger induced voltage differentials applied to nerve fibers at that location. As shown in FIG. 6, (a) disc electrodes represent a point-source electrically and allow higher selectivity through their ability of activating a nerve's fascicles with a higher probability in their proximity, and (b) ring electrodes 74 encircle a target provide more uniform electrical field lines and thereby more selectivity based on fiber size. FIG. 86 includes two diagrams showing the difference in electrical field lines between disc 74 (less uniform) and circumferential ring electrodes 75 (more uniform). These field lines can further be changed as needed by placing liquid mixture blobs 26 or rings 22 around, near or inside a nerve (or other target).

The present invention also allows a better electrical and mechanical fit for a prior art cuff electrode, thus modifying the electrical conduction between a conventional cuffs electrode contacts and the nerve. As indicated herein, cuff electrodes are often installed with a void 39 (see FIG. 48) between their electrode contacts and the neural target tissue. FIG. 84 is a diagram showing how encapsulation 52 with connective tissue grows in gaps between the electrodes and the neural target. As metallic electrodes often have recesses into the insulating carrier material (silicone, polyimide and others), connective tissue encapsulation 52 surrounds the nerve with a tight "wall" that is thicker at the location of the electrode (as it fills the void 39 between the recessed electrode and the nerve), thereby increasing stimulation thresholds and reducing SNR values for sensory applications.

Figure 87:
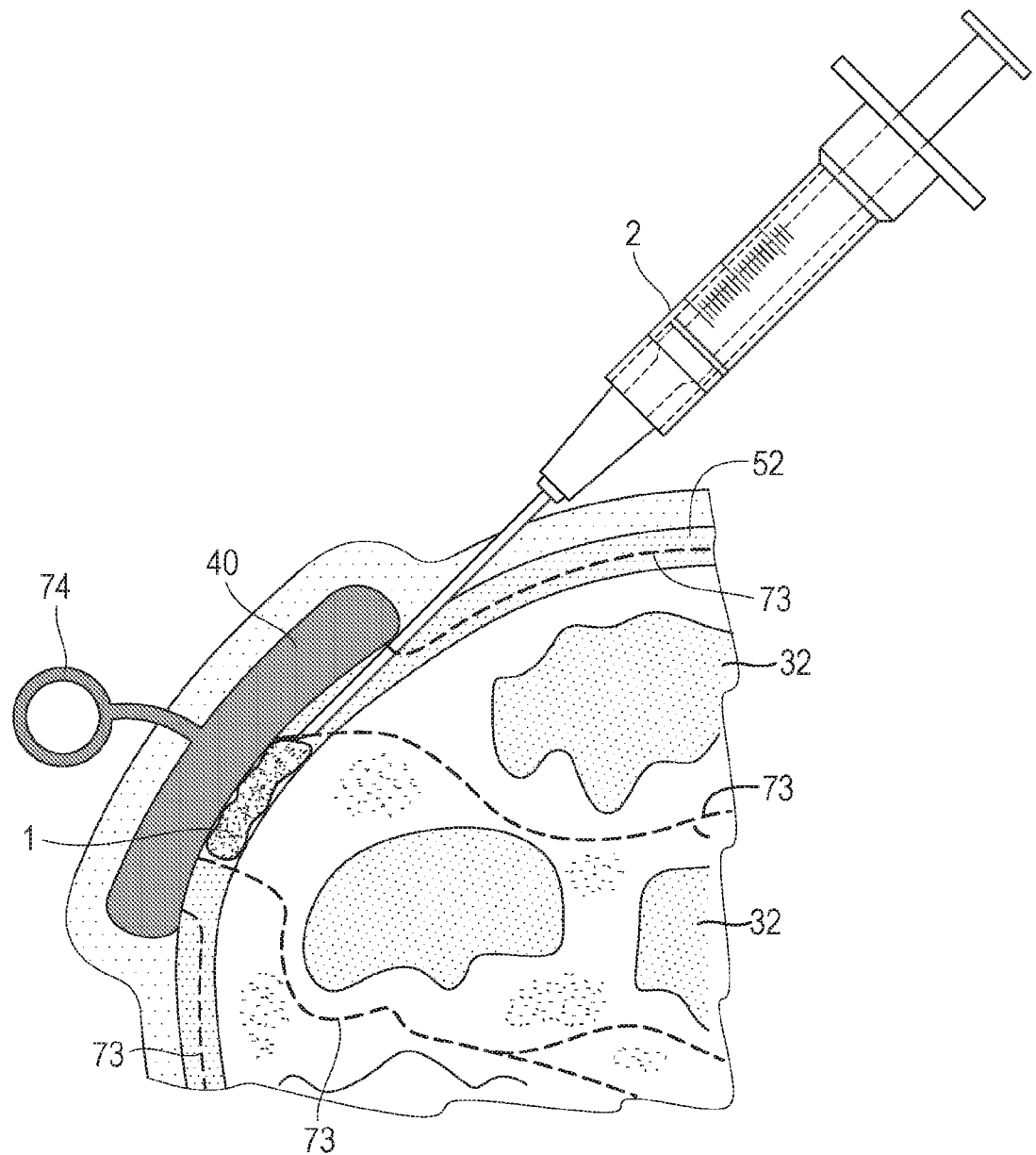
FIG. 87 is a diagram showing a procedure to create a gap in the fibrous tissue between the previously implanted prior art cuff electrode's contact pads and then to inject liquid conductor to fill that gap, thus bridging the encapsulation.

FIG. 87 is a diagram showing creation of a gap in the tissue between the prior art cuff electrode's contact pads and the nerve and then injection of liquid mixture to fill that gap, and also a bridging of encapsulation. A liquid mixture 1 may function as a bridge between a prior art metallic electrode contact 40 and the nerve 5 if liquid mixture is placed onto the contact prior to implantation of the cuff, as in FIG. 44-0. As shown in FIG. 87, this application of liquid mixture may also be placed post-implantation of the cuff if a fine needle is used to inject the liquid mixture 1 into and if the connective tissue right between the cuffs electrode contact and the nerve is removed by physical, biological or chemical means (FIG. 87). In FIG. 85-0 the electrical field lines 73 spreading inefficiently around the circumference of the nerve, will be redirected by a new application of liquid mixture added after original implantation jumps the void 39 and also cuts through the encapsulation 52.

The present invention may be used for re-establishing a cardiac conduction at locations where neural/muscle conduction of control signals to contract the heart is interrupted due to illness, injury or alike. A cardiac infarct can lead to the formation of scar tissue at a location that is required to transmit electrical signals from one location of the heart to another, thereby requiring the implantation of a cardiac pacemaker. The cardiac pacemaker senses the depolarization in one location of the heart (e.g. atrium) and then transmits this information to another location (e.g. the apex) that does not receive the command to contract any more due to injury, illness or alike. By injecting liquid mixture e.g. into the scar tissue within the septum that may conduct the control signal to the apex, the liquid mixture can reestablish the electrical conduction. Considering that cardiac pacemakers are more complicated than the re-establishing of conductive pathways, the injection of liquid mixture in the heart muscle provides a more reliable and efficient approach for patients than reinstalling a pacemaker.

Methods are disclosed herein for reestablishing connection as well as the materials used and the injection catheter with its specifics as cardiac catheter. For the right bundle branch block, the blockade is in the right bundle branch and is visible in the QRS complex. Conduction on the right side relies on cell-to-cell conduction which is slower and thus inefficient and badly coordinated. For the left bundle branch block, the blockade is in the left bundle branch (following the HELLOS bundle), and is visible in the QRS complex-→prolonged QRS complex. Conduction on the left side relies on cell-to-cell conduction which is slower and thus inefficient and badly coordinated. For the AV block, the atria depolarize normally and the ventricle depolarizes somewhat following the atria, or if it is type III block then there is a complete circuit between the atrium and the ventricle on both sides of the heart and the ventricle only pump through the escape beats every 2 seconds (aka 30 bpm). Type III requires a cardiac pacemaker, type II and type I can be ameliorated with medication. The treatment approach of old is for a Cardiac pacemaker for most, especially any symptomatic or severe cases. The new approach is a catheter-based injection of liquid mixture into the location believed to be the bundle block and conduction is reestablished without a cardiac pacemaker at all, resulting in cost savings without surgery, and a procedure can be performed as an out-patient procedure.

A further optional goal is to combat arrhythmias by utilizing a similar approach of injecting liquid mixture into the heart at locations of broken conductivity to prevent or combat arrhythmias, essentially providing parallels to the Purkinje fibers or hiss bundles and the like, using a fine needle to inject the liquid mixture, providing a conductive bypass around areas which should conduct but do not.

Bladder and Bowel

Bladder and bowel control utilizing the cured electrode and TENS stimulation is generally achieved by stimulating the efferent (or afferent) sacral S1, S2, or S3 roots with the aim to either modulate activity in the sacral spinal cord and thereby initiate bladder contraction or relaxation on this indirect route, or by stimulating at least one of these sacral roots for an efferent contraction of the bladder. Bladder activity may further be modulated by stimulating the hypogastric plexuses and nerves or the inferior hypogastric plexus, for these plexi are in direct and indirect connection with both, the bladder as well as the sacral nerve roots. Specifically, the bladder receives motor innervation from both sympathetic fibers, most of which arise from the hypogastric plexuses and nerves, and parasympathetic fibers, which come from the pelvic splanchnic nerves and the inferior hypogastric plexus. There are no prior art treatments available that place an electrode into, near or around one of these plexi. There are also no treatment approaches that just connect to the bladder wall for stimulation, as there are no general electrode systems available that are flexible enough or versatile enough to be placed on or into an organ that stretches and flexes continuously throughout the day. For similar reasons, gastric and lower gut applications are limited. The injectable and cured electrode provides a new way of connecting to the bladder (as well as other organs) on the outside as well as the option for an injection of some liquid mixture partially into the organ wall for better integration. The liquid mixture may be placed on or around nerves that innervate the bladder, but likewise a placement around and into the before-mentioned hypogastric and inferior hypogastric plexi becomes possible as the liquid mixture requires the surgeon to simply distribute the electrically liquid mixture where she perceives e.g. a bladder contraction following a low-level stimulation from the liquid mixture dispenser. The ability to immediately verify that the just injected liquid mixture equally causes e.g. a bladder contraction provides the ability to verify interoperatively that the connection target was indeed hit and the liquid mixture may be assumed to having been properly placed.

The liquid mixture may then be dispensed from the target to a location just below the skin to essentially provide a connection point for an externally applied TENS stimulator. Utilizing a variety of electrical waveforms from 0.5 to 10 Hz for bladder relaxation to i.e. 30 Hz for bladder contraction may be applied with a TENS unit and thereby provide a simple pathway for bladder control. Furthermore, this approach may be used to achieve a connection to the pudendal nerve innervating the external urethral sphincter to provide bladder control, prevent unintended bladder leakage, and aid with bladder voiding when intended by utilizing KHFAC, depletion or non-destructive DC nerve block bilaterally applied to the pudendal nerve.

A similar approach may be utilized for bowel control with connection targets in the lower pelvic floor, the lower intestine walls (the cured electrode may be glued as a meander around or along the intestinal tube), the pudendal nerve, plexi in the vicinity of the bowel, as well as PNS nerves entering and exiting from the sacral spinal cord.

Figure 88:
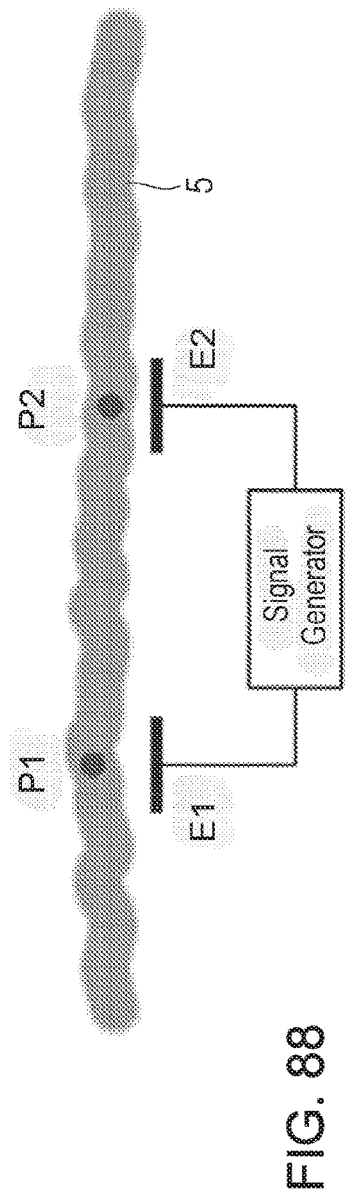
FIG. 88 is a schematic of a nerve with two electrodes being placed along the nerve.
Figure 89:
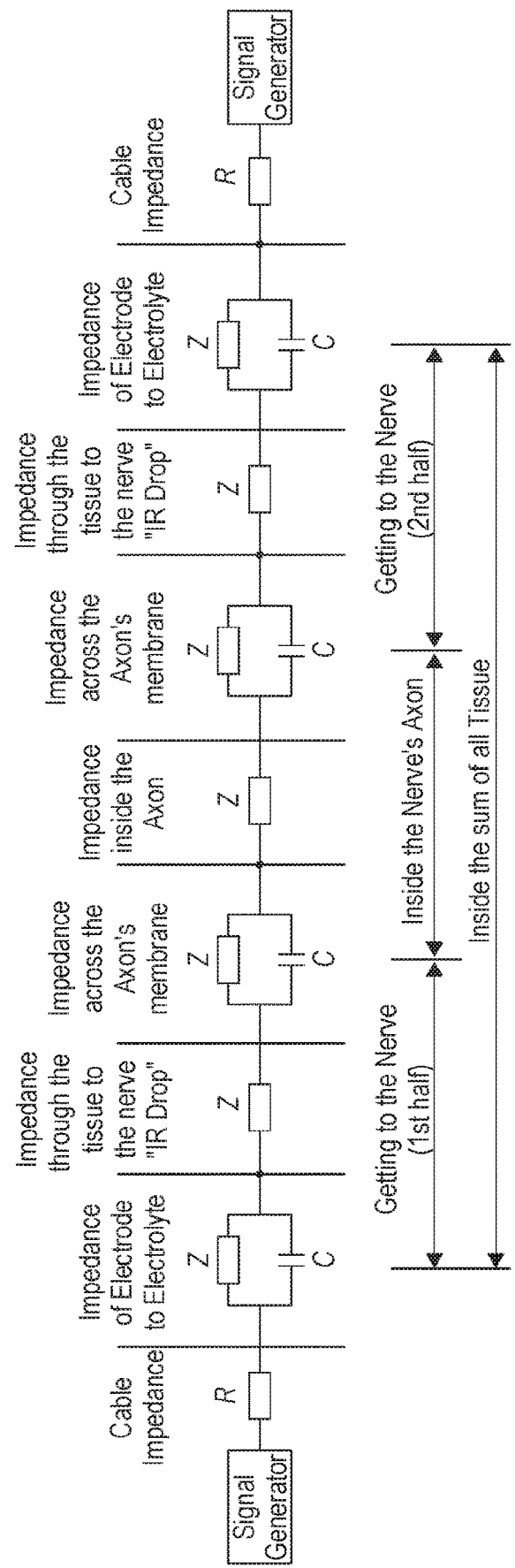
FIG. 89 is a schematic of resistive and capacitive impedance components on the path from one electrode through interstitial fluid to the axon within a nerve and back.

Reducing the IR drop is achievable with the present invention. In FIG. 88, it is assumed that two electrodes E1 and E2 from the signal generator are connected to the same signal generator and that a nerve is placed longitudinally between these electrodes. Of interest is the voltage between two points P1 and P2 inside the nerve, more specifically inside one of the axons of the nerve. FIG. 88 is a schematic of a nerve with two electrodes being placed along the nerve. When the voltage difference between P1 and P2 changes over a certain threshold at a specific (short) time then an action potential is evoked. In order for electric current to flow from point P1 to P2, an electrical difference in potential (voltage) must exist between P1 and P2 and a conductive medium must be present such as a metallic wire (electrons conducting) or an ionic liquid such as it is present inside a cell (ions conducting the electrical current). There are a several components to the final impedance from the signal generator to the electrode to the electrolyte, through the electrolyte to the nerve, across the membrane, inside the nerve, back across the membrane, through the electrolyte towards the electrode, the interface back from electrolyte to the electrode and from there back to the opposite end of the signal generator. FIG. 89 shows the total impedance from the electrical stimulator to the inside of the nerve and back.

FIG. 89 is a schematic of resistive and capacitive impedance components on the path from one electrode through interstitial fluid to the axon within a nerve and back. In other words, of the total applied voltage from one side of the signal generator to the other side of the signal generator, there is a complex sum of impedances in the path. The largest purely resistive component of that path is the ionic conduction of current through the electrolyte and the tissue made up of connective tissue between the electrode and the nerve's axonal membrane. This more or less purely resistive component is captured in the "IR-drop" of an applied square wave current-controlled signal, shown in the solid line of voltage over time in FIG. 90 which is a schematic of the voltage curve measured during current controlled stimulation showing the resistive component (solid curve: vertical lines=IR-drop) and the capacitive component (dV/dt indicating the charging of surface boundaries). Source: http://iopscience.iop.org/article/10.088/1741-2560/13/5/056011 via Google Images. If the voltage drop through the tissue and electrolyte were subtracted out, then the voltage measured to charge the electrode-to-electrolyte interface (and to a small degree the capacitance of the axon's membranes) is also shown in FIG. 89-0 as the dotted line.

Previously Unreachable Locations

Figure 90:
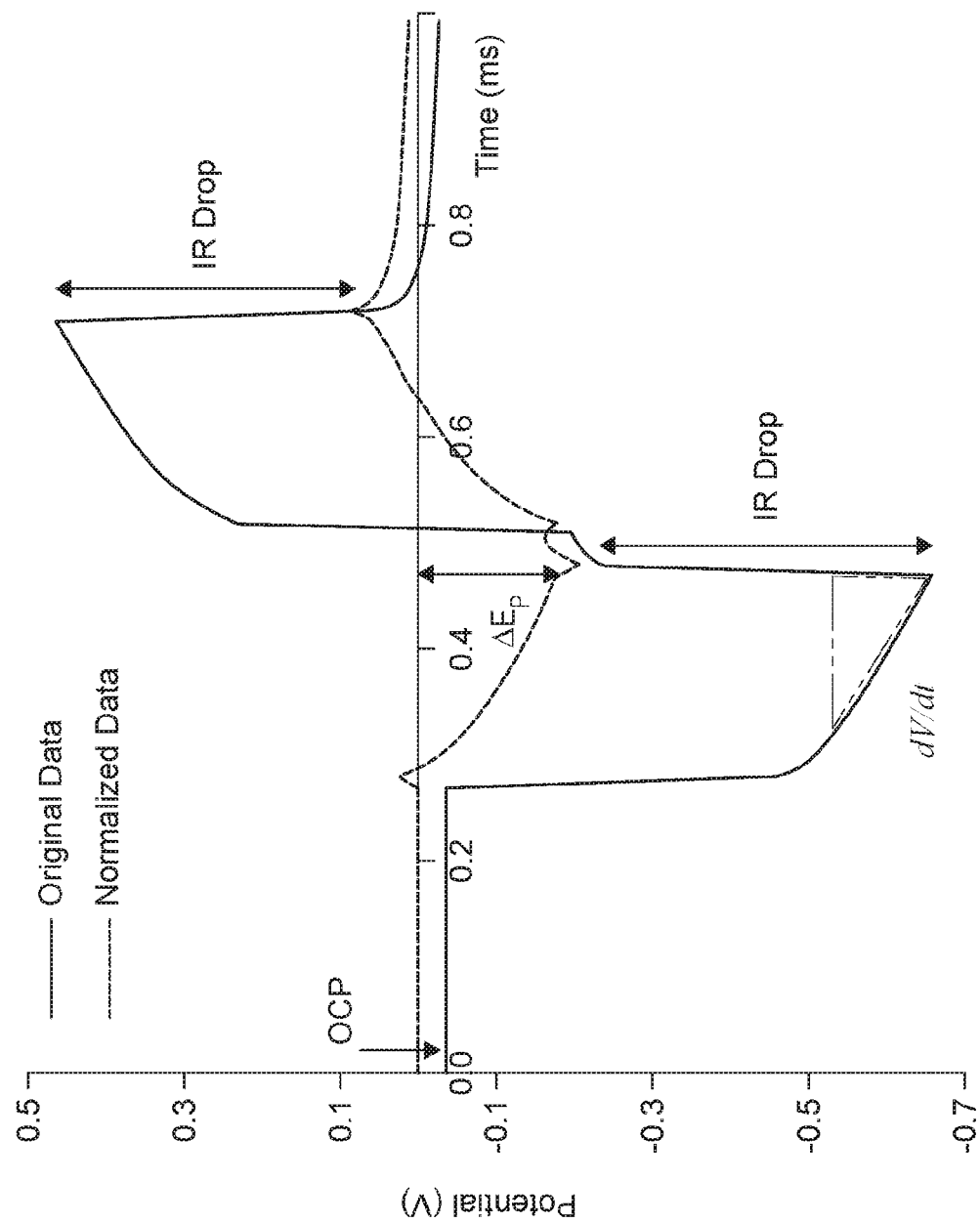
FIG. 90 is a schematic of the voltage curve measured during current controlled stimulation showing the resistive component (solid curve: vertical lines=IR-drop) and the capacitive component (dV/dt indicating the charging of surface boundaries).
Figure 91:
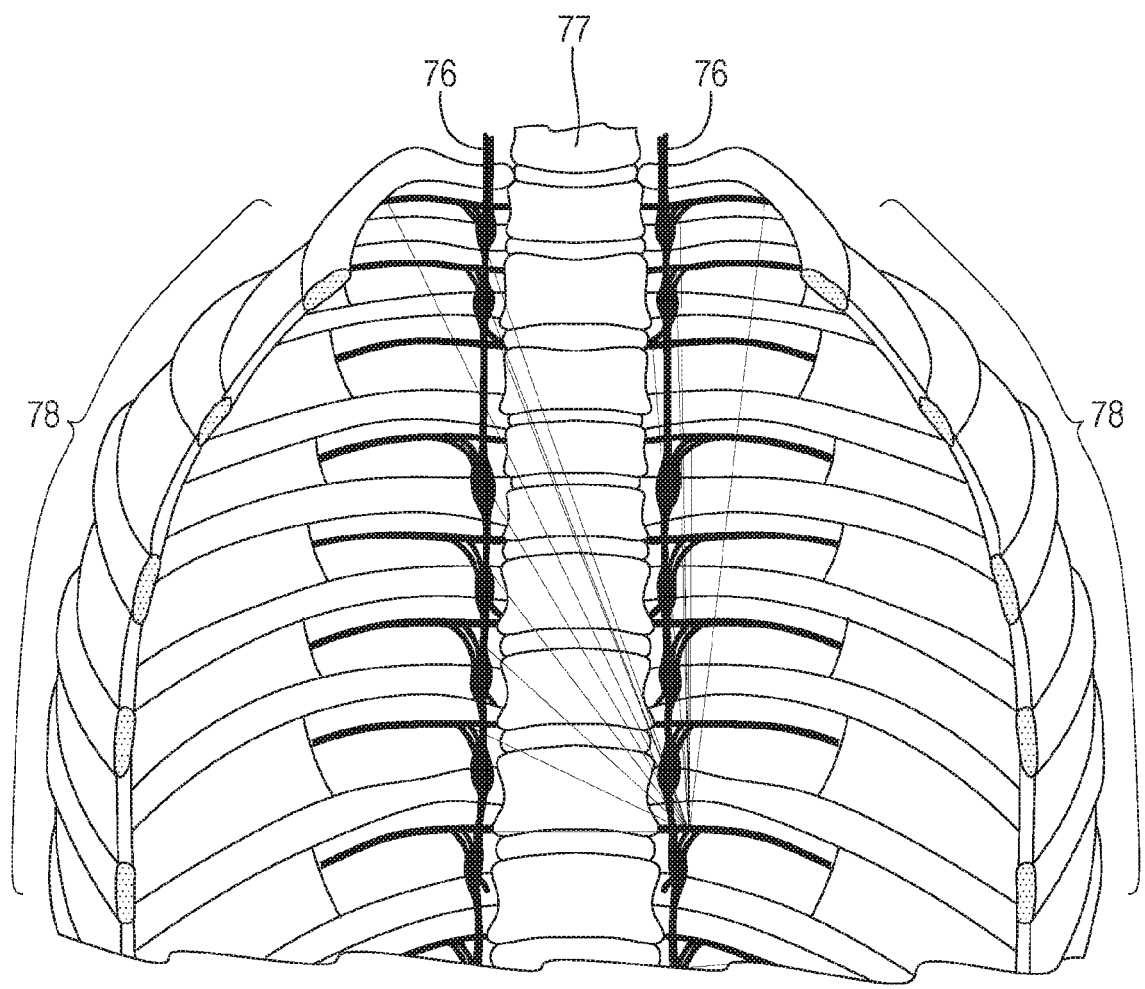
FIG. 91 is a schematic of a front view of a rib cage with sympathetic chain ganglia shown.

The injectability of the liquid mixture allows interfacing with the PNS at locations formerly not feasible with prior art devices. Many nerves of the PNS originate on the ventral side of the spine, running along the bones of the ribcage as intercostal nerves or diverge into the abdominal cavity. Most of these nerves may not be interfaced with current technologies, such as common cuff electrodes, unless a major surgery first grants access to such a deep tissue nerve, generally only possible from the ventral (abdominal) side, and then places the cuff electrode around the nerve with the need to then find a place to anchor the cuff electrode via suturing it to tissue that does not move much in relation to the nerve the cuff was placed on. Prior art devices do not allow a dorsal access as the surgical field required to gain access to a nerve in order to place a cuff electrode is simply not available between the bones of the rib cage or the muscles of the back without causing major damage to the movement and stabilization apparatus of the patient or subject in the process. Yet, many nerves of the autonomic nervous system ("ANS"), especially the majority of sympathetic nerves are located on the ventral side of the spine and run along as the ganglia of the sympathetic chain (FIG. 90-0). The sympathetic chain and its ganglia are depicted as positioned near to both sides laterally of the vertebrae at the rear of the thoracic cavity. To reach the sympathetic chain ganglia ventrally in this area would be massive surgery going around the heart and the lungs and the largest and most critical blood vessels, so the sympathetic chain is not reachable ventrally. Dorsally, though, through a thin needle may be placed through the muscles of the back through the ribs and so deliver injectable liquid mixture/cured electrodes to the sympathetic chain ganglia, instead of requiring an thoracic/abdominal surgical procedure. The present invention thus allows access to many locations formerly believed impossible to access such as, for example: (1) pre-ganglionic fibers exiting the spinal cord before synapsing in the ganglia of the sympathetic chain. (2) ganglia of the sympathetic chain. The liquid mixture/cured electrode may be injected to encase a specific ganglion allowing for the complete and or selective/partial depolarization using uniform electrical fields achieved by fully encapsulating the ganglion with the cured electrode and stimulation versus a distal return electrode. (3) connecting fibers between adjacent ganglia of the sympathetic chain. (4) post-ganglionic fibers that exit the ganglion of the sympathetic chain and travel to the inner organs, organ systems and neural ganglia or plexi inside the abdomen and other locations inside the body. (5) Foramen that Ganglia are located in. These foramen may function as mold pre-cure as well as added mechanical protection of the cured electrode. (6) Foramen that function as passage ways for nerves and nerve bundles. These foramen may equally function as mold pre-cure as well as added mechanical protection of the cured electrode. (7) tissue plains between muscle bundles that have nerves and nerve bundles pass in-between may become a mold to form a cured electrode in and attach a cured electrode to. The placement of the cured electrode does not require the same number of surgical steps needed to achieve a blunt separation of the nerve tissue from surrounding other tissue as well as may not require separate steps to anchor an electrode as the liquid electrode may provide this as an innate property, interfacing with the surrounding as well as the encapsulated neural tissue.

The present invention enables interface for ganglia in the PNS as never before. Ganglia are intersections of nerves in specific locations of the body. These intersections may be formed of afferent only, efferent only or combined afferent and efferent nerves. Ganglia contain axons and cell bodies of neurons and represent small processing units, somewhat similar to neural plexi, in the periphery of the body, meaning computational units that may perform signal analysis, combination, reduction and processing outside the central nervous system. Ganglia thus represent a highly desirable target for neural interfacing to stimulate or block activity within them fully or partially.

The prior art method of interfacing with a ganglion is to stab it, meaning injecting a sharp electrode, such as a microelectrode, into the ganglion. This unfortunately only allows for the interfacing with a few of the neurons passing through or connecting inside the ganglion. If a comparably large electrode were to be stabbed into a comparatively small ganglion then irreparable compression damage is to be expected for the ganglion, and injury from irritation during body movement.

Figure 92:
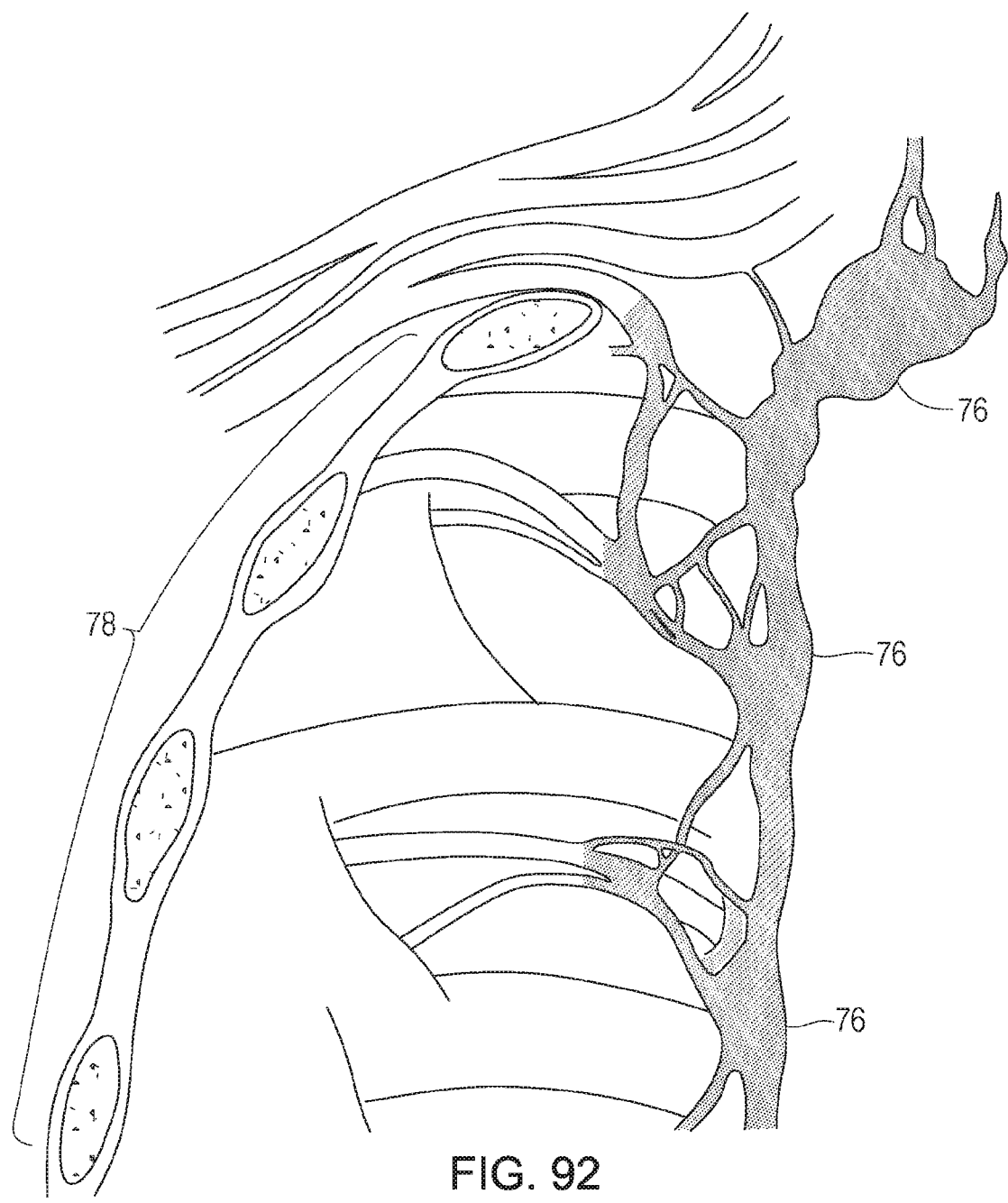
FIG. 92 is a schematic of a side view of a rib cage showing the irregular shapes of the sympathetic chain ganglia.

FIG. 92 shows greater detail of the highly irregular shapes of the sympathetic chain ganglia. Cuff electrodes for ganglia in contrast do not exist as such, for cuffs form a cylindrical volume when deployed. Cuff electrodes are not very desirable, but they can form a circular structure around a cylindrical nerve. They do not interface at all, however, with a ganglion that is irregularly shaped and has more than two neural entry points. If a cuff electrode were to exist for a ganglion, it would require substantial surgical access around the ganglion to encompass all entering and exiting nerve endings. Such a procedure would require more than a simple blunt dissection lasting less than 5 minutes. Prior art cuffs often require a suturing of the cuff around the nerve or to neighboring tissues which require the supporting mechanical biological environment as well as additional surgical time.

The advantages of the present invention in comparison include, without limitation, the ability to (1) provide a blunt dissection by placing the liquid mixture next to, behind and around a biological structure which reduces surgical time needed to free up a target from its surrounding tissue, (2) encase a irregularly shaped target inside the body with a liquid mixture that flows initially and, after undergoing a phase change, flows less (e.g. malleable) or even ceases to flow (fully cures) and allows to place a neural interface all or partially around a ganglion with the expectation of having a reliable mechanical interface in place, (3) place a connecting wire into the liquid mixture at any location within the liquid mixture to fit the anatomy of the patient, (4) place liquid mixture via needle, with added instruments using a laparoscopic approach and under ultrasound or angiographic/x-ray visualization, allowing minimally invasive placement of liquid mixture on/around ganglia not surgically accessible before, e.g., deep inside the abdomen such as the ganglia of the sympathetic chain adjacent to the spine and on the ventral (abdominal) side of the spine.

Dorsal root ganglia (DRG) at the spinal cord may be interfaced in a similar fashion, (a) requiring a blunt dissection of the DRG first, (b) or using the blunt separation abilities of the liquid mixture placement to save time on the OR table. The DRG may be encased with liquid mixture, then also fully or partially encased with liquid nonmixture anchored elsewhere to raise mechanical stability or improve selective neural stimulation of the DRG.

The present invention has the capability to provide electrical stimulation of ganglia and connecting nerves of the sympathetic chain. The sympathetic chain innervates virtually every organ in the body and, additionally, is connected to blood vessels throughout the body, allowing a coordinated, body-wide effect with one or more neural interfaces that stimulate or block either ganglia or the connecting nerve fibers between ganglia of the sympathetic chain or the nerves connecting ganglia with the organs in the body. The sympathetic chain is commonly understood to regulate the "fight-or-flight" response. Some of the applications resulting from stimulating the sympathetic chain with the present invention include, without limitation: (1) an "electronic caffeine," i.e., waking a person within seconds, (2) a "boost of energy" to the subject, including a raised heart rate, respiratory rate, sweat production, modulation of blood pressure and modulations of the iris diameter, (3) an antidepressant and mood regulator, (4) combating the sensation of hunger, (5) raising the body's base metabolism and metabolic rate when a subject exercises, (6) an electric analgesic, (there is a directly correlation between parasympathetic over activity and perception of pain and modulating sympathetic activity can reduce the duration and intensity of pain) (7) modulation of sympathetic activity indirectly leads to a modulation of parasympathetic activity in the body. By temporarily blocking sympathetic activity, parasympathetic activity will decrease as a response due to the body's own regulatory pathways, allowing a reduction of parasympathetic activity by both, fully stimulating, partially stimulation, partially blocking, fully blocking as well as partially blocking and partially activating specific ganglia and connecting nerve branches of the sympathetic chain. The present invention provides all three, a medical diagnostic, a medical treatment and an academic research tool to directly interface with the sympathetic chain of the human body, as well as animal preparations, while relying on a minimally invasive surgery to place the cured electrode.

The present invention enables neuromodulation of all the organs connected to the sympathetic chain, by attaching one or more embodiments of the present invention to the sympathetic ganglia. The ability of the present invention to encase a ganglion completely with all entry and exit nerve branches allows for the application of nerve block waveforms uniformly to depolarize or hyperpolarize fibers and cell bodies within the ganglion similar to the uniform depolarization that may be achieved with a 360-degree encased cuff on a PNS nerve trunk: while a partially encased nerve trunk may be partially depolarized and hyperpolarized with fibers close to the electrodes perceiving the effects of the electrical field first, it is the 360-degree encapsulation that allows for a uniform field (of rotational symmetry) within the nerve trunk inside the 360-degree coverage of the liquid mixture/cured electrode to provide the uniform depolarization and hyperpolarization. It is this ability to produce the uniform depolarization and hyperpolarization that is key to a controlled and reproducible nerve block, especially with chronically placed electrodes.

The ability of the present invention to adhere very closely to a neural stimulation or block target of interest in combination with the ability to fully encase said target is vital to achieving a controlled and reproducible (partial or full) nerve block using waveforms such as kHz-frequency for KHFAC nerve conduction block, 200 Hz (range: about 150 to 900 Hz) for neurotransmitter depletion block to anodic block without damaging the ganglion by penetrating it with an electrode. The present invention thus provides the only interface needed for a controlled, partial or full and repeatable nerve block without the need to breach the membrane of the ganglion. The present invention achieves this for every ganglion with a proper surgical placement around the ganglion, with a partial or a full covering/encasing of the ganglion to achieve the ability to block as described.

In one embodiment, the present invention is a much more feasible alternative to prior art methods of sympathetic ablation that uses an endoscopic approach with a dorsal access. Some patients receive a surgical cauterization/dissection of the sympathetic chain to treat autonomic disorders or intractable pain. While this may treat the initial underlying condition, sympathetic ablation will generally yield a non-reversible result for the patient: it may not be undone and any resulting side effects caused by ablating the wrong or too much neural tissue of either the chain links between the ganglia or the ganglia itself may not be reversed. In contrast, the cured electrode provides a means to deliver a therapy (with a dorsal or ventral or combined dorsally-ventral approach) to reversibly stimulate or block neural tissue of the sympathetic chain or ganglia in the periphery or neural plexi in the abdomen as well as other peripheral locations. Use of the cured electrode is fully reversible by switching the waveforms off and, further, may be adapted very specifically to the patient since waveforms may be changed by the physician by noninvasive means. Additionally, the present invention's cured electrodes may be removed more easily through a minimally-invasive procedure if the patient or physician desires so, an advantage over prior cuff-like electrodes or electrodes that would penetrate the membrane of a ganglion, thereby leaving an indentation and scar tissue inside the ganglion when removed.

The present invention enables stimulation of spinal nerves formerly not accessible. The ability of the cured electrode to be delivered via needles placed through keyhole incisions is vital to a new treatment paradigm presented to the neural engineering community. Surgery to place a prior art electrode on a neural target in the PNS required a comparatively large incision as well as a significant amount of spreading of tissue inside the body to gain access to the nerve and have enough space left to place the electrode into or around the nerve, the liquid mixture/cured electrode is capable of providing a minimally invasive procedure to access and interface neural tissue of interest for stimulation and block.

The present invention provides the first reliable interface for deep tissue nerves in the PNS at hard to reach locations such as the spinal nerves exiting the spinal foramen and running along the intercostal space between the ribs or along other bony structures of the body.

The present invention enables a neural interface for a foramina (plural, foramen 34) which are naturally occurring openings, holes, or passage ways for arteries, veins, nerves and alike in or through bony tissue. Foramen come in many forms, shapes and sizes and are different from one human to another. As such, it is very complicated to provide a one-size fits-all" pre-made electrode that may be placed into a foramen to interface with a nerve. On the other hand, a foramen may represent an ideal mechanical anchor point for a neurostimulation electrode to nerve interface, as electrodes that integrate with the foramen do not experience any movement in relationship to the nerve passing through the foramen. The presence of bony tissue around an electrode and nerve further adds protection for the fragile neural interface. One method of placing and securing a liquid mixture/cured electrode is the injection of liquid mixture around a nerve and also into a foramen. The procedure of placing a connecting wire into a foramen, injecting liquid mixture around that wire and the nerve, encasing both, in some embodiments, alleviates removal of bone near the cured electrode location (e.g., a laminectomy).

Figure 93:
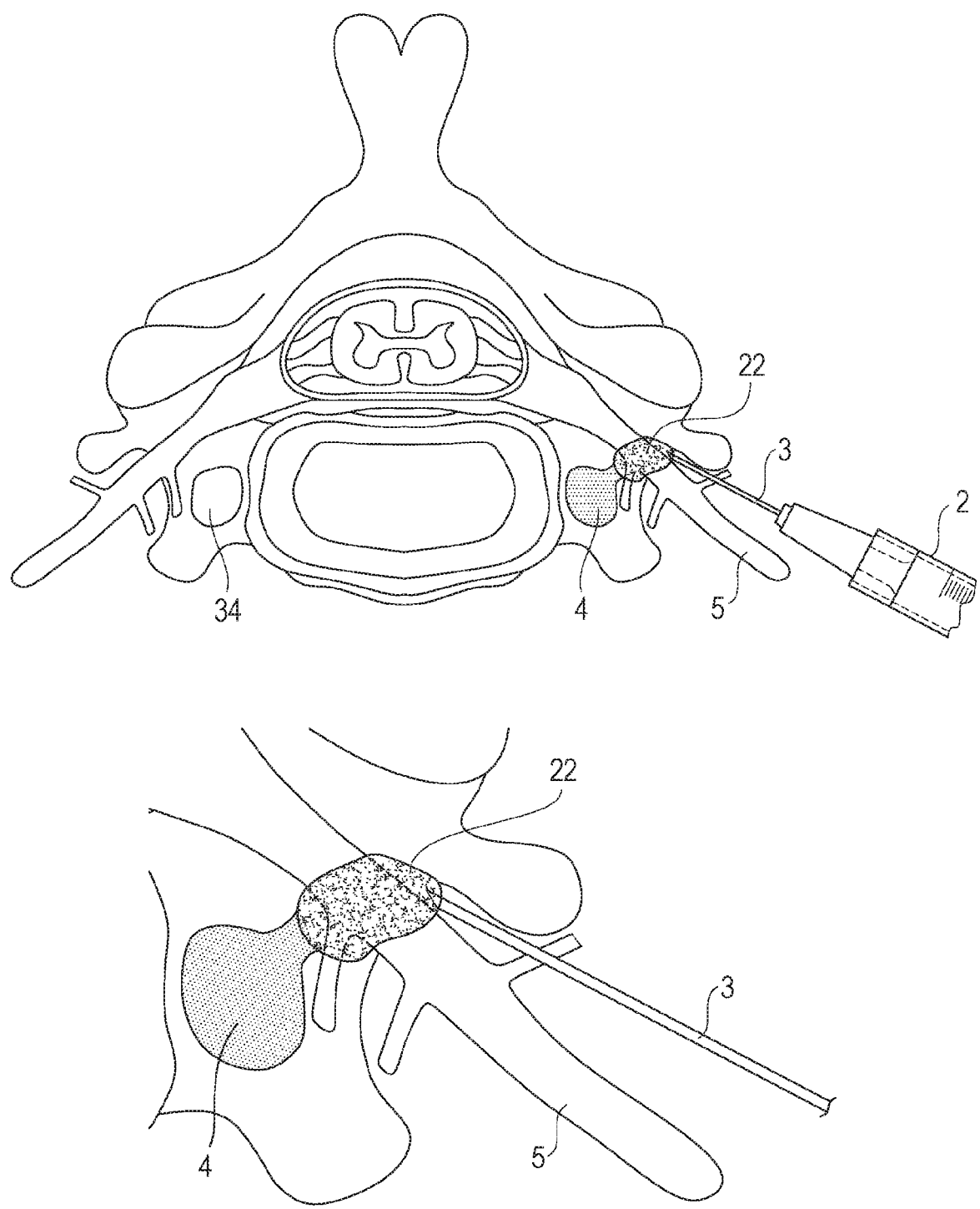
FIG. 93 contains two schematics depicting foramina as exit points for spinal nerves with placement of liquid mixture or non-mixture in a foramen. The lower schematic is an enlargement of the placement region of the upper schematic.

FIG. 93 is a drawing showing foramina as exit points for spinal nerves with placement of liquid mixture or nonmixture in a foramen.

The present invention enables interfacing sacral nerves and branches for parasympathetic and bladder control. The human body has two primary interface points to the parasympathetic nervous system: (a) several cranial nerves (vagal, trigeminal, occipital, auricular and others), and (b) nerves of the sacral level spinal cord. For lack of easy surgical access to the nerves to the sacral spinal nerves, most current neuromodulation technologies aiming to utilize a modulation of parasympathetic activity focus on interfacing primarily with the vagal nerve and to some degree with the trigeminal, occipital and auricular nerve. Current interfaces, such as the Medtronic Interstim device for bladder modulation or the Brindley Vocare System for bladder control in spinal cord injured individuals, require a major surgery to gain access to the sacral nerves (and/or nerve roots), in part requiring a laminectomy and removal of spinal bone structure to place prior art electrodes. In contrast, the present invention provides a minimally invasive approach that allows the injection of the primary interface as a liquid mixture around the target. This liquid mixture may then either connect to an injected signal generator, or it may encase the de-insulated tip of a lead wire that in turn may connect to an implantable signal generator, or it may be connected to a subcutaneous connection pad as described herein.

Additional embodiments for the present invention include, without limitation, (1) Stimulating parasympathetic fibers from the sacral level and modulate HR, BP etc. (2) producing calm under stress by being able to stimulate parasympathetic fibers (sacral and cranial level), (3) creating alertness when needed, (4) reducing hunger sensation even with food volume deprivation by stimulating the sympathetic chain, and (5) stimulation of the duodenum to provide the sensation of satiety for low-volume eating.

Figure 1A:
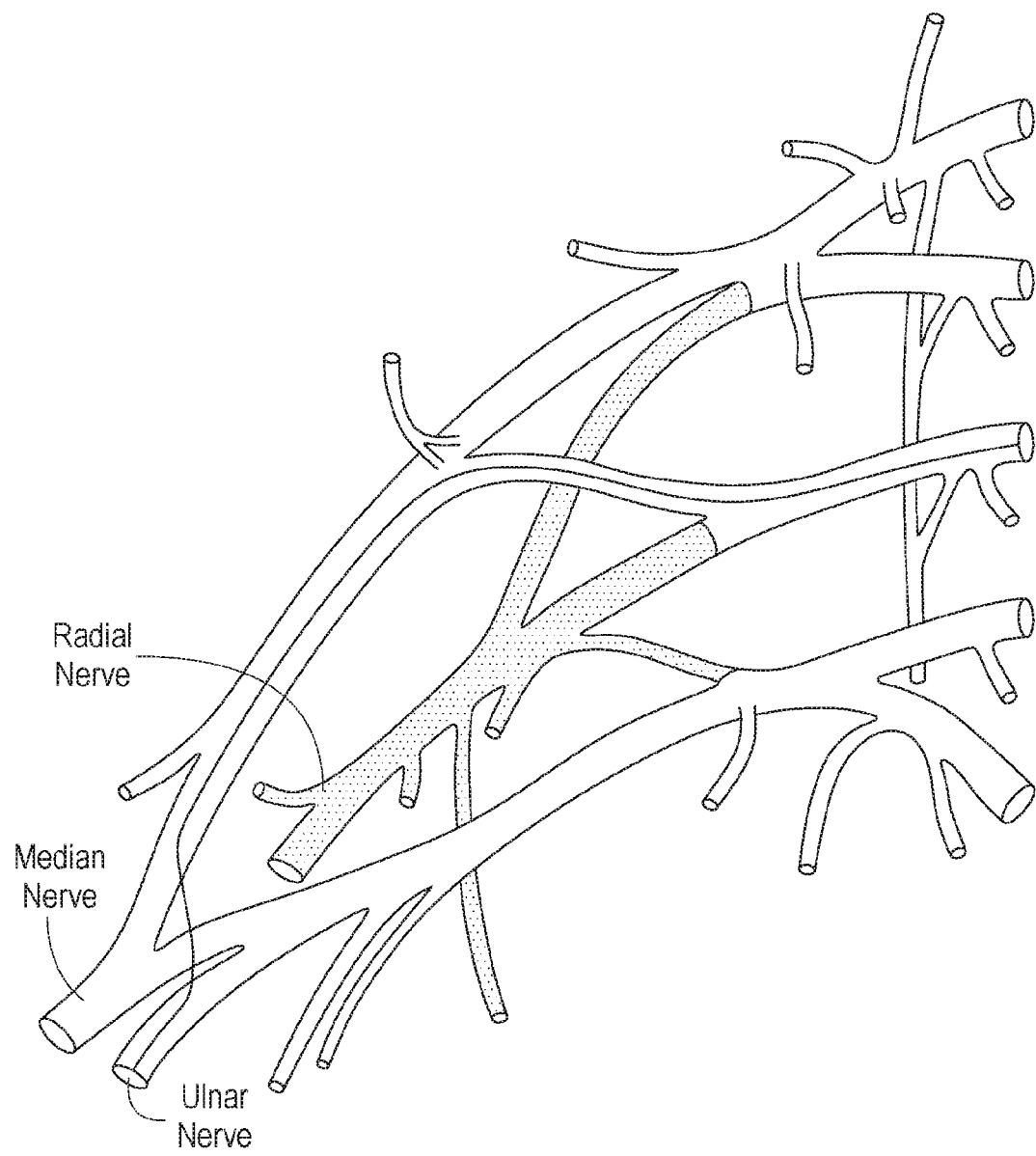
FIG. 1A shows the peripheral nervous system ("PNS") neural plexi of a human brachial plexus.
Figure 1B:
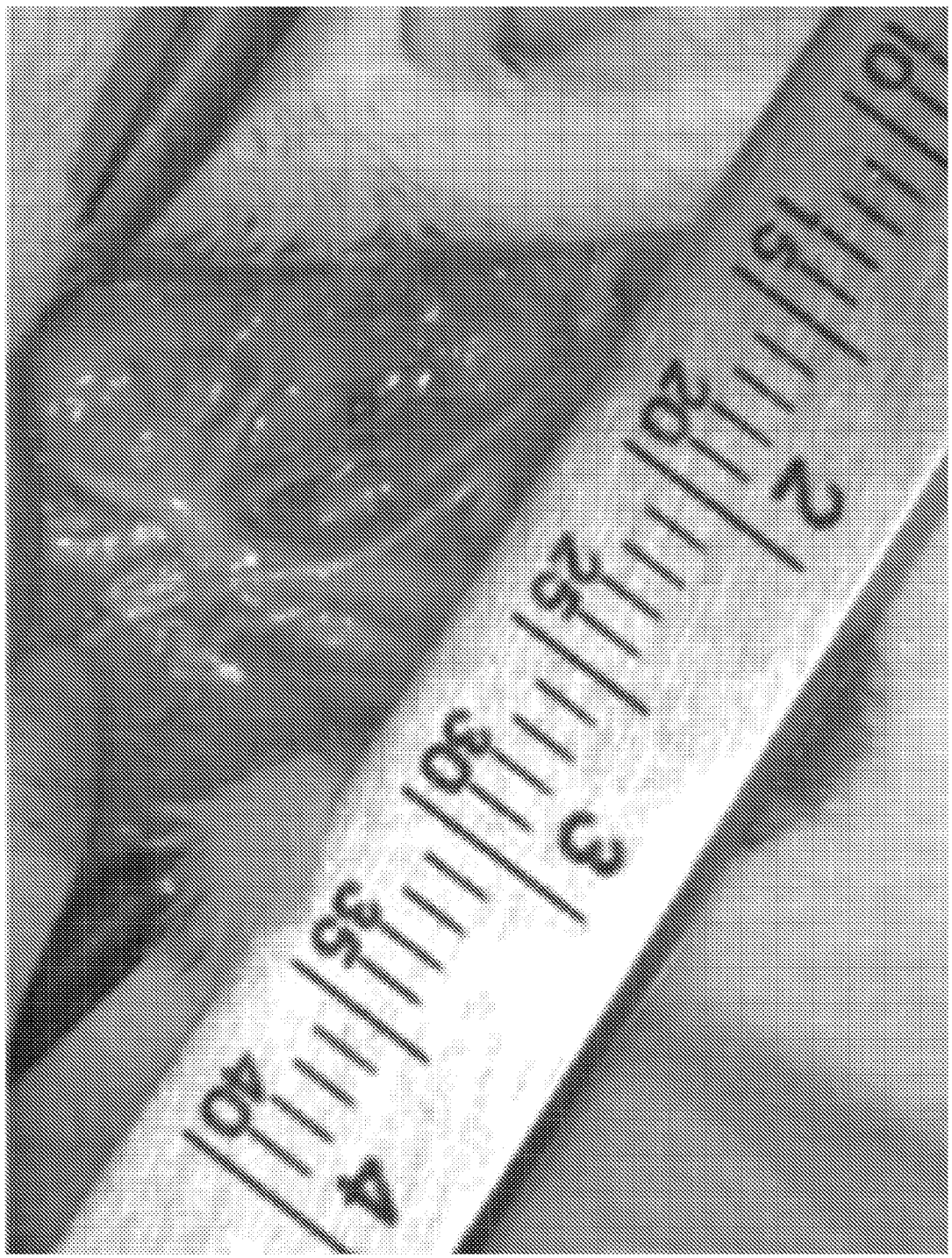
FIG. 1B is an image of a rat cranial nerve ganglion adjacent to a scale.

The present invention enables a novel neural interface for neural plexi in the PNS and CNS. A neural plexus is a collection of nerves in the same location, often with crossovers and interfacing between said nerves. Ganglia may be part of a neural plexus. All of these structures are shaped differently, have different nerve thicknesses and often slightly different contours and locations for nerve entrances and exits. It is virtually impossible with conventional technologies to interface in a simple and straight forward way with the nerves of a neural plexus and utilizing the exact same technology across multiple patients, each having unique anatomy. An example of the above application is for the brachial plexus, a collection of nerves near the clavicle bone towards the arm pit and from there innervate the entire arm, as shown in FIG. 1-0. The majority of nerves that innervate the arm are very easily accessible at the brachial plexus. The advantage of using the liquid mixture/cured electrode, as contrasted with prior art electrodes, is the capability of encasing one or more or nerves here. A patient suffering from chronic arm pain due a traumatic nerve injury, or from phantom limb pain, will benefit from the placement of a cured electrode on the nerves of the brachial plexus (image below). Especially for cases where the entire arm was lost due to traumatic injury it may be advantageous to utilize a neural interface that may stimulate all the nerves involved at one central interface location. The cured electrode, placed as injection at a perpendicular angle to the longitudinal axis of the involved nerves, aiming to inject the liquid mixture below and behind the nerves, offers an interface that may be adapted by the operating physician at runtime in the ER or and under localized anesthesia at the injection site alone. Wherever needed, nerve or fascicle specific selectivity may be increased by combining liquid mixture and nonmixture.

Figure 94A:
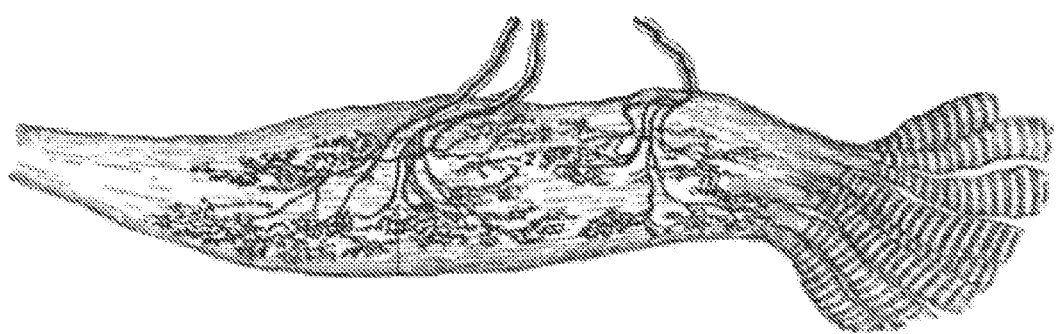
FIG. 94A is a schematic of Golgi Tendon Organs inside tendons.
Figure 94B:
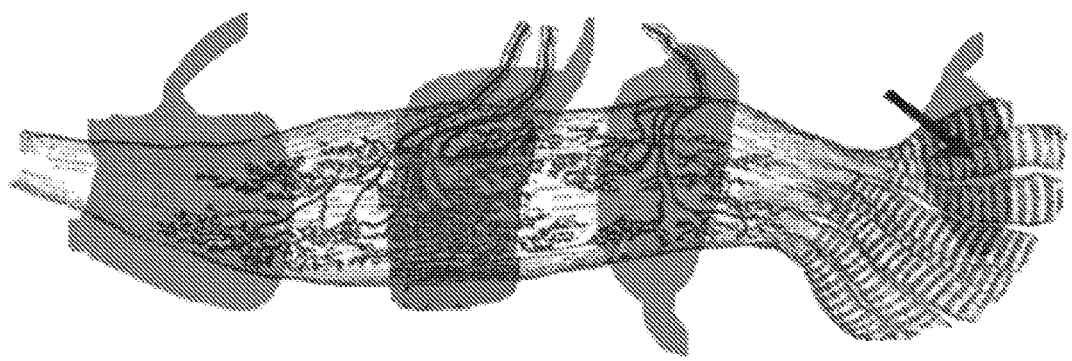
FIG. 94B is a schematic of Golgi Tendon Organs inside tendons as locations for the placement of four cured electrodes.
Figure 94C:
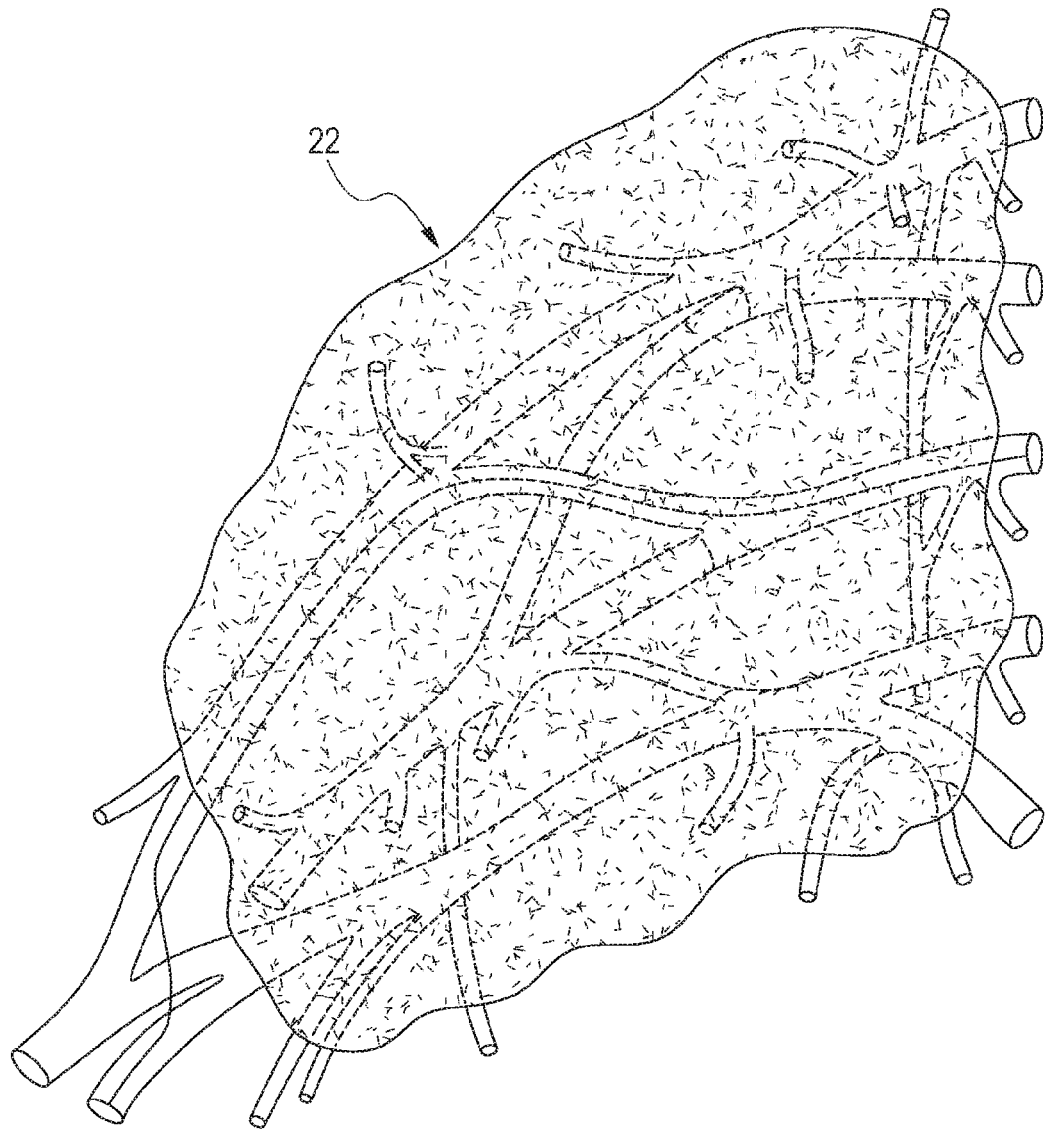
FIG. 94C is a schematic depicting the placement for a liquid mixture/cured electrode on a brachial plexus.

FIG. 94C is a drawing of placement location for a liquid mixture/cured electrode (blue) on the brachial plexus in a human with a IPG implanted to electrically connect to the cured electrode and thereby fully depolarize all fibers of the brachial plexus on demand.

Other targets for the present invention include the cervical, thoracic, abdominal, and pelvic plexi. Prior art electrodes are designed to interface, for example, with a cylindrical nerve fiber (via a cuff) or a nerve nucleus (via a needle). The distribution of many fine nerves connected together and forming a neural network in the physical structure of a mesh requires a different type of interface. The cured electrode provides such an interface by allowing the physician to spray, paint, inject below, through and on-top of the body's irregular structures. For example, the sacral plexus and other plexi in the abdominal cavity, especially within the pelvic region, represent neural stimulation targets for specific organs (e.g., bladder, bowel, sexual organs) or the dualism between the sympathetic and parasympathetic arm of the autonomic nervous system.

Another example of applications for the present invention is stimulating baroreceptors in the abdominal and thoracic cavity. The body utilizes baroreceptors in two locations to drive sympathetic inhibition and parasympathetic activation with the goal of causing a combination of bradycardia and vasodilation to lower blood pressure when needed: one group of baroreceptors sits on the carotid sinus, the second one on the aortic arch. The aortic arch catches system high blood pressure (body wide) whereas the carotid sinus catches a stronger component of blood pressure differences heading cranially.

A selective stimulation (and/or potential temporary partial or full nerve block) of the baroreceptors or innervating nerve fibers connecting to said baroreceptors of the Aortic arch may provide a simple and more effective way to lower systemic blood pressure as compared to stimulation (and/or potential temporary partial or full nerve block) of the baroreceptors or innervating nerve fibers connecting to said baroreceptors of the carotid sinus.

The aorta may be surrounded with a cured electrode, focusing the liquid at the aortic arch and liquid nonmixture as mechanical stabilizer without impeding the ability of the aorta to stretch and contract as cardiac contractions push pressure waves through the aorta. Such a cured electrode is one again achieved under ultrasound or angiographic visualization in a laparoscopic approach using sterile, minimal-invasive technique.

Additionally, stimulation of the baroreceptors is possible at tissues connected to the sternum. Sternal thrusts are commonly performed on patients for whom breathing has stopped and conventional means of resuscitation are unavailable, impractical, or exhausted. The inferior vena cava which extends from the heart and connects to the liver through the diaphragm, may stimulate the baroreceptor reflex when stretched.

Anchoring

The present invention prevents or minimizes migration of miniaturized prior art neural implants. Similar to the approach of securing a signal generator to a bone or other biological structures passing through or nearby a foramen, small neural signal generators may be secured very easily with liquid mixture or nonmixture at their specific neural interface location. Liquid nonmixture may be used to provide an optimal mechanical anchoring of the small neural signal generator, whereas the active electrode area to the neural target of interest or the distant return electrode (which may just be 5 to 25 mm away from the neural target of interest on the other end of the small signal generator) may be formed using the liquid mixture which may use the same carrier medium as used to form the liquid nonmixture to provide an optimal mechanical integration of the small neural signal generator. A neural signal generator, anchored with liquid nonmixture, and/or liquid mixture, retains its mechanical position better than when held in place by only one suture or by conforming to anatomical structures of the implantation target. This is true for placement locations near single small nerves, single large nerves, many collinear running nerves, near or inside a foramen, near or inside a neural plexus.

Follower Circuits

Follower-circuits may be used to pick up an electrical signal in the radio-frequency spectrum (e.g., 1 to 10 MHz) and they comprise a receiver coil, a diode, a transistor, a capacitor and a resistor, all of them passive components hermetically sealed, the product follower-circuit being encapsulated in silicone to provide some form of mechanical stability.

Instead of soldering the electronic components together, they may be glued together using liquid mixture, only to then be encased in liquid nonmixture to provide the mechanical stability. Such a circuit, constructed truly only from hermetically sealed components that are connected and encased only in liquid mixture or nonmixture, offers the advantage of being more mechanically stable, less chemically valent (no solder means less metals that may form half cells inside an aqueous medium), and be mass produced outside the body as fully cured system that may then relatively easily be implanted and then secured inside the body using the liquid mixture while connections to nerves may be utilized using the same liquid mixture that was used to connect the hermetically sealed components earlier to form the follower-circuit. Aside from follower-circuits, other electronics such as for sensing, amplification and stimulation can be constructed using such manufacturing principles.

Cardiac Applications

Many cardiac applications range from arrhythmias (heart not at correct rhythm, incorrect timing of contractions or of partial contractions of the heart), to bradycardia (slow heart), to tachycardia (fast heart), to bundle branch block before heart failure develops. In general, hearts age with each person/patient and as the muscle (and neuro-muscle) tissue in the heart undergoes small damages, fibrosis sets in and healthy heart tissue slowly becomes non-conductive and needs to be electrically bridged. Cardiac resynchronization pacemakers and other pacemakers as well as cardiac defibrillators are implanted to combat effects caused by this loss of conductivity inside the heart.

The present invention further comprises a dispenser and methods for improving electrical connectivity for the above cardiac pathologies:
(1) A dispenser is provided which comprises a catheter comprising a needle to sense electrical signals and stimulate cardiac muscles, with the dispenser being connected to a controller outside the body.
(2) A physician advances the catheter needle into the septum to a point where it senses the natural progression of the neural stimulation signal still reaching, and the physician location is marked as P1 on the controller.
(3) The catheter [needle?] is advanced into the septum at a point a few millimeters (2.5 mm) distally to a point where stimulation, coordinated in time with the sensed signal earlier at P1, provides normal cardiac rhythm, this location being marked as P2
(4) The physician then actuates a flow of liquid mixture between P1 and P2 through the catheter needle to establish the electrical connection again
(5) The physician uses ECG data to verify electrical connectivity between P1 and P2

In addition to injecting liquid mixture through the catheter into the heart, the physician may also dispense liquid mixture from the outside of the heart through another dispenser adapted from a syringe, to establish electrical connectivity in a manner analogous to that described above in the ER/OR at runtime. Alternatively, the liquid mixture may be dispensed to temporarily block nerve conduction for open heart surgery comparable to current techniques where a fork is used to bypass electrical conduction for a given region of the heart, rendering it still and allow a surgeon to complete a procedure.

Post-Surgical Pain

Many surgeries are associated with longer-lasting deep tissue pain, especially when bony structures, tendons and muscle pathways were re-aligned as part of the procedure. Examples are hip replacements, fixing and stabilizing a broken femur bone, knee and/or ankle surgeries, or procedures on the lower back such as fusing vertebrae or fixing a herniated disk. This pain may last several weeks as a result of a successful surgery and months to years as a result of a suboptimal surgical outcome. While post-op care generally involves the supply of opioids to the patient for follow-up pain treatment, the present invention provides to the localized pain block instead of systemic opioid use.

Some liquid mixture embodiments described herein provide a temporary cured electrode resorbed by the body over time. The temporary cured electrode, when placed as part of the surgery (likely towards the end of the procedure) and connected to nerves, tendons, or larger tissue groups within the surgical wound itself, does not require an excessive amount of surgeon time while providing the option for a local pain block relying on e.g. a transcutaneous stimulation paradigm later on with the added benefit that the waveforms needed for the specific patient's needs may more easily be designed and adjusted with a device outside the body.

In yet another implementation, liquid mixture not temporary and described herein is placed into the wound to connect to the same tissues when the physician determines that a long term electrical neural interface is required.

Abdominal Organs

There is a need for a stable mechanical interface to organs and/or organ systems which may flexibly or rigidly move with the organ within the body without putting excessive strain on the organ's walls.

Tendons and Muscles

Pain treatment via the cured electrode connected to tendons and muscles for proprioception. Tendons are innervated with Golgi Tendon Organs, reporting information on the tendon strain and thereby the strain (and in part the stretch) of the muscle connected to the tendon. Similarly, muscles are innervated by nerves connecting to muscle spindles that measure the amount of stretch of the muscle. Together, Golgi tendon organs and muscle spindles are the primary sensory input organs as part of the body's peripheral afferent innervation providing the proprioceptive input to the spinal cord and brain that allow the calculation of one's body's position. When phantom limb pain is present in an individual having suffered muscle loss or damage to the limb's neural, muscular, body or other tissue structures, then the amount of information provided by Golgi tendon organs and muscle spindles may be reduced or otherwise changed in comparison to the amount and type of signals that were presented to the CNS from the periphery before.

The present invention allows the placement of the liquid mixture around entire tendons as well as the surrounding or crisscrossing of muscles with liquid mixture to interface with the afferent nerves within the tendons and muscles of interest. This is especially of interest for cases where the afferent fibers form a mesh around and inside the tendon and/or muscle and do not allow a simple interface with prior art electrodes. FIG. 104-0 is a drawing of the basic anatomy of tendons and the Golgi tendon organs at the interface to the muscle fibers. These nerves are often small and a cuff electrode would only insufficiently cover the nerves as needed while micro-needle based electrode would need to be poked into the actual Golgi tendon organs or around the nerves to have any chance of effect. The present invention in contrast may be formed with conductive and non-conductive mixtures where needed to surround the tendon, the Golgi tendon organs as well as any muscle fibers of interest to provide a mechanically stable, flexible as needed, neural interface that lasts. FIG. 94A is a drawing of Golgi Tendon Organs (GTO) inside tendons which are locations for placement of cured electrodes. GTO are part of the Body's proprioceptive neural sensory input system. They acquire information about the tension of a tendon and the connected muscle, thereby allowing the body to assess muscle forces and indirectly through computation in the CNS the location and orientation of the body's arms, legs and other body parts. Image source: https://upload.wikimedia.org/wikipedia/commons/a/a1/Gray938.pn The liquid mixture may be placed as part of a surgery that takes place on the muscle, tendon or other tissues in an open wound or needle-based delivery approach; or liquid mixture may be placed separately with the needle-based or similar approaches. FIG. 94B is a diagram of Golgi Tendon Organs (GTO) with four cured electrode locations. Liquid mixture is visualized in blue, liquid nonmixture in grey. Cured electrode #1 interfaces with the tendon and some GTO inside the tendon. Cured electrode #2 interfaces electrically with the nerves connecting to the GTO while mechanical stability is provided by liquid nonmixture surrounding the tendon with GTO inside. Cured electrode #3 interfaces with both, the GTO inside the tendon and the nerves connecting to the same GTO on the outside of the tendon. Cured electrode #4 interfaces with muscle fibers to stimulate sensory fibers such as muscle stretch receptors primarily and efferent fibers to drive muscle contraction second.

Preclinical Cadaver, Animal Studies, Benchtop Studies

Study 1: Impedance—Tissue & Cadaver Study

Figure 95A:
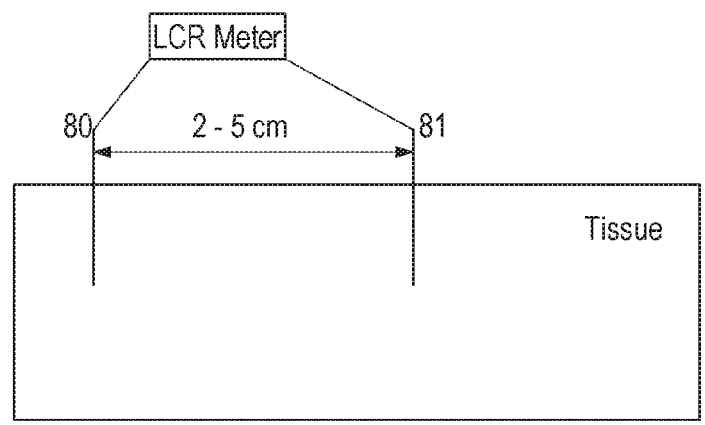
FIG. 95A is a schematic of a lab setup for Neurostimulation Study #1 with an LCR meter and a first and a second steel probe for measuring impedances in various animal tissues.

Tissue impedances of various samples were first measured without the present invention. Tissue impedances were measured with a LCR meter (DE-5000 Handheld LCR Meter; IET LABS, INC., Westbury, NY) using a 1 kHz sinusoid by recording the impedance between two stainless steel wire probes 80, 81 inserted in animal tissue. Tissues examined were chicken muscle tissue, chicken sub-cutaneous tissue, pork muscle tissue, ham (processed pork), beef (muscle) and rat muscle tissue. First, stainless steel wire (SS 316L, 26 ga, Fort Wayne Metals) was placed into the tissue at a distance of 2 cm. The location was chosen such that the distance could be varied up to 5 cm. Caution was used to insert approximately 1 cm of wire into the tissue for repeatable metal to tissue interface areas. The LCR meter was connected to the stainless steel wire probes 80, 81 at distances between 2 and 5 cm apart. (FIG. 95A). Result: All impedances between 2 and 5 cm distance were determined to be between approximately 300 and 700 Ohms with the majority of tissue impedances recorded in the 500 to 700 Ohm range.

Figure 95B:
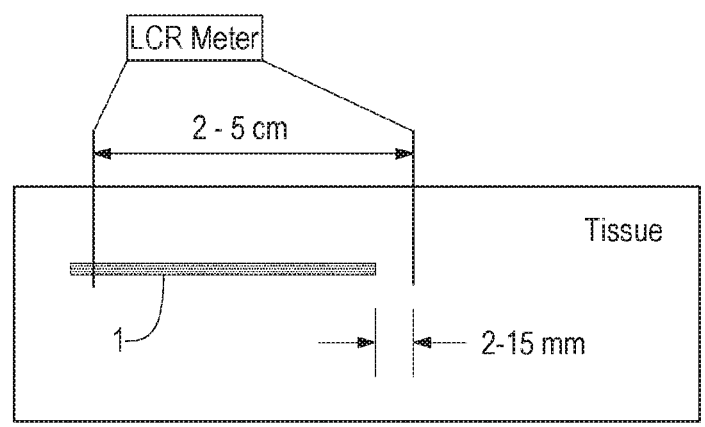
FIG. 95B is similar to 95A, with the addition of a cured electrode in direct contact with the first steel probe, but not in direct contact with the second steel probe.

Next, electric field modification and tissue impedances were observed with the present invention. Cured electrodes 1 were placed into the meat by needle injection, originating from the location of one stainless steel wire probe 80 and bridging the distance to the second stainless steel wire probe 81 with varying gap distances between 2 mm and 15 mm of tissue left un-touched between the end of the cured electrode and the second stainless steel wire probe 81. (FIG. 95B). Result: impedances across the entire 2 and 5 cm distance were determined to be between approximately 150 and 270 Ohms and dependent primarily on the length of the gap between the end of the cured electrode 1 and the second stainless steel wire probe.

Figure 95C:
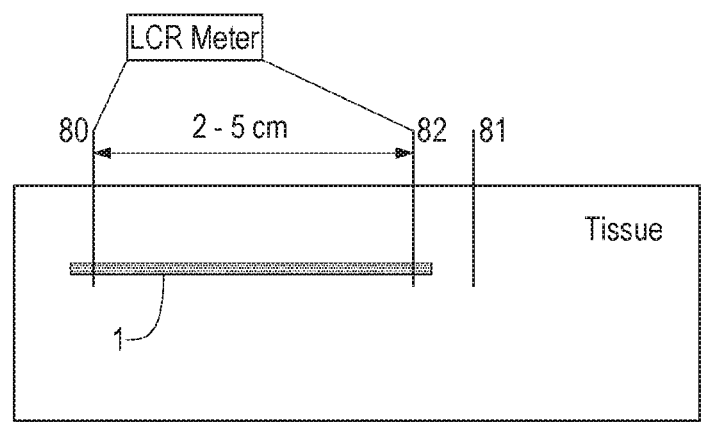
FIG. 95C is similar to 95B, with the second steel probe being in direct contact with the cured electrode to obtain the impedance of the cured electrode(s), and with the addition of a third probe not in direct contact with the cured electrode.

Finally, the Cured electrode impedance was determined by placing a third wire probe 82 directly through the end of the cured electrode 1 closest to the second probe 81. The impedance of the cured electrodes did vary by length from about 0.25 to about 0.45 Ohms with smaller impedances correlating with shorter cured electrode lengths (FIG. 95C).

Study 2: Voltage Drop—Tissue & Cadaver Study

Figure 96:
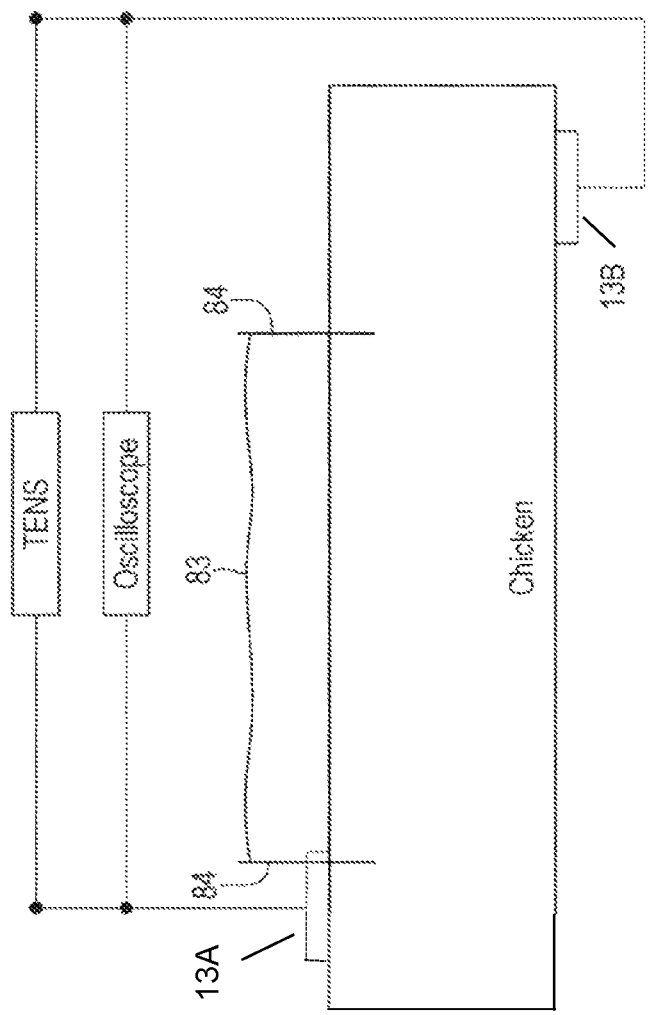
FIG. 96 is a schematic of a lab setup for Neurostimulation Study #2 with an oscilloscope to measure the voltage necessary to apply a current controlled biphasic waveform during TENS stimulation on chicken meat, with and without a cured electrode.
Figure 97A:
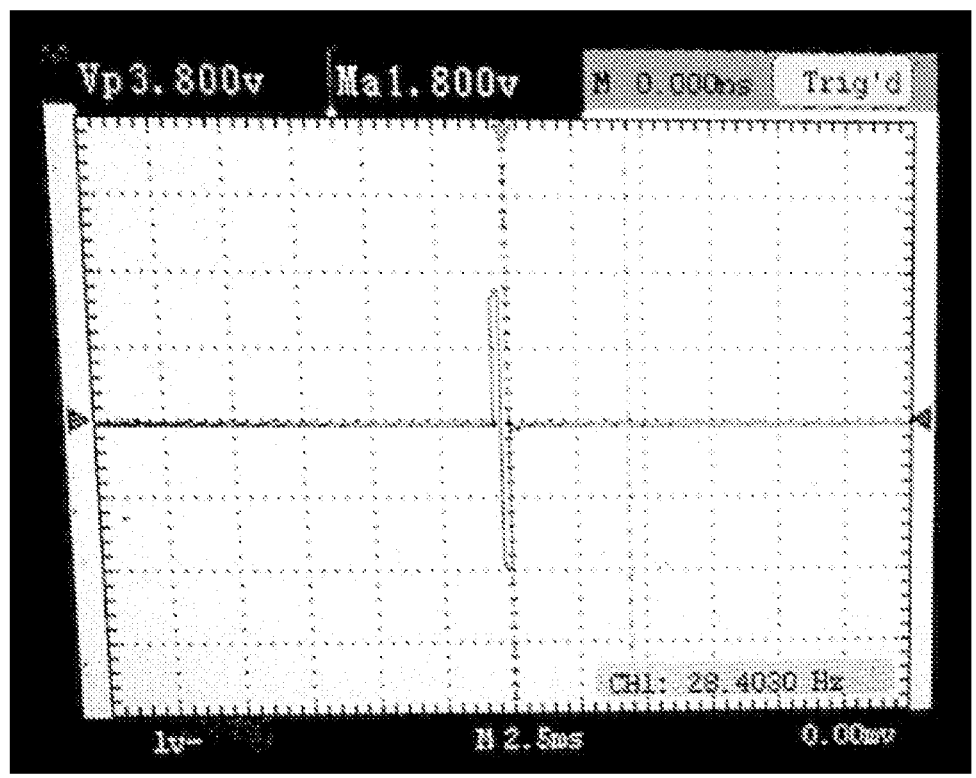
FIG. 97A is an image of an oscilloscope readout of 3.8 volts from the setup in FIG. 96 without a cured electrode injected into the chicken meat.

A voltage measurement was taken during TENS stimulation. A transcutaneous electrical nerve stimulator was applied with TENS electrodes 13 (cut to 1 cm square) to chicken meat (muscle, approximately 1 cm thick, 3 cm wide, 12 cm long). The electrodes 13 were placed approximately 8 cm apart and on opposite sides of the chicken meat. An oscilloscope was used to visualize the voltage needed to apply the current controlled biphasic stimulation waveform. A diagram of the setup is FIG. 96. The oscilloscope showed the voltage between the two TENS electrodes was 3.8 volts (FIG. 97A). The chicken tissue was wrapped into insulating foil to minimize dry out and parallel current paths through contacts on the table.

A 5 cm stainless steel wire 83 (line impedance <0.2 Ohm) with alligator clips was clipped to metal pins 84 and inserted through the short axis of the chicken and the wire placed into the chicken tissue. One pin 84 was placed in direct contact with one of the TENS electrodes 13A ("first electrode"), the other pin 84 was placed at varying distances along the long axis of the chicken tissue, but never the total distance to the second TENS electrode 13B. As the wire 83 produced a parallel low-impedance path along the long axis of the chicken tissue, the voltage measured by the oscilloscope dropped as driving the same current with the TENS unit was now possible through a lower impedance parallel path. The drop in voltage depended primarily on the size of the gap between the second TENS electrode 13B and pin 84 near it.

For gap distances larger than 50% of the distance (approximately 4 cm) between the two TENS electrodes, the voltage (e.g., 3.56 volts) needed to drive the current dropped some but not more than 30%. For small gap distances of about 1 cm of the distance between the second TENS electrode 13B and the nearest pin 84, the voltage (1.68 volts peak to peak) needed to drive the current dropped to values of about 50% of the total voltage needed if no shortening wire 83 was applied, as shown in the readout on the oscilloscope in FIG. 97B. For very small gap distances of <1 cm and especially <0.5 cm of the distance between the second TENS electrode and the pin, the voltage needed to drive the current dropped to values of about 20% of the total voltage needed if no shortening wire was applied.

Figure 97B:
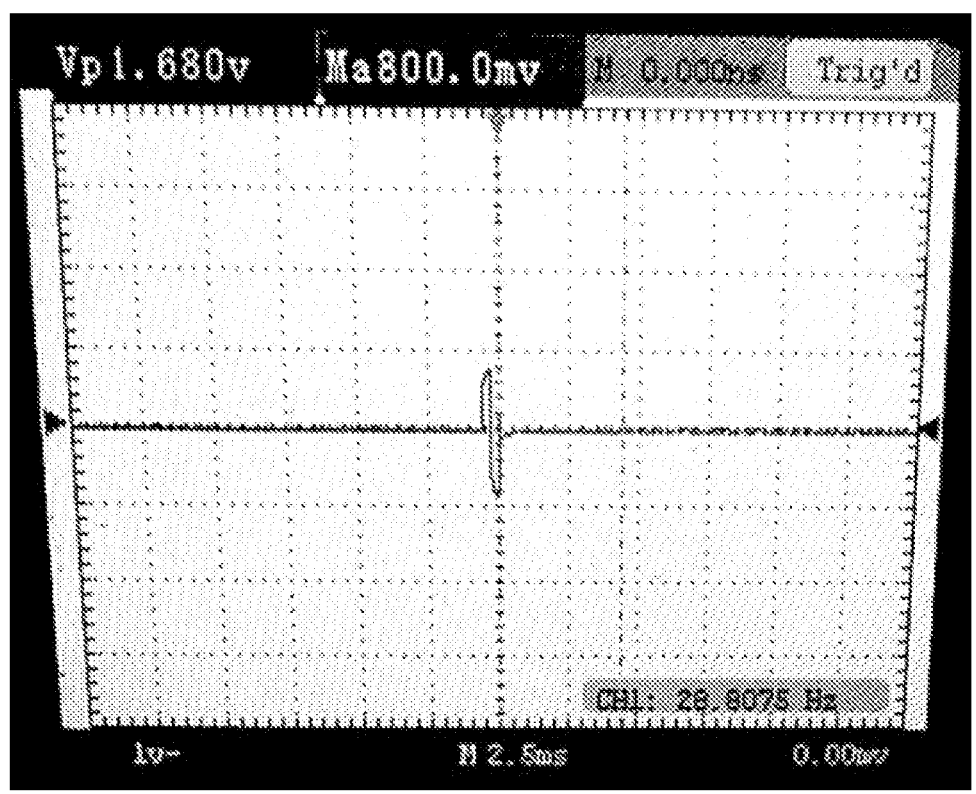
FIG. 97B is an image of an oscilloscope readout of 1.68 volts from the setup in FIG. 96 with a cured electrode injected into the chicken meat.

A cured electrode 1 was placed by needle injection for the distance of approximately 3 cm into the chicken tissue and the outside TENS electrodes 13A, 13B were repositioned to allow a direct connection of the first TENS electrode to the cured electrode 1 while the second TENS electrode remained approximately 0.7 cm away from the cured electrode and the results were similar to FIG. 97B. The voltage needed to drive the same current through the chicken tissue dropped by about 65%. The voltage needed with the wire placed in parallel, shortening gap by approximately 90% resulted in a voltage drop of about 65% from the original value of 3.68 volts peak to peak.

Study 3: Rat Study 1

Figure 98A:
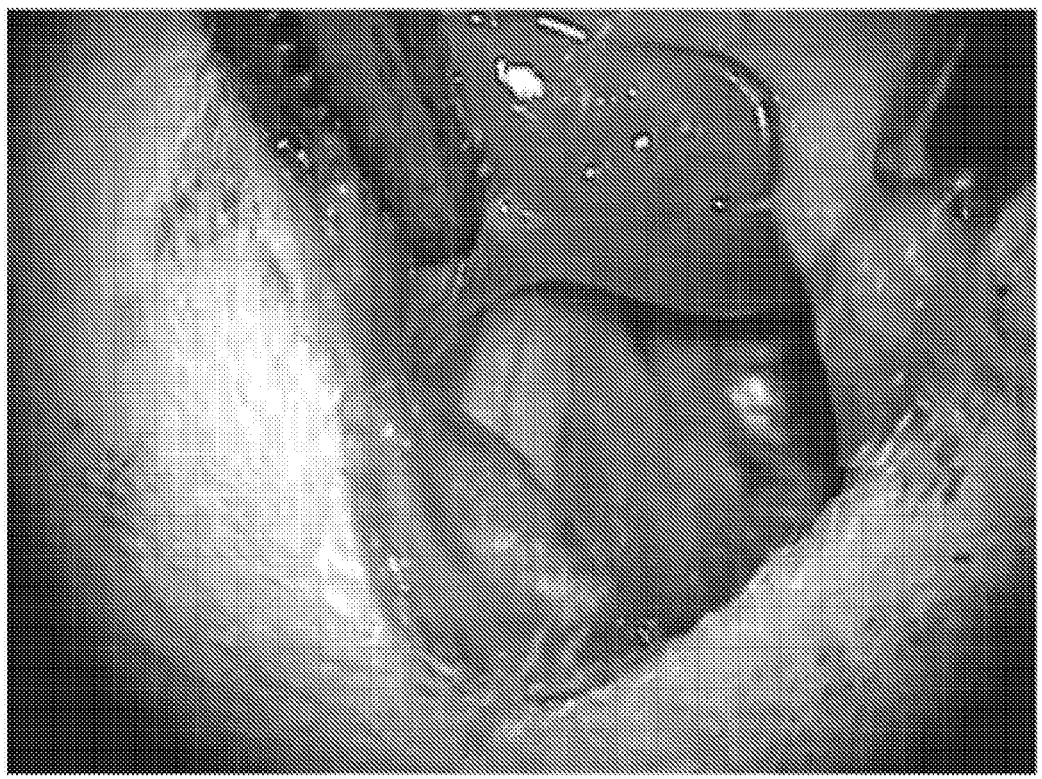
FIG. 98A is an image of a rat brachial plexus in Neurostimulation Study #3.
Figure 98B:
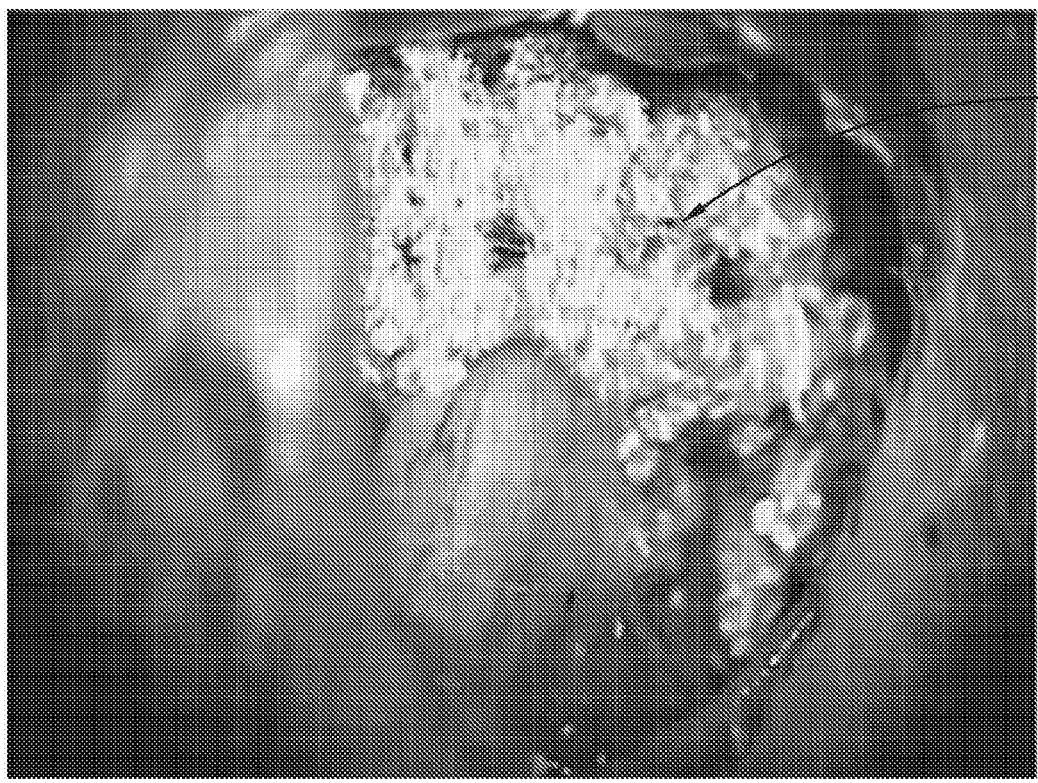
FIG. 98B is an image of the rat brachial plexus as in FIG. 98A, but with a cured electrode on the brachial plexus.
Figure 98C:
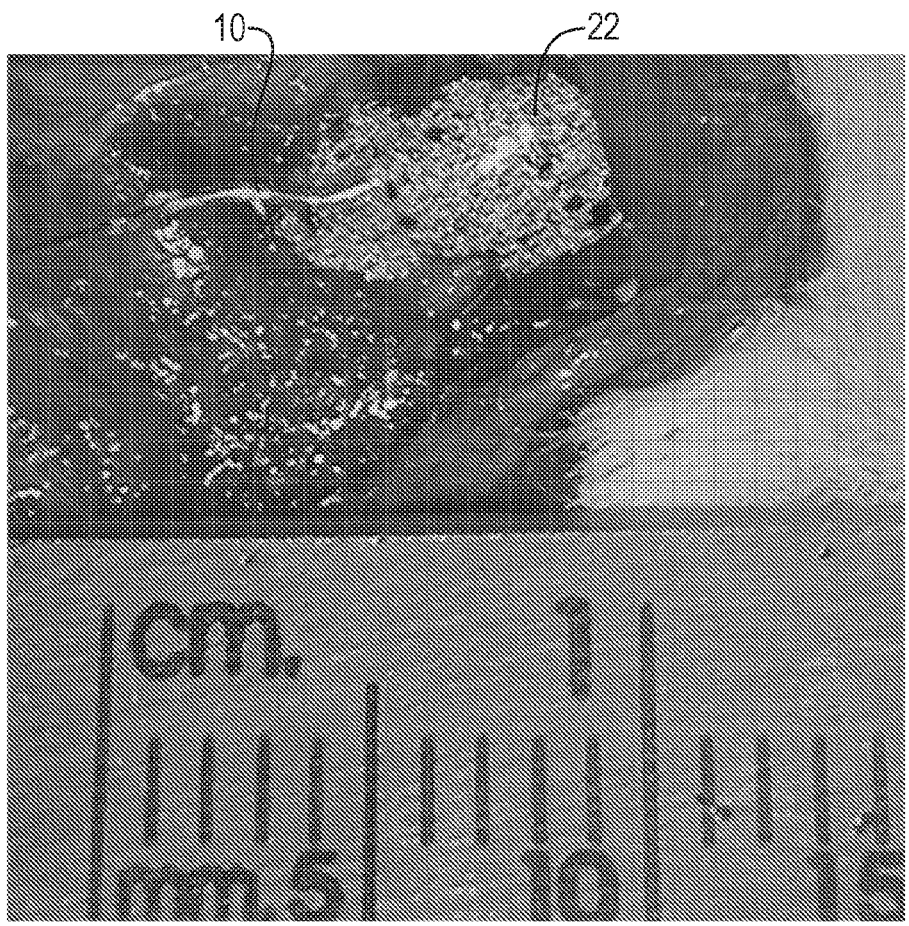
FIG. 98C is an image of a lead wire embedded in the cured electrode in FIG. 98B.
Figure 98D:
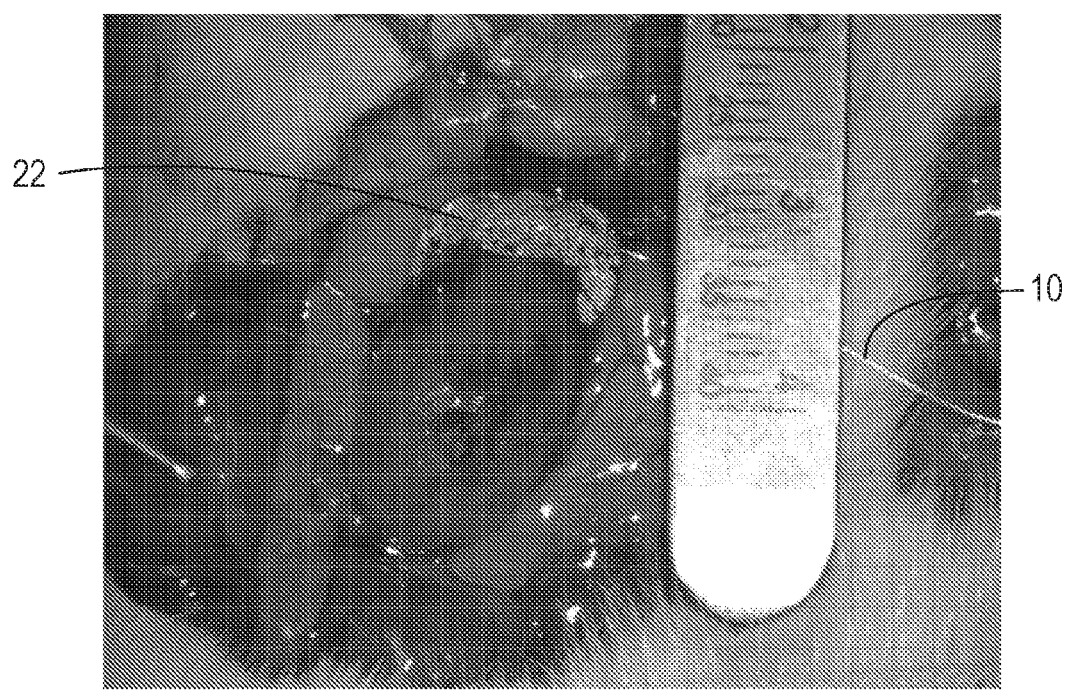
FIG. 98D is an image of a lead wire embedded in a cured electrode formed as a ring around a rat bladder neck and some more cured electrode material added for mechanical matching.

This study was performed on three rats, one animal at a time. Under deep anesthetic plane (anesthetic plane monitored using heart rate, breathing frequency, and paw withdrawal to toe pinch), the animal's left or right brachial plexus (sometimes "BP") or both brachial plexi (left and right arm) were exposed with a small 5 mm incision (FIG. 98A). (If both BP were tested, testing was done sequentially to avoid tissue dry out.) Median, Ulnar and Radial nerve were freed from surrounding tissue but not from their respective nerve sheath; in one case two nerves ran together and it was not clear if median and ulnar had not yet separated at the surgical site. A cured electrode 1 (silicone & silver based, line impedance range from 0.2 to 0.4 ohm*m) was formed as a ring-like portion 22 around the entire plexus. A lead wire 10 was sunken into the cured electrode material prior to curing (FIG. 98C). After the curing time of approx. 60 seconds, a signal generator 17 was attached to the wire 10 embedded into the cured electrode around the brachial plexus. A distal return electrode was achieved via a needle that was placed into the sub-cutaneous tissue near the lower back of the animal. Stimulation of the brachial plexus was achieved with signal waveforms of 1 Hz @ 0.5 mA, 30 Hz @ 0.5 mA, 30 Hz @ 1 mA, 30 Hz @ 2 mA, and 30 Hz @ 5 mA to differentiate various nerve fiber sizes. Nerve block was tested with 300 Hz ACh depletion block waveforms since the cured electrode provided a complete cuff. Parameters for block compared to stim were the same except for the frequency applied. To ensure stimulating and blocking all fibers, the parameters used were 30 Hz @ 5 mA for stimulation and 300 Hz @ 5 mA for block. Immediate block (onset duration <0.5 sec) was achieved successfully. In two animals, the incision was widened slightly and a second cured electrode was placed adjacent and more distally to the first one, about 1 mm away and without touching the first cured electrode placed earlier. A lead wire 10 was embedded before curing. Stimulation applied to the second cured electrode with the same as well as different parameters utilized for stimulation (1 to 30 Hz) showed different effects on lower arm, wrist, and paw movement. Stimulating both cured electrodes simultaneously provided combined movement resulting from the two cured electrodes. Applying stimulation waveforms to one of the cured electrodes while applying block waveforms (300 Hz at high amplitudes) to the second cured electrode led to flaccid paws and wrists as long as the block was applied. FIG. 98A is an image of obtaining access to the brachial plexus, with exposed nerves in the center. Cured electrode material was injected behind and around the nerves, and the brachial plexus was encased, as shown in FIG. 98B. FIG. 98C—is an image of a lead wire embedded in the rat cured electrode.

A rat cadaver study was performed with a cured electrode formed around the bladder neck (for access to nerves innervating the end organ). In FIG. 10D-0, a lead wire was embedded in the cured electrode formed as a ring 22 and some more cured electrode material added for mechanical matching, by letting cured electrode material flow around a moment with slower curing time. The bladder neck is the primary path for nerves innervating (entering) the bladder tissue from the surrounding tissue inside the abdominal cavity. Placing a mechanically flexible electrode that confirms to the anatomical shape of the tissue of interest around the bladder neck provides a neural interface that can stimulate and block neural tissue in locations conventional electrodes do not conform to and thus do not perform well. The bladder was filled for demonstration purposes after curing of the molded electrode; the molded electrode remained in place and did not show major movement.

After the rat brachial plexus data had been obtained, pig studies were also performed on the Brachial Plexus in three different designs. Materials used included: (1) Silicone electrodes: silicone, Kwik-Cast (World Precision Instruments), silver powder see powder specs below, and the surfactant, GLYMO; (2) PEG electrodes: CoSeal PEG 8 ml vial, Silver powder see powder specs below, and glycerol. Silver powder was the same as used in both formulations, conductive element sizes ranging from ~0.6 micron to ~6 micron, with aspect ratios ranging from ~1 to 6 in a polydisperse system. Number average for the mixture was approximately between 2-3 aspect ratio, given the larger number of roundish particles seen. The silicone cured electrodes 1 comprised ~73% wt % silver content: 200 mg Kwik-Cast (100 mg each of part A and part B), 800 mg silver powder, and 100 µl GLYMO. Silicone based cured electrodes were also provided a mixture with an added layer of Kwik-Cast added to the one surface to act as a selective insulator. The PEG cured electrodes 1 comprised ~73% wt % silver content: 200 mg CoSeal PEG Reconstituted Using Supplied Syringe system (100 mg each of part A and part B), 800 mg silver powder, and 100 µl Glycerol.

Figure 99A:
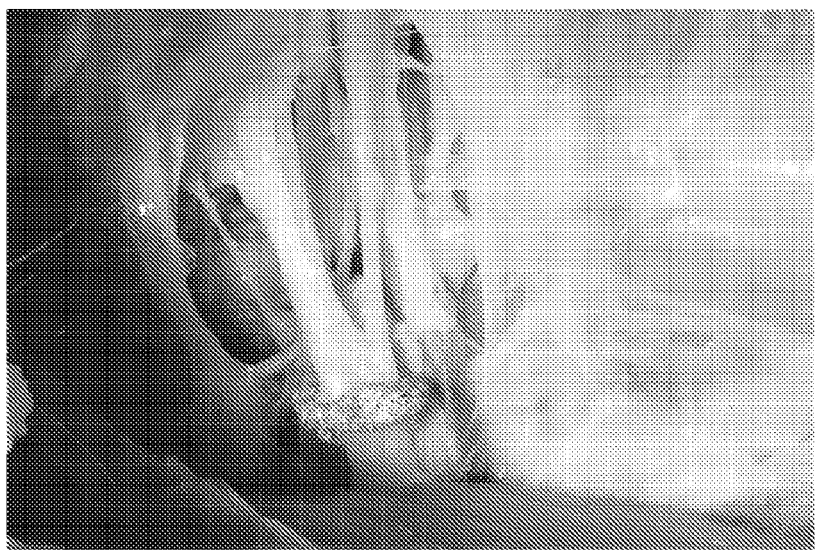
FIG. 99A is an image of a pig brachial plexus and a ring like cured electrode formed in open cut down.

Study 1: This study was performed on 2 pigs, one animal at a time. The animals had just expired (defining the situation as tissue study) and allowed approximately 10 minutes of study time prior to ATP depletion. The animal's left brachial plexus (BP) was exposed with a large 10 cm incision to allow optimal visualization for documentation purposes. The nerves of the BP were carefully exposed and freed from the tissue underneath, and n electrode material mix was molded around these nerves to form a cured electrode. The ring-like portion 22 of a cured electrode was allowed to cure fully within 60 seconds. FIG. 98A. A handheld TENS signal generator was used to stimulate the nerves with current controlled biphasic, charge balanced waveforms. The TENS unit electrode contact associated with the cathodic first pulse of the waveform was used to temporarily touch the nerves of the BP as well as the cured electrode around said nerves, while the anodic first (TENS counter) electrode was placed as distal return by clamping it into the open cutdown approximately 10 cm away from the cured electrode. Stimulation of the brachial plexus was achieved with signal waveforms of 2 Hz applied at a current amplitude that did cause the nerve to depolarize and arm muscles to twitch at 2 Hz when the cured electrode was touched, but not to depolarize when the nerve was touched with the probe contact coming from the TENS unit directly, either proximally or distally to the cured electrode. The study confirmed that the cured electrode is able to provide a low impedance interface and a concentration of the electric waveform energy to the nerve surrounded by cured electrode material and that activation thresholds are lowest with such a cuff configuration, lower than touching the nerve with the probe contact (probe tip surface area approximately 1 mm2). FIG. 99A is an image of the pig Brachial Plexus with the cured electrode molded during open cut-down. The proximal portion of the nerve is located south with respect to the cured electrode in the figure, the distal portions are north of it.

Figure 99B:
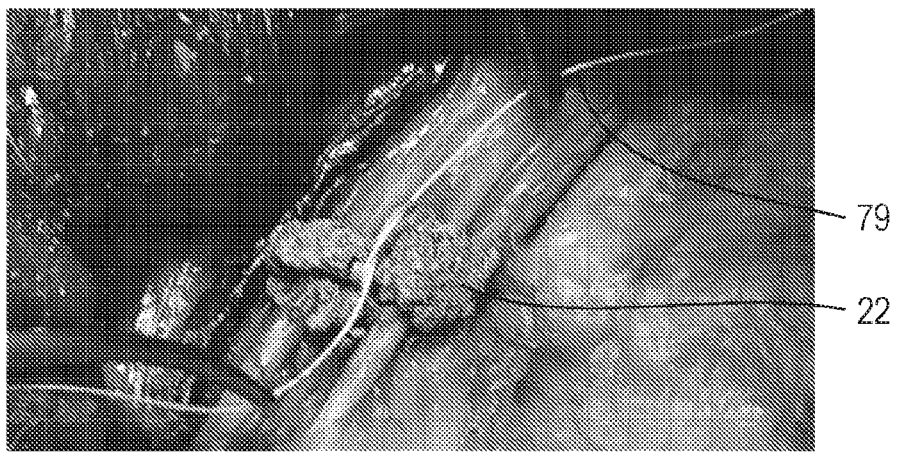
FIG. 99B is an image of forming a knot with a suture in a cured electrode and pulling on the knot with two surgical clamps.
Figure 99C:
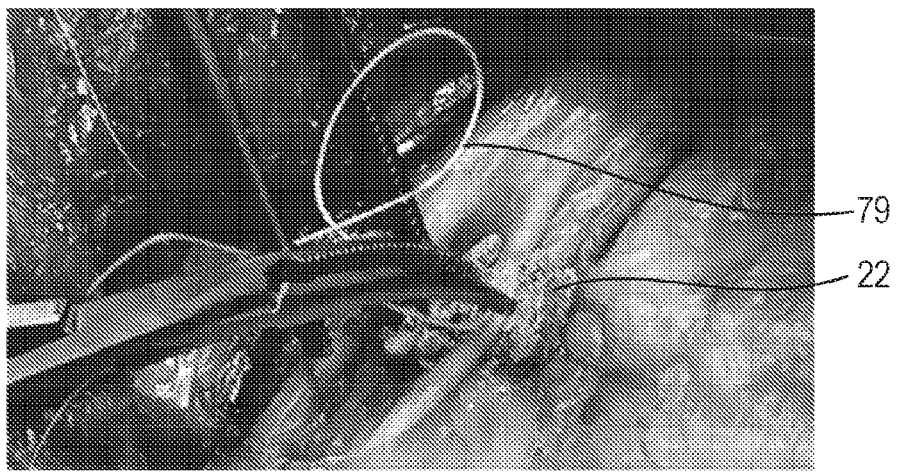
FIG. 99C is an image after pulling on the knot in 99B with two surgical clamps and the pieces of the cured electrode after the suture cut through the cured electrode.

Study 2: Following earlier benchtop studies and studies in chicken tissue, a study was performed on a pig cadaver to replicate the cutting of a cured electrode with a suture. FIG. 99B is an image of forming a knot with a suture 79 and pulling on the knot with two surgical clamps. FIG. 99C is an image of pulling on the knot with two surgical clamps and checking the path the suture took through the cured electrode. Note that pulling the knot split the cured electrode ring-like portion 22 into two sections, allowing this now C-shaped cured & cut electrode to be removed by grabbing it with tweezers and pulling it away from the nerve.

Figure 101:
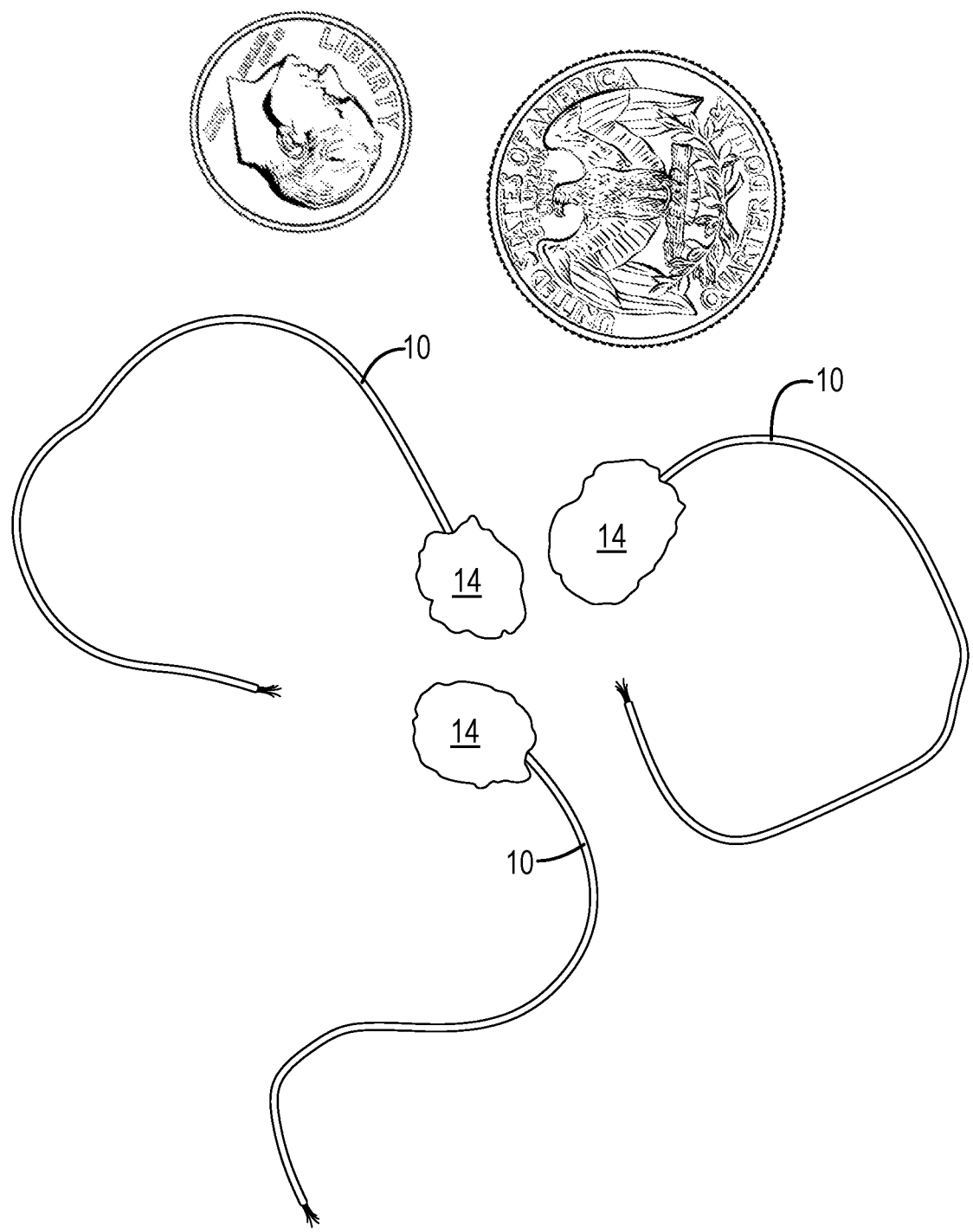
FIG. 101 is an image of the contact pads, from the setup in FIG. 100, next to coins for comparison of size.

Study 3: Following earlier studies on chicken (see above) and rat tissue demonstrating the ability to reduce voltage needed to bridge a current path through tissue by placing a cured electrode in parallel to the tissue, thereby shortening the distance between low-impedance elements of a circuit containing animal tissue in between opposite electrical potentials, a pig vagal study was performed in two pigs. This study was able to replicate the reduction of impedance by placing cured electrodes into the tissue, bridging distances to the nerve with low impedance materials (cured electrode and attached wire in this case). The study further demonstrated the ability to reduce Heart Rate with such a cured electrode and it demonstrated the ability to reduce Heart Rate with an external stimulator TENS unit that was never in direct contact with metal inside the animal. For the procedure, an animal on the table was placed into a deep plane of anesthesia. A vagal cut-down was performed to openly expose the vagus nerve. Two prior art cuff electrodes were placed around the vagus nerve and the lead wire from these cuffs was connected to a cured electrode placed into the subcutaneous tissue of the pig near the vagal exposure. TENS electrodes and a TENS stimulator were used to stimulate transcutaneously by electrically connecting to the sub-cutaneously placed cured electrodes through the skin (without a direct connection through the skin as the skin above the cured electrodes was never damaged) which in turn were connected to the cuffs around the vagal nerve. The study setup is diagrammed in FIG. 100A (showing only the elements internal to the animal) and FIG. 100B (with TENS patch electrodes placed on the outside of the animal). FIG. 100B is a diagram of the open vagus cut-down and two cured electrodes (image in FIG. 101 next to coins) placed subcutaneously, then connected to cuffs (either prior art cuffs 40 or formed as a ring-like portion 22 of a cured electrode live in pig. Each cured electrode and a corresponding patch above is diagrammed in. FIG. 100 is a diagram showing placement of the TENS patch electrodes on the outside of the skin, on-top of a corresponding subcutaneously placed contact pad 14 which allows electrical vagal stimulation through the skin without damaging the skin.

Five stimulation tests were performed: (1) low amplitude stimulation, (2) mid amplitude stimulation, (3) high amplitude stimulation, (4) removal of the subcutaneously placed collector cured electrode that connected to the cathode to test for leakage driving the HR reduction, with no leakage detected, and (5) removal of the subcutaneously placed collector cured electrode that connected to the anode to test for leakage driving the HR reduction, with no leakage detected. The results are shown in the chart, FIG. 113-0, which plots heart rate (bpm) versus time (seconds). The low amplitude stimulation (55 sec) provides a first response. The mid (200 sec) and large (305 sec) amplitude stimulation provide a strong HR reduction. Once the subcutaneously placed cured electrode under the cathodic TENS electrode was removed, stimulation did not result in changes to HR, indicating that the current flow had been via the cured electrodes and not via the open cut-down (430 sec and forward; control tests).

A comparison of electrodes was conducted for the cured electrode vs. a prior art cuff (LivaNova) as reported in FIG. 103A-B. The present invention had the larger capacitive charge injection capabilities. At frequencies of 2 kHz and above, the cured electrode was about ⅓ of the impedance of the Livanova cuff (100 ohms vs. 300 ohms), which may save battery energy for an implanted pulseform generator due to the lower voltage needed to drive the same stimulation current; one would expect a stimulator to require ⅔ less power to drive the same charge into surrounding tissue when using the present invention. The cured electrode demonstrated strong capacitive charge injection capabilities for the injection of current.

Very thin cured electrodes and wires (<1 mm) as extruded from a dispenser are shown in FIGS. 104B and 104A were manufactured. The impedance as shown on an LCR meter was 2.328 ohms, as in FIG. 115A-0, measured across the length of several turns and twists of the extruded electrode in the shape of a wire, further confirming that the impedance of each smaller section of the cured extruded shape is smaller than 1 Ohm.

Disclosed herein is a cured electrode for a target with contours in bodily tissue, said cured electrode comprising a mixture comprising fractional weights of conductive elements and a hydrogel comprising a liquid phase and a solid phase, said liquid phase curable to said solid phase, said mixture during said liquid and solid phases of the hydrogel capable of conducting current through the conductive elements, and said mixture being capable in the bodily tissue of being molded against and retaining at least a portion of the contours of the target. In further embodiments:

the hydrogel comprises a polyethylene glycol comprising the general structure X—(O—CH2-CH2)$_n$-Y where n is a variable number of repeat units and X and Y are functional groups at the terminal ends.

said current constitutes charge transfer by direct exchange of electrons between said conductive elements.

the cured electrode further comprises pores, and the cured electrode comprises outermost dimensions defining an overall volume, and the pores define spaces which together total a subset volume of the overall volume.

the subset volume is within a range of about 0.1% to 20% of the overall volume.

the subset volume is within a range of about 0.1% to 40% of the overall volume.

said conductive elements comprise a material selected from a group consisting of gold, gold bonding wire bits, silver, platinum, graphene, graphite, carbon tubes, stainless steel, 316 stainless steel, copper, aluminum oxides, bronze, vanadium, niobium, iron, rhodium, tungsten, titanium, tantalum, gallium, arsenic, antimony, bismuth, nitinol, diamond-coated sand, gold-coated steel or iron, iridium, iridium oxide, ionized proteins, and poly(3,4-ethylenedioxythiophene) polystyrene sulfonate.

the fractional weight of said conductive elements is within a range of about 65-85%.

the fractional weight of said conductive elements is within a range of about 50-64%.

the conductive elements comprise a longest and a shortest dimension, and the conductive elements comprise an aspect ratio of the longest dimension divided by the shortest dimension.

the shorter or longer dimensions of at least a portion of the conductive elements is at least one micron.

the aspect ratio of at least a portion of the conductive elements is less than 3:1.

the aspect ratio of at least a portion of the conductive elements is within a range between 3:1 and less than 1:1.

the aspect ratio of at least a portion of the conductive elements is at least 10:1.

at least a portion of said conductive elements comprise interlocking features selected from a group consisting of hook, loops and coils.

further comprises an immunoreactive agent selected from a group consisting of cells, whole blood, blood serum, biodegradable polymers sugars, amino acids, proteins, iron, lipopolysaccharides, collagen, hyaluronic acid, fibrin and pharmacological agents further comprises an anti-inflammatory agent selected from a group consisting of steroids, anti-oxidants, superoxide dismutase mimetics and non-steroidal anti-inflammatory drugs.

further comprises a hemostatic agent selected from a group consisting of microfibrillar collagen hemostat, chitosan, kaolin, zeolite, anhydrous aluminum sulfate and fibrin glue.

further comprises a pharmacological agent selected from a group consisting of an antibiotic, an analgesic and an anesthetic.

further comprises a radio-opaque agent selected from a group consisting of fluroscein and platinum.

an electrical resistance of the conductive elements does not exceed 10 ohms.

further comprises a nonconductive layer comprising the hydrogel capable of bonding to the mixture and the target and the bodily tissue.

the nonconductive layer further comprises nonconductive particles selected from a group consisting of ceramic and glass.

the hydrogel in the solid phase is capable of resorption by the bodily tissue, such that fibrous tissue is capable of attaching to the conductive elements.

further comprises a crosslinker for the hydrogel.

the crosslinker comprises trilysine further comprises glycerine.

Additionally disclosed herein is a cured electrode for a target with contours in bodily tissue, said cured electrode comprising a mixture of fractional weights of conductive elements and a cured hydrogel, said cured electrode capable of conducting current through the conductive elements, and said cured electrode being molded against and retaining at least a portion of the contours of the target. In further embodiments:

the hydrogel comprises a polyethylene glycol comprising the general structure X—(O—CH2-CH2)$_n$-Y where n is a variable number of repeat units and X and Y are functional groups at the terminal ends.

said current constitutes charge transfer by direct exchange of electrons between said conductive elements.

further comprises pores, and the cured electrode has outermost dimensions defining an overall volume, and the pores define spaces which together total a subset volume of the overall volume.

the subset volume is within a range of about 0.1% to 20% of the overall volume.

the subset volume is within a range of about 0.1% to 40% of the overall volume.

said conductive elements comprise a material selected from a group consisting of gold, gold bonding wire bits, silver, platinum, graphene, graphite, carbon tubes, stainless steel, 316 stainless steel, copper, aluminum oxides, bronze, vanadium, niobium, iron, rhodium, tungsten, titanium, tantalum, gallium, arsenic, antimony, bismuth, nitinol, diamond-coated sand, gold-coated steel or iron, iridium, iridium oxide, ionized proteins, and poly(3,4-ethylenedioxythiophene) polystyrene sulfonate.

the fractional weight of said conductive elements is within a range of about 65-85%.

the fractional weight of said conductive elements is within a range of about 50-64%.

the conductive elements comprise a longest and a shortest dimension, and the conductive elements comprise an aspect ratio of the longest dimension divided by the shortest dimension.

the shorter or longer dimensions of at least a portion of the conductive elements is at least one micron.

the aspect ratio of at least a portion of the conductive elements is less than 3:1.

the aspect ratio of at least a portion of the conductive elements is within a range between 3:1 and less than 1:1.

the aspect ratio of at least a portion of the conductive elements is at least 10:1.

at least a portion of said conductive elements comprise interlocking features selected from a group consisting of hook, loops and coils.

further comprises an immunoreactive agent selected from a group consisting of cells, whole blood, blood serum, biodegradable polymers sugars, amino acids, proteins, iron, lipopolysaccharides, collagen, hyaluronic acid, fibrin and pharmacological agents.

further comprises an anti-inflammatory agent selected from a group consisting of steroids, anti-oxidants, superoxide dismutase mimetics and non-steroidal anti-inflammatory drugs.

further comprises a hemostatic agent selected from a group consisting of microfibrillar collagen hemostat, chitosan, kaolin, zeolite, anhydrous aluminum sulfate and fibrin glue.

further comprises a pharmacological agent selected from a group consisting of an antibiotic, an analgesic and an anesthetic.

further comprises a radio-opaque agent selected from a group consisting of fluroscein and platinum.

an electrical resistance of the conductive elements does not exceed 10 ohms.

further comprises a nonconductive layer comprising the hydrogel capable of bonding to said mixture, the target and the bodily tissue.

the nonconductive layer further comprises nonconductive particles selected from a group consisting of ceramic and glass.

the cured hydrogel is capable of resorption by the bodily tissue, such that fibrous tissue is capable of attaching to the conductive elements.

further comprises a crosslinker for the hydrogel.

the crosslinker comprises trilysine

Further disclosed is liquid mixture comprising fractional weights of conductive elements and a hydrogel in a liquid phase in water, said mixture in the liquid phase being moldable to a target with contours in bodily tissue and curable to a solid phase, said mixture capable of conducting electrical current in the liquid and solid phases. In further embodiments:

the hydrogel comprises a polyethylene glycol comprising the general structure X—(O—CH2-CH2)n-Y where n is a variable number of repeat units and X and Y are functional groups at the terminal ends.

said current constitutes charge transfer by direct exchange of electrons between said conductive elements.

said conductive elements constitute a fractional weight of the mixture and comprise a material selected from a group consisting of gold, gold bonding wire bits, silver, platinum, graphene, graphite, carbon tubes, stainless steel, 316 stainless steel, copper, aluminum oxides, bronze, vanadium, niobium, iron, rhodium, tungsten, titanium, tantalum, gallium, arsenic, antimony, bismuth, nitinol, diamond-coated sand, gold-coated steel or iron, iridium, iridium oxide, ionized proteins, and poly(3,4-ethylenedioxythiophene) polystyrene sulfonate.

the fractional weight of said conductive elements is within a range of about 65-85%.

the fractional weight of said conductive elements is within a range of about 50-64%.

the conductive elements comprise a longest and a shortest dimension, and the conductive elements comprise an aspect ratio of the longest dimension divided by the shortest dimension.

the shorter or longer dimensions of at least a portion of the conductive elements is at least one micron.

the aspect ratio of at least a portion of the conductive elements is less than 3:1.

the aspect ratio of at least a portion of the conductive elements is within a range between 3:1 and less than 1:1.

the aspect ratio of at least a portion of the conductive elements is at least 10:1.

at least a portion of said conductive elements comprise interlocking features selected from a group consisting of hook, loops and coils.

further comprises an immunoreactive agent selected from a group consisting of cells, whole blood, blood serum, biodegradable polymers, sugars, amino acids, proteins, iron, lipopolysaccharides, collagen, hyaluronic acid, fibrin and pharmacological agents.

further comprises an anti-inflammatory agent selected from a group consisting of steroids, anti-oxidants, superoxide dismutase mimetics and non-steroidal anti-inflammatory drugs.

further comprises a hemostatic agent selected from a group consisting of microfibrillar collagen hemostat, chitosan, kaolin, zeolite, anhydrous aluminum sulfate and fibrin glue.

further comprises a pharmacological agent selected from a group consisting of an antibiotic, an analgesic and an anesthetic.

further comprises a radio-opaque agent selected from a group consisting of fluroscein and platinum.

an electrical resistance of the conductive elements does not exceed 10 ohms.

further comprises a crosslinker for the hydrogel.

the crosslinker comprises trilysine

Another embodiment of the invention is a mixture comprises conductive elements, a hydrogel and water, said hydrogel comprising a liquid phase responsive to a crosslinker for curing to a solid phase, said mixture capable of conducting current in the liquid and solid phases. Further embodiments include:

the hydrogel comprises a polyethylene glycol comprising the general structure X—(O—CH2-CH2)n-Y where n is a variable number of repeat units and X and Y are functional groups at the terminal ends.

the crosslinker comprises trilysine said current constitutes transfer by direct exchange of electrons between said conductive elements.

said conductive elements constitute a fractional weight of the mixture and comprise a material selected from a group consisting of gold, gold bonding wire bits, gold modified with sulfide/disulfide groups, silver, platinum, graphene, graphite, carbon tubes, stainless steel, 316 stainless steel, copper, aluminum oxides, bronze, vanadium, niobium, iron, rhodium, tungsten, titanium, tantalum, gallium, arsenic, antimony, bismuth, nitinol, diamond-coated sand, gold-coated steel or iron, iridium, iridium oxide, ionized proteins, and poly(3,4-ethylenedioxythiophene) polystyrene sulfonate.

the fractional weight of said conductive elements is within a range of about 50-64%.

the conductive elements comprise a longest and a shortest dimension, and the conductive elements comprise an aspect ratio of the longest dimension divided by the shortest dimension.

the shorter or longer dimension of at least a portion of the conductive elements is at least one micron.

the aspect ratio of at least a portion of the conductive elements is less than 3:1.

the aspect ratio of at least a portion of the conductive elements is within a range between 3:1 and less than 1:1.

the aspect ratio of at least a portion of the conductive elements is at least 10:1.

at least a portion of said conductive elements comprise interlocking features selected from a group consisting of hook, loops and coils.

further comprises an immunoreactive agent selected from a group consisting of cells, whole blood, blood serum, biodegradable polymers sugars, amino acids, proteins, iron, lipopolysaccharides, collagen, hyaluronic acid, fibrin and pharmacological agents further comprises an anti-inflammatory agent selected from a group consisting of steroids, anti-oxidants, superoxide dismutase mimetics and non-steroidal anti-inflammatory drugs.

further comprises a hemostatic agent selected from a group consisting of microfibrillar collagen hemostat, chitosan, kaolin, zeolite, anhydrous aluminum sulfate and fibrin glue.

further comprises a pharmacological agent selected from a group consisting of an antibiotic, an analgesic and an anesthetic.

further comprises a radio-opaque agent selected from a group consisting of fluroscein and platinum.

an electrical resistance of the conductive elements does not exceed 10 ohms.

An electrode after hydrogel resporption for a target with contours in bodily tissue comprising conductive elements, said conductive elements at least partially molded against the contours of the target, and said conductive elements capable of being encapsulated by the bodily tissue, and capable of conducting current. Further embodiments include:

said conductive elements comprise a material selected from a group consisting of gold, gold bonding wire bits, silver, platinum, graphene, graphite, carbon tubes, stainless steel, 316 stainless steel, copper, aluminum oxides, bronze, vanadium, niobium, iron, rhodium, tungsten, titanium, tantalum, gallium, arsenic, antimony, bismuth, nitinol, diamond-coated sand, gold-coated steel or iron, iridium, iridium oxide, ionized proteins, and poly(3,4-ethylenedioxythiophene) polystyrene sulfonate.

the conductive elements comprise a longest and a shortest dimension, and the conductive elements comprise an aspect ratio of the longest dimension divided by the shortest dimension.

the shorter or longer dimensions of at least a portion of the conductive elements is at least one micron.

the aspect ratio of at least a portion of the conductive elements is less than 3:1.

the aspect ratio of at least a portion of the conductive elements is within a range between 3:1 and less than 1:1.

the aspect ratio of at least a portion of the conductive elements is at least 10:1.

at least a portion of said conductive elements comprise interlocking features selected from a group consisting of hook, loops and coils.

further comprises an immunoreactive agent selected from a group consisting of cells, whole blood, blood serum, biodegradable polymers, sugars, amino acids, proteins, iron, lipopolysaccharides, collagen, hyaluronic acid, fibrin and pharmacological agents further comprises an anti-inflammatory agent selected from a group consisting of steroids, anti-oxidants, superoxide dismutase mimetics and non-steroidal anti-inflammatory drugs.

further comprises a hemostatic agent selected from a group consisting of microfibrillar collagen hemostat, chitosan, kaolin, zeolite, anhydrous aluminum sulfate and fibrin glue.

further comprises a pharmacological agent selected from a group consisting of an antibiotic, an analgesic and an anesthetic.

further comprises a radio-opaque agent selected from a group consisting of fluroscein and platinum an electrical resistance of the conductive elements does not exceed 10 ohms.

A method of forming an electrode in bodily tissue for a target with contours comprising the steps of
 a. introducing into the bodily tissue a liquid mixture comprising conductive elements and a carrier material in a liquid phase, said carrier material capable of curing to a solid phase, said conductive elements being capable of conducting current,
 b. placing the mixture in the bodily tissue against at least a portion of the contours of the target,
 c. molding the mixture against at least a portion of the contours of the target, and
 e. allowing the carrier material to cure to the solid phase,
such that the mixture during the solid phase of the carrier material is capable of retaining at least a portion of the contours of the target, and the conductive elements are capable of conducting current to the target. Further embodiments include:
 further comprising step z, prior to step a, of cooling the carrier material in the liquid phase to retard curing.
 further comprising step x, between steps b and c, of supplying symmetrical charge balanced pulse trains at 10 Hz, 10V to 50V amplitude voltage, controlled cathodic first.
 further comprising step u, between steps d and e, of placing a line of the mixture in the liquid phase of the carrier material from the target to a subcutaneous region.
 further comprising a step, after the previous step, of forming a contact pad in the subcutaneous region.
 the carrier material is selected from a group consisting of a hydrogel, fibrin glue, a cyanoacrylate, bone cement, and dental resin.

An additional method disclosed herein is a method of forming an electrode in bodily tissue for a target with contours and connecting the electrode to a transcutaneous electrical nerve stimulator, comprising the steps of
 a. providing a dispenser containing a mixture comprising conductive elements and a carrier material in a liquid phase, said conductive elements being capable of conducting current,
 b. inserting the dispenser through skin into the bodily tissue to the contours of the target,
 c. dispensing the mixture from an exit point of the dispenser to at least a portion of the contours of the target,
 d. molding the mixture against at least a portion of the contours of the target,
 e. dispensing a line of the mixture toward a subcutaneous region,
 f. forming the mixture into a contact pad in the subcutaneous region,
 g. curing the mixture to a solid phase,
 h. placing a transcutaneous electrical nerve stimulator on the skin above the contact pad, and
 i. stimulating the conductive elements by the transcutaneous electrical nerve stimulator,
such that the transcutaneous electrical nerve stimulator is capable of electrically stimulating the contact pad. Further embodiments include:
 further comprising step z, prior to step a, of cooling the carrier material in the liquid phase to retard curing.
 further comprising step v, between steps b and c, of vibrating the liquid mixture at a frequency within a range of 50 to 100 Hz by means selected from a group consisting of a sound transducer, an ultrasound transducer or a mass out of midline.
 the carrier material is selected from a group consisting of a hydrogel, fibrin glue, a cyanoacrylate, bone cement, and dental resin.

A method of restoring or supplementing function for an electronic device in bodily tissue comprising
 a. locating the electronic device in the bodily tissue,
 b. placing on the electronic device a mixture comprising conductive elements and a carrier material in a liquid phase, said liquid carrier material capable of curing to a solid phase, said conductive elements being capable of conducting current,
 c. positioning the mixture so as to restore or supplement a current flow between the electronic device and a target in the bodily tissue, and
 d. allowing the carrier material to cure to the solid phase,
such that conductive elements are capable or restoring or supplementing the current flow between the electronic device and the target. Further embodiments include:
 the carrier material is selected from a group consisting of a hydrogel, fibrin glue, a cyanoacrylate, bone cement, and dental resin.
 further comprising step z, prior to step a, of cooling the carrier material in the liquid phase to retard curing.

Another method is disclosed for finding a target for stimulation in bodily tissue comprising
 a. introducing into the bodily tissue a liquid mixture comprising conductive elements and a carrier material in a liquid phase, said carrier material capable of curing to a solid phase, and said conductive elements being capable of conducting current,
 b. placing the liquid mixture in the bodily tissue against at least a portion of the contours of the target,
 c. providing the current through the liquid mixture, and
 d. verifying that the target has been stimulated by the current through the liquid mixture.
Further embodiments include:
 the carrier material is selected from a group consisting of a hydrogel, fibrin glue, a cyanoacrylate, bone cement, and dental resin.
 the current is a repetitive (or intermittent) neurostimulation pulse (200 µs pulse width, 1 mA current amplitude, cathodic first vs. distal return, symmetrical charge balanced.

Another method disclosed for the present invention is that of providing current while manufacturing an electrode in bodily tissue for a target with contours comprising the steps of
 a. providing a dispenser comprising an exit point, a chamber containing a liquid mixture comprising conductive elements and a carrier material in a liquid phase, and an electrical stimulator near the exit point, said chamber communicating fluidly with the exit point, said electrical stimulator connected to a current source, said conductive elements being capable of conducting current,
 b. placing the exit point of the dispenser in the bodily tissue against the contours of the target, c. dispensing the liquid mixture from the exit point of the dispenser, d. molding the liquid mixture against the contours of the target, and e. providing current to the electrical stimulator in contact with the liquid mixture against the contours of the target, such that the electrical stimulator is capable of stimulating the conductive elements and the conductive elements are capable of conducting current to the target.

Further embodiments include:

wherein the current comprises anodic current wherein the current comprises cathodic current wherein the current comprises a repetitive or intermittent pulse of approximately 200 μs width, 1 mA current amplitude, cathodic first vs. distal return, symmetrical charge for nerves.

Also disclosed herein is a dispenser for injecting a liquid or a liquid mixture into a bodily tissue against a target with contours, said dispenser comprising a first and a second chamber, a needle comprising a tip, a first and a second exit point near the tip, and a first plunger seated slideably with the first chamber and communicating fluidly with the first exit point, a second plunger seated slideably with the second chamber and communicating fluidly with the second exit point, so that when a user pushes the first plunger the said liquid or liquid mixture exits the first exit point and when the user pushes the second plunger the said liquid or liquid mixture exits the second exit point.

Further aspects include:

wherein the first and second chambers are coaxial.

wherein the first and second chambers each comprise a conical frustum connected to the needle.

wherein the dispenser comprises means for vibrating the dispenser or the liquid or liquid mixture, said means is selected from a group consisting of a sound transducer, an ultrasound transducer or a mass out of midline.

further comprising an electrical stimulator near the tip.

further comprising a light near the tip for curing the liquid or liquid mixture in the bodily tissue.

further comprising an auger in the first or second chamber.

further comprising a sensor for detecting speed of dispensing of the liquid or liquid mixture.

further comprising a third chamber for dispensing wire connected to a third exit point near the tip, said third chamber receiving a feed of the dispensing wire.

A method of implanting an electrode with an anchor in a bodily tissue comprising a. placing an electrode near a target in the bodily tissue, b. introducing into the bodily tissue a liquid mixture comprising conductive elements and a carrier material in a liquid phase, said carrier material capable of curing to a solid phase, and said conductive elements being capable of conducting current, c. placing the liquid mixture in the bodily tissue against at least a portion of the contours of the target, d. placing a liquid nonmixture in a first area in the bodily tissue which is secure, e. connecting the liquid nonmixture to the liquid mixture, and f. allowing the liquid mixture and the liquid nonmixture to cure and bond together.

For the method above, the carrier material is selected from a group consisting of a hydrogel, fibrin glue, a cyanoacrylate, bone cement, and dental resin.

Further disclosed herein is a method of delivering a liquid mixture with vibration to a target in bodily tissue comprising a. providing a dispenser containing a liquid mixture comprising conductive elements and a carrier material in a liquid phase, said carrier material capable of curing to a solid phase, and said conductive elements being capable of conducting current, and b. vibrating the dispenser or the liquid mixture, such that the liquid mixture is capable of flowing to the target in bodily tissue.

The carrier material may be selected from a group consisting of a hydrogel, fibrin glue, a cyanoacrylate, bone cement, and dental resin.

Also disclosed is a method of installing a Suture for removal of a cured electrode comprising a. introducing into the bodily tissue a liquid mixture comprising conductive elements and a carrier material in a liquid phase, said carrier material capable of curing to a solid phase, said conductive elements being capable of conducting current, b. placing the liquid mixture in the bodily tissue against at least a portion of the contours of the target, c. molding the liquid mixture against at least a portion of the contours of the target, d. tying a suture on the liquid mixture, and e. allowing the carrier material to cure to the solid phase, such that by pulling the suture during the solid phase of the carrier material is capable of severing at least a portion of the cured electrode.

In this method the carrier material is selected from a group consisting of a hydrogel, fibrin glue, a cyanoacrylate, bone cement, and dental resin.

Further disclosed is a method of forming an electrode at a target in a bodily tissue, the method comprising a. providing a curable electrode mixture comprising liquid carrier material and conductive elements, the mixture comprising fractional weights of a conductive element;

b. introducing the curable electrode mixture into the bodily tissue to contact the target;

c. allowing the curable electrode mixture to transform into the electrode in the bodily tissue.

Further aspects include:

the target comprises a contour and the curable electrode mixture contacts at least a portion of the contour of the target.

the target comprises a contour and the electrode is molded against at least a portion of the contour of the target.

Further disclosed is a method of forming an electrode at a target in a bodily tissue, the method comprising a. providing a curable electrode mixture comprising a liquid hydrogel composition, a crosslinking agent and conductive elements, b. introducing the curable electrode mixture into the bodily tissue to contact the target;

c. allowing the curable electrode mixture to transform into the electrode in the bodily tissue.

Further aspects include:

the target comprises a contour and the curable electrode mixture contacts at least a portion of the contour of the target.

the target comprises a contour and the electrode is molded against at least a portion of the contour of the target.

A kit for forming a moldable electrode that adapts at least a portion of a contour of a target in a bodily tissue, the kit comprising:

a. a hydrogel composition in a liquid phase;
b. conductive elements, and
c. optionally a set of instructions for forming a moldable electrode from the hydrogel composition and the conductive elements in a subject.

Further aspects include:
the hydrogel composition comprises polyethylene glycol.
said conductive elements comprise a material selected from a group consisting of gold, gold bonding wire bits, silver, platinum, graphene, graphite, carbon tubes, stainless steel, 316 stainless steel, copper, aluminum oxides, bronze, vanadium, niobium, iron, rhodium, tungsten, titanium, tantalum, gallium, arsenic, antimony, bismuth, nitinol, diamond-coated sand, gold-coated steel, iridium, iridium oxide, ionized proteins, and poly(3,4-ethylenedioxythiophene) polystyrene sulfonate.
further comprising at least two conductive elements.
further comprising a crosslinking agent.
further comprising a dispenser for the liquid hydrogel composition and the conductive elements.
further comprising the set of instructions.

We claim:

1. An implantable electrode adapted to be injected into a body for electrical interfacing with a target within said body, said implantable electrode comprising a mixture of solid conductive elements and a biocompatible non-conductive carrier, said biocompatible non-conductive carrier is configured to transition from a liquid phase to a solid phase, wherein said mixture is adapted to be injected into the body to the target through at least one needle such that the biocompatible non-conductive carrier of said mixture is in the liquid phase during the injection of the mixture into the body, and wherein the biocompatible non-conductive carrier of said mixture is adapted to transition to the solid phase by a phase transition and cured within the body such that said mixture forms said implantable electrode that is conformable to a three-dimensional shape of contours of the target and adapted to conduct electricity through the conductive elements to the target within the body.

2. The cured electrode as in claim 1, wherein the carrier is selected from a group consisting of a silicone, a hydrogel, a bone cement, a cyanoacrylate, a dental resin and a fibrin mix.

3. The cured electrode as in claim 2, wherein when the carrier is silicone, the silicone comprises a formula of [R2SiO]n, where R is a silicone branch, a hydrogen or a group attached by a carbon including —CH$_3$ and n is a number of repeats.

4. The cured electrode as in claim 2, wherein the fibrin mix comprises a fibrinogen and a thrombin.

5. The cured electrode as in claim 1, wherein the phase transition is achieved by a process selected from a group consisting of polymerization, cross linking (chemical, ionic or other), gelation, self-assembly, fusion/solidification, precipitation, and solvent phase inversion.

6. The cured electrode as in claim 2 wherein when the carrier is silicone, the liquid phase of the silicone results from a combination of a vinyl terminated siloxane and a polyfunctional hydride.

7. The cured electrode as in claim 2, wherein when the carrier is silicone, the solid phase of the silicone occurs in presence of a catalyst.

8. The cured electrode as in claim 7, wherein the catalyst comprises platinum.

9. The cured electrode as in claim 2, wherein when the carrier is silicone, the mixture further comprises an additive for increasing contact between conductive elements.

10. The cured electrode as in claim 9, wherein the additive for increasing contact between conductive elements is selected from a group consisting of 3-Glycidyloxypropyltrimethoxysilane, water and ethanol.

11. The cured electrode as in claim 2, wherein the hydrogel comprises a polyethylene glycol having a structure of X—(O-Ch2-Ch2)n-Y, where n is a variable number of repeat units and X and Y are functional groups at terminal ends.

12. The cured electrode as in claim 11, further comprising glycerine.

13. The cured electrode as in claim 2, wherein when the carrier is hydrogel the mixture further comprises a cross linker.

14. The cured electrode as in claim 13, wherein the cross linker is selected from a group consisting of trilysine, quadlysine, pentalysine, Lys-tryp-lys, polylysine, and polyarginine.

15. The cured electrode as in claim 2, wherein the bone cement comprises poly(methyl methacylate).

16. The cured electrode as in claim 2, wherein when the silicone is the carrier the solid phase has a rubbery consistency.

17. The cured electrode as in claim 2, wherein the dental resin comprises a dimethylacrylate monomer and a silica.

18. The cured electrode as in claim 17, wherein the dimethylacrylate monomer is selected from a group consisting of Bis-GMA, TEGMA, UDMA and HDDMA.

19. The cured electrode as in claim 17, further comprising a photo-initiator.

20. The cured electrode as in claim 17, further comprising dimethylglyoxime.

21. The cured electrode as in claim 1, wherein the carrier in the liquid phase comprises monomers and/or oligomers.

22. The cured electrode as in claim 1, wherein in the solid phase of the carrier the conductive elements contribute primarily to electrical resistance of the cured electrode.

23. The cured electrode as in claim 22, wherein the electrical resistance of the conductive elements does not exceed 1 ohm meter.

24. The cured electrode as in claim 22, wherein the electrical resistance of the cured electrode does not exceed 10 ohm meters.

25. The cured electrode as in claim 1, wherein in the solid phase the carrier contributes primarily to mechanical strength of the mixture.

26. The cured electrode as in claim 1, wherein said current constitutes charge transfer by direct contact electron exchange between said conductive elements.

27. The cured electrode as in claim 1, wherein the cured electrode further comprises pores, and the cured electrode comprises outermost dimensions defining an overall volume, and the pores define spaces which together total a subset volume of the overall volume.

28. The cured electrode as in claim 27, wherein the subset volume is within a range of about 0.1% to 20% of the overall volume.

29. The cured electrode as in claim 27, wherein the subset volume is within a range of about 0.1% to 40% of the overall volume.

30. The cured electrode as in claim 1, wherein said conductive elements comprise a material selected from a group consisting of gold, gold bonding wire bits, silver, platinum, graphene, graphite, carbon tubes, stainless steel, 316 stainless steel, carbon doped polymer, aluminum oxides, vanadium, niobium, iron, rhodium, tungsten, titanium, tantalum, gallium, arsenic, antimony, bismuth, nitinol, diamond-coated sand, gold-coated steel or iron, iridium, iridium oxide, ionized proteins, and poly(3,4-ethylenedioxythiophene) polystyrene sulfonate.

31. The cured electrode as in claim 1, wherein conductive elements constitute a range of about 65-85% of the mixture by volume.

32. The cured electrode as in claim 1, wherein the conductive elements constitute a range of about 50-64% of the mixture by volume.

33. The cured electrode as in claim 1, wherein the conductive elements comprise a longest and a shortest dimension, and the conductive elements comprise an aspect ratio of the longest dimension divided by the shortest dimension.

34. The cured electrode as in claim 33, wherein the shortest or longest dimensions of at least a portion of the conductive elements is at least one micron.

35. The cured electrode as in claim 33, wherein the aspect ratio of at least a portion of the conductive elements is less than 3:1.

36. The cured electrode as in claim 33, wherein the aspect ratio of at least a portion of the conductive elements is within a range between 3:1 and less than 10:1.

37. The cured electrode as in claim 33, wherein the aspect ratio of at least a portion of the conductive elements is at least 10:1.

38. The cured electrode as in claim 1, wherein at least a portion of said conductive elements comprise interlocking features selected from a group consisting of hook, loops and coils.

39. The cured electrode as in claim 1, further comprising at least one immunoreactive agent selected from a group consisting of cells, whole blood, blood serum, biodegradable polymers sugars, amino acids, proteins, iron, lipopolysaccharides, collagen and hyaluronic acid.

40. The cured electrode as in claim 39, further comprising at least one of the pharmacological agents selected from a group consisting of an antibiotic, an anti-fungal, an analgesic and an anesthetic.

41. The cured electrode as in claim 1, further comprising at least one anti-inflammatory agent selected from a group consisting of steroids, anti-oxidants, superoxide dismutase mimetics and non-steroidal anti-inflammatory drugs.

42. The cured electrode as in claim 1, further comprising at least one hemostatic agent selected from a group consisting of microfibrillar collagen hemostat, chitosan, kaolin, zeolite, anhydrous aluminum and sulfate.

43. The cured electrode as in claim 1, further comprising a contrast agent for visualization during ultrasound, fluoroscopy or x-ray selected from a group consisting of fluroscein and platinum.

44. The cured electrode as in claim 1, further comprising a nonconductive layer comprising the carrier capable of bonding to the mixture and the target, said nonconductive layer not containing the conductive elements.

45. The cured electrode as in claim 44, wherein the nonconductive layer further comprises nonconductive particles selected from a group consisting of ceramic and glass.

* * * * *